US011919970B2

(12) United States Patent
Chen et al.

(10) Patent No.: US 11,919,970 B2
(45) Date of Patent: Mar. 5, 2024

(54) ANTIBODIES AND CHIMERIC ANTIGEN RECEPTORS SPECIFIC FOR ROR1

(71) Applicant: Juno Therapeutics, Inc., Seattle, WA (US)

(72) Inventors: Yan Chen, Seattle, WA (US); Steven M. Shamah, Seattle, WA (US); Csaba Pazmany, Seattle, WA (US); Jui Dutta-Simmons, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 435 days.

(21) Appl. No.: 17/121,549

(22) Filed: Dec. 14, 2020

(65) Prior Publication Data

US 2021/0238309 A1 Aug. 5, 2021

Related U.S. Application Data

(60) Division of application No. 15/997,635, filed on Jun. 4, 2018, now Pat. No. 10,889,652, which is a continuation of application No. 14/997,991, filed on Jan. 18, 2016, now abandoned.

(60) Provisional application No. 62/104,664, filed on Jan. 16, 2015.

(51) Int. Cl.

| | |
|---|---|
| ***C07K 14/705*** | (2006.01) |
| ***A61K 39/395*** | (2006.01) |
| ***C07K 14/71*** | (2006.01) |
| ***C07K 16/28*** | (2006.01) |
| ***C07K 16/40*** | (2006.01) |

(52) U.S. Cl.

CPC ............ *C07K 16/40* (2013.01); *A61K 39/395* (2013.01); *C07K 14/70596* (2013.01); *C07K 14/71* (2013.01); *C07K 16/2803* (2013.01); *C07K 2317/21* (2013.01); *C07K 2317/92* (2013.01); *C07K 2319/30* (2013.01)

(58) Field of Classification Search

CPC ........................ C07K 14/705; A61K 39/39558
USPC ...................................................... 424/135.1
See application file for complete search history.

(56) References Cited

U.S. PATENT DOCUMENTS 4,235,871 A 11/1980 Papahadjopoulos et al.
4,452,773 A 6/1984 Molday
4,501,728 A 2/1985 Geho et al.
4,690,915 A 9/1987 Rosenberg
4,795,698 A 1/1989 Owen et al.
4,837,028 A 6/1989 Allen
5,019,369 A 5/1991 Presant et al.
5,087,616 A 2/1992 Myers et al.
5,200,084 A 4/1993 Liberti et al.
5,208,020 A 5/1993 Chari et al.
5,219,740 A 6/1993 Miller et al.
5,416,064 A 5/1995 Chari et al.
5,635,483 A 6/1997 Pettit et al.
5,712,374 A 1/1998 Kuntsmann et al.
5,714,586 A 2/1998 Kunstmann et al.
5,739,116 A 4/1998 Hamann et al.
5,767,285 A 6/1998 Hamann et al.
5,770,701 A 6/1998 McGahren et al.
5,770,710 A 6/1998 McGahren et al.
5,773,001 A 6/1998 Hamann et al.
5,780,588 A 7/1998 Pettit et al.
5,877,296 A 3/1999 Hamann et al.
6,040,177 A 3/2000 Riddell et al.
6,207,453 B1 3/2001 Maass et al.
6,410,319 B1 6/2002 Raubitschek et al.
6,451,995 B1 9/2002 Cheung et al.
6,602,684 B1 8/2003 Umana et al.
6,630,579 B2 10/2003 Chari et al.
7,070,995 B2 7/2006 Jensen
7,265,209 B2 9/2007 Jensen
7,354,762 B2 4/2008 Jensen
7,446,179 B2 11/2008 Jensen et al.
7,446,190 B2 11/2008 Sadelain et al.
7,446,191 B2 11/2008 Jensen
7,498,298 B2 3/2009 Doronina et al.
7,521,541 B2 4/2009 Eigenbrot et al.
7,855,275 B2 12/2010 Eigenbrot et al.
8,324,353 B2 12/2012 Jensen
8,389,282 B2 3/2013 Sadelain et al.
8,399,645 B2 3/2013 Campana et al.

(Continued)

FOREIGN PATENT DOCUMENTS

CN 107557337 1/2018
EP 0425235 5/1991

(Continued)

OTHER PUBLICATIONS

US 8,252,592 B2, 08/2012, Sadelain (withdrawn)

(Continued)

*Primary Examiner* — Lynn A Bristol

(74) *Attorney, Agent, or Firm* — Morrison & Foerster LLP

(57) ABSTRACT

Provided are ROR1 binding molecules, including anti-ROR1 antibodies, including antibody fragments such as variable heavy chain (VH) regions, single-chain fragments, and chimeric receptors including the antibodies, such as chimeric antigen receptors (CARs). In some embodiments, the antibodies specifically bind to ROR1. Among the antibodies are human antibodies, including those that compete for binding to ROR1 with reference antibodies, such as a non-human reference antibody. Also provided are genetically engineered cells expressing the chimeric receptors, and uses of the binding molecules and cells adoptive cell therapy.

40 Claims, 2 Drawing Sheets

Specification includes a Sequence Listing.

(56) References Cited

U.S. PATENT DOCUMENTS

| | | | |
|---|---|---|---|
| 8,497,118 B2 | 7/2013 | Jensen | |
| 8,911,993 B2 | 12/2014 | June et al. | |
| 10,889,265 B2 | 1/2021 | Sobecki et al. | |
| 10,889,652 B2 * | 1/2021 | Chen | A61K 39/395 |
| 10,968,275 B2 | 4/2021 | Balakrishnan et al. | |
| 2002/0131960 A1 | 9/2002 | Sadelain et al. | |
| 2002/0164328 A1 | 11/2002 | Shinkawa et al. | |
| 2003/0115614 A1 | 6/2003 | Kanda et al. | |
| 2003/0157108 A1 | 8/2003 | Presta | |
| 2003/0170238 A1 | 9/2003 | Gruenberg et al. | |
| 2004/0093621 A1 | 5/2004 | Shitara et al. | |
| 2004/0109865 A1 | 6/2004 | Niwa et al. | |
| 2004/0110282 A1 | 6/2004 | Kanda et al. | |
| 2004/0110704 A1 | 6/2004 | Yamane et al. | |
| 2004/0132140 A1 | 7/2004 | Satoh et al. | |
| 2005/0009136 A1 | 1/2005 | Nixon et al. | |
| 2005/0123546 A1 | 6/2005 | Umana et al. | |
| 2005/0232921 A1 | 10/2005 | Rosen et al. | |
| 2006/0270045 A1 | 11/2006 | Cregg et al. | |
| 2009/0041784 A1 | 2/2009 | Yan et al. | |
| 2011/0003380 A1 | 1/2011 | Miltenyi et al. | |
| 2011/0129478 A1 | 6/2011 | Okano et al. | |
| 2012/0058051 A1 | 3/2012 | Rader et al. | |
| 2013/0149337 A1 | 6/2013 | Cooper et al. | |
| 2013/0202622 A1 | 8/2013 | Riddell et al. | |
| 2013/0251642 A1 | 9/2013 | Rader et al. | |
| 2013/0287748 A1 | 10/2013 | June et al. | |
| 2014/0314795 A1 | 10/2014 | Riddell et al. | |
| 2015/0306141 A1 | 10/2015 | Jensen et al. | |
| 2016/0208018 A1 | 7/2016 | Chen et al. | |
| 2018/0200298 A1 | 7/2018 | Jensen et al. | |
| 2018/0265593 A1 | 9/2018 | Chen et al. | |
| 2019/0040132 A1 | 2/2019 | Balakrishnan et al. | |
| 2021/0147540 A1 | 5/2021 | Balakrishnan et al. | |
| 2022/0096651 A1 | 3/2022 | Costa et al. | |

FOREIGN PATENT DOCUMENTS

| | | |
|---|---|---|
| EP | 0452342 | 10/1991 |
| EP | 2537416 | 12/2012 |
| WO | WO 1992/008796 | 5/1992 |
| WO | WO 1994/011026 | 5/1994 |
| WO | WO 1994/028143 | 12/1994 |
| WO | WO 1997/030087 | 8/1997 |
| WO | WO 1998/058964 | 12/1998 |
| WO | WO 1999/022764 | 5/1999 |
| WO | WO 2000/014257 | 3/2000 |
| WO | WO 2000/061739 | 10/2000 |
| WO | WO 2001/029246 | 4/2001 |
| WO | WO 2002/002641 | 1/2002 |
| WO | WO 2002/031140 | 4/2002 |
| WO | WO 2003/011878 | 2/2003 |
| WO | WO 2003/084570 | 10/2003 |
| WO | WO 2003/085093 | 10/2003 |
| WO | WO 2003/085107 | 10/2003 |
| WO | WO 2003/085119 | 10/2003 |
| WO | WO 2004/056312 | 7/2004 |
| WO | WO 2005/035586 | 4/2005 |
| WO | WO 2005/035732 | 4/2005 |
| WO | WO 2005/035778 | 4/2005 |
| WO | WO 2005/037235 | 4/2005 |
| WO | WO 2005/053742 | 6/2005 |
| WO | WO 2005/097184 | 10/2005 |
| WO | WO 2009/072003 | 6/2009 |
| WO | WO 2010/033140 | 3/2010 |
| WO | WO 2010/075238 | 7/2010 |
| WO | WO 2010/124188 | 10/2010 |
| WO | WO 2011/014469 | 3/2011 |
| WO | WO 2011/159847 | 12/2011 |
| WO | WO 2012/012695 | 1/2012 |
| WO | WO 2012/045085 | 4/2012 |
| WO | WO 2012/076066 | 6/2012 |
| WO | WO 2012/079000 | 6/2012 |
| WO | WO 2012/129514 | 9/2012 |
| WO | WO 2013/022968 | 2/2013 |
| WO | WO 2013/043933 | 3/2013 |
| WO | WO 2013/071154 | 5/2013 |
| WO | WO 2013/123061 | 8/2013 |
| WO | WO 2013/126712 | 8/2013 |
| WO | WO 2013/126726 | 8/2013 |
| WO | WO 2013/166321 | 11/2013 |
| WO | WO 2014/031174 | 2/2014 |
| WO | WO 2014/031687 | 2/2014 |
| WO | WO 2014/055668 | 4/2014 |
| WO | WO 2014/164554 | 10/2014 |
| WO | WO 2015/066551 | 5/2015 |
| WO | WO 2015/157399 | 10/2015 |
| WO | WO 2015/184203 | 12/2015 |
| WO | WO 2016/016344 | 2/2016 |
| WO | WO 2016/069647 | 5/2016 |
| WO | WO 2016/115559 | 7/2016 |
| WO | WO 2016/187216 | 11/2016 |
| WO | WO 2017/072361 | 5/2017 |
| WO | WO 2017/136607 | 8/2017 |
| WO | WO 2017/214207 | 12/2017 |
| WO | WO 2018/197675 | 11/2018 |
| WO | WO 2020/160050 | 8/2020 |

OTHER PUBLICATIONS

George et al. (Circulation. 1998; 97: 900-906).*

Specht et al (Cancer Research, (Jul. 2018) vol. 78, No. 13, Supp. Supplement 1. Abstract No. CT131. Meeting Info: 2018 Annual Meeting of the American Association for Cancer Research, AACR 2018. Chicago, IL, United States. Apr. 14, 2018-Apr. 18, 2018).*

Specth et al (Cancer Research, (Feb. 2019) vol. 79, No. 4, Supp. Supplement 1. Abstract No. P2-09-13. Meeting Info: 2018 San Antonio Breast Cancer Symposium. San Antonio, TX, United States. Dec. 4, 2018-Dec. 8, 2018).*

U.S. Appl. No. 17/157,810, filed Jan. 25, 2021, by Balakrishnan et al. (Copy not provided). (Copy not submitted herewith pursuant to the waiver of 37 C.F.R. § 1.98(a)(2)(iii) issued by the Office on Sep. 21, 2004).

Al-Lazikani et al., "Standard conformations for the canonical structures of immunoglobulins," JMB (1997) 273:927-948.

Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.

Anonymous, "A ROR1 antibody (Receptor Tyrosine Kinase-Like Orphan Receptor 1) (C-Term) Antigen: Receptor Tyrosine Kinase-Like Orphan Receptor 1(ROR1)" retrieved from the internet www.antibodies-online.com [retrieved Sep. 10, 2019].

Anonymous, "Product Data sheet: ARP63925 P050—RORI Antibody—C-terminal region (ARP63925 P050)—Aviva Systems Biology" Retrieved from the internet: URL:http://www.avivasysbio.com/sd/tds/html_datasheet.php?sku=ARP63925_P050 [retrieved on Sep. 9, 2019].

Baskar et al., "Targeting malignant B cells with an immunotoxin against ROR1," MAbs. May-Jun. 2012;4(3):349-61.

Berger et al., "Safety of targeting ROR1 for cancer immunotherapy with chimeric antigen receptor-modified T cells in a primate model," J. ImmunoTherapy of Cancer (2014);2(Suppl 3):3.

Berger, et al. "Safety of targeting ROR1 in primates with chimeric antigen receptor-modified T cells," Cancer Immunol Res. Feb. 2015;3(2):206-16.

Boris-Lawrie et al., "Recent advances in retrovirus vector technology," Cur. Opin. Genet. Develop. (1993) 3:102-109.

Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.

Bruggeman et al., "Human antibody production in transgenic animals," Arch Immunol. Ther. Exp. (2015) 63:101-08.

Brummell et al. (Biochemistry 32:1180-1187 (1993)).

Burks et al. (PNAS 94:412-417 (1997)).

(56) References Cited

OTHER PUBLICATIONS

Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.
Carlens et al., "Ex vivo T lymphocyte expansion for retroviral transduction: influence of serum-free media on variations in cell expansion rates and lymphocyte subset distribution," Exp Hematol (2000) 28(10): 1137-46.
Casset et al."A peptide mimetic of an anti-CD4 monoclonal antibody by rational design." BBRC, 307: 198-205 (2003).
Cavalieri et al., "Human T lymphocytes transduced by lentiviral vectors in the absence of TCR activation maintain an intact immune competence," Blood (2003) 102(2): 497-505.
Chari et al., "Immunoconjugates containing novel maytansinoids: promising anticancer drugs," Cancer Res. (1992) 52:127-131.
Chen et al. J. Mol. Bio. (1999) 293, 865-881.
Chen et al., "Cirmtuzumab blocks Wnt5a/ROR1 stimulation of NF-κB to repress autocrine STAT3 activation in chronic lymphocytic leukemia," Blood (2019) 134(13):1084-94.
Chicaybam et al., "An efficient low cost method for gene transfer to T lymphocytes," PLoS ONE (2013) 8(3): e60298.
Cho et al., "Human mammalian cell sorting using a highly integrated micro-fabricated fluorescence-activated cell sorter (microFACS)," Lab Chip (2010) 10: 1567-1573.
Choi et al., "Phase I Trial: Cirmtuzumab Inhibits ROR1 Signaling and Stemness Signatures in Patients with Chronic Lymphocytic Leukemia," Cell Stem Cell (2018) 22(6);951-9.
Chowdhury et al, "Engineering hot spots for affinity enhancement of antibodies," Methods Mol. Biol. (2008) 207:179-196.
Clackson et al., "Making antibody fragments using phage display libraries," Nature (1991) 352:624-628.
Clarke and Davies in: Methods in Molecular Medicine, vol. 58: Metastasis Research Protocols, vol. 2: Cell Behavior In Vitro and In Vivo, Edited by: S. A. Brooks and U. Schumacher © Humana Press Inc., Totowa, NJ (2001) pp. 17-25.
Clinical Trial Identifier NCT02194374, "Autologous ROR1R-CAR-T cells for chronic lymphocytic leukemia (CLL)," published Jul. 18, 2014, retrieved from: https://clinicaltrials.gov/ct2/show/NCT02194374.
Coleman (Research in Immunol. 145:33-36 (1994)).
Cooper et al., "T-cell clones can be rendered specific for CD19: toward the selective augmentation of the graft-versus-B-lineage leukemia effect," Blood. (2003) 101:1637-1644.
Daneshmanesh et al., "Monoclonal antibodies against ROR1 induce apoptosis of chronic lymphocytic leukemia (CLL) cells," Leukemia. Jun. 2012;26(6):1348-55.
Daneshmanesh et al., "Ror1, a cell surface receptor tyrosine kinase is expressed in chronic lymphocytic leukemia and may serve as a putative target for therapy," International Journal of Cancer (2008) 123:1190-1195.
Davila et al., "CD19 CAR-targeted T cells induce long-term remission and B Cell Aplasia in an immunocompetent mouse model of B cell acute lymphoblastic leukemia," PLoS ONE (2013) 8(4): e61338.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology 169:3076-3084 (2002).
Dubowchik et al., "Doxorubicin immunoconjugates containing bivalent, lysosomally-cleavable dipeptide linkages," Bioorg. & Med. Chem. Letters (2002) 12:1529-1532.
Endo et al., "High-throughput, genome-scale protein production method based on the wheat germ cell-free expression system," Biotechnol. Adv. (2003) 21: 695-713.
Fedorov et al., "PD-1- and CTLA-4-based inhibitory chimeric antigen receptors (iCARs) divert off-target immunotherapy responses," Sci. Transl. Medicine (2013) 5(215).
Flatman et al., "Process analytics for purification of monoclonal antibodies," J. Chromatogr. (2007) B 848:79-87.
Gerngross et al, "Advances in the production of human therapeutic proteins in yeasts and filamentous fungi," Nat. Biotech. (2004) 22:1409-1414.
Godin et al., "Microfluidics and photonics for Bio-System-on-a-Chip: a review of advancements in technology towards a microfluidic flow cytometry chip," J Biophoton. (2008) 1(5):355-376.
Hermans et al., "The VITAL assay: a versatile fluorometric technique for assessing CTL- and NKT-mediated cytotoxicity against multiple targets in vitro and in vivo," J. Immunological Methods (2004) 285(1): 25-40.
Hinman et al., "Preparation and characterization of monoclonal antibody conjugates of the calicheamicins: a novel and potent family of antitumor antibiotics," Cancer Res. (1993) 53:3336-3342.
Hojjat-Farsangi et al., "Inhibition of the receptor tyrosine kinase ROR1 by anti-ROR1 monoclonal antibodies and siRNA induced apoptosis of melanoma cells," PLoS One. Apr. 8, 2013;8(4):e61167.
Holm et al ((2007) Mol. Immunol. 44: 1075-1084).
Honegger A and Plückthun A, "Yet another numbering scheme for immunoglobulin variable domains: an automatic modeling and analysis tool," J Mol Biol, (2001) 8;309(3):657-70.
Hoogenboom et al., "Overview of antibody phage-display technology and its applications," Methods in Molecular Biology (2002) 178:1-37.
Huang et al., "Dna transposons for modification of human primary T lymphocytes," Methods Mol Biol (2009) 506: 115-126.
Hudecek et al., "Naïve CD4+T cells modified to express a ROR1-specific CAR mediate anti-tumor activity and provide superior help to CD8+ROR1-CAR T cells," Blood (2011) 118:643.
Hudecek et al., "Receptor affinity and extracellular domain modifications affect tumor recognition by ROR1-specific chimeric antigen receptor T cells," Clin. Cancer Res. (2013) 19:3153.
Hudecek et al., "The anti-tumor reactivity of ROR1-CAR modified T cells depends on the targeted epitope, CAR affinity and design of the CAR extracellular domain," Clinical Lymphoma, Myeloma and Leukemia Supplement (2011) 11(2):s280-s281.
Hudecek et al., "The B-cell tumor-associated antigen ROR1 can be targeted with T cells modified to express a ROR1-specific chimeric antigen receptor," Blood. Nov. 25, 2010;116(22):4532-41.
Jeffrey et al., "Dipeptide-based highly potent doxorubicin antibody conjugates," Bioorganic & Med. Chem. Letters (2006) 16:358-362.
Johnston, et al., "Biolistic transformation: microbes to mice," Nature (1990) 346: 776-777.
Junghans et al., "Anti-Tac-H, a humanized antibody to the interleukin 2 receptor with new features for immunotherapy in malignant and immune disorders," Cancer Res. (1990) 50:1495-1502.
Matsumoto, "How far has the development and application of human antibodies progressed," Chemistry and Biology (1998) vol. 38, No. 7, pp. 448-456 (Including English translation).
Kanda, Y. et al., "Comparison of cell lines for stable production of fucose-negative antibodies with enhanced ADCC," Biotechnol. Bioeng. (2006) 94(4):680-688.
Karachaliou et al., "ROR1 as a novel therapeutic target for EGFR-mutant non-small-cell lung cancer patients with the EGFR T790M mutation," Translational Lung Cancer Research (2014) 3(3):122-130.
Kindt et al., Kuby Immunology 6th ed., W.H. Freeman and Co. (2007) p. 91.
King et al., "Monoclonal antibody conjugates of doxorubicin prepared with branched peptide linkers: inhibition of aggregation by methoxytriethyleneglycol chains," J. Med. Chem. (2002) 45:4336-4343.
Klebanoff et al., "Sorting through subsets: which T-cell populations mediate highly effective adoptive immunotherapy?," J Immunother. (2012) 35(9): 651-660.
Kobayashi et al. (Protein Engineering 12:879-844 (1999)).
Kochenderfer et al., "Construction and preclinical evaluation of an anti-CD19 chimeric antigen receptor," J. Immunotherapy (2009) 32(7): 689-702.
Koehler et al., "Engineered T Cells for the Adoptive Therapy of B-Cell Chronic Lymphocytic Leukaemia." Advances in Hematology. (2011) v.2012, p. 1-13.
Koste et al., "T-cell receptor transfer into human T cells with ecotropic retroviral vectors," Gene Therapy (2014) 21: 533-538.

(56) References Cited

OTHER PUBLICATIONS

Kratz et al., "Prodrugs of anthracyclines in cancer chemotherapy," Current Med. Chem. (2006) 13:477-523.
Kumar et al. (J. Biol. Chem. 275:35129-35136 (2000)).
Lefranc et al., "IMGT unique numbering for immunoglobulin and T cell receptor variable domains and Ig superfamily V-like domains," Dev Comp Immunol (2003) 27(1):55-77.
Li et al., "Optimization of humanized IgGs in glycoengineered Pichia pastoris," Nat. Biotech. (2006) 24:210-215.
Liu et al., "Silencing of Receptor Tyrosine Kinase ROR1 Inhibits Tumor-Cell Proliferation via PI3K/AKT/mTOR Signaling Pathway in Lung Adenocarcinoma," PLOS One (2015) 10(5):e0127092.
Lode et al., "Targeted therapy with a novel enediyene antibiotic calicheamicin theta(I)1 effectively suppresses growth and dissemination of liver metastases in a syngeneic model of murine neuroblastoma," Cancer Res. (1998) 58:2925-2928.
Lupton S. D. et al., "Dominant positive and negative selection using a hygromycin phosphotransferase-thymidine kinase fusion gene," Mol. and Cell Biol. (1991) 11:6.
MacCallum et al., "Antibody-antigen interactions: Contact analysis and binding site topography," J. Mol. Biol. (1996) 262, 732-745.
Manuri et al., "piggyBac transposon/transposase system to generate CD19-specific T cells for the treatment of B-lineage malignancies," Hum Gene Ther (2010) 21(4): 427-437.
Martin et al., "Modeling antibody hypervariable loops: a combined algorithm," Proc Natl Acad Sci U S A. Dec. 1989;86(23):9268-72.
Miller et al., "Improved retroviral vectors for gene transfer and expression," BioTechniques (1989) 7:980-990.
Miller et al., "Retrovirus packaging cells," Human Gene Therapy (1990) 1:5-14.
Mullen et al., "Transfer of the bacterial gene for cytosine deaminase to mammalian cells confers lethal sensitivity to 5-fluorocytosine: a negative selection system," Proc. Natl. Acad. Sci. USA (1992) 89:33.
Nagy et al., "Stability of cytotoxic luteinizing hormone-releasing hormone conjugate (AN-152) containing doxorubicin 14-O-hemiglutarate in mouse and human serum in vitro: implications for the design of preclinical studies," Proc. Natl. Acad. Sci. USA (2000) 97:829-834.
Okazaki et al., "Fucose depletion from human IgG1 oligosaccharide enhances binding enthalpy and association rate between IgG1 and FcgammaRIIIa," J. Mol. Biol. (2004) 336:1239-1249.
Park et al., "Treating cancer with genetically engineered T cells," Trends Biotechnol. (2011) 29(11): 550-557.
Portolano et al., "Lack of promiscuity in autoantigen-specific H and L chain combinations as revealed by human H and L chain "roulette"," J. Immunol. (1993) 150:880-887.
Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3:319-338.
Ripka et al., "Two Chinese hamster ovary glycosylation mutants affected in the conversion of GDP-mannose to GDP-fucose," Arch. Biochem. Biophys. (1986) 249:533-545.
Rosenberg, et al., "Cell transfer immunotherapy for metastatic solid cancer—what clinicians need to know," Nat Rev Clin Oncol. (2011) 8(10):577-85).
Sadelain et al., "The basic principles of chimeric antigen receptor design," Cancer Discov. (2013) 3(4): 388-398.
Scarpa et al., "Characterization of recombinant helper retroviruses from Moloney-based vectors in ecotropic and amphotropic packaging cell lines," Virology (1991) 180:849-852.
Sharma et al., "Efficient sleeping beauty DNA transposition from DNA minicircles," Molec Ther Nucl Acids (2013) 2, e74.
Sitaraman et al., "High-throughput protein expression using cell-free system," Methods Mol. Biol. (2009) 498: 229-44.
Smith-Gill et al., (J. Immunol. 139:4135-4144 (1987).
Song et al. (Biochem Biophys Res Comm 268:390-394 (2000)).
Spirin, et al., "High-throughput cell-free systems for synthesis of functionally active proteins," Trends Biotechnol. (2004) 22: 538-45.
Szoka et al., "Comparative properties and methods of preparation of lipid vesicles (liposomes)," Ann. Rev. Biophys. Bioeng. (1980) 9: 467.
Terakura et al., "Generation of CD19-chimeric antigen receptor modified CD8+ T cells derived from virus-specific central memory T cells," Blood (2012) 1:72-82.
Themeli et al., "Generation of tumor-targeted human T lymphocytes from induced pluripotent stem cells for cancer therapy," Nat Biotechnol. (2013) 31(10): 928-933.
Torgov et al., "Generation of an intensely potent anthracycline by a monoclonal antibody-beta-galactosidase conjugate," Bioconj. Chem. (2005) 16:717-721.
Tsukahara et al., "CD19 target-engineered T-cells accumulate at tumor lesions in human B-cell lymphoma xenograft mouse models," Biochem Biophys Res Commun (2013) 438(1): 84-9.
Turtle et al., "Engineered T cells for anti-cancer therapy," Curr. Opin. Immunol. (2012) 24(5): 633-39.
Vajdos et al. "Comprehensive functional maps of the antigen-binding site of an anti-ErbB2 antibody obtained with shotgun scanning mutagenesis." J. Mol. Biol. 320, 415-428 (2002).
Van Tendeloo et al., "High-level transgene expression in primary human T lymphocytes and adult bone marrow CD34+ cells via electroporation-mediated gene delivery," Gene Therapy (2000) 7(16): 1431-1437).
Verhoeyen et al., "Lentiviral vector gene transfer into human T cells," Methods Mol Biol. (2009) 506: 97-114.
Vitetta et al., "Redesigning nature's poisons to create anti-tumor reagents," Science (1987) 238:1098.
Wadhwa et al., "Receptor mediated glycotargeting," J. Drug Targeting (1995) 3: 111.
Wang et al., "Phenotypic and functional attributes of lentivirus-modified CD19-specific human CD8+ central memory T cells manufactured at clinical scale," J Immunother. (2012) 35(9):689-701.
Ward et al. (Nature 341 :544-546 (1989);).
Wigler et al., "Transfer of purified herpes virus thymidine kinase gene to cultured mouse cells," Cell (1997) 11: 223-232.
Wu et al. "Humanization of a murine monoclonal antibody by simultaneous optimization of framework and CDR residues." J. Mol. Biol. 294, 151-162 (1999).
Wu et al., "Adoptive T-cell therapy using autologous tumor-infiltrating lymphocytes for metastatic melanoma: current status and future outlook," Cancer (2012) 18(2): 160-75.
Yamane-Ohnuki et al., "Establishment of FUT8 knockout Chinese hamster ovary cells: an ideal host cell line for producing completely defucosylated antibodies with enhanced antibody-dependent cellular cytotoxicity," Biotech. Bioeng. (2004) 87: 614.
Yang et al., "Therapeutic potential and challenges of targeting receptor tyrosine kinase ROR1 with monoclonal antibodies in B-cell malignancies," PLoS One. (2011);6(6):e21018.
Yu et al., "Cirmtuzumab inhibits Wnt5a-induced Rac1 activation in chronic lymphocytic leukemia treated with ibrutinib," Leukemia (2016) 31(6):1333-9.
Zhang et al., "ROR1 expression correlated with poor clinical outcome in human ovarian cancer," Scientific Reports (2014) 4:5811.
Zhang et al., "ROR1 Is Expressed in Human Breast Cancer and Associated with Enhanced Tumor-Cell Growth," PloS One (2012) 7(3): e31127.
Zhang et al., "The onco-embryonic antigen ROR1 is expressed by a variety of human cancers," The American Journal of Pathology. (2012) 181(6):1903-1910.
Zola in: Monoclonal Antibodies: A Manual of Techniques, © CRC Press Inc., Boca Raton, FL (1987) pp. 147-158.
Anonymous, "Autologous ROR1R-CAR-T cells for chronic lymphocytic leukemia (CLL)," NIH Clinical Trials, NCT02194374; Jul. 18, 2014, p. 1-8, retrieved from the internet: https://clinicaltrials.gov/ct2/show/NCT02194374.
Anonymous, "Anti ROR1 Antibody (Receptor Tyrosine Kinase Like Orphan Receptor 1) (C Term)," Online, Sep. 1, 2008, pp. 1-4, URL, https://www.antibodiesonline.com/productsheets/ABIN5539753.pdf.
Anonymous, "Genetically modified T-cell therapy in treating patients with advanced ROR1+ malignancies", NIH Clinical Trials,

(56) References Cited

OTHER PUBLICATIONS

NCT02706392; Mar. 11, 2016, retrieved from the internet: https://clinicaltrials.gov/ct2/show/NCT02706392.
Baskar et al., "Unique cell surface expression of receptor tyrosine kinase ROR1 in human B-cell chronic lymphocytic leukemia," Clinical Cancer Research (2008) 14(2): 396-404.
Chien et al., "Expression of ROR1 has prognostic significance in triple negative breast cancer," Virchows Arch. (2016) 468(5):589-595.
Choi et al., "Pre-clinical Specificity and Safety of UC-961, a First-In-Class Monoclonal Antibody Targeting ROR1," Clinical Lymphoma, Myeloma & Leukemia (2015) 15(Suppl. 1):S167-S169.
Cui et al., "Targeting ROR1 inhibits epithelial-mesenchymal transition and metastasis," Cancer Research (2013) 73(12):3649-3660.
Dave et al., "Restricted cell surface expression of receptor tyrosine kinase ROR1 in pediatric B-lineage acute lymphoblastic leukemia suggests targetability with therapeutic monoclonal antibodies," PLoS One (2012) 7(12):e52655.
Fukuda et al.,"Antisera induced by infusions of autologous Ad-CD154-leukemia B cells identify ROR1 as an oncofetal antigen and receptor for Wnt5a," PNAS (2008) 105(8):3047-3052.
Hudecek et al., "Receptor affinity and extracellular domain modifications affect tumor recognition by ROR1-specific chimeric antigen receptor T cells," Clin. Cancer Res. 19(12):3153-3164, 2013. Supplementary Data.
Kaucka et al., "Post-translational modifications regulate signalling by Ror1," Acta Physiologica (2011) 203(3):351-362.
Kunik et al., "Structural consensus among antibodies defines the antigen binding site," PLoS Comput Biol. (2012) 8(2):e1002388.
Kussie et al., "Single Engineered Amino Acid Substitution Changes Antibody Fine Specificity," J Immunol. (1994) 152(1):146-52.
Rudikoff et al., "Single amino acid substitution altering antigen-binding specificity," PNAS (1982) 79(6):1979-1983.
Specht et al., "Phase I study of immunotherapy for advanced ROR1+ malignancies with autologous ROR1-specific chimeric antigen receptor-modified (CAR)-T cells," J. Clin. Onc. 2018, 36(5):supplement 1; TPS79.
Yamaguchi et al., "NKX2-1/TITF1/TTF-1-Induced ROR1 is required to sustain EGFR survival signaling in lung adenocarcinoma," Cancer Cell (2012) 21(3):348-361.

* cited by examiner

SEQUENCE LISTING

<160> NUMBER OF SEQ ID NOS: 318

<210> SEQ ID NO 1
<211> LENGTH: 720
<212> TYPE: DNA
<213> ORGANISM: Homo sapiens
<220> FEATURE:
<223> OTHER INFORMATION: Clone 83 scFv

<400> SEQUENCE: 1
caggtccagc ttgtgcagtc tggggctgag gtgaagaagc ctggggcctc agtgaaggtt 60
tcctgcaagg catctggata caccttcacc agctactata tgcactgggt gcgacaggcc 120
cctggacaag ggcttgagtg gatgggaata atcaacccta gtggtggtag cacaagctac 180
gcacagaagt tccagggcag agtcaccatg accagggaca cgtccacgag cacagtctac 240
atggagctga gcagcctgag atctgaggac acggccgtgt attactgtgc gagagatagc 300
agctatgatg cttttgatat ctggggccaa gggacaatgg tcaccgtctc ctcaggtgga 360
ggcggttcag gcggaggtgg ctctggcggt ggcggatcgg ccatccagtt gacccaatct 420
ccttccaccc tgtctgcatc tgtaggagac agagtcacca tcacttgcca ggcgagtcag 480
gacatcagca attatttaaa ttggtatcag cagaaaccag ggaaagcccc taaactcctg 540
atcaacgatg catcctattt ggagacaggg gtcccatcaa ggttcagtgg aagtggatct 600
gggacagatt ttactttaac catcagcagc ctgcagcctg aagatattgc aacatattac 660
tgtcaacagt atgaaagtct cccgtacact tttggccagg ggaccaagct ggagatcaaa 720

<210> SEQ ID NO 2
<211> LENGTH: 240
<212> TYPE: PRT
<213> ORGANISM: Homo sapiens
<220> FEATURE:

<223> OTHER INFORMATION: Clone 83 scFv

<400> SEQUENCE: 2

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Tyr Asp Ala Phe Asp Ile Trp Gly Gln Gly Thr
            100                 105                 110

Met Val Thr Val Ser Ser Gly Gly Gly Gly Ser Gly Gly Gly Gly Ser
        115                 120                 125

Gly Gly Gly Gly Ser Ala Ile Gln Leu Thr Gln Ser Pro Ser Thr Leu
    130                 135                 140

Ser Ala Ser Val Gly Asp Arg Val Thr Ile Thr Cys Gln Ala Ser Gln
145                 150                 155                 160

Asp Ile Ser Asn Tyr Leu Asn Trp Tyr Gln Gln Lys Pro Gly Lys Ala
                165                 170                 175

Pro Lys Leu Leu Ile Asn Asp Ala Ser Tyr Leu Glu Thr Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Ile Ala Thr Tyr Tyr Cys Gln Gln Tyr
    210                 215                 220

Glu Ser Leu Pro Tyr Thr Phe Gly Gln Gly Thr Lys Leu Glu Ile Lys
225                 230                 235                 240
```

<210> SEQ ID NO 3
<211> LENGTH: 726
<212> TYPE: DNA
<213> ORGANISM: Homo sapiens
<220> FEATURE:
<223> OTHER INFORMATION: Clone 298 scFv

<400> SEQUENCE: 3

```
gaggtgcagc tggtggagtc tgggggaggc ttggtacagc cagggcggtc cctgagactc      60

tcctgtacag cttctggatt cacctttggt gattatgcga tgagctgggt ccgccaggct     120

ccagggaagg ggctggagtg ggtctcaagt attagtggta gtggtcgtag cacagaccac     180

gcagactacg tgaagggccg gttcaccatc tccagagaca attccaagaa cacggtatat     240

ctgcaaatga acaggctgag agccgaggac acggccgtgt attactgtgc aaaagtcagt     300

aactacgagt attactttga ctactgggcc cagggaaccc tggtcaccgt ctcctcaggt     360

ggaggcggtt caggcggagg tggctctggc ggtggcggat cggaaattgt gctgactcag     420

tctccctcgg tgtcagtggc cccaggacag acggccagaa ttacctgtgg gggaagcaac     480

attggatctg agagtgtcaa ctggtaccag tggaagtcgg gccaggttcc tgtcttggtc     540

gtctctgaca ctaccgaccg accctcaggg atccctgggc gattcactgg cacccggtct     600
```

-continued

```
gggaccacgg ccaccttgac catcagtggg gtcgaagccg gggatgaggc cgactatcac    660

tgtcaggtgt gggatgacac tggtgatcat cctgtcttcg gcggagggac caagctgacc    720

gtccta                                                               726


<210> SEQ ID NO 4
<211> LENGTH: 242
<212> TYPE: PRT
<213> ORGANISM: Homo sapiens
<220> FEATURE:
<223> OTHER INFORMATION: Clone 298 scFv

<400> SEQUENCE: 4

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Arg Ser Thr Asp His Ala Asp Tyr Val
    50                  55                  60

Lys Gly Arg Phe Thr Ile Ser Arg Asp Asn Ser Lys Asn Thr Val Tyr
65                  70                  75                  80

Leu Gln Met Asn Arg Leu Arg Ala Glu Asp Thr Ala Val Tyr Tyr Cys
                85                  90                  95

Ala Lys Val Ser Asn Tyr Glu Tyr Tyr Phe Asp Tyr Trp Ala Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Glu Ile Val Leu Thr Gln Ser Pro Ser Val
    130                 135                 140

Ser Val Ala Pro Gly Gln Thr Ala Arg Ile Thr Cys Gly Gly Ser Asn
145                 150                 155                 160

Ile Gly Ser Glu Ser Val Asn Trp Tyr Gln Trp Lys Ser Gly Gln Val
                165                 170                 175

Pro Val Leu Val Val Ser Asp Thr Thr Asp Arg Pro Ser Gly Ile Pro
            180                 185                 190

Gly Arg Phe Thr Gly Thr Arg Ser Gly Thr Thr Ala Thr Leu Thr Ile
        195                 200                 205

Ser Gly Val Glu Ala Gly Asp Glu Ala Asp Tyr His Cys Gln Val Trp
    210                 215                 220

Asp Asp Thr Gly Asp His Pro Val Phe Gly Gly Gly Thr Lys Leu Thr
225                 230                 235                 240

Val Leu


<210> SEQ ID NO 5
<211> LENGTH: 741
<212> TYPE: DNA
<213> ORGANISM: Homo sapiens
<220> FEATURE:
<223> OTHER INFORMATION: Clone 48 scFv

<400> SEQUENCE: 5

caggtcacct tgaaggagtc tgggggaggc ttggtaaagc ctgggggggtc ccttagactc     60

tcctgtgcag cctctggatt cactttcagt aacgcctgga tgagctgggt ccgccaggct    120

ccagggaagg ggctggagtg ggttggccgt attaaaagca aaactgatgg tgggacaaca    180
```

-continued

```
gactacgctg cacccgtgaa aggcagattc accatctcaa gagatgattc aaaaaacacg    240

ctgtatctgc aaatgaacag cctgaaaacc gaggacacag ccgtgtatta ctgtgcgaga    300

gatttcggac gatggagcta ctactttgac tactggagcc agggaaccct ggtcaccgtc    360

tcctcaggtg gaggcggttc aggcggaggt ggctctggcg gtggcggatc gcagtctgtg    420

ctgactcagc catcctcagt gtctgggacc cccgggcaga gggtcaccat ctcttgttct    480

ggaagcagct ccaacatcgg aagtaattat gtatactggt accagcagct cccaggaacg    540

gcccccaaac tcctcatcta taggaataat cagcggccct caggggtccc tgaccgattc    600

tctggctcca agtctggcac ctcagcctcc ctggccatca gtgggctccg gtccgaggat    660

gaggctgatt attactgtgc agcatgggat gacagcctga gtggtgtggt attcggcgga    720

gggaccaagc tcaccgtcct a                                              741
```

```
<210> SEQ ID NO 6
<211> LENGTH: 247
<212> TYPE: PRT
<213> ORGANISM: Homo sapiens
<220> FEATURE:
<223> OTHER INFORMATION: Clone 48 scFv

<400> SEQUENCE: 6

Gln Val Thr Leu Lys Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Gly Arg Trp Ser Tyr Tyr Phe Asp Tyr Trp
            100                 105                 110

Ser Gln Gly Thr Leu Val Thr Val Ser Ser Gly Gly Gly Gly Ser Gly
        115                 120                 125

Gly Gly Gly Ser Gly Gly Gly Gly Ser Gln Ser Val Leu Thr Gln Pro
    130                 135                 140

Ser Ser Val Ser Gly Thr Pro Gly Gln Arg Val Thr Ile Ser Cys Ser
145                 150                 155                 160

Gly Ser Ser Ser Asn Ile Gly Ser Asn Tyr Val Tyr Trp Tyr Gln Gln
                165                 170                 175

Leu Pro Gly Thr Ala Pro Lys Leu Leu Ile Tyr Arg Asn Asn Gln Arg
            180                 185                 190

Pro Ser Gly Val Pro Asp Arg Phe Ser Gly Ser Lys Ser Gly Thr Ser
        195                 200                 205

Ala Ser Leu Ala Ile Ser Gly Leu Arg Ser Glu Asp Glu Ala Asp Tyr
    210                 215                 220

Tyr Cys Ala Ala Trp Asp Asp Ser Leu Ser Gly Val Val Phe Gly Gly
225                 230                 235                 240

Gly Thr Lys Leu Thr Val Leu
                245
```

<210> SEQ ID NO 7
<211> LENGTH: 357
<212> TYPE: DNA
<213> ORGANISM: Homo sapiens
<220> FEATURE:
<223> OTHER INFORMATION: Clone V70 VH

<400> SEQUENCE: 7
caggtgcagc tgttggagtc tgggggaggc ttggtacagc cagggcggtc cctgagactc 60
tcctgtacag cttctggatt cacctttggt gattatgcga tgagctgggt ccgccaggct 120
ccagggaagg ggctggagtg ggtctcaagt attagtggta gtggtcgtag cacagaccac 180
gcagactacg tgaagggccg gttcaccatc tccagagaca attccaagaa cacggtatat 240
ctgcaaatga acaggctgag agccgaggac acggccgtgt attactgtgc aaaagtcagt 300
aactacgagt attactttga ctactgggcc cagggaaccc tggtcaccgt ctcctca 357

<210> SEQ ID NO 8
<211> LENGTH: 119
<212> TYPE: PRT
<213> ORGANISM: Homo sapiens
<220> FEATURE:
<223> OTHER INFORMATION: Clone V70 VH

<400> SEQUENCE: 8

Gln Val Gln Leu Leu Glu Ser Gly Gly Gly Leu Val Gln Pro Gly Arg
1 5 10 15

Ser Leu Arg Leu Ser Cys Thr Ala Ser Gly Phe Thr Phe Gly Asp Tyr
20 25 30

Ala Met Ser Trp Val Arg Gln Ala Pro Gly Lys Gly Leu Glu Trp Val
35 40 45

Ser Ser Ile Ser Gly Ser Gly Arg Ser Thr Asp His Ala Asp Tyr Val
50 55 60

Lys Gly Arg Phe Thr Ile Ser Arg Asp Asn Ser Lys Asn Thr Val Tyr
65 70 75 80

Leu Gln Met Asn Arg Leu Arg Ala Glu Asp Thr Ala Val Tyr Tyr Cys
85 90 95

Ala Lys Val Ser Asn Tyr Glu Tyr Tyr Phe Asp Tyr Trp Ala Gln Gly
100 105 110

Thr Leu Val Thr Val Ser Ser
115

<210> SEQ ID NO 9
<211> LENGTH: 366
<212> TYPE: DNA
<213> ORGANISM: Homo sapiens
<220> FEATURE:
<223> OTHER INFORMATION: Clone V353 VH

<400> SEQUENCE: 9
caggtcacct tgaaggagtc tgggggaggc ttggtaaagc ctgggggggtc ccttagactc 60 tcctgtgcag cctctggatt cactttcagt aacgcctgga tgagctgggt ccgccaggct 120
ccagggaagg ggctggagtg ggttggccgt attaaaagca aaactgatgg tgggacaaca 180
gactacgctg cacccgtgaa aggcagattc accatctcaa gagatgattc aaaaaacacg 240
ctgtatctgc aaatgaacag cctgaaaacc gaggacacag ccgtgtatta ctgtgcgaga 300
gatttcggac gatggggcta ctactttgac tactggagcc agggaaccct ggtcaccgtc 360
tcctca 366

<210> SEQ ID NO 10
<211> LENGTH: 122
<212> TYPE: PRT
<213> ORGANISM: Homo sapiens
<220> FEATURE:
<223> OTHER INFORMATION: Clone V353 VH

<400> SEQUENCE: 10

```
Gln Val Thr Leu Lys Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Gly Arg Trp Gly Tyr Tyr Phe Asp Tyr Trp
            100                 105                 110

Ser Gln Gly Thr Leu Val Thr Val Ser Ser
        115                 120
```

<210> SEQ ID NO 11
<211> LENGTH: 720
<212> TYPE: DNA
<213> ORGANISM: Homo sapiens
<220> FEATURE:
<223> OTHER INFORMATION: Clone 83B scFv

<400> SEQUENCE: 11

```
caggtccagc ttgtgcagtc tggggctgag gtgaagaagc ctggggcctc agtgaaggtt     60

tcctgcaagg catctggata caccttcacc agctactata tgcactgggt gcgacaggcc    120

cctggacaag ggcttgagtg gatgggaata atcaacccta atggtggtag cacaagctac    180

gcacagaagt tccagggcag agtcaccatg accagggaca cgtccacgag cacagtctac    240

atggagctga gcagcctgag atctgaggac acggccgtgt attactgtgc gagagatagc    300

agctatgatg cttttgatat ctggggccaa gggacaatgg tcaccgtctc ctcaggtgga    360

ggcggttcag gcggaggtgg ctctggcggt ggcggatcgg ccatccagtt gacccaatct    420

ccttccaccc tgtctgcatc tgtaggagac agagtcacca tcacttgcca ggcgagtcag    480

gacatcagca attatttaaa ttggtatcag cagaaaccag ggaaagcccc taaactcctg    540

atcaacgatg catcctattt ggagacaggg gtcccatcaa ggttcagtgg aagtggatct    600

gggacagatt ttactttaac catcagcagc ctgcagcctg aagatattgc aacatattac    660

tgtcaacagt atgaaagtct cccgtacact tttggccagg ggaccaagct ggagatcaaa    720
```

<210> SEQ ID NO 12
<211> LENGTH: 240
<212> TYPE: PRT
<213> ORGANISM: Homo sapiens
<220> FEATURE:
<223> OTHER INFORMATION: Clone 83B scFv

<400> SEQUENCE: 12

```
Gln Val Gln Leu Val Gln Ser Gly Ala Glu Val Lys Lys Pro Gly Ala
```

```
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Asn Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Tyr Asp Ala Phe Asp Ile Trp Gly Gln Gly Thr
            100                 105                 110

Met Val Thr Val Ser Ser Gly Gly Gly Gly Ser Gly Gly Gly Gly Ser
        115                 120                 125

Gly Gly Gly Gly Ser Ala Ile Gln Leu Thr Gln Ser Pro Ser Thr Leu
    130                 135                 140

Ser Ala Ser Val Gly Asp Arg Val Thr Ile Thr Cys Gln Ala Ser Gln
145                 150                 155                 160

Asp Ile Ser Asn Tyr Leu Asn Trp Tyr Gln Gln Lys Pro Gly Lys Ala
                165                 170                 175

Pro Lys Leu Leu Ile Asn Asp Ala Ser Tyr Leu Glu Thr Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Ile Ala Thr Tyr Tyr Cys Gln Gln Tyr
    210                 215                 220

Glu Ser Leu Pro Tyr Thr Phe Gly Gln Gly Thr Lys Leu Glu Ile Lys
225                 230                 235                 240


<210> SEQ ID NO 13
<211> LENGTH: 122
<212> TYPE: PRT
<213> ORGANISM: Homo sapiens
<220> FEATURE:
<223> OTHER INFORMATION: Clone 48 VH

<400> SEQUENCE: 13

Gln Val Thr Leu Lys Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Gly Arg Trp Ser Tyr Tyr Phe Asp Tyr Trp
            100                 105                 110

Ser Gln Gly Thr Leu Val Thr Val Ser Ser
        115                 120
```

<210> SEQ ID NO 14
<211> LENGTH: 110
<212> TYPE: PRT
<213> ORGANISM: Homo sapiens
<220> FEATURE:
<223> OTHER INFORMATION: Clone 48 VL

<400> SEQUENCE: 14

```
Gln Ser Val Leu Thr Gln Pro Ser Ser Val Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Val Val Phe Gly Gly Gly Thr Lys Leu Thr Val Leu
            100                 105                 110
```

<210> SEQ ID NO 15
<211> LENGTH: 119
<212> TYPE: PRT
<213> ORGANISM: Homo sapiens
<220> FEATURE:
<223> OTHER INFORMATION: Clone 298 VH

<400> SEQUENCE: 15

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Arg Ser Thr Asp His Ala Asp Tyr Val
    50                  55                  60

Lys Gly Arg Phe Thr Ile Ser Arg Asp Asn Ser Lys Asn Thr Val Tyr
65                  70                  75                  80

Leu Gln Met Asn Arg Leu Arg Ala Glu Asp Thr Ala Val Tyr Tyr Cys
                85                  90                  95

Ala Lys Val Ser Asn Tyr Glu Tyr Tyr Phe Asp Tyr Trp Ala Gln Gly
            100                 105                 110

Thr Leu Val Thr Val Ser Ser
        115
```

<210> SEQ ID NO 16
<211> LENGTH: 108
<212> TYPE: PRT
<213> ORGANISM: Homo sapiens
<220> FEATURE:
<223> OTHER INFORMATION: Clone 298 VL

<400> SEQUENCE: 16

```
Glu Ile Val Leu Thr Gln Ser Pro Ser Val Ser Val Ala Pro Gly Gln
1               5                   10                  15

Thr Ala Arg Ile Thr Cys Gly Gly Ser Asn Ile Gly Ser Glu Ser Val
            20                  25                  30
```

```
Asn Trp Tyr Gln Trp Lys Ser Gly Gln Val Pro Val Leu Val Val Ser
        35                  40                  45

Asp Thr Thr Asp Arg Pro Ser Gly Ile Pro Gly Arg Phe Thr Gly Thr
    50                  55                  60

Arg Ser Gly Thr Thr Ala Thr Leu Thr Ile Ser Gly Val Glu Ala Gly
65                  70                  75                  80

Asp Glu Ala Asp Tyr His Cys Gln Val Trp Asp Asp Thr Gly Asp His
                85                  90                  95

Pro Val Phe Gly Gly Gly Thr Lys Leu Thr Val Leu
            100                 105


<210> SEQ ID NO 17
<211> LENGTH: 118
<212> TYPE: PRT
<213> ORGANISM: Homo sapiens
<220> FEATURE:
<223> OTHER INFORMATION: Clone 83 VH

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Tyr Asp Ala Phe Asp Ile Trp Gly Gln Gly Thr
            100                 105                 110

Met Val Thr Val Ser Ser
        115


<210> SEQ ID NO 18
<211> LENGTH: 107
<212> TYPE: PRT
<213> ORGANISM: Homo sapiens
<220> FEATURE:
<223> OTHER INFORMATION: Clone 83, 83B VL

<400> SEQUENCE: 18

Ala Ile Gln Leu Thr Gln Ser Pro Ser Thr Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Asn Asp Ala Ser Tyr Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Tyr Glu Ser Leu Pro Tyr
                85                  90                  95

Thr Phe Gly Gln Gly Thr Lys Leu Glu Ile Lys
```

100 105

<210> SEQ ID NO 19
<211> LENGTH: 118
<212> TYPE: PRT
<213> ORGANISM: Homo sapiens
<220> FEATURE:
<223> OTHER INFORMATION: Clone 83B VH

<400> SEQUENCE: 19

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Tyr Met His Trp Val Arg Gln Ala Pro Gly Gln Gly Leu Glu Trp Met
35 40 45

Gly Ile Ile Asn Pro Asn Gly Gly Ser Thr Ser Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Asp Ser Ser Tyr Asp Ala Phe Asp Ile Trp Gly Gln Gly Thr
100 105 110

Met Val Thr Val Ser Ser
115

<210> SEQ ID NO 20
<211> LENGTH: 5
<212> TYPE: PRT
<213> ORGANISM: Homo sapiens
<220> FEATURE:
<223> OTHER INFORMATION: Clone 83, 83B CDR-H1

<400> SEQUENCE: 20

Ser Tyr Tyr Met His
1 5

<210> SEQ ID NO 21
<211> LENGTH: 17
<212> TYPE: PRT
<213> ORGANISM: Homo sapiens
<220> FEATURE:
<223> OTHER INFORMATION: Clone 83 CDR-H2

<400> SEQUENCE: 21

Ile Ile Asn Pro Ser Gly Gly Ser Thr Ser Tyr Ala Gln Lys Phe Gln
1 5 10 15

Gly

<210> SEQ ID NO 22
<211> LENGTH: 9
<212> TYPE: PRT
<213> ORGANISM: Homo sapiens
<220> FEATURE:
<223> OTHER INFORMATION: Clone 83, 83B CDR-H3

<400> SEQUENCE: 22

Asp Ser Ser Tyr Asp Ala Phe Asp Ile
1 5

<210> SEQ ID NO 23

<211> LENGTH: 11
<212> TYPE: PRT
<213> ORGANISM: Homo sapiens
<220> FEATURE:
<223> OTHER INFORMATION: Clone 83, 83B CDR-L1

<400> SEQUENCE: 23

Gln Ala Ser Gln Asp Ile Ser Asn Tyr Leu Asn
1 5 10

<210> SEQ ID NO 24
<211> LENGTH: 7
<212> TYPE: PRT
<213> ORGANISM: Homo sapiens
<220> FEATURE:
<223> OTHER INFORMATION: Clone 83, 83B CDR-L2

<400> SEQUENCE: 24

Asp Ala Ser Tyr Leu Glu Thr
1 5

<210> SEQ ID NO 25
<211> LENGTH: 9
<212> TYPE: PRT
<213> ORGANISM: Homo sapiens
<220> FEATURE:
<223> OTHER INFORMATION: Clone 83, 83B CDR-L3

<400> SEQUENCE: 25

Gln Gln Tyr Glu Ser Leu Pro Tyr Thr
1 5

<210> SEQ ID NO 26
<211> LENGTH: 17
<212> TYPE: PRT
<213> ORGANISM: Homo sapiens
<220> FEATURE:
<223> OTHER INFORMATION: Clone 83B CDR-H2

<400> SEQUENCE: 26

Ile Ile Asn Pro Asn Gly Gly Ser Thr Ser Tyr Ala Gln Lys Phe Gln
1 5 10 15

Gly

<210> SEQ ID NO 27
<211> LENGTH: 5
<212> TYPE: PRT
<213> ORGANISM: Homo sapiens
<220> FEATURE:
<223> OTHER INFORMATION: Clone 298, V70 CDR-H1

<400> SEQUENCE: 27

Asp Tyr Ala Met Ser
1 5

<210> SEQ ID NO 28
<211> LENGTH: 17
<212> TYPE: PRT
<213> ORGANISM: Homo sapiens
<220> FEATURE:
<223> OTHER INFORMATION: Clone 298, V70 CDR-H2

<400> SEQUENCE: 28

Ser Ile Ser Gly Ser Gly Arg Ser Thr Asp His Ala Asp Tyr Val Lys
1 5 10 15

Gly

<210> SEQ ID NO 29
<211> LENGTH: 10
<212> TYPE: PRT
<213> ORGANISM: Homo sapiens
<220> FEATURE:
<223> OTHER INFORMATION: Clone 298, 305, 350, 366, V70 CDR-H3

<400> SEQUENCE: 29

Val Ser Asn Tyr Glu Tyr Tyr Phe Asp Tyr
1 5 10

<210> SEQ ID NO 30
<211> LENGTH: 11
<212> TYPE: PRT
<213> ORGANISM: Homo sapiens
<220> FEATURE:
<223> OTHER INFORMATION: Clone 298 CDR-L1

<400> SEQUENCE: 30

Gly Gly Ser Asn Ile Gly Ser Glu Ser Val Asn
1 5 10

<210> SEQ ID NO 31
<211> LENGTH: 7
<212> TYPE: PRT
<213> ORGANISM: Homo sapiens
<220> FEATURE:
<223> OTHER INFORMATION: Clone 298 CDR-L2

<400> SEQUENCE: 31

Asp Thr Thr Asp Arg Pro Ser
1 5

<210> SEQ ID NO 32
<211> LENGTH: 11
<212> TYPE: PRT
<213> ORGANISM: Homo sapiens
<220> FEATURE:
<223> OTHER INFORMATION: Clone 298 CDR-L3

<400> SEQUENCE: 32

Gln Val Trp Asp Asp Thr Gly Asp His Pro Val
1 5 10

<210> SEQ ID NO 33
<211> LENGTH: 5
<212> TYPE: PRT
<213> ORGANISM: Homo sapiens
<220> FEATURE:
<223> OTHER INFORMATION: Clone 48, V353 CDR-H1

<400> SEQUENCE: 33

Asn Ala Trp Met Ser
1 5

<210> SEQ ID NO 34
<211> LENGTH: 19
<212> TYPE: PRT
<213> ORGANISM: Homo sapiens
<220> FEATURE:
<223> OTHER INFORMATION: Clone 48, V353 CDR-H2

<400> SEQUENCE: 34

Arg Ile Lys Ser Lys Thr Asp Gly Gly Thr Thr Asp Tyr Ala Ala Pro
1 5 10 15

Val Lys Gly

<210> SEQ ID NO 35
<211> LENGTH: 11
<212> TYPE: PRT
<213> ORGANISM: Homo sapiens
<220> FEATURE:
<223> OTHER INFORMATION: Clones 16, 20, 43, 48, 40, 65, 81, 7, V128, V18
CDR-H3

<400> SEQUENCE: 35

Asp Phe Gly Arg Trp Ser Tyr Tyr Phe Asp Tyr
1 5 10

<210> SEQ ID NO 36
<211> LENGTH: 13
<212> TYPE: PRT
<213> ORGANISM: Homo sapiens
<220> FEATURE:
<223> OTHER INFORMATION: Clone 48 CDR-L1

<400> SEQUENCE: 36

Ser Gly Ser Ser Ser Asn Ile Gly Ser Asn Tyr Val Tyr
1 5 10

<210> SEQ ID NO 37
<211> LENGTH: 7
<212> TYPE: PRT
<213> ORGANISM: Homo sapiens
<220> FEATURE:
<223> OTHER INFORMATION: Clone 48 CDR-L2

<400> SEQUENCE: 37

Arg Asn Asn Gln Arg Pro Ser
1 5

<210> SEQ ID NO 38
<211> LENGTH: 11
<212> TYPE: PRT
<213> ORGANISM: Homo sapiens
<220> FEATURE:
<223> OTHER INFORMATION: Clones 43, 48 CDR-L3

<400> SEQUENCE: 38

Ala Ala Trp Asp Asp Ser Leu Ser Gly Val Val
1 5 10

<210> SEQ ID NO 39
<211> LENGTH: 11
<212> TYPE: PRT
<213> ORGANISM: Homo sapiens
<220> FEATURE:
<223> OTHER INFORMATION: Clone 305 CDR-L3

<400> SEQUENCE: 39

Gln Val Trp Asp Asn Asp Ser Asp His Arg Val
1 5 10

<210> SEQ ID NO 40
<211> LENGTH: 9
<212> TYPE: PRT
<213> ORGANISM: Homo sapiens
<220> FEATURE:
<223> OTHER INFORMATION: Clone 350 CDR-L3

<400> SEQUENCE: 40

Gln Ser Tyr Asp Ser Ser Asn His Val 1 5

<210> SEQ ID NO 41
<211> LENGTH: 9
<212> TYPE: PRT
<213> ORGANISM: Homo sapiens
<220> FEATURE:
<223> OTHER INFORMATION: Clone 20 CDR-L3

<400> SEQUENCE: 41

Gln Gln Leu Lys Ser Arg Pro Leu Ser
1 5

<210> SEQ ID NO 42
<211> LENGTH: 9
<212> TYPE: PRT
<213> ORGANISM: Homo sapiens
<220> FEATURE:
<223> OTHER INFORMATION: Clone 16 CDR-L3

<400> SEQUENCE: 42

Gln Gln Leu Asn Ser Tyr Pro Leu Thr
1 5

<210> SEQ ID NO 43
<211> LENGTH: 11
<212> TYPE: PRT
<213> ORGANISM: Homo sapiens
<220> FEATURE:
<223> OTHER INFORMATION: Clone 366 CDR-L3

<400> SEQUENCE: 43

Ala Ala Trp Asp Asp Ser Leu Asn Gly Tyr Val
1 5 10

<210> SEQ ID NO 44
<211> LENGTH: 9
<212> TYPE: PRT
<213> ORGANISM: Homo sapiens
<220> FEATURE:
<223> OTHER INFORMATION: Clone 40 CDR-L3

<400> SEQUENCE: 44

Gln Ser Tyr Asp Gly Arg Asn Leu Met
1 5

<210> SEQ ID NO 45
<211> LENGTH: 14
<212> TYPE: PRT
<213> ORGANISM: Homo sapiens
<220> FEATURE:
<223> OTHER INFORMATION: Clone 461 CDR-H3

<400> SEQUENCE: 45

Asp Phe Glu Val Arg Glu Ala His Leu Ser Tyr Phe Asp Tyr
1 5 10

<210> SEQ ID NO 46
<211> LENGTH: 11
<212> TYPE: PRT
<213> ORGANISM: Homo sapiens
<220> FEATURE:
<223> OTHER INFORMATION: Clone 461 CDR-L3

<400> SEQUENCE: 46

Gln Val Trp Asp Ser Ser Ser Asp His Arg Val
1 5 10

<210> SEQ ID NO 47
<211> LENGTH: 11
<212> TYPE: PRT
<213> ORGANISM: Homo sapiens
<220> FEATURE:
<223> OTHER INFORMATION: Clone 65 CDR-L3

<400> SEQUENCE: 47

Lys Ser Trp Asp Ser Ser Gly Ser Leu Tyr Val
1 5 10

<210> SEQ ID NO 48
<211> LENGTH: 11
<212> TYPE: PRT
<213> ORGANISM: Homo sapiens
<220> FEATURE:
<223> OTHER INFORMATION: Clone 81 CDR-L3

<400> SEQUENCE: 48

Gln Val Trp Asp Ser Ser Ser Asp His Tyr Val
1 5 10

<210> SEQ ID NO 49
<211> LENGTH: 9
<212> TYPE: PRT
<213> ORGANISM: Homo sapiens
<220> FEATURE:
<223> OTHER INFORMATION: Clone 7 CDR-L3

<400> SEQUENCE: 49

Gln Ala Trp Asp Ser Ser Thr Val Val
1 5

<210> SEQ ID NO 50
<211> LENGTH: 10
<212> TYPE: PRT
<213> ORGANISM: Homo sapiens
<220> FEATURE:
<223> OTHER INFORMATION: Clone V420 CDR-H3

<400> SEQUENCE: 50

Val Asn Gly Gly Glu Tyr Tyr Phe Asp Tyr
1 5 10

<210> SEQ ID NO 51
<211> LENGTH: 10
<212> TYPE: PRT
<213> ORGANISM: Homo sapiens
<220> FEATURE:
<223> OTHER INFORMATION: Clone V282 CDR-H3

<400> SEQUENCE: 51

Val Arg Gly Ser Glu Tyr Tyr Phe Asp Tyr
1 5 10

<210> SEQ ID NO 52
<211> LENGTH: 11
<212> TYPE: PRT
<213> ORGANISM: Homo sapiens
<220> FEATURE:
<223> OTHER INFORMATION: Clone V353 CDR-H3

<400> SEQUENCE: 52

Asp Phe Gly Arg Trp Gly Tyr Tyr Phe Asp Tyr
1 5 10

<210> SEQ ID NO 53
<211> LENGTH: 16
<212> TYPE: PRT
<213> ORGANISM: Homo sapiens
<220> FEATURE:
<223> OTHER INFORMATION: Clone V163 CDR-H3

<400> SEQUENCE: 53

Gln Gly Asp Ser Ser Ser Trp Tyr Val Glu Val Tyr Tyr Phe Asp Tyr
1 5 10 15

<210> SEQ ID NO 54
<211> LENGTH: 9
<212> TYPE: PRT
<213> ORGANISM: Homo sapiens
<220> FEATURE:
<223> OTHER INFORMATION: Clone V355 CDR-H3

<400> SEQUENCE: 54

Ile Thr Pro Pro Asp Ala Phe Asp Ile
1 5

<210> SEQ ID NO 55
<211> LENGTH: 14
<212> TYPE: PRT
<213> ORGANISM: Homo sapiens
<220> FEATURE:
<223> OTHER INFORMATION: Clone V224 CDR-H3

<400> SEQUENCE: 55

Thr Tyr Ser Ser Ser Trp Tyr Glu Ser Leu Leu Phe Asp Tyr
1 5 10

<210> SEQ ID NO 56
<211> LENGTH: 15
<212> TYPE: PRT
<213> ORGANISM: Homo sapiens
<220> FEATURE:
<223> OTHER INFORMATION: Clone V95 CDR-H3

<400> SEQUENCE: 56

Gly Ser Gly Glu Leu Arg Phe Leu Glu Ser Tyr Tyr Phe Asp Tyr
1 5 10 15

<210> SEQ ID NO 57
<211> LENGTH: 14
<212> TYPE: PRT
<213> ORGANISM: Homo sapiens
<220> FEATURE:
<223> OTHER INFORMATION: Clone V316 CDR-H3

<400> SEQUENCE: 57

Val Asp Ser Glu Arg Phe Leu Glu Trp Tyr Tyr Phe Asp Tyr
1 5 10

<210> SEQ ID NO 58
<211> LENGTH: 13
<212> TYPE: PRT
<213> ORGANISM: Homo sapiens
<220> FEATURE:
<223> OTHER INFORMATION: Clone V331 CDR-H3

<400> SEQUENCE: 58

Gly Gln Ile Ala Ala His Val Trp Gly Trp Phe Asp Pro
1 5 10

-continued

<210> SEQ ID NO 59
<211> LENGTH: 14
<212> TYPE: PRT
<213> ORGANISM: Homo sapiens
<220> FEATURE:
<223> OTHER INFORMATION: Clone V357 CDR-H3

<400> SEQUENCE: 59

Asp Met Val Gly Ala Trp Leu Val Leu Ser Tyr Phe Asp Tyr
1               5                   10

<210> SEQ ID NO 60
<211> LENGTH: 14
<212> TYPE: PRT
<213> ORGANISM: Homo sapiens
<220> FEATURE:
<223> OTHER INFORMATION: Clone V397 CDR-H3

<400> SEQUENCE: 60

Ala Lys Gly Leu Trp Phe Gly Glu Ser Tyr Tyr Phe Asp Tyr
1               5                   10

<210> SEQ ID NO 61
<211> LENGTH: 14
<212> TYPE: PRT
<213> ORGANISM: Homo sapiens
<220> FEATURE:
<223> OTHER INFORMATION: Clone V312 CDR-H3

<400> SEQUENCE: 61

Thr Ser Arg Gly Arg Phe Leu Glu Trp Leu Leu Phe Asp Tyr
1               5                   10

<210> SEQ ID NO 62
<211> LENGTH: 12
<212> TYPE: PRT
<213> ORGANISM: Homo sapiens
<220> FEATURE:
<223> OTHER INFORMATION: Clone V278 CDR-H3

<400> SEQUENCE: 62

Glu Arg Ser Arg Trp Gly Asp Asn Trp Phe Asp Pro
1               5                   10

<210> SEQ ID NO 63
<211> LENGTH: 11
<212> TYPE: PRT
<213> ORGANISM: Homo sapiens
<220> FEATURE:
<223> OTHER INFORMATION: Clone V86 CDR-H3

<400> SEQUENCE: 63

Val Ile Phe Gly Val Val Asn Ile Pro Asp Tyr
1               5                   10

<210> SEQ ID NO 64
<211> LENGTH: 11
<212> TYPE: PRT
<213> ORGANISM: Homo sapiens
<220> FEATURE:
<223> OTHER INFORMATION: Clone V102 CDR-H3

<400> SEQUENCE: 64

Val Gly Pro Ser Trp Asp Tyr Tyr Phe Asp Tyr
1               5                   10

<210> SEQ ID NO 65

<211> LENGTH: 16
<212> TYPE: PRT
<213> ORGANISM: Homo sapiens
<220> FEATURE:
<223> OTHER INFORMATION: Clone V365 CDR-H3

<400> SEQUENCE: 65

Gly Ile Gly Tyr Ser Ser Ser Trp Tyr Glu Ile Trp Thr Phe Asp Tyr
1 5 10 15

<210> SEQ ID NO 66
<211> LENGTH: 14
<212> TYPE: PRT
<213> ORGANISM: Homo sapiens
<220> FEATURE:
<223> OTHER INFORMATION: Clone V181 CDR-H3

<400> SEQUENCE: 66

Asp Phe Glu Val Arg Glu Ala His Leu Ser Tyr Phe Asp Tyr
1 5 10

<210> SEQ ID NO 67
<211> LENGTH: 14
<212> TYPE: PRT
<213> ORGANISM: Homo sapiens
<220> FEATURE:
<223> OTHER INFORMATION: Clone V71 CDR-H3

<400> SEQUENCE: 67

Val Leu Arg Ser Gly Phe Leu Glu Trp Asn Leu Phe Asp Tyr
1 5 10

<210> SEQ ID NO 68
<211> LENGTH: 14
<212> TYPE: PRT
<213> ORGANISM: Homo sapiens
<220> FEATURE:
<223> OTHER INFORMATION: Clone V68 CDR-H3

<400> SEQUENCE: 68

Asp Phe Glu Val Arg Gly Ala His Leu Ser Tyr Phe Asp Tyr
1 5 10

<210> SEQ ID NO 69
<211> LENGTH: 14
<212> TYPE: PRT
<213> ORGANISM: Homo sapiens
<220> FEATURE:
<223> OTHER INFORMATION: Clone V336 CDR-H3

<400> SEQUENCE: 69

Val Tyr Gly Tyr Asp Tyr Arg Asp Phe Gly Trp Phe Asp Pro
1 5 10

<210> SEQ ID NO 70
<211> LENGTH: 14
<212> TYPE: PRT
<213> ORGANISM: Homo sapiens
<220> FEATURE:
<223> OTHER INFORMATION: Clone V9 CDR-H3

<400> SEQUENCE: 70

Gly Ser Asn Glu Arg Phe Leu Glu Trp Leu Asn Phe Asp Tyr
1 5 10

<210> SEQ ID NO 71
<211> LENGTH: 13

<212> TYPE: PRT
<213> ORGANISM: Homo sapiens
<220> FEATURE:
<223> OTHER INFORMATION: Clone V345 CDR-H3

<400> SEQUENCE: 71

Gly Pro Leu Arg Pro Gln Lys Val Leu Pro Phe Gln Ile
1               5                   10

<210> SEQ ID NO 72
<211> LENGTH: 12
<212> TYPE: PRT
<213> ORGANISM: Rabbit
<220> FEATURE:
<223> OTHER INFORMATION: R12 CDR-H3

<400> SEQUENCE: 72

Asp Ser Tyr Ala Asp Asp Gly Ala Leu Phe Asn Ile
1               5                   10

<210> SEQ ID NO 73
<211> LENGTH: 9
<212> TYPE: PRT
<213> ORGANISM: Rabbit
<220> FEATURE:
<223> OTHER INFORMATION: R12 CDR-L3

<400> SEQUENCE: 73

Gly Ala Asp Tyr Ile Gly Gly Tyr Val
1               5

<210> SEQ ID NO 74
<211> LENGTH: 6
<212> TYPE: PRT
<213> ORGANISM: Homo sapiens
<220> FEATURE:
<223> OTHER INFORMATION: Clone 83, 83B CDR-H1

<400> SEQUENCE: 74

Gly Tyr Thr Phe Thr Ser
1               5

<210> SEQ ID NO 75
<211> LENGTH: 10
<212> TYPE: PRT
<213> ORGANISM: Homo sapiens
<220> FEATURE:
<223> OTHER INFORMATION: Clone 83, 83B CDR-H1

<400> SEQUENCE: 75

Gly Tyr Thr Phe Thr Ser Tyr Tyr Met His
1               5                   10

<210> SEQ ID NO 76
<211> LENGTH: 6
<212> TYPE: PRT
<213> ORGANISM: Homo sapiens
<220> FEATURE:
<223> OTHER INFORMATION: Clone 298, V70 CDR-H1

<400> SEQUENCE: 76

Gly Phe Thr Phe Gly Asp
1               5

<210> SEQ ID NO 77
<211> LENGTH: 10
<212> TYPE: PRT

<213> ORGANISM: Homo sapiens
<220> FEATURE:
<223> OTHER INFORMATION: Clone 298, V70 CDR-H1

<400> SEQUENCE: 77

Gly Phe Thr Phe Gly Asp Tyr Ala Met Ser
1 5 10

<210> SEQ ID NO 78
<211> LENGTH: 6
<212> TYPE: PRT
<213> ORGANISM: Homo sapiens
<220> FEATURE:
<223> OTHER INFORMATION: Clone 48, V353 CDR-H1

<400> SEQUENCE: 78

Gly Phe Thr Phe Ser Asn
1 5

<210> SEQ ID NO 79
<211> LENGTH: 10
<212> TYPE: PRT
<213> ORGANISM: Homo sapiens
<220> FEATURE:
<223> OTHER INFORMATION: Clone 48, V353 CDR-H1

<400> SEQUENCE: 79

Gly Phe Thr Phe Ser Asn Ala Trp Met Ser
1 5 10

<210> SEQ ID NO 80
<211> LENGTH: 8
<212> TYPE: PRT
<213> ORGANISM: Homo sapiens
<220> FEATURE:
<223> OTHER INFORMATION: Clone 83 CDR-H2

<400> SEQUENCE: 80

Ile Ile Asn Pro Ser Gly Gly Ser
1 5

<210> SEQ ID NO 81
<211> LENGTH: 8
<212> TYPE: PRT
<213> ORGANISM: Homo sapiens
<220> FEATURE:
<223> OTHER INFORMATION: Clone 298, V70 CDR-H2

<400> SEQUENCE: 81

Ser Ile Ser Gly Ser Gly Arg Ser
1 5

<210> SEQ ID NO 82
<211> LENGTH: 10
<212> TYPE: PRT
<213> ORGANISM: Homo sapiens
<220> FEATURE:
<223> OTHER INFORMATION: Clone 48, V353 CDR -H2

<400> SEQUENCE: 82

Arg Ile Lys Ser Lys Thr Asp Gly Gly Thr
1 5 10

<210> SEQ ID NO 83
<211> LENGTH: 8
<212> TYPE: PRT
<213> ORGANISM: Homo sapiens

<220> FEATURE:
<223> OTHER INFORMATION: Clone 83B CDR-H2

<400> SEQUENCE: 83

Ile Ile Asn Pro Asn Gly Gly Ser
1               5

<210> SEQ ID NO 84
<211> LENGTH: 248
<212> TYPE: PRT
<213> ORGANISM: Rabbit
<220> FEATURE:
<223> OTHER INFORMATION: R12 scFv

<400> SEQUENCE: 84

Gln Glu Gln Leu Val Glu Ser Gly Gly Arg Leu Val Thr Pro Gly Gly
1               5                   10                  15

Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile
        35                  40                  45

Ala Thr Ile Tyr Pro Ser Ser Gly Lys Thr Tyr Tyr Ala Thr Trp Val
    50                  55                  60

Asn Gly Arg Phe Thr Ile Ser Ser Asp Asn Ala Gln Asn Thr Val Asp
65                  70                  75                  80

Leu Gln Met Asn Ser Leu Thr Ala Ala Asp Arg Ala Thr Tyr Phe Cys
                85                  90                  95

Ala Arg Asp Ser Tyr Ala Asp Asp Gly Ala Leu Phe Asn Ile Trp Gly
            100                 105                 110

Pro Gly Thr Leu Val Thr Ile Ser Ser Gly Gly Gly Gly Ser Gly Gly
        115                 120                 125

Gly Gly Ser Gly Gly Gly Gly Ser Glu Leu Val Leu Thr Gln Ser Pro
    130                 135                 140

Ser Val Ser Ala Ala Leu Gly Ser Pro Ala Lys Ile Thr Cys Thr Leu
145                 150                 155                 160

Ser Ser Ala His Lys Thr Asp Thr Ile Asp Trp Tyr Gln Gln Leu Gln
                165                 170                 175

Gly Glu Ala Pro Arg Tyr Leu Met Gln Val Gln Ser Asp Gly Ser Tyr
            180                 185                 190

Thr Lys Arg Pro Gly Val Pro Asp Arg Phe Ser Gly Ser Ser Ser Gly
        195                 200                 205

Ala Asp Arg Tyr Leu Ile Ile Pro Ser Val Gln Ala Asp Asp Glu Ala
    210                 215                 220

Asp Tyr Tyr Cys Gly Ala Asp Tyr Ile Gly Gly Tyr Val Phe Gly Gly
225                 230                 235                 240

Gly Thr Gln Leu Thr Val Thr Gly
                245

<210> SEQ ID NO 85
<211> LENGTH: 121
<212> TYPE: PRT
<213> ORGANISM: Rabbit
<220> FEATURE:
<223> OTHER INFORMATION: R12 VH

<400> SEQUENCE: 85

Gln Glu Gln Leu Val Glu Ser Gly Gly Arg Leu Val Thr Pro Gly Gly
1               5                   10                  15

-continued

Ser Leu Thr Leu Ser Cys Lys Ala Ser Gly Phe Asp Phe Ser Ala Tyr
20 25 30

Tyr Met Ser Trp Val Arg Gln Ala Pro Gly Lys Gly Leu Glu Trp Ile
35 40 45

Ala Thr Ile Tyr Pro Ser Ser Gly Lys Thr Tyr Tyr Ala Thr Trp Val
50 55 60

Asn Gly Arg Phe Thr Ile Ser Ser Asp Asn Ala Gln Asn Thr Val Asp
65 70 75 80

Leu Gln Met Asn Ser Leu Thr Ala Ala Asp Arg Ala Thr Tyr Phe Cys
85 90 95

Ala Arg Asp Ser Tyr Ala Asp Asp Gly Ala Leu Phe Asn Ile Trp Gly
100 105 110

Pro Gly Thr Leu Val Thr Ile Ser Ser
115 120

<210> SEQ ID NO 86
<211> LENGTH: 112
<212> TYPE: PRT
<213> ORGANISM: Rabbit
<220> FEATURE:
<223> OTHER INFORMATION: R12 VL

<400> SEQUENCE: 86

Glu Leu Val Leu Thr Gln Ser Pro Ser Val Ser Ala Ala Leu Gly Ser
1 5 10 15

Pro Ala Lys Ile Thr Cys Thr Leu Ser Ser Ala His Lys Thr Asp Thr
20 25 30

Ile Asp Trp Tyr Gln Gln Leu Gln Gly Glu Ala Pro Arg Tyr Leu Met
35 40 45

Gln Val Gln Ser Asp Gly Ser Tyr Thr Lys Arg Pro Gly Val Pro Asp
50 55 60

Arg Phe Ser Gly Ser Ser Ser Gly Ala Asp Arg Tyr Leu Ile Ile Pro
65 70 75 80

Ser Val Gln Ala Asp Asp Glu Ala Asp Tyr Tyr Cys Gly Ala Asp Tyr
85 90 95

Ile Gly Gly Tyr Val Phe Gly Gly Gly Thr Gln Leu Thr Val Thr Gly
100 105 110

<210> SEQ ID NO 87
<211> LENGTH: 5
<212> TYPE: PRT
<213> ORGANISM: Rabbit
<220> FEATURE:
<223> OTHER INFORMATION: R12 CDR-H1

<400> SEQUENCE: 87

Ala Tyr Tyr Met Ser
1 5

<210> SEQ ID NO 88
<211> LENGTH: 17
<212> TYPE: PRT
<213> ORGANISM: Rabbit
<220> FEATURE:
<223> OTHER INFORMATION: R12 CDR-H2

<400> SEQUENCE: 88

Thr Ile Tyr Pro Ser Ser Gly Lys Thr Tyr Tyr Ala Thr Trp Val Asn
1 5 10 15

Gly

-continued

<210> SEQ ID NO 89
<211> LENGTH: 12
<212> TYPE: PRT
<213> ORGANISM: Rabbit
<220> FEATURE:
<223> OTHER INFORMATION: R12 CDR-L1

<400> SEQUENCE: 89

Thr Leu Ser Ser Ala His Lys Thr Asp Thr Ile Asp
1 5 10

<210> SEQ ID NO 90
<211> LENGTH: 7
<212> TYPE: PRT
<213> ORGANISM: Rabbit
<220> FEATURE:
<223> OTHER INFORMATION: R12 CDR-L2

<400> SEQUENCE: 90

Gly Ser Tyr Thr Lys Arg Pro
1 5

<210> SEQ ID NO 91
<211> LENGTH: 15
<212> TYPE: PRT
<213> ORGANISM: Artificial Sequence
<220> FEATURE:
<223> OTHER INFORMATION: Synthetic linker

<400> SEQUENCE: 91

Gly Gly Gly Gly Ser Gly Gly Gly Gly Ser Gly Gly Gly Gly Ser
1 5 10 15

<210> SEQ ID NO 92
<211> LENGTH: 16
<212> TYPE: PRT
<213> ORGANISM: Homo sapiens
<220> FEATURE:
<223> OTHER INFORMATION: Consensus CDR-H3
<220> FEATURE:
<221> NAME/KEY: VARIANT
<222> LOCATION: 1
<223> OTHER INFORMATION: Xaa = D, V, Q, I, T, G, A, or E
<220> FEATURE:
<221> NAME/KEY: VARIANT
<222> LOCATION: 2
<223> OTHER INFORMATION: Xaa = S, F, N, R, G, T, Y, D, Q, M, K, I, L, or P
<220> FEATURE:
<221> NAME/KEY: VARIANT
<222> LOCATION: 3
<223> OTHER INFORMATION: Xaa = S, N, G, E, D, P, I, V, R, F, N, or L
<220> FEATURE:
<221> NAME/KEY: VARIANT
<222> LOCATION: 4
<223> OTHER INFORMATION: Xaa = Y, R, V, G, S, P, E, A, or L
<220> FEATURE:
<221> NAME/KEY: VARIANT
<222> LOCATION: 5
<223> OTHER INFORMATION: Xaa = D, E, W, R, S, L, A, V, G, or P
<220> FEATURE:
<221> NAME/KEY: VARIANT
<222> LOCATION: 6
<223> OTHER INFORMATION: Xaa = A, W, S, E, G, Y, R, F, H, V, D, S, or Q
<220> FEATURE:
<221> NAME/KEY: VARIANT
<222> LOCATION: 7
<223> OTHER INFORMATION: Xaa = F, Y, A, W, L, G, D, V, N, S, K, or R
<220> FEATURE:
<221> NAME/KEY: VARIANT
<222> LOCATION: 8

<223> OTHER INFORMATION: Xaa = F, Y, H, E, L, W, V, N, I, D, or null
<220> FEATURE:
<221> NAME/KEY: VARIANT
<222> LOCATION: 9
<223> OTHER INFORMATION: Xaa = F, L, V, S, E, W, G, P, Y, or null
<220> FEATURE:
<221> NAME/KEY: VARIANT
<222> LOCATION: 10
<223> OTHER INFORMATION: Xaa = S, E, L, Y, W, F, N, G, P, or null
<220> FEATURE:
<221> NAME/KEY: VARIANT
<222> LOCATION: 11
<223> OTHER INFORMATION: Xaa = Y, V, L, F, I, W, N, or null
<220> FEATURE:
<221> NAME/KEY: VARIANT
<222> LOCATION: 12
<223> OTHER INFORMATION: Xaa = F, Y, W, or null
<220> FEATURE:
<221> NAME/KEY: VARIANT
<222> LOCATION: 13
<223> OTHER INFORMATION: Xaa = Y, F, T, or null
<220> FEATURE:
<221> NAME/KEY: VARIANT
<222> LOCATION: 14
<223> OTHER INFORMATION: Xaa = F or null
<220> FEATURE:
<221> NAME/KEY: VARIANT
<222> LOCATION: 15
<223> OTHER INFORMATION: Xaa = D or Q
<220> FEATURE:
<221> NAME/KEY: VARIANT
<222> LOCATION: 16
<223> OTHER INFORMATION: Xaa = I, Y, or P

<400> SEQUENCE: 92

```
Xaa Xaa Xaa Xaa Xaa Xaa Xaa Xaa Xaa Xaa Xaa Xaa Xaa Xaa Xaa Xaa
1               5                   10                  15
```

<210> SEQ ID NO 93
<211> LENGTH: 14
<212> TYPE: PRT
<213> ORGANISM: Homo sapiens
<220> FEATURE:
<223> OTHER INFORMATION: Consensus CDR-H3
<220> FEATURE:
<221> NAME/KEY: VARIANT
<222> LOCATION: 1
<223> OTHER INFORMATION: Xaa = D or V
<220> FEATURE:
<221> NAME/KEY: VARIANT
<222> LOCATION: 2
<223> OTHER INFORMATION: Xaa = S or F
<220> FEATURE:
<221> NAME/KEY: VARIANT
<222> LOCATION: 3
<223> OTHER INFORMATION: Xaa = S, N, G, or E
<220> FEATURE:
<221> NAME/KEY: VARIANT
<222> LOCATION: 4
<223> OTHER INFORMATION: Xaa = Y, R, or V
<220> FEATURE:
<221> NAME/KEY: VARIANT
<222> LOCATION: 5
<223> OTHER INFORMATION: Xaa = D, E, W, or R
<220> FEATURE:
<221> NAME/KEY: VARIANT
<222> LOCATION: 6
<223> OTHER INFORMATION: Xaa = A, Y, S, or E
<220> FEATURE:
<221> NAME/KEY: VARIANT
<222> LOCATION: 7
<223> OTHER INFORMATION: Xaa = F, Y, or A
<220> FEATURE:
<221> NAME/KEY: VARIANT
<222> LOCATION: 8
<223> OTHER INFORMATION: Xaa = F, Y, H, or null
<220> FEATURE:

<221> NAME/KEY: VARIANT
<222> LOCATION: 9
<223> OTHER INFORMATION: Xaa = F, L, or null
<220> FEATURE:
<221> NAME/KEY: VARIANT
<222> LOCATION: 10
<223> OTHER INFORMATION: Xaa = S or null
<220> FEATURE:
<221> NAME/KEY: VARIANT
<222> LOCATION: 11
<223> OTHER INFORMATION: Xaa = Y or null
<220> FEATURE:
<221> NAME/KEY: VARIANT
<222> LOCATION: 12
<223> OTHER INFORMATION: Xaa = F or null
<220> FEATURE:
<221> NAME/KEY: VARIANT
<222> LOCATION: 14
<223> OTHER INFORMATION: Xaa = I or Y

<400> SEQUENCE: 93

Xaa Xaa Xaa Xaa Xaa Xaa Xaa Xaa Xaa Xaa Xaa Xaa Asp Xaa
1               5                   10

<210> SEQ ID NO 94
<211> LENGTH: 11
<212> TYPE: PRT
<213> ORGANISM: Homo sapiens
<220> FEATURE:
<223> OTHER INFORMATION: Consensus CDR-H3
<220> FEATURE:
<221> NAME/KEY: VARIANT
<222> LOCATION: 1
<223> OTHER INFORMATION: Xaa = V or D
<220> FEATURE:
<221> NAME/KEY: VARIANT
<222> LOCATION: 2
<223> OTHER INFORMATION: Xaa = S or F
<220> FEATURE:
<221> NAME/KEY: VARIANT
<222> LOCATION: 3
<223> OTHER INFORMATION: Xaa = N or G
<220> FEATURE:
<221> NAME/KEY: VARIANT
<222> LOCATION: 4
<223> OTHER INFORMATION: Xaa = Y or R
<220> FEATURE:
<221> NAME/KEY: VARIANT
<222> LOCATION: 5
<223> OTHER INFORMATION: Xaa = E or W
<220> FEATURE:
<221> NAME/KEY: VARIANT
<222> LOCATION: 6
<223> OTHER INFORMATION: Xaa = Y or G
<220> FEATURE:
<221> NAME/KEY: VARIANT
<222> LOCATION: 8
<223> OTHER INFORMATION: Xaa = F or Y
<220> FEATURE:
<221> NAME/KEY: VARIANT
<222> LOCATION: 9
<223> OTHER INFORMATION: Xaa = F or null

<400> SEQUENCE: 94

Xaa Xaa Xaa Xaa Xaa Xaa Tyr Xaa Xaa Asp Tyr
1               5                   10

<210> SEQ ID NO 95
<211> LENGTH: 5
<212> TYPE: PRT
<213> ORGANISM: Homo sapiens
<220> FEATURE:
<223> OTHER INFORMATION: Consensus CDR-H1
<220> FEATURE:
<221> NAME/KEY: VARIANT
<222> LOCATION: 1
<223> OTHER INFORMATION: Xaa = S, D, or N
<220> FEATURE:
<221> NAME/KEY: VARIANT
<222> LOCATION: 2
<223> OTHER INFORMATION: Xaa = Y or A
<220> FEATURE:
<221> NAME/KEY: VARIANT
<222> LOCATION: 3
<223> OTHER INFORMATION: Xaa = Y, A, or W
<220> FEATURE:
<221> NAME/KEY: VARIANT
<222> LOCATION: 5
<223> OTHER INFORMATION: Xaa = H or S

<400> SEQUENCE: 95

Xaa Xaa Xaa Met Xaa
1               5

<210> SEQ ID NO 96
<211> LENGTH: 19
<212> TYPE: PRT
<213> ORGANISM: Homo sapiens
<220> FEATURE:
<223> OTHER INFORMATION: Consensus CDR-H2
<220> FEATURE:
<221> NAME/KEY: VARIANT
<222> LOCATION: 1
<223> OTHER INFORMATION: Xaa = I, S, or R
<220> FEATURE:
<221> NAME/KEY: VARIANT
<222> LOCATION: 3
<223> OTHER INFORMATION: Xaa = N, S, or K
<220> FEATURE:
<221> NAME/KEY: VARIANT
<222> LOCATION: 4
<223> OTHER INFORMATION: Xaa = P, G, or S
<220> FEATURE:
<221> NAME/KEY: VARIANT
<222> LOCATION: 5
<223> OTHER INFORMATION: Xaa = K or null
<220> FEATURE:
<221> NAME/KEY: VARIANT
<222> LOCATION: 6
<223> OTHER INFORMATION: Xaa = T or null
<220> FEATURE:
<221> NAME/KEY: VARIANT
<222> LOCATION: 7
<223> OTHER INFORMATION: Xaa = S, D, or N
<220> FEATURE:
<221> NAME/KEY: VARIANT
<222> LOCATION: 9
<223> OTHER INFORMATION: Xaa = G or R
<220> FEATURE:
<221> NAME/KEY: VARIANT
<222> LOCATION: 10
<223> OTHER INFORMATION: Xaa = S or T
<220> FEATURE:
<221> NAME/KEY: VARIANT
<222> LOCATION: 12
<223> OTHER INFORMATION: Xaa = S or D
<220> FEATURE:
<221> NAME/KEY: VARIANT
<222> LOCATION: 13
<223> OTHER INFORMATION: Xaa = Y or H
<220> FEATURE:
<221> NAME/KEY: VARIANT
<222> LOCATION: 15
<223> OTHER INFORMATION: Xaa = Q, D, or A
<220> FEATURE:
<221> NAME/KEY: VARIANT
<222> LOCATION: 16
<223> OTHER INFORMATION: Xaa = K, Y, or P
<220> FEATURE:
<221> NAME/KEY: VARIANT
<222> LOCATION: 17
<223> OTHER INFORMATION: Xaa = F or V
<220> FEATURE:
<221> NAME/KEY: VARIANT
<222> LOCATION: 18
<223> OTHER INFORMATION: Xaa = Q or K

<400> SEQUENCE: 96

Xaa Ile Xaa Xaa Xaa Xaa Xaa Gly Xaa Xaa Thr Xaa Xaa Ala Xaa Xaa
1 5 10 15

Xaa Xaa Gly

<210> SEQ ID NO 97
<211> LENGTH: 5
<212> TYPE: PRT
<213> ORGANISM: Homo sapiens
<220> FEATURE:
<223> OTHER INFORMATION: Consensus CDR-H1
<220> FEATURE:
<221> NAME/KEY: VARIANT
<222> LOCATION: 1
<223> OTHER INFORMATION: Xaa = D or N
<220> FEATURE:
<221> NAME/KEY: VARIANT
<222> LOCATION: 2
<223> OTHER INFORMATION: Xaa = Y or A
<220> FEATURE:
<221> NAME/KEY: VARIANT
<222> LOCATION: 3
<223> OTHER INFORMATION: Xaa = A or W

<400> SEQUENCE: 97

Xaa Xaa Xaa Met Ser
1 5

<210> SEQ ID NO 98
<211> LENGTH: 19
<212> TYPE: PRT
<213> ORGANISM: Homo sapiens
<220> FEATURE:
<223> OTHER INFORMATION: Consensus CDR-H2
<220> FEATURE:
<221> NAME/KEY: VARIANT
<222> LOCATION: 1
<223> OTHER INFORMATION: Xaa = I, S, or R
<220> FEATURE:
<221> NAME/KEY: VARIANT
<222> LOCATION: 3
<223> OTHER INFORMATION: Xaa = N, S, or K
<220> FEATURE:
<221> NAME/KEY: VARIANT
<222> LOCATION: 4
<223> OTHER INFORMATION: Xaa = P, G, or S
<220> FEATURE:
<221> NAME/KEY: VARIANT
<222> LOCATION: 5
<223> OTHER INFORMATION: Xaa = K or null
<220> FEATURE:
<221> NAME/KEY: VARIANT
<222> LOCATION: 6
<223> OTHER INFORMATION: Xaa = T or null
<220> FEATURE:
<221> NAME/KEY: VARIANT
<222> LOCATION: 7
<223> OTHER INFORMATION: Xaa = S, D, or N
<220> FEATURE:
<221> NAME/KEY: VARIANT
<222> LOCATION: 9
<223> OTHER INFORMATION: Xaa = G or R
<220> FEATURE:
<221> NAME/KEY: VARIANT
<222> LOCATION: 10
<223> OTHER INFORMATION: Xaa = S or T
<220> FEATURE:
<221> NAME/KEY: VARIANT
<222> LOCATION: 12

<223> OTHER INFORMATION: Xaa = S or D
<220> FEATURE:
<221> NAME/KEY: VARIANT
<222> LOCATION: 13
<223> OTHER INFORMATION: Xaa = Y or H
<220> FEATURE:
<221> NAME/KEY: VARIANT
<222> LOCATION: 15
<223> OTHER INFORMATION: Xaa = Q, D, or A
<220> FEATURE:
<221> NAME/KEY: VARIANT
<222> LOCATION: 16
<223> OTHER INFORMATION: Xaa = K, Y, or P
<220> FEATURE:
<221> NAME/KEY: VARIANT
<222> LOCATION: 17
<223> OTHER INFORMATION: Xaa = F or V
<220> FEATURE:
<221> NAME/KEY: VARIANT
<222> LOCATION: 18
<223> OTHER INFORMATION: Xaa = Q or K

<400> SEQUENCE: 98

Xaa Ile Xaa Xaa Xaa Xaa Xaa Gly Xaa Xaa Thr Xaa Xaa Ala Xaa Xaa
1               5                   10                  15

Xaa Xaa Gly

<210> SEQ ID NO 99
<211> LENGTH: 11
<212> TYPE: PRT
<213> ORGANISM: Homo sapiens
<220> FEATURE:
<223> OTHER INFORMATION: Consensus CDR-L3
<220> FEATURE:
<221> NAME/KEY: VARIANT
<222> LOCATION: 1
<223> OTHER INFORMATION: Xaa = Q, A, or K
<220> FEATURE:
<221> NAME/KEY: VARIANT
<222> LOCATION: 2
<223> OTHER INFORMATION: Xaa = Q, V, A, or S
<220> FEATURE:
<221> NAME/KEY: VARIANT
<222> LOCATION: 3
<223> OTHER INFORMATION: Xaa = Y, W, or L
<220> FEATURE:
<221> NAME/KEY: VARIANT
<222> LOCATION: 4
<223> OTHER INFORMATION: Xaa = E, D, K, or N
<220> FEATURE:
<221> NAME/KEY: VARIANT
<222> LOCATION: 5
<223> OTHER INFORMATION: Xaa = S, D, N, or G
<220> FEATURE:
<221> NAME/KEY: VARIANT
<222> LOCATION: 6
<223> OTHER INFORMATION: Xaa = L, T, S, D, R, or Y
<220> FEATURE:
<221> NAME/KEY: VARIANT
<222> LOCATION: 7
<223> OTHER INFORMATION: Xaa = P, G, L, S, N, or T
<220> FEATURE:
<221> NAME/KEY: VARIANT
<222> LOCATION: 8
<223> OTHER INFORMATION: Xaa = D, S, N, or null
<220> FEATURE:
<221> NAME/KEY: VARIANT
<222> LOCATION: 9
<223> OTHER INFORMATION: Xaa = H, G, L, or null
<220> FEATURE:
<221> NAME/KEY: VARIANT
<222> LOCATION: 10
<223> OTHER INFORMATION: Xaa = Y, P, V, R, H, or L
<220> FEATURE:
<221> NAME/KEY: VARIANT
<222> LOCATION: 11

<223> OTHER INFORMATION: Xaa = T, V, S, or M

<400> SEQUENCE: 99

Xaa Xaa Xaa Xaa Xaa Xaa Xaa Xaa Xaa Xaa Xaa
1 5 10

<210> SEQ ID NO 100
<211> LENGTH: 11
<212> TYPE: PRT
<213> ORGANISM: Homo sapiens
<220> FEATURE:
<223> OTHER INFORMATION: Consensus CDR-L3
<220> FEATURE:
<221> NAME/KEY: VARIANT
<222> LOCATION: 1
<223> OTHER INFORMATION: Xaa = Q or A
<220> FEATURE:
<221> NAME/KEY: VARIANT
<222> LOCATION: 2
<223> OTHER INFORMATION: Xaa = Q, V, or A
<220> FEATURE:
<221> NAME/KEY: VARIANT
<222> LOCATION: 3
<223> OTHER INFORMATION: Xaa = Y or W
<220> FEATURE:
<221> NAME/KEY: VARIANT
<222> LOCATION: 4
<223> OTHER INFORMATION: Xaa = E or D
<220> FEATURE:
<221> NAME/KEY: VARIANT
<222> LOCATION: 5
<223> OTHER INFORMATION: Xaa = S or D
<220> FEATURE:
<221> NAME/KEY: VARIANT
<222> LOCATION: 6
<223> OTHER INFORMATION: Xaa = L, T, or S
<220> FEATURE:
<221> NAME/KEY: VARIANT
<222> LOCATION: 7
<223> OTHER INFORMATION: Xaa = P, G, or L
<220> FEATURE:
<221> NAME/KEY: VARIANT
<222> LOCATION: 8
<223> OTHER INFORMATION: Xaa = D, S, or null
<220> FEATURE:
<221> NAME/KEY: VARIANT
<222> LOCATION: 9
<223> OTHER INFORMATION: Xaa = H, G, or null
<220> FEATURE:
<221> NAME/KEY: VARIANT
<222> LOCATION: 10
<223> OTHER INFORMATION: Xaa = Y, P, or V
<220> FEATURE:
<221> NAME/KEY: VARIANT
<222> LOCATION: 11
<223> OTHER INFORMATION: Xaa = T or V

<400> SEQUENCE: 100

Xaa Xaa Xaa Xaa Xaa Xaa Xaa Xaa Xaa Xaa Xaa
1 5 10

<210> SEQ ID NO 101
<211> LENGTH: 13
<212> TYPE: PRT
<213> ORGANISM: Homo sapiens
<220> FEATURE:
<223> OTHER INFORMATION: Consensus CDR-L1
<220> FEATURE:
<221> NAME/KEY: VARIANT
<222> LOCATION: 1
<223> OTHER INFORMATION: Xaa = Q, G, or S
<220> FEATURE:
<221> NAME/KEY: VARIANT
<222> LOCATION: 2
<223> OTHER INFORMATION: Xaa = A or G
<220> FEATURE:
<221> NAME/KEY: VARIANT
<222> LOCATION: 4
<223> OTHER INFORMATION: Xaa = Q, N, or S
<220> FEATURE:
<221> NAME/KEY: VARIANT
<222> LOCATION: 5
<223> OTHER INFORMATION: Xaa = S or null
<220> FEATURE:
<221> NAME/KEY: VARIANT
<222> LOCATION: 6
<223> OTHER INFORMATION: Xaa = N or null
<220> FEATURE:
<221> NAME/KEY: VARIANT
<222> LOCATION: 7
<223> OTHER INFORMATION: Xaa = D or I
<220> FEATURE:
<221> NAME/KEY: VARIANT
<222> LOCATION: 8
<223> OTHER INFORMATION: Xaa = I or G
<220> FEATURE:
<221> NAME/KEY: VARIANT
<222> LOCATION: 10
<223> OTHER INFORMATION: Xaa = N or E
<220> FEATURE:
<221> NAME/KEY: VARIANT
<222> LOCATION: 11
<223> OTHER INFORMATION: Xaa = Y or S
<220> FEATURE:
<221> NAME/KEY: VARIANT
<222> LOCATION: 12
<223> OTHER INFORMATION: Xaa = L or V
<220> FEATURE:
<221> NAME/KEY: VARIANT
<222> LOCATION: 13
<223> OTHER INFORMATION: Xaa = N or Y

<400> SEQUENCE: 101

```
Xaa Xaa Ser Xaa Xaa Xaa Xaa Xaa Ser Xaa Xaa Xaa Xaa
1               5                   10
```

<210> SEQ ID NO 102
<211> LENGTH: 7
<212> TYPE: PRT
<213> ORGANISM: Homo sapiens
<220> FEATURE:
<223> OTHER INFORMATION: Consensus CDR-L2
<220> FEATURE:
<221> NAME/KEY: VARIANT
<222> LOCATION: 1
<223> OTHER INFORMATION: Xaa = D or R
<220> FEATURE:
<221> NAME/KEY: VARIANT
<222> LOCATION: 2
<223> OTHER INFORMATION: Xaa = A, T, or N
<220> FEATURE:
<221> NAME/KEY: VARIANT
<222> LOCATION: 3
<223> OTHER INFORMATION: Xaa = S, T, or N
<220> FEATURE:
<221> NAME/KEY: VARIANT
<222> LOCATION: 4
<223> OTHER INFORMATION: Xaa = Y, D, or Q
<220> FEATURE:
<221> NAME/KEY: VARIANT
<222> LOCATION: 5
<223> OTHER INFORMATION: Xaa = L or R
<220> FEATURE:
<221> NAME/KEY: VARIANT
<222> LOCATION: 6
<223> OTHER INFORMATION: Xaa = E or P
<220> FEATURE:
<221> NAME/KEY: VARIANT
<222> LOCATION: 7
<223> OTHER INFORMATION: Xaa = T or S

<400> SEQUENCE: 102

Xaa Xaa Xaa Xaa Xaa Xaa Xaa
1               5

<210> SEQ ID NO 103
<211> LENGTH: 908
<212> TYPE: PRT
<213> ORGANISM: Homo sapiens
<220> FEATURE:
<223> OTHER INFORMATION: Human ROR1, GenBank No. NP_005003.2

<400> SEQUENCE: 103

Gln Glu Thr Glu Leu Ser Val Ser Ala Glu Leu Val Pro Thr Ser Ser
1               5                   10                  15

Trp Asn Ile Ser Ser Glu Leu Asn Lys Asp Ser Tyr Leu Thr Leu Asp
            20                  25                  30

Glu Pro Met Asn Asn Ile Thr Thr Ser Leu Gly Gln Thr Ala Glu Leu
        35                  40                  45

His Cys Lys Val Ser Gly Asn Pro Pro Pro Thr Ile Arg Trp Phe Lys
    50                  55                  60

Asn Asp Ala Pro Val Val Gln Glu Pro Arg Arg Leu Ser Phe Arg Ser
65                  70                  75                  80

Thr Ile Tyr Gly Ser Arg Leu Arg Ile Arg Asn Leu Asp Thr Thr Asp
                85                  90                  95

Thr Gly Tyr Phe Gln Cys Val Ala Thr Asn Gly Lys Glu Val Val Ser
            100                 105                 110

Ser Thr Gly Val Leu Phe Val Lys Phe Gly Pro Pro Pro Thr Ala Ser
        115                 120                 125

Pro Gly Tyr Ser Asp Glu Tyr Glu Glu Asp Gly Phe Cys Gln Pro Tyr
    130                 135                 140

Arg Gly Ile Ala Cys Ala Arg Phe Ile Gly Asn Arg Thr Val Tyr Met
145                 150                 155                 160

Glu Ser Leu His Met Gln Gly Glu Ile Glu Asn Gln Ile Thr Ala Ala
                165                 170                 175

Phe Thr Met Ile Gly Thr Ser Ser His Leu Ser Asp Lys Cys Ser Gln
            180                 185                 190

Phe Ala Ile Pro Ser Leu Cys His Tyr Ala Phe Pro Tyr Cys Asp Glu
        195                 200                 205

Thr Ser Ser Val Pro Lys Pro Arg Asp Leu Cys Arg Asp Glu Cys Glu
    210                 215                 220

Ile Leu Glu Asn Val Leu Cys Gln Thr Glu Tyr Ile Phe Ala Arg Ser
225                 230                 235                 240

Asn Pro Met Ile Leu Met Arg Leu Lys Leu Pro Asn Cys Glu Asp Leu
                245                 250                 255

Pro Gln Pro Glu Ser Pro Glu Ala Ala Asn Cys Ile Arg Ile Gly Ile
            260                 265                 270

Pro Met Ala Asp Pro Ile Asn Lys Asn His Lys Cys Tyr Asn Ser Thr
        275                 280                 285

Gly Val Asp Tyr Arg Gly Thr Val Ser Val Thr Lys Ser Gly Arg Gln
    290                 295                 300

Cys Gln Pro Trp Asn Ser Gln Tyr Pro His Thr His Thr Phe Thr Ala
305                 310                 315                 320

Leu Arg Phe Pro Glu Leu Asn Gly Gly His Ser Tyr Cys Arg Asn Pro
                325                 330                 335

Gly Asn Gln Lys Glu Ala Pro Trp Cys Phe Thr Leu Asp Glu Asn Phe
            340                 345                 350

-continued

```
Lys Ser Asp Leu Cys Asp Ile Pro Ala Cys Asp Ser Lys Asp Ser Lys
        355                 360                 365

Glu Lys Asn Lys Met Glu Ile Leu Tyr Ile Leu Val Pro Ser Val Ala
    370                 375                 380

Ile Pro Leu Ala Ile Ala Leu Leu Phe Phe Phe Ile Cys Val Cys Arg
385                 390                 395                 400

Asn Asn Gln Lys Ser Ser Ser Ala Pro Val Gln Arg Gln Pro Lys His
                405                 410                 415

Val Arg Gly Gln Asn Val Glu Met Ser Met Leu Asn Ala Tyr Lys Pro
            420                 425                 430

Lys Ser Lys Ala Lys Glu Leu Pro Leu Ser Ala Val Arg Phe Met Glu
        435                 440                 445

Glu Leu Gly Glu Cys Ala Phe Gly Lys Ile Tyr Lys Gly His Leu Tyr
    450                 455                 460

Leu Pro Gly Met Asp His Ala Gln Leu Val Ala Ile Lys Thr Leu Lys
465                 470                 475                 480

Asp Tyr Asn Asn Pro Gln Gln Trp Thr Glu Phe Gln Gln Glu Ala Ser
                485                 490                 495

Leu Met Ala Glu Leu His His Pro Asn Ile Val Cys Leu Leu Gly Ala
            500                 505                 510

Val Thr Gln Glu Gln Pro Val Cys Met Leu Phe Glu Tyr Ile Asn Gln
        515                 520                 525

Gly Asp Leu His Glu Phe Leu Ile Met Arg Ser Pro His Ser Asp Val
    530                 535                 540

Gly Cys Ser Ser Asp Glu Asp Gly Thr Val Lys Ser Ser Leu Asp His
545                 550                 555                 560

Gly Asp Phe Leu His Ile Ala Ile Gln Ile Ala Ala Gly Met Glu Tyr
                565                 570                 575

Leu Ser Ser His Phe Phe Val His Lys Asp Leu Ala Ala Arg Asn Ile
            580                 585                 590

Leu Ile Gly Glu Gln Leu His Val Lys Ile Ser Asp Leu Gly Leu Ser
        595                 600                 605

Arg Glu Ile Tyr Ser Ala Asp Tyr Tyr Arg Val Gln Ser Lys Ser Leu
    610                 615                 620

Leu Pro Ile Arg Trp Met Pro Pro Glu Ala Ile Met Tyr Gly Lys Phe
625                 630                 635                 640

Ser Ser Asp Ser Asp Ile Trp Ser Phe Gly Val Val Leu Trp Glu Ile
                645                 650                 655

Phe Ser Phe Gly Leu Gln Pro Tyr Tyr Gly Phe Ser Asn Gln Glu Val
            660                 665                 670

Ile Glu Met Val Arg Lys Arg Gln Leu Leu Pro Cys Ser Glu Asp Cys
        675                 680                 685

Pro Pro Arg Met Tyr Ser Leu Met Thr Glu Cys Trp Asn Glu Ile Pro
    690                 695                 700

Ser Arg Arg Pro Arg Phe Lys Asp Ile His Val Arg Leu Arg Ser Trp
705                 710                 715                 720

Glu Gly Leu Ser Ser His Thr Ser Ser Thr Thr Pro Ser Gly Gly Asn
                725                 730                 735

Ala Thr Thr Gln Thr Thr Ser Leu Ser Ala Ser Pro Val Ser Asn Leu
            740                 745                 750

Ser Asn Pro Arg Tyr Pro Asn Tyr Met Phe Pro Ser Gln Gly Ile Thr
        755                 760                 765
```

```
Pro Gln Gly Gln Ile Ala Gly Phe Ile Gly Pro Pro Ile Pro Gln Asn
    770                 775                 780

Gln Arg Phe Ile Pro Ile Asn Gly Tyr Pro Ile Pro Pro Gly Tyr Ala
785                 790                 795                 800

Ala Phe Pro Ala Ala His Tyr Gln Pro Thr Gly Pro Pro Arg Val Ile
                805                 810                 815

Gln His Cys Pro Pro Pro Lys Ser Arg Ser Pro Ser Ser Ala Ser Gly
            820                 825                 830

Ser Thr Ser Thr Gly His Val Thr Ser Leu Pro Ser Ser Gly Ser Asn
        835                 840                 845

Gln Glu Ala Asn Ile Pro Leu Leu Pro His Met Ser Ile Pro Asn His
    850                 855                 860

Pro Gly Gly Met Gly Ile Thr Val Phe Gly Asn Lys Ser Gln Lys Pro
865                 870                 875                 880

Tyr Lys Ile Asp Ser Lys Gln Ala Ser Leu Leu Gly Asp Ala Asn Ile
                885                 890                 895

His Gly His Thr Glu Ser Met Ile Ser Ala Glu Leu
            900                 905


<210> SEQ ID NO 104
<211> LENGTH: 520
<212> TYPE: PRT
<213> ORGANISM: Homo sapiens
<220> FEATURE:
<223> OTHER INFORMATION: ROR1 Isoform short

<400> SEQUENCE: 104

Gln Glu Thr Glu Leu Ser Val Ser Ala Glu Leu Val Pro Thr Ser Ser
1               5                   10                  15

Trp Asn Ile Ser Ser Glu Leu Asn Lys Asp Ser Tyr Leu Thr Leu Asp
            20                  25                  30

Glu Pro Met Asn Asn Ile Thr Thr Ser Leu Gly Gln Thr Ala Glu Leu
        35                  40                  45

His Cys Lys Val Ser Gly Asn Pro Pro Pro Thr Ile Arg Trp Phe Lys
    50                  55                  60

Asn Asp Ala Pro Val Val Gln Glu Pro Arg Arg Leu Ser Phe Arg Ser
65                  70                  75                  80

Thr Ile Tyr Gly Ser Arg Leu Arg Ile Arg Asn Leu Asp Thr Thr Asp
                85                  90                  95

Thr Gly Tyr Phe Gln Cys Val Ala Thr Asn Gly Lys Glu Val Val Ser
            100                 105                 110

Ser Thr Gly Val Leu Phe Val Lys Phe Gly Pro Pro Pro Thr Ala Ser
        115                 120                 125

Pro Gly Tyr Ser Asp Glu Tyr Glu Glu Asp Gly Phe Cys Gln Pro Tyr
    130                 135                 140

Arg Gly Ile Ala Cys Ala Arg Phe Ile Gly Asn Arg Thr Val Tyr Met
145                 150                 155                 160

Glu Ser Leu His Met Gln Gly Glu Ile Glu Asn Gln Ile Thr Ala Ala
                165                 170                 175

Phe Thr Met Ile Gly Thr Ser Ser His Leu Ser Asp Lys Cys Ser Gln
            180                 185                 190

Phe Ala Ile Pro Ser Leu Cys His Tyr Ala Phe Pro Tyr Cys Asp Glu
        195                 200                 205

Thr Ser Ser Val Pro Lys Pro Arg Asp Leu Cys Arg Asp Glu Cys Glu
    210                 215                 220
```

```
Ile Leu Glu Asn Val Leu Cys Gln Thr Glu Tyr Ile Phe Ala Arg Ser
225                 230                 235                 240

Asn Pro Met Ile Leu Met Arg Leu Lys Leu Pro Asn Cys Glu Asp Leu
                245                 250                 255

Pro Gln Pro Glu Ser Pro Glu Ala Ala Asn Cys Ile Arg Ile Gly Ile
            260                 265                 270

Pro Met Ala Asp Pro Ile Asn Lys Asn His Lys Cys Tyr Asn Ser Thr
        275                 280                 285

Gly Val Asp Tyr Arg Gly Thr Val Ser Val Thr Lys Ser Gly Arg Gln
    290                 295                 300

Cys Gln Pro Trp Asn Ser Gln Tyr Pro His Thr His Thr Phe Thr Ala
305                 310                 315                 320

Leu Arg Phe Pro Glu Leu Asn Gly Gly His Ser Tyr Cys Arg Asn Pro
                325                 330                 335

Gly Asn Gln Lys Glu Ala Pro Trp Cys Phe Thr Leu Asp Glu Asn Phe
            340                 345                 350

Lys Ser Asp Leu Cys Asp Ile Pro Ala Cys Asp Ser Lys Asp Ser Lys
        355                 360                 365

Glu Lys Asn Lys Met Glu Ile Leu Tyr Ile Leu Val Pro Ser Val Ala
    370                 375                 380

Ile Pro Leu Ala Ile Ala Leu Leu Phe Phe Phe Ile Cys Val Cys Arg
385                 390                 395                 400

Asn Asn Gln Lys Ser Ser Ser Ala Pro Val Gln Arg Gln Pro Lys His
                405                 410                 415

Val Arg Gly Gln Asn Val Glu Met Ser Met Leu Asn Ala Tyr Lys Pro
            420                 425                 430

Lys Ser Lys Ala Lys Glu Leu Pro Leu Ser Ala Val Arg Phe Met Glu
        435                 440                 445

Glu Leu Gly Glu Cys Ala Phe Gly Lys Ile Tyr Lys Gly His Leu Tyr
    450                 455                 460

Leu Pro Gly Met Asp His Ala Gln Leu Val Ala Ile Lys Thr Leu Lys
465                 470                 475                 480

Asp Tyr Asn Asn Pro Gln Gln Trp Thr Glu Phe Gln Gln Glu Ala Ser
                485                 490                 495

Leu Met Ala Glu Leu His His Pro Asn Ile Val Cys Leu Leu Gly Ala
            500                 505                 510

Val Thr Gln Glu Gln Pro Val Cys
        515                 520


<210> SEQ ID NO 105
<211> LENGTH: 364
<212> TYPE: PRT
<213> ORGANISM: Homo sapiens
<220> FEATURE:
<223> OTHER INFORMATION: ROR1 isoform 3

<400> SEQUENCE: 105

Gln Glu Thr Glu Leu Ser Val Ser Ala Glu Leu Val Pro Thr Ser Ser
1               5                   10                  15

Trp Asn Ile Ser Ser Glu Leu Asn Lys Asp Ser Tyr Leu Thr Leu Asp
            20                  25                  30

Glu Pro Met Asn Asn Ile Thr Thr Ser Leu Gly Gln Thr Ala Glu Leu
        35                  40                  45

His Cys Lys Val Ser Gly Asn Pro Pro Pro Thr Ile Arg Trp Phe Lys
    50                  55                  60
```

-continued

Asn Asp Ala Pro Val Val Gln Glu Pro Arg Arg Leu Ser Phe Arg Ser
65 70 75 80

Thr Ile Tyr Gly Ser Arg Leu Arg Ile Arg Asn Leu Asp Thr Thr Asp
85 90 95

Thr Gly Tyr Phe Gln Cys Val Ala Thr Asn Gly Lys Glu Val Val Ser
100 105 110

Ser Thr Gly Val Leu Phe Val Lys Phe Gly Pro Pro Pro Thr Ala Ser
115 120 125

Pro Gly Tyr Ser Asp Glu Tyr Glu Glu Asp Gly Phe Cys Gln Pro Tyr
130 135 140

Arg Gly Ile Ala Cys Ala Arg Phe Ile Gly Asn Arg Thr Val Tyr Met
145 150 155 160

Glu Ser Leu His Met Gln Gly Glu Ile Glu Asn Gln Ile Thr Ala Ala
165 170 175

Phe Thr Met Ile Gly Thr Ser Ser His Leu Ser Asp Lys Cys Ser Gln
180 185 190

Phe Ala Ile Pro Ser Leu Cys His Tyr Ala Phe Pro Tyr Cys Asp Glu
195 200 205

Thr Ser Ser Val Pro Lys Pro Arg Asp Leu Cys Arg Asp Glu Cys Glu
210 215 220

Ile Leu Glu Asn Val Leu Cys Gln Thr Glu Tyr Ile Phe Ala Arg Ser
225 230 235 240

Asn Pro Met Ile Leu Met Arg Leu Lys Leu Pro Asn Cys Glu Asp Leu
245 250 255

Pro Gln Pro Glu Ser Pro Glu Ala Ala Asn Cys Ile Arg Ile Gly Ile
260 265 270

Pro Met Ala Asp Pro Ile Asn Lys Asn His Lys Cys Tyr Asn Ser Thr
275 280 285

Gly Val Asp Tyr Arg Gly Thr Val Ser Val Thr Lys Ser Gly Arg Gln
290 295 300

Cys Gln Pro Trp Asn Ser Gln Tyr Pro His Thr His Thr Phe Thr Ala
305 310 315 320

Leu Arg Phe Pro Glu Leu Asn Gly Gly His Ser Tyr Cys Arg Asn Pro
325 330 335

Gly Asn Gln Lys Glu Ala Pro Trp Cys Phe Thr Leu Asp Glu Asn Phe
340 345 350

Lys Ser Asp Leu Cys Asp Ile Pro Ala Cys Gly Lys
355 360

<210> SEQ ID NO 106
<211> LENGTH: 908
<212> TYPE: PRT
<213> ORGANISM: Mus musculus
<220> FEATURE:
<223> OTHER INFORMATION: Mouse ROR1, GenBank No. NP_038873

<400> SEQUENCE: 106

Gln Glu Thr Glu Leu Ser Val Ser Ala Glu Leu Val Pro Thr Ser Ser
1 5 10 15

Trp Asn Thr Ser Ser Glu Ile Asp Lys Gly Ser Tyr Leu Thr Leu Asp
20 25 30

Glu Pro Met Asn Asn Ile Thr Thr Ser Leu Gly Gln Thr Ala Glu Leu
35 40 45

His Cys Lys Val Ser Gly Asn Pro Pro Pro Ser Ile Arg Trp Phe Lys
50 55 60

-continued

```
Asn Asp Ala Pro Val Val Gln Glu Pro Arg Arg Ile Ser Phe Arg Ala
65                  70                  75                  80

Thr Asn Tyr Gly Ser Arg Leu Arg Ile Arg Asn Leu Asp Thr Thr Asp
                85                  90                  95

Thr Gly Tyr Phe Gln Cys Val Ala Thr Asn Gly Lys Lys Val Val Ser
            100                 105                 110

Thr Thr Gly Val Leu Phe Val Lys Phe Gly Pro Pro Pro Thr Ala Ser
        115                 120                 125

Pro Gly Ser Ser Asp Glu Tyr Glu Glu Asp Gly Phe Cys Gln Pro Tyr
    130                 135                 140

Arg Gly Ile Ala Cys Ala Arg Phe Ile Gly Asn Arg Thr Val Tyr Met
145                 150                 155                 160

Glu Ser Leu His Met Gln Gly Glu Ile Glu Asn Gln Ile Thr Ala Ala
                165                 170                 175

Phe Thr Met Ile Gly Thr Ser Ser His Leu Ser Asp Lys Cys Ser Gln
            180                 185                 190

Phe Ala Ile Pro Ser Leu Cys His Tyr Ala Phe Pro Tyr Cys Asp Glu
        195                 200                 205

Thr Ser Ser Val Pro Lys Pro Arg Asp Leu Cys Arg Asp Glu Cys Glu
    210                 215                 220

Val Leu Glu Asn Val Leu Cys Gln Thr Glu Tyr Ile Phe Ala Arg Ser
225                 230                 235                 240

Asn Pro Met Ile Leu Met Arg Leu Lys Leu Pro Asn Cys Glu Asp Leu
                245                 250                 255

Pro Gln Pro Glu Ser Pro Glu Ala Ala Asn Cys Ile Arg Ile Gly Ile
            260                 265                 270

Pro Met Ala Asp Pro Ile Asn Lys Asn His Lys Cys Tyr Asn Ser Thr
        275                 280                 285

Gly Val Asp Tyr Arg Gly Thr Val Ser Val Thr Lys Ser Gly Arg Gln
    290                 295                 300

Cys Gln Pro Trp Asn Ser Gln Tyr Pro His Thr His Ser Phe Thr Ala
305                 310                 315                 320

Leu Arg Phe Pro Glu Leu Asn Gly Gly His Ser Tyr Cys Arg Asn Pro
                325                 330                 335

Gly Asn Gln Lys Glu Ala Pro Trp Cys Phe Thr Leu Asp Glu Asn Phe
            340                 345                 350

Lys Ser Asp Leu Cys Asp Ile Pro Ala Cys Asp Ser Lys Asp Ser Lys
        355                 360                 365

Glu Lys Asn Lys Met Glu Ile Leu Tyr Ile Leu Val Pro Ser Val Ala
    370                 375                 380

Ile Pro Leu Ala Ile Ala Phe Leu Phe Phe Phe Ile Cys Val Cys Arg
385                 390                 395                 400

Asn Asn Gln Lys Ser Ser Ser Pro Pro Val Gln Arg Gln Pro Lys Pro
                405                 410                 415

Val Arg Gly Gln Asn Val Glu Met Ser Met Leu Asn Ala Tyr Lys Pro
            420                 425                 430

Lys Ser Lys Ala Lys Glu Leu Pro Leu Ser Ala Val Arg Phe Met Glu
        435                 440                 445

Glu Leu Gly Glu Cys Thr Phe Gly Lys Ile Tyr Lys Gly His Leu Tyr
    450                 455                 460

Leu Pro Gly Met Asp His Ala Gln Leu Val Ala Ile Lys Thr Leu Lys
465                 470                 475                 480

Asp Tyr Asn Asn Pro Gln Gln Trp Thr Glu Phe Gln Gln Glu Ala Ser
```

```
                485                 490                 495

Leu Met Ala Glu Leu His His Pro Asn Ile Val Cys Leu Leu Gly Ala
            500                 505                 510

Val Thr Gln Glu Gln Pro Val Cys Met Leu Phe Glu Tyr Met Asn Gln
        515                 520                 525

Gly Asp Leu His Glu Phe Leu Ile Met Arg Ser Pro His Ser Asp Val
    530                 535                 540

Gly Cys Ser Ser Asp Glu Asp Gly Thr Val Lys Ser Ser Leu Asp His
545                 550                 555                 560

Gly Asp Phe Leu His Ile Ala Ile Gln Ile Ala Ala Gly Met Glu Tyr
                565                 570                 575

Leu Ser Ser His Phe Phe Val His Lys Asp Leu Ala Ala Arg Asn Ile
            580                 585                 590

Leu Ile Gly Glu Gln Leu His Val Lys Ile Ser Asp Leu Gly Leu Ser
        595                 600                 605

Arg Glu Ile Tyr Ser Ala Asp Tyr Tyr Arg Val Gln Ser Lys Ser Ser
    610                 615                 620

Leu Pro Ile Arg Trp Met Pro Pro Glu Ala Ile Met Tyr Gly Lys Phe
625                 630                 635                 640

Ser Ser Asp Ser Asp Ile Trp Ser Phe Gly Val Val Leu Trp Glu Ile
                645                 650                 655

Phe Ser Phe Gly Leu Gln Pro Tyr Tyr Gly Phe Ser Asn Gln Glu Val
            660                 665                 670

Ile Glu Met Val Arg Lys Arg Gln Leu Leu Pro Cys Ser Glu Asp Cys
        675                 680                 685

Pro Pro Arg Met Tyr Ser Leu Met Thr Glu Cys Trp Asn Glu Ile Pro
    690                 695                 700

Ser Arg Arg Pro Arg Phe Lys Asp Ile His Val Arg Leu Arg Ser Trp
705                 710                 715                 720

Glu Gly Leu Ser Ser His Thr Ser Ser Thr Thr Pro Ser Gly Gly Asn
                725                 730                 735

Ala Thr Thr Gln Thr Thr Ser Leu Ser Ala Ser Pro Val Ser Asn Leu
            740                 745                 750

Ser Asn Pro Arg Phe Pro Asn Tyr Met Phe Pro Ser Gln Gly Ile Thr
        755                 760                 765

Pro Gln Gly Gln Ile Ala Gly Phe Ile Gly Pro Ala Ile Pro Gln Asn
    770                 775                 780

Gln Arg Phe Ile Pro Ile Asn Gly Tyr Pro Ile Pro Pro Gly Tyr Ala
785                 790                 795                 800

Ala Phe Pro Ala Ala His Tyr Gln Pro Ala Gly Pro Pro Arg Val Ile
                805                 810                 815

Gln His Cys Pro Pro Pro Lys Ser Arg Ser Pro Ser Ser Ala Ser Gly
            820                 825                 830

Ser Thr Ser Thr Gly His Val Ala Ser Leu Pro Ser Ser Gly Ser Asn
        835                 840                 845

Gln Glu Ala Asn Val Pro Leu Leu Pro His Met Ser Ile Pro Asn His
    850                 855                 860

Pro Gly Gly Met Gly Ile Thr Val Phe Gly Asn Lys Ser Gln Lys Pro
865                 870                 875                 880

Tyr Lys Ile Asp Ser Lys Gln Ser Ser Leu Leu Gly Asp Ser His Ile
                885                 890                 895

His Gly His Thr Glu Ser Met Ile Ser Ala Glu Val
            900                 905
```

<210> SEQ ID NO 107
<211> LENGTH: 36
<212> TYPE: DNA
<213> ORGANISM: Artificial Sequence
<220> FEATURE:
<223> OTHER INFORMATION: Synthetic
<220> FEATURE:
<223> OTHER INFORMATION: spacer (IgG4hinge)

<400> SEQUENCE: 107
gaatctaagt acggaccgcc ctgcccccct tgccct 36

<210> SEQ ID NO 108
<211> LENGTH: 12
<212> TYPE: PRT
<213> ORGANISM: Artificial Sequence
<220> FEATURE:
<223> OTHER INFORMATION: Synthetic
<220> FEATURE:
<223> OTHER INFORMATION: spacer (IgG4hinge)

<400> SEQUENCE: 108

Glu Ser Lys Tyr Gly Pro Pro Cys Pro Pro Cys Pro
1 5 10

<210> SEQ ID NO 109
<211> LENGTH: 10
<212> TYPE: PRT
<213> ORGANISM: Homo sapiens
<220> FEATURE:
<223> OTHER INFORMATION: Consensus CDR-H3
<220> FEATURE:
<221> NAME/KEY: VARIANT
<222> LOCATION: 1
<223> OTHER INFORMATION: Xaa = V or D
<220> FEATURE:
<221> NAME/KEY: VARIANT
<222> LOCATION: 3
<223> OTHER INFORMATION: Xaa = S or N
<220> FEATURE:
<221> NAME/KEY: VARIANT
<222> LOCATION: 5
<223> OTHER INFORMATION: Xaa = D or E
<220> FEATURE:
<221> NAME/KEY: VARIANT
<222> LOCATION: 6
<223> OTHER INFORMATION: Xaa = Y or A
<220> FEATURE:
<221> NAME/KEY: VARIANT
<222> LOCATION: 7
<223> OTHER INFORMATION: Xaa = F or Y
<220> FEATURE:
<221> NAME/KEY: VARIANT
<222> LOCATION: 8
<223> OTHER INFORMATION: Xaa = F or null
<220> FEATURE:
<221> NAME/KEY: VARIANT
<222> LOCATION: 10
<223> OTHER INFORMATION: Xaa = I or Y

<400> SEQUENCE: 109

Xaa Ser Xaa Tyr Xaa Xaa Xaa Xaa Asp Xaa
1 5 10

<210> SEQ ID NO 110
<211> LENGTH: 10
<212> TYPE: PRT
<213> ORGANISM: Homo sapiens
<220> FEATURE:
<223> OTHER INFORMATION: Consensus CDR-H3
<220> FEATURE:

<221> NAME/KEY: VARIANT
<222> LOCATION: 2
<223> OTHER INFORMATION: Xaa = S, N, or R
<220> FEATURE:
<221> NAME/KEY: VARIANT
<222> LOCATION: 3
<223> OTHER INFORMATION: Xaa = N or G
<220> FEATURE:
<221> NAME/KEY: VARIANT
<222> LOCATION: 4
<223> OTHER INFORMATION: Xaa = Y, G, or S

<400> SEQUENCE: 110

Val Xaa Xaa Xaa Glu Tyr Tyr Phe Asp Tyr
1 5 10

<210> SEQ ID NO 111
<211> LENGTH: 5
<212> TYPE: PRT
<213> ORGANISM: Artificial Sequence
<220> FEATURE:
<223> OTHER INFORMATION: Synthetic
<220> FEATURE:
<223> OTHER INFORMATION: 4GS linker

<400> SEQUENCE: 111

Gly Gly Gly Gly Ser
1 5

<210> SEQ ID NO 112
<211> LENGTH: 4
<212> TYPE: PRT
<213> ORGANISM: Artificial Sequence
<220> FEATURE:
<223> OTHER INFORMATION: Synthetic
<220> FEATURE:
<223> OTHER INFORMATION: 3GS linker

<400> SEQUENCE: 112

Gly Gly Gly Ser
1

<210> SEQ ID NO 113
<211> LENGTH: 18
<212> TYPE: PRT
<213> ORGANISM: Artificial Sequence
<220> FEATURE:
<223> OTHER INFORMATION: Synthetic
<220> FEATURE:
<223> OTHER INFORMATION: Linker

<400> SEQUENCE: 113

Gly Ser Thr Ser Gly Ser Gly Lys Pro Gly Ser Gly Glu Gly Ser Thr
1 5 10 15

Lys Gly

<210> SEQ ID NO 114
<211> LENGTH: 118
<212> TYPE: PRT
<213> ORGANISM: Mus musculus
<220> FEATURE:
<223> OTHER INFORMATION: 2A2 VH

<400> SEQUENCE: 114

Gln Val Gln Leu Gln Gln Ser Gly Ala Glu Leu Val Arg Pro Gly Ala
1 5 10 15

Ser Val Thr Leu Ser Cys Lys Ala Ser Gly Tyr Thr Phe Ser Asp Tyr
20 25 30

```
Glu Met His Trp Val Ile Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Gly Tyr Tyr Asp Tyr Asp Ser Phe Thr Tyr Trp Gly Gln Gly Thr
            100                 105                 110

Leu Val Thr Val Ser Ala
        115


<210> SEQ ID NO 115
<211> LENGTH: 107
<212> TYPE: PRT
<213> ORGANISM: Mus musculus
<220> FEATURE:
<223> OTHER INFORMATION: 2A2 VL

<400> SEQUENCE: 115

Asp Ile Val Met Thr Gln Ser Gln Lys Ile Met Ser Thr Thr Val Gly
1               5                   10                  15

Asp Arg Val Ser Ile Thr Cys Lys Ala Ser Gln Asn Val Asp Ala Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Asp Ile Tyr Pro Tyr
                85                  90                  95

Thr Phe Gly Gly Gly Thr Lys Leu Glu Ile Lys
            100                 105


<210> SEQ ID NO 116
<211> LENGTH: 5
<212> TYPE: PRT
<213> ORGANISM: Mus musculus
<220> FEATURE:
<223> OTHER INFORMATION: 2A2 CDR-H1

<400> SEQUENCE: 116

Asp Tyr Glu Met His
1               5


<210> SEQ ID NO 117
<211> LENGTH: 17
<212> TYPE: PRT
<213> ORGANISM: Mus musculus
<220> FEATURE:
<223> OTHER INFORMATION: 2A2 CDR-H2

<400> SEQUENCE: 117

Ala Ile Asp Pro Glu Thr Gly Gly Thr Ala Tyr Asn Gln Lys Phe Lys
1               5                   10                  15

Gly
```

<210> SEQ ID NO 118
<211> LENGTH: 9
<212> TYPE: PRT
<213> ORGANISM: Mus musculus
<220> FEATURE:
<223> OTHER INFORMATION: 2A2 CDR-H3

<400> SEQUENCE: 118

Tyr Tyr Asp Tyr Asp Ser Phe Thr Tyr
1               5

<210> SEQ ID NO 119
<211> LENGTH: 11
<212> TYPE: PRT
<213> ORGANISM: Mus musculus
<220> FEATURE:
<223> OTHER INFORMATION: 2A2 CDR-L1

<400> SEQUENCE: 119

Lys Ala Ser Gln Asn Val Asp Ala Ala Val Ala
1               5                   10

<210> SEQ ID NO 120
<211> LENGTH: 7
<212> TYPE: PRT
<213> ORGANISM: Mus musculus
<220> FEATURE:
<223> OTHER INFORMATION: 2A2 CDR-L2

<400> SEQUENCE: 120

Ser Ala Ser Asn Arg Tyr Thr
1               5

<210> SEQ ID NO 121
<211> LENGTH: 9
<212> TYPE: PRT
<213> ORGANISM: Mus musculus
<220> FEATURE:
<223> OTHER INFORMATION: 2A2 CDR-L3

<400> SEQUENCE: 121

Gln Gln Tyr Asp Ile Tyr Pro Tyr Thr
1               5

<210> SEQ ID NO 122
<211> LENGTH: 116
<212> TYPE: PRT
<213> ORGANISM: Artificial Sequence
<220> FEATURE:
<223> OTHER INFORMATION: Synthetic
<220> FEATURE:
<223> OTHER INFORMATION: 99961 humanized VH

<400> SEQUENCE: 122

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
            20                  25                  30

Asn Ile His Trp Val Arg Gln Ala Pro Gly Gln Gly Leu Glu Trp Met
        35                  40                  45

Gly Ser Phe Asp Pro Tyr Asp Gly Gly Ser Ser Tyr Asn Gln Lys Phe
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys

```
                85                  90                  95

Ala Arg Gly Trp Tyr Tyr Phe Asp Tyr Trp Gly His Gly Thr Leu Val
            100                 105                 110

Thr Val Ser Ser
        115
```

<210> SEQ ID NO 123
<211> LENGTH: 116
<212> TYPE: PRT
<213> ORGANISM: Artificial Sequence
<220> FEATURE:
<223> OTHER INFORMATION: Synthetic
<220> FEATURE:
<223> OTHER INFORMATION: 99961 humanized VH

<400> SEQUENCE: 123

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
            20                  25                  30

Asn Ile His Trp Val Arg Gln Ala Pro Gly Gln Gly Leu Glu Trp Met
        35                  40                  45

Gly Ser Phe Asp Pro Tyr Asp Gly Gly Ser Ser Tyr Asn Gln Lys Phe
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser
        115
```

<210> SEQ ID NO 124
<211> LENGTH: 116
<212> TYPE: PRT
<213> ORGANISM: Artificial Sequence
<220> FEATURE:
<223> OTHER INFORMATION: Synthetic
<220> FEATURE:
<223> OTHER INFORMATION: 99961 humanized VH

<400> SEQUENCE: 124

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
            20                  25                  30

Asn Ile His Trp Ile Arg Gln Pro Pro Gly Lys Gly Leu Glu Trp Ile
        35                  40                  45

Gly Ser Phe Asp Pro Tyr Asp Gly Gly Ser Ser Tyr Asn Gln Lys Phe
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser
        115
```

```
<210> SEQ ID NO 125
<211> LENGTH: 116
<212> TYPE: PRT
<213> ORGANISM: Artificial Sequence
<220> FEATURE:
<223> OTHER INFORMATION: Synthetic
<220> FEATURE:
<223> OTHER INFORMATION: 99961 humanized VH

<400> SEQUENCE: 125

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
            20                  25                  30

Asn Ile His Trp Ile Arg Gln Pro Pro Gly Lys Gly Leu Glu Trp Ile
        35                  40                  45

Gly Ser Phe Asp Pro Tyr Asp Gly Gly Ser Ser Tyr Asn Gln Lys Phe
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser
        115


<210> SEQ ID NO 126
<211> LENGTH: 107
<212> TYPE: PRT
<213> ORGANISM: Artificial Sequence
<220> FEATURE:
<223> OTHER INFORMATION: Synthetic
<220> FEATURE:
<223> OTHER INFORMATION: 99961 humanized VL

<400> SEQUENCE: 126

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Ser Ile Ser Lys Tyr
            20                  25                  30

Leu Ala Trp Tyr Gln Gln Lys Pro Gly Gln Ala Pro Arg Leu Leu Ile
        35                  40                  45

Tyr Ser Gly Ser Thr Leu Gln Ser Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys
            100                 105


<210> SEQ ID NO 127
<211> LENGTH: 107
<212> TYPE: PRT
<213> ORGANISM: Artificial Sequence
<220> FEATURE:
<223> OTHER INFORMATION: Synthetic

<400> SEQUENCE: 127
```

Asp Val Val Met Thr Gln Ser Pro Leu Ser Leu Pro Val Thr Leu Gly
1 5 10 15

Gln Pro Ala Ser Ile Ser Cys Arg Ala Ser Lys Ser Ile Ser Lys Tyr
20 25 30

Leu Ala Trp Tyr Gln Gln Lys Pro Gly Lys Ala Pro Lys Leu Leu Ile
35 40 45

Tyr Ser Gly Ser Thr Leu Gln Ser Gly Ile Pro Pro Arg Phe Ser Gly
50 55 60

Ser Gly Tyr Gly Thr Asp Phe Thr Leu Thr Ile Asn Asn Ile Glu Ser
65 70 75 80

Glu Asp Ala Ala Tyr Tyr Phe Cys Gln Gln His Asp Glu Ser Pro Tyr
85 90 95

Thr Phe Gly Glu Gly Thr Lys Val Glu Ile Lys
100 105

<210> SEQ ID NO 128
<211> LENGTH: 107
<212> TYPE: PRT
<213> ORGANISM: Artificial Sequence
<220> FEATURE:
<223> OTHER INFORMATION: Synthetic
<220> FEATURE:
<223> OTHER INFORMATION: 99961 humanized VL

<400> SEQUENCE: 128

Asp Ile Val Met Thr Gln Thr Pro Leu Ser Leu Pro Val Thr Pro Gly
1 5 10 15

Glu Pro Ala Ser Ile Ser Cys Arg Ala Ser Lys Ser Ile Ser Lys Tyr
20 25 30

Leu Ala Trp Tyr Gln Gln Lys Pro Gly Gln Ala Pro Arg Leu Leu Ile
35 40 45

Tyr Ser Gly Ser Thr Leu Gln Ser Gly Ile Pro Pro Arg Phe Ser Gly
50 55 60

Ser Gly Tyr Gly Thr Asp Phe Thr Leu Thr Ile Asn Asn Ile Glu Ser
65 70 75 80

Glu Asp Ala Ala Tyr Tyr Phe Cys Gln Gln His Asp Glu Ser Pro Tyr
85 90 95

Thr Phe Gly Glu Gly Thr Lys Val Glu Ile Lys
100 105

<210> SEQ ID NO 129
<211> LENGTH: 107
<212> TYPE: PRT
<213> ORGANISM: Artificial Sequence
<220> FEATURE:
<223> OTHER INFORMATION: Synthetic
<220> FEATURE:
<223> OTHER INFORMATION: 99961 humanized VL

<400> SEQUENCE: 129

Asp Val Val Met Thr Gln Ser Pro Leu Ser Leu Pro Val Thr Leu Gly
1 5 10 15

Gln Pro Ala Ser Ile Ser Cys Arg Ala Ser Lys Ser Ile Ser Lys Tyr
20 25 30

Leu Ala Trp Tyr Gln Gln Lys Pro Gly Lys Ala Pro Lys Leu Leu Ile
35 40 45

Tyr Ser Gly Ser Thr Leu Gln Ser Gly Ile Pro Pro Arg Phe Ser Gly
50 55 60

Ser Gly Tyr Gly Thr Asp Phe Thr Leu Thr Ile Asn Asn Ile Glu Ser
65 70 75 80

Glu Asp Ala Ala Tyr Tyr Phe Cys Gln Gln His Asp Glu Ser Pro Tyr
85 90 95

Thr Phe Gly Glu Gly Thr Lys Val Glu Ile Lys
100 105

<210> SEQ ID NO 130
<211> LENGTH: 15
<212> TYPE: PRT
<213> ORGANISM: Artificial Sequence
<220> FEATURE:
<223> OTHER INFORMATION: Synthetic
<220> FEATURE:
<223> OTHER INFORMATION: 99961 humanized CDR-H1

<400> SEQUENCE: 130

Ser Gly Tyr Ala Phe Thr Ala Tyr Asn Ile His Trp Val Arg Gln
1 5 10 15

<210> SEQ ID NO 131
<211> LENGTH: 18
<212> TYPE: PRT
<213> ORGANISM: Artificial Sequence
<220> FEATURE:
<223> OTHER INFORMATION: Synthetic
<220> FEATURE:
<223> OTHER INFORMATION: 99961 humanized CDR-H2

<400> SEQUENCE: 131

Gly Ser Phe Asp Pro Tyr Asp Gly Gly Ser Ser Tyr Asn Gln Lys Phe
1 5 10 15

Lys Asp

<210> SEQ ID NO 132
<211> LENGTH: 23
<212> TYPE: PRT
<213> ORGANISM: Artificial Sequence
<220> FEATURE:
<223> OTHER INFORMATION: Synthetic
<220> FEATURE:
<223> OTHER INFORMATION: 99961 humanized CDR-H3

<400> SEQUENCE: 132

Tyr Tyr Cys Ala Arg Gly Trp Tyr Tyr Phe Asp Tyr Trp Gly His Gly
1 5 10 15

Thr Leu Val Thr Val Ser Ser
20

<210> SEQ ID NO 133
<211> LENGTH: 8
<212> TYPE: PRT
<213> ORGANISM: Artificial Sequence
<220> FEATURE:
<223> OTHER INFORMATION: Synthetic
<220> FEATURE:
<223> OTHER INFORMATION: 99961 humanized CDR-H1

<400> SEQUENCE: 133

Gly Tyr Ala Phe Thr Ala Tyr Asn
1 5

<210> SEQ ID NO 134
<211> LENGTH: 8
<212> TYPE: PRT
<213> ORGANISM: Artificial Sequence
<220> FEATURE:
<223> OTHER INFORMATION: Synthetic
<220> FEATURE:
<223> OTHER INFORMATION: 99961 humanized CDR-H2

<400> SEQUENCE: 134

Phe Asp Pro Tyr Asp Gly Gly Ser
1               5

<210> SEQ ID NO 135
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: 99961 humanized CDR-H3

<400> SEQUENCE: 135

Gly Trp Tyr Tyr Phe Asp Tyr
1               5

<210> SEQ ID NO 136
<211> LENGTH: 14
<212> TYPE: PRT
<213> ORGANISM: Artificial Sequence
<220> FEATURE:
<223> OTHER INFORMATION: Synthetic
<220> FEATURE:
<223> OTHER INFORMATION: 99961 humanized CDR-L1

<400> SEQUENCE: 136

Cys Arg Ala Ser Lys Ser Ile Ser Lys Tyr Leu Ala Trp Tyr
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Synthetic
<220> FEATURE:
<223> OTHER INFORMATION: 99961 humanized CDR-L2

<400> SEQUENCE: 137

Leu Leu Ile Tyr Ser Gly Ser Thr Leu Gln Ser Gly
1               5                   10

<210> SEQ ID NO 138
<211> LENGTH: 16
<212> TYPE: PRT
<213> ORGANISM: Artificial Sequence
<220> FEATURE:
<223> OTHER INFORMATION: Synthetic
<220> FEATURE:
<223> OTHER INFORMATION: 99961 humanized CDR-L3

<400> SEQUENCE: 138

Cys Gln Gln His Asp Glu Ser Pro Tyr Thr Phe Gly Glu Gly Thr Lys
1               5                   10                  15

<210> SEQ ID NO 139
<211> LENGTH: 6
<212> TYPE: PRT
<213> ORGANISM: Artificial Sequence
<220> FEATURE:
<223> OTHER INFORMATION: Synthetic
<220> FEATURE:
<223> OTHER INFORMATION: 99961 humanized CDR-L1

<400> SEQUENCE: 139

Lys Ser Ile Ser Lys Tyr
1 5

<210> SEQ ID NO 140
<211> LENGTH: 3
<212> TYPE: PRT
<213> ORGANISM: Artificial Sequence
<220> FEATURE:
<223> OTHER INFORMATION: Synthetic
<220> FEATURE:
<223> OTHER INFORMATION: 99961 humanized CDR-L2

<400> SEQUENCE: 140

Ser Gly Ser
1

<210> SEQ ID NO 141
<211> LENGTH: 8
<212> TYPE: PRT
<213> ORGANISM: Artificial Sequence
<220> FEATURE:
<223> OTHER INFORMATION: Synthetic
<220> FEATURE:
<223> OTHER INFORMATION: 99961 humanized CDR-L3

<400> SEQUENCE: 141

Gln Gln His Asp Glu Ser Pro Tyr
1 5

<210> SEQ ID NO 142
<211> LENGTH: 119
<212> TYPE: PRT
<213> ORGANISM: Artificial Sequence
<220> FEATURE:
<223> OTHER INFORMATION: Synthetic
<220> FEATURE:
<223> OTHER INFORMATION: Hinge-CH3 spacer

<400> SEQUENCE: 142

Glu Ser Lys Tyr Gly Pro Pro Cys Pro Pro Cys Pro Gly Gln Pro Arg
1 5 10 15

Glu Pro Gln Val Tyr Thr Leu Pro Pro Ser Gln Glu Glu Met Thr Lys
20 25 30

Asn Gln Val Ser Leu Thr Cys Leu Val Lys Gly Phe Tyr Pro Ser Asp
35 40 45

Ile Ala Val Glu Trp Glu Ser Asn Gly Gln Pro Glu Asn Asn Tyr Lys
50 55 60

Thr Thr Pro Pro Val Leu Asp Ser Asp Gly Ser Phe Phe Leu Tyr Ser
65 70 75 80

Arg Leu Thr Val Asp Lys Ser Arg Trp Gln Glu Gly Asn Val Phe Ser
85 90 95

Cys Ser Val Met His Glu Ala Leu His Asn His Tyr Thr Gln Lys Ser
100 105 110

Leu Ser Leu Ser Leu Gly Lys
115

<210> SEQ ID NO 143
<211> LENGTH: 229
<212> TYPE: PRT
<213> ORGANISM: Artificial Sequence
<220> FEATURE:
<223> OTHER INFORMATION: Synthetic
<220> FEATURE:
<223> OTHER INFORMATION: Hinge-CH2-CH3 spacer

<400> SEQUENCE: 143

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 144
<211> LENGTH: 282
<212> TYPE: PRT
<213> ORGANISM: Homo sapiens
<220> FEATURE:
<223> OTHER INFORMATION: IgD-hinge-Fc

<400> SEQUENCE: 144

```
Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
```

100 105 110

Pro Thr Gly Gly Val Glu Glu Gly Leu Leu Glu Arg His Ser Asn Gly
115 120 125

Ser Gln Ser Gln His Ser Arg Leu Thr Leu Pro Arg Ser Leu Trp Asn
130 135 140

Ala Gly Thr Ser Val Thr Cys Thr Leu Asn His Pro Ser Leu Pro Pro
145 150 155 160

Gln Arg Leu Met Ala Leu Arg Glu Pro Ala Ala Gln Ala Pro Val Lys
165 170 175

Leu Ser Leu Asn Leu Leu Ala Ser Ser Asp Pro Pro Glu Ala Ala Ser
180 185 190

Trp Leu Leu Cys Glu Val Ser Gly Phe Ser Pro Pro Asn Ile Leu Leu
195 200 205

Met Trp Leu Glu Asp Gln Arg Glu Val Asn Thr Ser Gly Phe Ala Pro
210 215 220

Ala Arg Pro Pro Pro Gln Pro Gly Ser Thr Thr Phe Trp Ala Trp Ser
225 230 235 240

Val Leu Arg Val Pro Ala Pro Pro Ser Pro Gln Pro Ala Thr Tyr Thr
245 250 255

Cys Val Val Ser His Glu Asp Ser Arg Thr Leu Leu Asn Ala Ser Arg
260 265 270

Ser Leu Glu Val Ser Tyr Val Thr Asp His
275 280

<210> SEQ ID NO 145
<211> LENGTH: 27
<212> TYPE: PRT
<213> ORGANISM: Homo sapiens
<220> FEATURE:
<223> OTHER INFORMATION: CD28, Accession No. P10747

<400> SEQUENCE: 145

Phe Trp Val Leu Val Val Val Gly Gly Val Leu Ala Cys Tyr Ser Leu
1 5 10 15

Leu Val Thr Val Ala Phe Ile Ile Phe Trp Val
20 25

<210> SEQ ID NO 146
<211> LENGTH: 66
<212> TYPE: PRT
<213> ORGANISM: Homo sapiens
<220> FEATURE:
<223> OTHER INFORMATION: CD28, Accession No. P10747

<400> SEQUENCE: 146

Ile Glu Val Met Tyr Pro Pro Pro Tyr Leu Asp Asn Glu Lys Ser Asn
1 5 10 15

Gly Thr Ile Ile His Val Lys Gly Lys His Leu Cys Pro Ser Pro Leu
20 25 30

Phe Pro Gly Pro Ser Lys Pro Phe Trp Val Leu Val Val Val Gly Gly
35 40 45

Val Leu Ala Cys Tyr Ser Leu Leu Val Thr Val Ala Phe Ile Ile Phe
50 55 60

Trp Val
65

<210> SEQ ID NO 147
<211> LENGTH: 41

<212> TYPE: PRT
<213> ORGANISM: Homo sapiens
<220> FEATURE:
<223> OTHER INFORMATION: CD28, Accession No. P10747

<400> SEQUENCE: 147

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 148
<211> LENGTH: 41
<212> TYPE: PRT
<213> ORGANISM: Homo sapiens
<220> FEATURE:
<223> OTHER INFORMATION: CD28, LL to GG

<400> SEQUENCE: 148

```
Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 149
<211> LENGTH: 42
<212> TYPE: PRT
<213> ORGANISM: Homo sapiens
<220> FEATURE:
<223> OTHER INFORMATION: 4-1BB, Accession No. Q07011.1

<400> SEQUENCE: 149

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 150
<211> LENGTH: 112
<212> TYPE: PRT
<213> ORGANISM: Homo sapiens
<220> FEATURE:
<223> OTHER INFORMATION: CD3 zeta

<400> SEQUENCE: 150

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80
```

```
Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 151
<211> LENGTH: 112
<212> TYPE: PRT
<213> ORGANISM: Homo sapiens
<220> FEATURE:
<223> OTHER INFORMATION: CD3 zeta

<400> SEQUENCE: 151

```
Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 152
<211> LENGTH: 112
<212> TYPE: PRT
<213> ORGANISM: Homo sapiens
<220> FEATURE:
<223> OTHER INFORMATION: CD3 zeta

<400> SEQUENCE: 152

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 153
<211> LENGTH: 24
<212> TYPE: PRT
<213> ORGANISM: Artificial Sequence
<220> FEATURE:
<223> OTHER INFORMATION: Synthetic
<220> FEATURE:
<223> OTHER INFORMATION: T2A

<400> SEQUENCE: 153

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 154
<211> LENGTH: 357
<212> TYPE: PRT
<213> ORGANISM: Artificial Sequence
<220> FEATURE:
<223> OTHER INFORMATION: Synthetic
<220> FEATURE:
<223> OTHER INFORMATION: tEGFR

<400> SEQUENCE: 154

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

-continued

```
Gly Leu Glu Gly Cys Pro Thr Asn Gly Pro Lys Ile Pro Ser Ile Ala
                325                 330                 335

Thr Gly Met Val Gly Ala Leu Leu Leu Leu Leu Val Val Ala Leu Gly
            340                 345                 350

Ile Gly Leu Phe Met
        355


<210> SEQ ID NO 155
<211> LENGTH: 5
<212> TYPE: PRT
<213> ORGANISM: Homo sapiens
<220> FEATURE:
<223> OTHER INFORMATION: Clone 65 CDR-H1
<220> FEATURE:
<221> NAME/KEY: VARIANT
<222> LOCATION: 1
<223> OTHER INFORMATION: Xaa = any amino acid

<400> SEQUENCE: 155

Xaa Arg Leu Asp Glu
1               5


<210> SEQ ID NO 156
<211> LENGTH: 5
<212> TYPE: PRT
<213> ORGANISM: Homo sapiens
<220> FEATURE:
<223> OTHER INFORMATION: Clone V128 CDR-H1

<400> SEQUENCE: 156

Thr Phe Trp Met Ser
1               5


<210> SEQ ID NO 157
<211> LENGTH: 5
<212> TYPE: PRT
<213> ORGANISM: Homo sapiens
<220> FEATURE:
<223> OTHER INFORMATION: Clone V71 CDR-H1

<400> SEQUENCE: 157

Thr Ser Ala Met Ser
1               5


<210> SEQ ID NO 158
<211> LENGTH: 5
<212> TYPE: PRT
<213> ORGANISM: Homo sapiens
<220> FEATURE:
<223> OTHER INFORMATION: Clone V86, V278, V365 CDR-H1

<400> SEQUENCE: 158

Ser Tyr Ala Met Ser
1               5


<210> SEQ ID NO 159
<211> LENGTH: 5
<212> TYPE: PRT
<213> ORGANISM: Homo sapiens
<220> FEATURE:
<223> OTHER INFORMATION: Clone V316 CDR-H1

<400> SEQUENCE: 159

Arg Thr Trp Met Ser
1               5
```

-continued

<210> SEQ ID NO 160
<211> LENGTH: 5
<212> TYPE: PRT
<213> ORGANISM: Homo sapiens
<220> FEATURE:
<223> OTHER INFORMATION: Clone V331, V345 CDR-H1

<400> SEQUENCE: 160

Gly Tyr Tyr Trp Ser
1 5

<210> SEQ ID NO 161
<211> LENGTH: 5
<212> TYPE: PRT
<213> ORGANISM: Homo sapiens
<220> FEATURE:
<223> OTHER INFORMATION: Clone V355 CDR-H1

<400> SEQUENCE: 161

Ser Tyr Ala Ile Ser
1 5

<210> SEQ ID NO 162
<211> LENGTH: 5
<212> TYPE: PRT
<213> ORGANISM: Homo sapiens
<220> FEATURE:
<223> OTHER INFORMATION: Clone V420, V282 CDR-H1

<400> SEQUENCE: 162

Ser Tyr Trp Met Ser
1 5

<210> SEQ ID NO 163
<211> LENGTH: 5
<212> TYPE: PRT
<213> ORGANISM: Homo sapiens
<220> FEATURE:
<223> OTHER INFORMATION: Clone V336 CDR-H1

<400> SEQUENCE: 163

Ser Tyr Ala Met His
1 5

<210> SEQ ID NO 164
<211> LENGTH: 19
<212> TYPE: PRT
<213> ORGANISM: Homo sapiens
<220> FEATURE:
<223> OTHER INFORMATION: Clone 461, V68, V102, V181 CDR-H2

<400> SEQUENCE: 164

Phe Ile Arg Ser Lys Ala Tyr Gly Gly Thr Thr Glu Tyr Ala Ala Ser
1 5 10 15

Val Lys Gly

<210> SEQ ID NO 165
<211> LENGTH: 17
<212> TYPE: PRT
<213> ORGANISM: Homo sapiens
<220> FEATURE:
<223> OTHER INFORMATION: Clone V71 CDR-H2

<400> SEQUENCE: 165

Thr Ile Ser Thr Asp Gly Ala Thr Thr Trp Tyr Ala Asp Ser Val Arg
1 5 10 15

Gly

<210> SEQ ID NO 166
<211> LENGTH: 17
<212> TYPE: PRT
<213> ORGANISM: Homo sapiens
<220> FEATURE:
<223> OTHER INFORMATION: Clone V86, V278, V365 CDR-H2

<400> SEQUENCE: 166

Ala Ile Ser Gly Ser Gly Gly Ser Thr Tyr Tyr Ala Asp Ser Val Lys
1 5 10 15

Gly

<210> SEQ ID NO 167
<211> LENGTH: 17
<212> TYPE: PRT
<213> ORGANISM: Homo sapiens
<220> FEATURE:
<223> OTHER INFORMATION: Clone V316 CDR-H2

<400> SEQUENCE: 167

Ser Ile Asn Asp Asp Gly Ser Glu Lys Tyr Tyr Val Asp Ser Val Lys
1 5 10 15

Gly

<210> SEQ ID NO 168
<211> LENGTH: 16
<212> TYPE: PRT
<213> ORGANISM: Homo sapiens
<220> FEATURE:
<223> OTHER INFORMATION: Clone V331 CDR-H2

<400> SEQUENCE: 168

Lys Ile Asn His Ser Gly Ser Thr Asn Tyr Asn Pro Ser Leu Lys Ser
1 5 10 15

<210> SEQ ID NO 169
<211> LENGTH: 17
<212> TYPE: PRT
<213> ORGANISM: Homo sapiens
<220> FEATURE:
<223> OTHER INFORMATION: Clone V355 CDR-H2

<400> SEQUENCE: 169

Gly Ile Ile Pro Ile Phe Gly Thr Ala Asn Tyr Ala Gln Lys Phe Gln
1 5 10 15

Gly

<210> SEQ ID NO 170
<211> LENGTH: 17
<212> TYPE: PRT
<213> ORGANISM: Homo sapiens
<220> FEATURE:
<223> OTHER INFORMATION: Clone V282, V420 CDR-H2

<400> SEQUENCE: 170

Asn Ile Lys Gln Asp Gly Ser Glu Lys Tyr Tyr Val Asp Ser Val Lys
1 5 10 15

Gly

<210> SEQ ID NO 171
<211> LENGTH: 19
<212> TYPE: PRT

<213> ORGANISM: Homo sapiens
<220> FEATURE:
<223> OTHER INFORMATION: Clone V397 CDR-H2

<400> SEQUENCE: 171

```
Arg Ile Lys Ser Lys Thr Asp Gly Gly Thr Thr Asp Tyr Ala Ala Pro
1               5                   10                  15

Leu Lys Gly
```

<210> SEQ ID NO 172
<211> LENGTH: 16
<212> TYPE: PRT
<213> ORGANISM: Homo sapiens
<220> FEATURE:
<223> OTHER INFORMATION: Clone V345 CDR-H2

<400> SEQUENCE: 172

```
Glu Ile Asn His Ser Gly Ser Thr Asn Tyr Asn Pro Ser Leu Lys Ser
1               5                   10                  15
```

<210> SEQ ID NO 173
<211> LENGTH: 16
<212> TYPE: PRT
<213> ORGANISM: Homo sapiens
<220> FEATURE:
<223> OTHER INFORMATION: Clone V336 CDR-H2
<220> FEATURE:
<221> NAME/KEY: VARIANT
<222> LOCATION: 15
<223> OTHER INFORMATION: Xaa = any amino acid

<400> SEQUENCE: 173

```
Val Ile Ser Tyr Asp Gly Ser Thr Asn Tyr Asn Pro Ser Leu Xaa Ser
1               5                   10                  15
```

<210> SEQ ID NO 174
<211> LENGTH: 14
<212> TYPE: PRT
<213> ORGANISM: Homo sapiens
<220> FEATURE:
<223> OTHER INFORMATION: Clone V336 CDR-H3
<220> FEATURE:
<221> NAME/KEY: VARIANT
<222> LOCATION: 7
<223> OTHER INFORMATION: Xaa = any amino acid

<400> SEQUENCE: 174

```
Val Tyr Gly Tyr Asp Tyr Xaa Asp Phe Gly Trp Phe Asp Pro
1               5                   10
```

<210> SEQ ID NO 175
<211> LENGTH: 122
<212> TYPE: PRT
<213> ORGANISM: Homo sapiens
<220> FEATURE:
<223> OTHER INFORMATION: Clone 7 VH

<400> SEQUENCE: 175

```
Gln Ile Thr Leu Lys Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Arg Ser Lys Thr Asp Gly Gly Thr Thr Asp Tyr Ala Ala
    50                  55                  60
```

```
Leu Val Lys Gly Arg Phe Thr Ile Ser Arg Asp Asp Ser Glu Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Gly Arg Trp Ser Tyr Tyr Phe Asp Tyr Trp
            100                 105                 110

Ser Gln Gly Thr Leu Val Thr Val Ser Ser
        115                 120


<210> SEQ ID NO 176
<211> LENGTH: 122
<212> TYPE: PRT
<213> ORGANISM: Homo sapiens
<220> FEATURE:
<223> OTHER INFORMATION: Clone 81 VH

<400> SEQUENCE: 176

Gln Ile Thr Leu Lys Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Gly Arg Trp Ser Tyr Tyr Phe Asp Tyr Trp
            100                 105                 110

Ser Gln Gly Thr Leu Val Thr Val Ser Ser
        115                 120


<210> SEQ ID NO 177
<211> LENGTH: 122
<212> TYPE: PRT
<213> ORGANISM: Homo sapiens
<220> FEATURE:
<223> OTHER INFORMATION: Clone 16 VH
<220> FEATURE:
<221> NAME/KEY: VARIANT
<222> LOCATION: 4, 11
<223> OTHER INFORMATION: Xaa = any amino acid

<400> SEQUENCE: 177

Arg Ser Pro Xaa Arg Ser Leu Gly Glu Ala Xaa Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Gly Ser Ala Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95
```

Tyr Cys Ala Arg Asp Phe Gly Arg Trp Ser Tyr Tyr Phe Asp Tyr Trp
            100                 105                 110

Ser Gln Gly Thr Leu Val Thr Val Ser Ser
        115                 120

<210> SEQ ID NO 178
<211> LENGTH: 122
<212> TYPE: PRT
<213> ORGANISM: Homo sapiens
<220> FEATURE:
<223> OTHER INFORMATION: Clone 65 VH
<220> FEATURE:
<221> NAME/KEY: VARIANT
<222> LOCATION: 31
<223> OTHER INFORMATION: Xaa = any amino acid

<400> SEQUENCE: 178

Gln Val Thr Leu Lys Glu Ser Gly Gly Gly Leu Val Lys Pro Gly Gly
1               5                   10                  15

Ser Leu Arg Leu Ser Cys Ala Ala Ser Gly Phe Thr Phe Gln Xaa Arg
            20                  25                  30

Leu Asp Glu Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Gly Arg Trp Ser Tyr Tyr Phe Asp Tyr Trp
            100                 105                 110

Ser Gln Gly Thr Leu Val Thr Val Ser Ser
        115                 120

<210> SEQ ID NO 179
<211> LENGTH: 122
<212> TYPE: PRT
<213> ORGANISM: Homo sapiens
<220> FEATURE:
<223> OTHER INFORMATION: Clone V18 VH

<400> SEQUENCE: 179

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Gly Arg Trp Ser Tyr Tyr Phe Asp Tyr Trp
            100                 105                 110

Gly Gln Gly Thr Leu Val Thr Val Ser Ser
        115                 120

<210> SEQ ID NO 180
<211> LENGTH: 122
<212> TYPE: PRT
<213> ORGANISM: Homo sapiens
<220> FEATURE:
<223> OTHER INFORMATION: Clone 40 VH

<400> SEQUENCE: 180

```
Gln Val Thr Leu Lys Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Arg Thr Glu Asp Thr Ala Val Tyr
                85                  90                  95

Tyr Cys Ala Arg Asp Phe Gly Arg Trp Ser Tyr Tyr Phe Asp Tyr Trp
            100                 105                 110

Ser Gln Gly Thr Leu Val Thr Val Ser Ser
        115                 120
```

<210> SEQ ID NO 181
<211> LENGTH: 122
<212> TYPE: PRT
<213> ORGANISM: Homo sapiens
<220> FEATURE:
<223> OTHER INFORMATION: Clone 40 VH

<400> SEQUENCE: 181

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Arg Thr Glu Asp Thr Ala Val Tyr
                85                  90                  95

Tyr Cys Ala Arg Asp Phe Gly Arg Trp Ser Tyr Tyr Phe Asp Tyr Trp
            100                 105                 110

Ser Gln Gly Thr Leu Val Thr Val Ser Ser
        115                 120
```

<210> SEQ ID NO 182
<211> LENGTH: 119
<212> TYPE: PRT
<213> ORGANISM: Homo sapiens
<220> FEATURE:
<223> OTHER INFORMATION: Clone 350, 305, 366 VH

<400> SEQUENCE: 182

```
Glu Val Gln Leu Val Glu Ser Gly Gly Gly Leu Val Gln Pro Gly Arg
1               5                   10                  15
```

Ser Leu Arg Leu Ser Cys Thr Ala Ser Gly Phe Thr Phe Gly Asp Tyr
20 25 30

Ala Met Ser Trp Val Arg Gln Ala Pro Gly Lys Gly Leu Glu Trp Val
35 40 45

Ser Ser Ile Ser Gly Ser Gly Arg Ser Thr Asp His Ala Asp Tyr Val
50 55 60

Lys Gly Arg Phe Thr Ile Ser Arg Asp Asn Ser Lys Asn Thr Val Tyr
65 70 75 80

Leu Gln Met Asn Arg Leu Arg Ala Glu Asp Thr Ala Val Tyr Tyr Cys
85 90 95

Ala Lys Val Ser Asn Tyr Glu Tyr Tyr Phe Asp Tyr Trp Ala Gln Gly
100 105 110

Thr Leu Val Thr Val Ser Ser
115

<210> SEQ ID NO 183
<211> LENGTH: 122
<212> TYPE: PRT
<213> ORGANISM: Homo sapiens
<220> FEATURE:
<223> OTHER INFORMATION: Clone 20, 43 VH

<400> SEQUENCE: 183

Gln Val Thr Leu Lys Glu Ser Gly Gly Gly Leu Val Lys Pro Gly Gly
1 5 10 15

Ser Leu Arg Leu Ser Cys Ala Ala Ser Gly Phe Thr Phe Ser Asn Ala
20 25 30

Trp Met Ser Trp Val Arg Gln Ala Pro Gly Lys Gly Leu Glu Trp Val
35 40 45

Gly Arg Ile Lys Ser Lys Thr Asp Gly Gly Thr Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu Lys Thr Glu Asp Thr Ala Val Tyr
85 90 95

Tyr Cys Ala Arg Asp Phe Gly Arg Trp Ser Tyr Tyr Phe Asp Tyr Trp
100 105 110

Ser Gln Gly Thr Leu Val Thr Val Ser Ser
115 120

<210> SEQ ID NO 184
<211> LENGTH: 122
<212> TYPE: PRT
<213> ORGANISM: Homo sapiens
<220> FEATURE:
<223> OTHER INFORMATION: Clone 20, 43 VH

<400> SEQUENCE: 184

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asn Ala
20 25 30

Trp Met Ser Trp Val Arg Gln Ala Pro Gly Lys Gly Leu Glu Trp Val
35 40 45

Gly Arg Ile Lys Ser Lys Thr Asp Gly Gly Thr Thr Asp Tyr Ala Ala
50 55 60

Pro Val Lys Gly Arg Phe Thr Ile Ser Arg Asp Asp Ser Lys Asn Thr

```
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Gly Arg Trp Ser Tyr Tyr Phe Asp Tyr Trp
            100                 105                 110

Ser Gln Gly Thr Leu Val Thr Val Ser Ser
        115                 120
```

<210> SEQ ID NO 185
<211> LENGTH: 125
<212> TYPE: PRT
<213> ORGANISM: Homo sapiens
<220> FEATURE:
<223> OTHER INFORMATION: Clone 461 VH

<400> SEQUENCE: 185

```
Gln Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Lys Asp Phe Glu Val Arg Glu Ala His Leu Ser Tyr Phe
            100                 105                 110

Asp Tyr Trp Gly Gln Gly Thr Leu Val Thr Val Ser Ser
        115                 120                 125
```

<210> SEQ ID NO 186
<211> LENGTH: 125
<212> TYPE: PRT
<213> ORGANISM: Homo sapiens
<220> FEATURE:
<223> OTHER INFORMATION: Clone 461 VH

<400> SEQUENCE: 186

```
Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Lys Asp Phe Glu Val Arg Glu Ala His Leu Ser Tyr Phe
            100                 105                 110

Asp Tyr Trp Gly Gln Gly Thr Leu Val Thr Val Ser Ser
        115                 120                 125
```

<210> SEQ ID NO 187
<211> LENGTH: 125
<212> TYPE: PRT
<213> ORGANISM: Homo sapiens
<220> FEATURE:
<223> OTHER INFORMATION: Clone V9 VH

<400> SEQUENCE: 187

Gln Val Thr Leu Lys Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Glu Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Lys Thr
65                  70                  75                  80

Leu Tyr Leu Gln Met Asn Ser Leu Lys Thr Glu Asp Thr Ala Val Tyr
                85                  90                  95

Tyr Cys Ala Arg Gly Ser Asn Glu Arg Phe Leu Glu Trp Leu Asn Phe
            100                 105                 110

Asp Tyr Trp Gly Gln Gly Thr Leu Val Thr Val Ser Ser
        115                 120                 125

<210> SEQ ID NO 188
<211> LENGTH: 122
<212> TYPE: PRT
<213> ORGANISM: Homo sapiens
<220> FEATURE:
<223> OTHER INFORMATION: Clone V128 VH

<400> SEQUENCE: 188

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Phe
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Gly Arg Trp Ser Tyr Tyr Phe Asp Tyr Trp
            100                 105                 110

Ser Gln Gly Thr Leu Val Thr Val Ser Ser
        115                 120

<210> SEQ ID NO 189
<211> LENGTH: 125
<212> TYPE: PRT
<213> ORGANISM: Homo sapiens
<220> FEATURE:
<223> OTHER INFORMATION: Clone V68 VH

<400> SEQUENCE: 189

Gln Ile Thr Leu Lys Glu Ser Gly Gly Gly Leu Val Lys Pro Gly Arg 1 5 10 15

Ser Leu Arg Leu Ser Cys Thr Ala Ser Gly Phe Thr Phe Gly Asp Tyr
20 25 30

Ala Met Ser Trp Phe Arg Gln Ala Pro Gly Lys Gly Leu Glu Trp Val
35 40 45

Gly Phe Ile Arg Ser Lys Ala Tyr Gly Gly Thr Thr Glu Tyr Ala Ala
50 55 60

Ser Val Lys Gly Arg Phe Thr Ile Ser Arg Asp Asp Ser Lys Ser Ile
65 70 75 80

Ala Tyr Leu Gln Met Asn Ser Leu Lys Thr Glu Asp Thr Ala Val Tyr
85 90 95

Tyr Cys Ala Lys Asp Phe Glu Val Arg Gly Ala His Leu Ser Tyr Phe
100 105 110

Asp Tyr Trp Gly Gln Gly Thr Leu Val Thr Val Ser Ser
115 120 125

<210> SEQ ID NO 190
<211> LENGTH: 123
<212> TYPE: PRT
<213> ORGANISM: Homo sapiens
<220> FEATURE:
<223> OTHER INFORMATION: Clone V71 VH

<400> SEQUENCE: 190

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Thr Ser
20 25 30

Ala Met Ser Trp Val Arg Gln Ala Pro Gly Lys Gly Leu Glu Trp Val
35 40 45

Ser Thr Ile Ser Thr Asp Gly Ala Thr Thr Trp Tyr Ala Asp Ser Val
50 55 60

Arg Gly Arg Phe Ser Val Ser Arg Asp Asn Ser Lys Asn Thr Leu Tyr
65 70 75 80

Leu Gln Met Thr Gly Leu Arg Ala Glu Asp Thr Ala Val Tyr Tyr Cys
85 90 95

Ala Arg Val Leu Arg Ser Gly Phe Leu Glu Trp Asn Leu Phe Asp Tyr
100 105 110

Trp Gly Gln Gly Thr Leu Val Thr Val Ser Ser
115 120

<210> SEQ ID NO 191
<211> LENGTH: 120
<212> TYPE: PRT
<213> ORGANISM: Homo sapiens
<220> FEATURE:
<223> OTHER INFORMATION: Clone V86 VH

<400> SEQUENCE: 191

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ile Phe Gly Val Val Asn Ile Pro Asp Tyr Trp Gly Gln
            100                 105                 110

Gly Thr Leu Val Thr Val Ser Ser
        115                 120


<210> SEQ ID NO 192
<211> LENGTH: 125
<212> TYPE: PRT
<213> ORGANISM: Homo sapiens
<220> FEATURE:
<223> OTHER INFORMATION: Clone V224 VH

<400> SEQUENCE: 192

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ile Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Thr Tyr Ser Ser Ser Trp Tyr Glu Ser Leu Leu Phe
            100                 105                 110

Asp Tyr Trp Gly Gln Gly Thr Leu Val Thr Val Ser Ser
        115                 120                 125


<210> SEQ ID NO 193
<211> LENGTH: 127
<212> TYPE: PRT
<213> ORGANISM: Homo sapiens
<220> FEATURE:
<223> OTHER INFORMATION: Clone V163 VH

<400> SEQUENCE: 193

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Gln Gly Asp Ser Ser Ser Trp Tyr Val Glu Val Tyr
            100                 105                 110

Tyr Phe Asp Tyr Trp Gly Gln Gly Thr Leu Val Thr Val Ser Ser
        115                 120                 125
```

<210> SEQ ID NO 194
<211> LENGTH: 126
<212> TYPE: PRT
<213> ORGANISM: Homo sapiens
<220> FEATURE:
<223> OTHER INFORMATION: Clone V95 VH

<400> SEQUENCE: 194

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asn Ala
20 25 30

Trp Met Ser Trp Val Arg Gln Ala Pro Gly Lys Gly Leu Glu Trp Val
35 40 45

Gly Arg Ile Lys Ser Lys Thr Asp Gly Gly Thr Thr Asp Tyr Ala Ala
50 55 60

Pro Val Lys Gly Arg Phe Thr Ile Ser Arg Asp Asp Ser Lys Lys Thr
65 70 75 80

Leu Tyr Leu Gln Met Asn Ser Leu Lys Thr Glu Asp Thr Ala Val Tyr
85 90 95

Tyr Cys Ala Arg Gly Ser Gly Glu Leu Arg Phe Leu Glu Ser Tyr Tyr
100 105 110

Phe Asp Tyr Trp Gly Gln Gly Thr Leu Val Thr Val Ser Ser
115 120 125

<210> SEQ ID NO 195
<211> LENGTH: 122
<212> TYPE: PRT
<213> ORGANISM: Homo sapiens
<220> FEATURE:
<223> OTHER INFORMATION: Clone V102 VH

<400> SEQUENCE: 195

Gln Val Gln Leu Val Glu Ser Gly Gly Gly Leu Val Gln Pro Gly Arg
1 5 10 15

Ser Leu Arg Leu Ser Cys Thr Ala Ser Gly Phe Thr Phe Gly Asp Tyr
20 25 30

Ala Met Ser Trp Val Arg Gln Ala Pro Gly Lys Gly Leu Glu Trp Val
35 40 45

Gly Phe Ile Arg Ser Lys Ala Tyr Gly Gly Thr Thr Glu Tyr Ala Ala
50 55 60

Ser Val Lys Gly Arg Phe Thr Ile Ser Arg Asp Asp Ser Gln Ser Ile
65 70 75 80

Ala Tyr Leu Gln Met Asp Ser Leu Lys Thr Glu Asp Thr Ala Val Tyr
85 90 95

Tyr Cys Ala Lys Val Gly Pro Ser Trp Asp Tyr Tyr Phe Asp Tyr Trp
100 105 110

Gly Gln Gly Thr Leu Val Thr Val Ser Ser
115 120

<210> SEQ ID NO 196
<211> LENGTH: 125
<212> TYPE: PRT
<213> ORGANISM: Homo sapiens
<220> FEATURE:
<223> OTHER INFORMATION: Clone V181 VH

<400> SEQUENCE: 196

```
Gln Ile Thr Leu Lys Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Lys Asp Phe Glu Val Arg Glu Ala His Leu Ser Tyr Phe
            100                 105                 110

Asp Tyr Trp Gly Gln Gly Thr Leu Val Thr Val Ser Ser
        115                 120                 125
```

<210> SEQ ID NO 197
<211> LENGTH: 125
<212> TYPE: PRT
<213> ORGANISM: Homo sapiens
<220> FEATURE:
<223> OTHER INFORMATION: Clone V312 VH

<400> SEQUENCE: 197

```
Glu Val Gln Leu Val Glu Ser Gly Gly Gly Leu Val Lys Pro Arg Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Thr Ser Arg Gly Arg Phe Leu Glu Trp Leu Leu Phe
            100                 105                 110

Asp Tyr Trp Gly Gln Gly Thr Leu Val Thr Val Ser Ser
        115                 120                 125
```

<210> SEQ ID NO 198
<211> LENGTH: 123
<212> TYPE: PRT
<213> ORGANISM: Homo sapiens
<220> FEATURE:
<223> OTHER INFORMATION: Clone V316 VH

<400> SEQUENCE: 198

```
Glu Val Gln Leu Val Glu Ser Gly Gly Gly Leu Val Arg Pro Gly Gly
1               5                   10                  15

Ser Leu Arg Leu Ser Cys Ala Ala Ser Gly Leu Thr Phe Ser Arg Thr
            20                  25                  30

Trp Met Ser Trp Val Arg Gln Ala Pro Gly Lys Gly Leu Glu Trp Val
        35                  40                  45

Ala Ser Ile Asn Asp Asp Gly Ser Glu Lys Tyr Tyr Val Asp Ser Val
    50                  55                  60
```

Lys Gly Arg Phe Thr Ile Ser Arg Asp Asn Ala Arg Asn Ser Leu Tyr
65 70 75 80

Leu Gln Met Asn Arg Leu Arg Ala Glu Asp Thr Ala Val Tyr Tyr Cys
85 90 95

Ala Arg Val Asp Ser Glu Arg Phe Leu Glu Trp Tyr Tyr Phe Asp Tyr
100 105 110

Trp Gly Gln Gly Thr Leu Val Thr Val Ser Ser
115 120

<210> SEQ ID NO 199
<211> LENGTH: 121
<212> TYPE: PRT
<213> ORGANISM: Homo sapiens
<220> FEATURE:
<223> OTHER INFORMATION: Clone V331 VH

<400> SEQUENCE: 199

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

Gly Lys Ile Asn His Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Gly Gln Ile Ala Ala His Val Trp Gly Trp Phe Asp Pro Trp Gly
100 105 110

Gln Gly Thr Leu Val Thr Val Ser Ser
115 120

<210> SEQ ID NO 200
<211> LENGTH: 121
<212> TYPE: PRT
<213> ORGANISM: Homo sapiens
<220> FEATURE:
<223> OTHER INFORMATION: Clone V278 VH

<400> SEQUENCE: 200

Gln Ile Thr Leu Lys Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Glu Arg Ser Arg Trp Gly Asp Asn Trp Phe Asp Pro Trp Gly
100 105 110

Gln Gly Thr Leu Val Thr Val Ser Ser 115 120

<210> SEQ ID NO 201
<211> LENGTH: 118
<212> TYPE: PRT
<213> ORGANISM: Homo sapiens
<220> FEATURE:
<223> OTHER INFORMATION: Clone V355 VH

<400> SEQUENCE: 201

Glu Val Gln Leu Val Glu Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Ile Tyr Pro Pro Asp Ala Phe Asp Ile Trp Gly Gln Gly Thr
100 105 110

Met Val Thr Val Ser Ser
115

<210> SEQ ID NO 202
<211> LENGTH: 125
<212> TYPE: PRT
<213> ORGANISM: Homo sapiens
<220> FEATURE:
<223> OTHER INFORMATION: Clone V357 VH

<400> SEQUENCE: 202

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asn Ala
20 25 30

Trp Met Ser Trp Val Arg Gln Ala Pro Gly Lys Gly Leu Glu Trp Val
35 40 45

Gly Arg Ile Lys Ser Lys Thr Asp Gly Gly Thr Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu Lys Thr Glu Asp Thr Ala Val Tyr
85 90 95

Tyr Cys Ala Arg Asp Met Val Gly Ala Trp Leu Val Leu Ser Tyr Phe
100 105 110

Asp Tyr Trp Gly Gln Gly Thr Leu Val Thr Val Ser Ser
115 120 125

<210> SEQ ID NO 203
<211> LENGTH: 119
<212> TYPE: PRT
<213> ORGANISM: Homo sapiens
<220> FEATURE:
<223> OTHER INFORMATION: Clone V282 VH

<400> SEQUENCE: 203

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Arg Gly Ser Glu Tyr Tyr Phe Asp Tyr Trp Gly Gln Gly
            100                 105                 110

Thr Leu Val Thr Val Ser Ser
        115
```

<210> SEQ ID NO 204
<211> LENGTH: 125
<212> TYPE: PRT
<213> ORGANISM: Homo sapiens
<220> FEATURE:
<223> OTHER INFORMATION: Clone V365 VH

<400> SEQUENCE: 204

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ile Gly Tyr Ser Ser Ser Trp Tyr Glu Ile Trp Thr Phe
            100                 105                 110

Asp Tyr Trp Gly Gln Gly Thr Leu Val Thr Val Ser Ser
        115                 120                 125
```

<210> SEQ ID NO 205
<211> LENGTH: 125
<212> TYPE: PRT
<213> ORGANISM: Homo sapiens
<220> FEATURE:
<223> OTHER INFORMATION: Clone V397 VH

<400> SEQUENCE: 205

```
Gln Ile Thr Leu Lys Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
```

50 55 60

Pro Leu Lys Gly Arg Phe Thr Ile Ser Arg Asp Asp Ser Lys Asn Thr
65 70 75 80

Leu Tyr Leu Gln Met Asn Ser Leu Lys Thr Glu Asp Thr Ala Val Tyr
85 90 95

Tyr Cys Ala Arg Ala Lys Gly Leu Trp Phe Gly Glu Ser Tyr Tyr Phe
100 105 110

Asp Tyr Trp Gly Gln Gly Thr Leu Val Thr Val Ser Ser
115 120 125

<210> SEQ ID NO 206
<211> LENGTH: 119
<212> TYPE: PRT
<213> ORGANISM: Homo sapiens
<220> FEATURE:
<223> OTHER INFORMATION: Clone V420 VH

<400> SEQUENCE: 206

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Met Ser Trp Val Arg Gln Ala Pro Gly Lys Gly Leu Glu Trp Val
35 40 45

Ala Asn Ile Lys Gln Asp Gly Ser Glu Lys Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Val Asn Gly Gly Glu Tyr Tyr Phe Asp Tyr Trp Gly Gln Gly
100 105 110

Thr Leu Val Thr Val Ser Ser
115

<210> SEQ ID NO 207
<211> LENGTH: 121
<212> TYPE: PRT
<213> ORGANISM: Homo sapiens
<220> FEATURE:
<223> OTHER INFORMATION: Clone V345 VH

<400> SEQUENCE: 207

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

Gly Glu Ile Asn His Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Glu Asp Thr Ala Val Tyr Tyr Cys Ala
85 90 95

Arg Gly Pro Leu Arg Pro Gln Lys Val Leu Pro Phe Gln Ile Gly Ala
100 105 110

```
Gln Gly Thr Leu Val Thr Val Ser Ser
        115                 120


<210> SEQ ID NO 208
<211> LENGTH: 122
<212> TYPE: PRT
<213> ORGANISM: Homo sapiens
<220> FEATURE:
<223> OTHER INFORMATION: Clone V336 VH
<220> FEATURE:
<221> NAME/KEY: VARIANT
<222> LOCATION: 64
<223> OTHER INFORMATION: Xaa = any amino acid

<400> SEQUENCE: 208

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Thr Asn Tyr Asn Pro Ser Leu Xaa
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Tyr Gly Tyr Asp Tyr Arg Asp Phe Gly Trp Phe Asp Pro Trp
            100                 105                 110

Gly Gln Gly Thr Leu Val Thr Val Ser Ser
        115                 120


<210> SEQ ID NO 209
<211> LENGTH: 122
<212> TYPE: PRT
<213> ORGANISM: Homo sapiens
<220> FEATURE:
<223> OTHER INFORMATION: Clone V336 VH
<220> FEATURE:
<221> NAME/KEY: VARIANT
<222> LOCATION: 64, 104
<223> OTHER INFORMATION: Xaa = any amino acid

<400> SEQUENCE: 209

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Thr Asn Tyr Asn Pro Ser Leu Xaa
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Tyr Gly Tyr Asp Tyr Xaa Asp Phe Gly Trp Phe Asp Pro Trp
            100                 105                 110

Gly Gln Gly Thr Leu Val Thr Val Ser Ser
        115                 120
```

```
<210> SEQ ID NO 210
<211> LENGTH: 11
<212> TYPE: PRT
<213> ORGANISM: Homo sapiens
<220> FEATURE:
<223> OTHER INFORMATION: Clone 7 CDR-L1

<400> SEQUENCE: 210

Ser Gly Asp Lys Leu Gly Asp Lys Tyr Ala Cys
1               5                   10


<210> SEQ ID NO 211
<211> LENGTH: 11
<212> TYPE: PRT
<213> ORGANISM: Homo sapiens
<220> FEATURE:
<223> OTHER INFORMATION: Clone 81 CDR-L1

<400> SEQUENCE: 211

Gly Gly Asn Asn Ile Gly Thr Lys Ser Val His
1               5                   10


<210> SEQ ID NO 212
<211> LENGTH: 11
<212> TYPE: PRT
<213> ORGANISM: Homo sapiens
<220> FEATURE:
<223> OTHER INFORMATION: Clone 16 CDR-L1

<400> SEQUENCE: 212

Arg Ala Ser Gln Gly Ile Ser Ser Tyr Leu Ala
1               5                   10


<210> SEQ ID NO 213
<211> LENGTH: 11
<212> TYPE: PRT
<213> ORGANISM: Homo sapiens
<220> FEATURE:
<223> OTHER INFORMATION: Clone 65 CDR-L1

<400> SEQUENCE: 213

Pro Arg Arg Gln Pro Gln Lys Thr Ile Met Gln
1               5                   10


<210> SEQ ID NO 214
<211> LENGTH: 11
<212> TYPE: PRT
<213> ORGANISM: Homo sapiens
<220> FEATURE:
<223> OTHER INFORMATION: Clone V18 CDR-L1

<400> SEQUENCE: 214

Gly Gly Asn Asn Leu Gly Ser Lys Asn Val His
1               5                   10


<210> SEQ ID NO 215
<211> LENGTH: 13
<212> TYPE: PRT
<213> ORGANISM: Homo sapiens
<220> FEATURE:
<223> OTHER INFORMATION: Clone 40 CDR-L1

<400> SEQUENCE: 215

Thr Arg Ser Ser Gly Asn Ile Ala Ser Asn Phe Val Gln
1               5                   10
```

<210> SEQ ID NO 216
<211> LENGTH: 13
<212> TYPE: PRT
<213> ORGANISM: Homo sapiens
<220> FEATURE:
<223> OTHER INFORMATION: Clone 350 CDR-L1

<400> SEQUENCE: 216

Thr Arg Ser Ser Gly Ser Ile Ala Ser Asn Tyr Val Gln
1 5 10

<210> SEQ ID NO 217
<211> LENGTH: 11
<212> TYPE: PRT
<213> ORGANISM: Homo sapiens
<220> FEATURE:
<223> OTHER INFORMATION: Clone 20 CDR-L1

<400> SEQUENCE: 217

Arg Ala Ser Gln Ser Ile Asn Lys Trp Leu Ala
1 5 10

<210> SEQ ID NO 218
<211> LENGTH: 11
<212> TYPE: PRT
<213> ORGANISM: Homo sapiens
<220> FEATURE:
<223> OTHER INFORMATION: Clone 305 CDR-L1

<400> SEQUENCE: 218

Gly Gly Asn Asn Ile Gly Ser Thr Ser Val His
1 5 10

<210> SEQ ID NO 219
<211> LENGTH: 13
<212> TYPE: PRT
<213> ORGANISM: Homo sapiens
<220> FEATURE:
<223> OTHER INFORMATION: Clone 366 CDR-L1

<400> SEQUENCE: 219

Ser Gly Ser Arg Phe Asn Ile Gly Ser Asn Thr Val Asn
1 5 10

<210> SEQ ID NO 220
<211> LENGTH: 11
<212> TYPE: PRT
<213> ORGANISM: Homo sapiens
<220> FEATURE:
<223> OTHER INFORMATION: Clone 461 CDR-L1

<400> SEQUENCE: 220

Gly Gly Asn Arg Ile Gly Thr Lys Ala Val His
1 5 10

<210> SEQ ID NO 221
<211> LENGTH: 7
<212> TYPE: PRT
<213> ORGANISM: Homo sapiens
<220> FEATURE:
<223> OTHER INFORMATION: Clone 7 CDR-L2

<400> SEQUENCE: 221

Gln Asp Ser Lys Arg Pro Ser
1 5

<210> SEQ ID NO 222

<211> LENGTH: 7
<212> TYPE: PRT
<213> ORGANISM: Homo sapiens
<220> FEATURE:
<223> OTHER INFORMATION: Clone 81 CDR-L2

<400> SEQUENCE: 222

Asp Glu Ser Asp Arg Pro Ser
1               5

<210> SEQ ID NO 223
<211> LENGTH: 7
<212> TYPE: PRT
<213> ORGANISM: Homo sapiens
<220> FEATURE:
<223> OTHER INFORMATION: Clone 16 CDR-L2

<400> SEQUENCE: 223

Ala Ala Ser Thr Leu Gln Ser
1               5

<210> SEQ ID NO 224
<211> LENGTH: 7
<212> TYPE: PRT
<213> ORGANISM: Homo sapiens
<220> FEATURE:
<223> OTHER INFORMATION: Clone 65 CDR-L2

<400> SEQUENCE: 224

Gly Lys Asn Asp Arg Pro Ser
1               5

<210> SEQ ID NO 225
<211> LENGTH: 7
<212> TYPE: PRT
<213> ORGANISM: Homo sapiens
<220> FEATURE:
<223> OTHER INFORMATION: Clone V18 CDR-L2

<400> SEQUENCE: 225

Asp Asp Asp Asn Arg Pro Ser
1               5

<210> SEQ ID NO 226
<211> LENGTH: 7
<212> TYPE: PRT
<213> ORGANISM: Homo sapiens
<220> FEATURE:
<223> OTHER INFORMATION: Clone 40 CDR-L2

<400> SEQUENCE: 226

Glu Asp Thr Gln Arg Pro Ser
1               5

<210> SEQ ID NO 227
<211> LENGTH: 7
<212> TYPE: PRT
<213> ORGANISM: Homo sapiens
<220> FEATURE:
<223> OTHER INFORMATION: Clone 350 CDR-L2

<400> SEQUENCE: 227

Glu Asp Asn Gln Arg Pro Ser
1               5

<210> SEQ ID NO 228
<211> LENGTH: 7

<212> TYPE: PRT
<213> ORGANISM: Homo sapiens
<220> FEATURE:
<223> OTHER INFORMATION: Clone 20 CDR-L2

<400> SEQUENCE: 228

Asp Ala Ser Thr Leu Glu Ser
1               5

<210> SEQ ID NO 229
<211> LENGTH: 7
<212> TYPE: PRT
<213> ORGANISM: Homo sapiens
<220> FEATURE:
<223> OTHER INFORMATION: Clone 305 CDR-L2

<400> SEQUENCE: 229

Asp Asp Ser Asp Arg Pro Ser
1               5

<210> SEQ ID NO 230
<211> LENGTH: 7
<212> TYPE: PRT
<213> ORGANISM: Homo sapiens
<220> FEATURE:
<223> OTHER INFORMATION: Clone 366 CDR-L2

<400> SEQUENCE: 230

Ser Asn Asn Gln Arg Pro Ser
1               5

<210> SEQ ID NO 231
<211> LENGTH: 7
<212> TYPE: PRT
<213> ORGANISM: Homo sapiens
<220> FEATURE:
<223> OTHER INFORMATION: Clone 461 CDR-L2

<400> SEQUENCE: 231

Asp Asp Thr Asp Arg Pro Ser
1               5

<210> SEQ ID NO 232
<211> LENGTH: 11
<212> TYPE: PRT
<213> ORGANISM: Homo sapiens
<220> FEATURE:
<223> OTHER INFORMATION: Clone V18 CDR-L3

<400> SEQUENCE: 232

Gln Val Trp Asp Ser Ser Ser Arg His Val Val
1               5                   10

<210> SEQ ID NO 233
<211> LENGTH: 9
<212> TYPE: PRT
<213> ORGANISM: Homo sapiens
<220> FEATURE:
<223> OTHER INFORMATION: Clone 7 CDR-L3
<220> FEATURE:
<221> NAME/KEY: VARIANT
<222> LOCATION: 1
<223> OTHER INFORMATION: Xaa = any amino acid

<400> SEQUENCE: 233

Xaa Ala Trp Asp Ser Ser Thr Val Val
1               5

<210> SEQ ID NO 234
<211> LENGTH: 106
<212> TYPE: PRT
<213> ORGANISM: Homo sapiens
<220> FEATURE:
<223> OTHER INFORMATION: Clone 7 VL
<220> FEATURE:
<221> NAME/KEY: VARIANT
<222> LOCATION: (86)...(88)
<223> OTHER INFORMATION: Xaa = any amino acid

<400> SEQUENCE: 234

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Xaa Xaa Xaa Ala Trp Asp Ser Ser Thr Val Val
                85                  90                  95

Phe Gly Gly Gly Thr Lys Leu Thr Val Leu
            100                 105
```

<210> SEQ ID NO 235
<211> LENGTH: 106
<212> TYPE: PRT
<213> ORGANISM: Homo sapiens
<220> FEATURE:
<223> OTHER INFORMATION: Clone 7 VL
<220> FEATURE:
<221> NAME/KEY: VARIANT
<222> LOCATION: (86)...(87)
<223> OTHER INFORMATION: Xaa = any amino acid

<400> SEQUENCE: 235

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Xaa Xaa Gln Ala Trp Asp Ser Ser Thr Val Val
                85                  90                  95

Phe Gly Gly Gly Thr Lys Leu Thr Val Leu
            100                 105
```

<210> SEQ ID NO 236
<211> LENGTH: 108
<212> TYPE: PRT
<213> ORGANISM: Homo sapiens
<220> FEATURE:
<223> OTHER INFORMATION: Clone 81 VL
<220> FEATURE:
<221> NAME/KEY: VARIANT
<222> LOCATION: 65, 85, 92, 93, 94, 95
<223> OTHER INFORMATION: Xaa = any amino acid

<400> SEQUENCE: 236

```
Gln Ser Val Leu Thr Gln Pro Pro Ser Val Ser Val Ala Pro Gly Gln
1               5                   10                  15

Thr Ala Arg Ile Thr Cys Gly Gly Asn Asn Ile Gly Thr Lys Ser Val
            20                  25                  30

His Trp Tyr Gln Gln Lys Pro Gly Gln Ala Pro Val Leu Val Leu Tyr
        35                  40                  45

Asp Glu Ser Asp Arg Pro Ser Gly Ile Pro Glu Arg Phe Ser Gly Ser
    50                  55                  60

Xaa Ser Gly Asn Thr Ala Thr Leu Thr Ile Ser Arg Val Glu Ala Gly
65                  70                  75                  80

Asp Glu Ala Asp Xaa Leu Leu Ser Gly Val Gly Xaa Xaa Xaa Xaa Ser
                85                  90                  95

Leu Cys Phe Gly Ser Gly Thr Lys Leu Thr Val Leu
            100                 105
```

<210> SEQ ID NO 237
<211> LENGTH: 108
<212> TYPE: PRT
<213> ORGANISM: Homo sapiens
<220> FEATURE:
<223> OTHER INFORMATION: Clone 81 VL
<220> FEATURE:
<221> NAME/KEY: VARIANT
<222> LOCATION: 65, 85
<223> OTHER INFORMATION: Xaa = any amino acid

<400> SEQUENCE: 237

```
Gln Ser Val Leu Thr Gln Pro Pro Ser Val Ser Val Ala Pro Gly Gln
1               5                   10                  15

Thr Ala Arg Ile Thr Cys Gly Gly Asn Asn Ile Gly Thr Lys Ser Val
            20                  25                  30

His Trp Tyr Gln Gln Lys Pro Gly Gln Ala Pro Val Leu Val Leu Tyr
        35                  40                  45

Asp Glu Ser Asp Arg Pro Ser Gly Ile Pro Glu Arg Phe Ser Gly Ser
    50                  55                  60

Xaa Ser Gly Asn Thr Ala Thr Leu Thr Ile Ser Arg Val Glu Ala Gly
65                  70                  75                  80

Asp Glu Ala Asp Xaa Leu Leu Gln Val Trp Asp Ser Ser Ser Asp His
                85                  90                  95

Tyr Val Phe Gly Ser Gly Thr Lys Leu Thr Val Leu
            100                 105
```

<210> SEQ ID NO 238
<211> LENGTH: 88
<212> TYPE: PRT
<213> ORGANISM: Homo sapiens
<220> FEATURE:
<223> OTHER INFORMATION: Clone 16 VL

<400> SEQUENCE: 238

```
Glu Ile Val Met Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45
```

```
Tyr Ala Ala Ser Thr Leu Gln Ser Gly Ser His Gln Gly Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys
                85
```

<210> SEQ ID NO 239
<211> LENGTH: 87
<212> TYPE: PRT
<213> ORGANISM: Homo sapiens
<220> FEATURE:
<223> OTHER INFORMATION: Clone 65 VL
<220> FEATURE:
<221> NAME/KEY: VARIANT
<222> LOCATION: 87
<223> OTHER INFORMATION: Xaa = any amino acid

<400> SEQUENCE: 239

```
Gln Ser Ala Leu Thr Gln Asp Pro Ala Val Ser Val Ala Leu Gly Thr
1               5                   10                  15

Asp Ser Gln Asp His Met Pro Arg Arg Gln Pro Gln Lys Thr Ile Met
            20                  25                  30

Gln Trp Tyr Gln Gln Lys Pro Gly Gln Ala Pro Ala Leu Val Ile Tyr
        35                  40                  45

Gly Lys Asn Asp Arg Pro Ser Gly Ile Pro Asp Arg Phe Ser Gly Ser
    50                  55                  60

Thr Ser Gly Asn Thr Ala Ser Leu Thr Ile Thr Gly Ala Gln Ala Glu
65                  70                  75                  80

Asp Glu Ala Asp Tyr Tyr Xaa
                85
```

<210> SEQ ID NO 240
<211> LENGTH: 106
<212> TYPE: PRT
<213> ORGANISM: Homo sapiens
<220> FEATURE:
<223> OTHER INFORMATION: Clone V18 VL

<400> SEQUENCE: 240

```
Val Leu Thr Gln Pro Pro Ser Val Ser Val Ala Pro Gly Lys Thr Ala
1               5                   10                  15

Arg Ile Thr Cys Gly Gly Asn Asn Leu Gly Ser Lys Asn Val His Trp
            20                  25                  30

Tyr Gln Gln Lys Pro Gly Gln Ala Pro Val Leu Val Ile Tyr Asp Asp
        35                  40                  45

Asp Asn Arg Pro Ser Gly Ile Pro Glu Arg Phe Ser Gly Ser Asn Ser
    50                  55                  60

Gly Asn Thr Ala Thr Leu Thr Ile Ser Arg Val Glu Ala Gly Asp Glu
65                  70                  75                  80

Ala Asp Tyr Tyr Cys Gln Val Trp Asp Ser Ser Ser Arg His Val Val
                85                  90                  95

Phe Gly Gly Gly Thr Lys Leu Thr Val Leu
            100                 105
```

<210> SEQ ID NO 241
<211> LENGTH: 110
<212> TYPE: PRT
<213> ORGANISM: Homo sapiens
<220> FEATURE:

<223> OTHER INFORMATION: Clone 40 VL

<400> SEQUENCE: 241

Gln Pro Val Leu Thr Gln Pro His Ser Val Ser Glu Ser Pro Gly Lys
1               5                   10                  15

Thr Val Thr Ile Ser Cys Thr Arg Ser Ser Gly Asn Ile Ala Ser Asn
            20                  25                  30

Phe Val Gln Trp Tyr Gln Arg Arg Pro Asp Gly Ala Thr Thr Asn Val
        35                  40                  45

Ile Tyr Glu Asp Thr Gln Arg Pro Ser Gly Val Ser Gly Arg Phe Ser
    50                  55                  60

Gly Ser Ile Asp Arg Ser Ser Asn Ser Ala Ser Leu Thr Ile Ser Gly
65                  70                  75                  80

Leu Arg Ala Glu Asp Glu Ala Asp Tyr Tyr Cys Gln Ser Tyr Asp Gly
                85                  90                  95

Arg Asn Leu Met Phe Gly Gly Gly Thr Lys Val Thr Val Leu
            100                 105                 110

<210> SEQ ID NO 242
<211> LENGTH: 110
<212> TYPE: PRT
<213> ORGANISM: Homo sapiens
<220> FEATURE:
<223> OTHER INFORMATION: Clone 350 VL

<400> SEQUENCE: 242

Gln Pro Val Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn His Val Phe Gly Thr Gly Thr Lys Leu Thr Val Leu
            100                 105                 110

<210> SEQ ID NO 243
<211> LENGTH: 107
<212> TYPE: PRT
<213> ORGANISM: Homo sapiens
<220> FEATURE:
<223> OTHER INFORMATION: Clone 20 VL

<400> SEQUENCE: 243

Asn Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Lys Trp
            20                  25                  30

Leu Ala Trp Tyr Gln Gln Lys Pro Gly Lys Ala Pro Lys Leu Leu Ile
        35                  40                  45

His Asp Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu His Pro 65 70 75 80

Asp Asp Ser Ala Thr Tyr Tyr Cys Gln Gln Leu Lys Ser Pro Pro Ala
85 90 95

Gln Phe Gly Glu Gly Thr Lys Leu Glu Ile Lys
100 105

<210> SEQ ID NO 244
<211> LENGTH: 107
<212> TYPE: PRT
<213> ORGANISM: Homo sapiens
<220> FEATURE:
<223> OTHER INFORMATION: Clone 20 VL

<400> SEQUENCE: 244

Asn Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Asn Lys Trp
20 25 30

Leu Ala Trp Tyr Gln Gln Lys Pro Gly Lys Ala Pro Lys Leu Leu Ile
35 40 45

His Asp Ala Ser Thr Leu Glu Ser Gly Val Pro Ser Arg Phe Ser Gly
50 55 60

Ser Gly Ser Gly Thr Glu Phe Thr Leu Thr Ile Ser Ser Leu His Pro
65 70 75 80

Asp Asp Ser Ala Thr Tyr Tyr Cys Gln Gln Leu Lys Ser Arg Pro Leu
85 90 95

Ser Phe Gly Glu Gly Thr Lys Leu Glu Ile Lys
100 105

<210> SEQ ID NO 245
<211> LENGTH: 110
<212> TYPE: PRT
<213> ORGANISM: Homo sapiens
<220> FEATURE:
<223> OTHER INFORMATION: Clone 43 VL

<400> SEQUENCE: 245

Gln Ser Val Leu Thr Gln Pro Ser Ser Val Ser Gly Thr Pro Gly Gln
1 5 10 15

Arg Val Thr Ile Ser Cys Ser Gly Ser Ser Ser Asn Ile Gly Ser Asn
20 25 30

Tyr Val Tyr Trp Tyr Gln Gln Leu Pro Gly Thr Ala Pro Lys Leu Leu
35 40 45

Ile Tyr Arg Asn Asn Gln Arg Pro Ser Gly Val Pro Asp Arg Phe Ser
50 55 60

Gly Ser Lys Ser Gly Thr Ser Ala Ser Leu Gly His Gln Trp Ala Pro
65 70 75 80

Gly Pro Arg Met Arg Leu Ile Ile Thr Ala Ala Trp Asp Asp Ser Leu
85 90 95

Ser Gly Val Val Phe Gly Gly Gly Thr Lys Leu Thr Val Leu
100 105 110

<210> SEQ ID NO 246
<211> LENGTH: 108
<212> TYPE: PRT
<213> ORGANISM: Homo sapiens
<220> FEATURE:
<223> OTHER INFORMATION: Clone 305 VL

<400> SEQUENCE: 246

```
Gln Ser Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Thr Ser Val
            20                  25                  30

His Trp Phe Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Asn Asp Ser Asp His
                85                  90                  95

Arg Val Phe Gly Gly Gly Thr Lys Leu Thr Val Leu
            100                 105


<210> SEQ ID NO 247
<211> LENGTH: 110
<212> TYPE: PRT
<213> ORGANISM: Homo sapiens
<220> FEATURE:
<223> OTHER INFORMATION: Clone 366 VL

<400> SEQUENCE: 247

Gln Ser Val Leu Thr Gln Pro Pro Ser Val Pro Gly Thr Pro Gly Gln
1               5                   10                  15

Arg Val Thr Ile Thr Cys Ser Gly Ser Arg Phe Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Leu Thr Val Leu
            100                 105                 110


<210> SEQ ID NO 248
<211> LENGTH: 107
<212> TYPE: PRT
<213> ORGANISM: Homo sapiens
<220> FEATURE:
<223> OTHER INFORMATION: Clone 461 VL
<220> FEATURE:
<221> NAME/KEY: VARIANT
<222> LOCATION: 69
<223> OTHER INFORMATION: Xaa = any amino acid

<400> SEQUENCE: 248

Gln Ser Val Leu Thr Gln Pro Pro Ser Val Ser Val Ala Pro Gly Gln
1               5                   10                  15

Thr Ala Arg Ile Thr Cys Gly Gly Asn Arg Ile Gly Thr Lys Ala Val
            20                  25                  30

His Trp Tyr Gln Gln Lys Ser Gly Gln Ala Pro Val Leu Val Val Arg
        35                  40                  45

Asp Asp Thr Asp Arg Pro Ser Gly Ser Leu Arg Asp Ser Leu Ala Pro
    50                  55                  60
```

```
Thr Leu Gly Thr Xaa Ala Thr Leu Thr Ile Ser Gly Val Glu Ala Gly
65                  70                  75                  80

Asp Glu Ala Asp Tyr Tyr Gln Val Trp Asp Ser Ser Ser Asp His Arg
                85                  90                  95

Val Phe Gly Gly Gly Thr Lys Leu Thr Val Leu
            100                 105


<210> SEQ ID NO 249
<211> LENGTH: 228
<212> TYPE: PRT
<213> ORGANISM: Homo sapiens
<220> FEATURE:
<223> OTHER INFORMATION: Clone 7 scFv
<220> FEATURE:
<221> NAME/KEY: VARIANT
<222> LOCATION: (208)...(210)
<223> OTHER INFORMATION: Xaa = any amino acid

<400> SEQUENCE: 249

Gln Ile Thr Leu Lys Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Arg Ser Lys Thr Asp Gly Gly Thr Thr Asp Tyr Ala Ala
    50                  55                  60

Leu Val Lys Gly Arg Phe Thr Ile Ser Arg Asp Asp Ser Glu Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Gly Arg Trp Ser Tyr Tyr Phe Asp Tyr Trp
            100                 105                 110

Ser Gln Gly Thr Leu Val Thr Val Ser Ser Ser Tyr Glu Leu Thr Gln
        115                 120                 125

Pro Pro Ser Val Ser Val Ser Pro Gly Gln Thr Ala Ser Ile Thr Cys
    130                 135                 140

Ser Gly Asp Lys Leu Gly Asp Lys Tyr Ala Cys Trp Tyr Gln Gln Lys
145                 150                 155                 160

Pro Gly Gln Ser Pro Val Leu Val Ile Tyr Gln Asp Ser Lys Arg Pro
                165                 170                 175

Ser Gly Ile Pro Glu Arg Phe Ser Gly Ser Asn Ser Gly Asn Thr Ala
            180                 185                 190

Thr Leu Thr Ile Ser Gly Thr Gln Ala Met Asp Glu Ala Asp Tyr Xaa
        195                 200                 205

Xaa Xaa Ala Trp Asp Ser Ser Thr Val Val Phe Gly Gly Gly Thr Lys
    210                 215                 220

Leu Thr Val Leu
225


<210> SEQ ID NO 250
<211> LENGTH: 228
<212> TYPE: PRT
<213> ORGANISM: Homo sapiens
<220> FEATURE:
<223> OTHER INFORMATION: Clone 7 scFv
<220> FEATURE:
<221> NAME/KEY: VARIANT
<222> LOCATION: (208)...(209)
<223> OTHER INFORMATION: Xaa = any amino acid
```

<400> SEQUENCE: 250

Gln Ile Thr Leu Lys Glu Ser Gly Gly Gly Leu Val Lys Pro Gly Gly
1 5 10 15

Ser Leu Arg Leu Ser Cys Ala Ala Ser Gly Phe Thr Phe Ser Asn Ala
20 25 30

Trp Met Ser Trp Val Arg Gln Ala Pro Gly Lys Gly Leu Glu Trp Val
35 40 45

Gly Arg Ile Arg Ser Lys Thr Asp Gly Gly Thr Thr Asp Tyr Ala Ala
50 55 60

Leu Val Lys Gly Arg Phe Thr Ile Ser Arg Asp Asp Ser Glu Asn Thr
65 70 75 80

Leu Tyr Leu Gln Met Asn Ser Leu Lys Thr Glu Asp Thr Ala Val Tyr
85 90 95

Tyr Cys Ala Arg Asp Phe Gly Arg Trp Ser Tyr Tyr Phe Asp Tyr Trp
100 105 110

Ser Gln Gly Thr Leu Val Thr Val Ser Ser Ser Tyr Glu Leu Thr Gln
115 120 125

Pro Pro Ser Val Ser Val Ser Pro Gly Gln Thr Ala Ser Ile Thr Cys
130 135 140

Ser Gly Asp Lys Leu Gly Asp Lys Tyr Ala Cys Trp Tyr Gln Gln Lys
145 150 155 160

Pro Gly Gln Ser Pro Val Leu Val Ile Tyr Gln Asp Ser Lys Arg Pro
165 170 175

Ser Gly Ile Pro Glu Arg Phe Ser Gly Ser Asn Ser Gly Asn Thr Ala
180 185 190

Thr Leu Thr Ile Ser Gly Thr Gln Ala Met Asp Glu Ala Asp Tyr Xaa
195 200 205

Xaa Gln Ala Trp Asp Ser Ser Thr Val Val Phe Gly Gly Gly Thr Lys
210 215 220

Leu Thr Val Leu
225

<210> SEQ ID NO 251
<211> LENGTH: 230
<212> TYPE: PRT
<213> ORGANISM: Homo sapiens
<220> FEATURE:
<223> OTHER INFORMATION: Clone 81 scFv
<220> FEATURE:
<221> NAME/KEY: VARIANT
<222> LOCATION: 187, 207, 214, 215, 216, 217
<223> OTHER INFORMATION: Xaa = any amino acid

<400> SEQUENCE: 251

Gln Ile Thr Leu Lys Glu Ser Gly Gly Gly Leu Val Lys Pro Gly Gly
1 5 10 15

Ser Leu Arg Leu Ser Cys Ala Ala Ser Gly Phe Thr Phe Ser Asn Ala
20 25 30

Trp Met Ser Trp Val Arg Gln Ala Pro Gly Lys Gly Leu Glu Trp Val
35 40 45

Gly Arg Ile Lys Ser Lys Thr Asp Gly Gly Thr Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu Lys Thr Glu Asp Thr Ala Val Tyr
85 90 95

Tyr Cys Ala Arg Asp Phe Gly Arg Trp Ser Tyr Tyr Phe Asp Tyr Trp
100 105 110

Ser Gln Gly Thr Leu Val Thr Val Ser Ser Gln Ser Val Leu Thr Gln
115 120 125

Pro Pro Ser Val Ser Val Ala Pro Gly Gln Thr Ala Arg Ile Thr Cys
130 135 140

Gly Gly Asn Asn Ile Gly Thr Lys Ser Val His Trp Tyr Gln Gln Lys
145 150 155 160

Pro Gly Gln Ala Pro Val Leu Val Leu Tyr Asp Glu Ser Asp Arg Pro
165 170 175

Ser Gly Ile Pro Glu Arg Phe Ser Gly Ser Xaa Ser Gly Asn Thr Ala
180 185 190

Thr Leu Thr Ile Ser Arg Val Glu Ala Gly Asp Glu Ala Asp Xaa Leu
195 200 205

Leu Ser Gly Val Gly Xaa Xaa Xaa Xaa Ser Leu Cys Phe Gly Ser Gly
210 215 220

Thr Lys Leu Thr Val Leu
225 230

<210> SEQ ID NO 252
<211> LENGTH: 230
<212> TYPE: PRT
<213> ORGANISM: Homo sapiens
<220> FEATURE:
<223> OTHER INFORMATION: Clone 81 scFv
<220> FEATURE:
<221> NAME/KEY: VARIANT
<222> LOCATION: 187, 207
<223> OTHER INFORMATION: Xaa = any amino acid

<400> SEQUENCE: 252

Gln Ile Thr Leu Lys Glu Ser Gly Gly Gly Leu Val Lys Pro Gly Gly
1 5 10 15

Ser Leu Arg Leu Ser Cys Ala Ala Ser Gly Phe Thr Phe Ser Asn Ala
20 25 30

Trp Met Ser Trp Val Arg Gln Ala Pro Gly Lys Gly Leu Glu Trp Val
35 40 45

Gly Arg Ile Lys Ser Lys Thr Asp Gly Gly Thr Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu Lys Thr Glu Asp Thr Ala Val Tyr
85 90 95

Tyr Cys Ala Arg Asp Phe Gly Arg Trp Ser Tyr Tyr Phe Asp Tyr Trp
100 105 110

Ser Gln Gly Thr Leu Val Thr Val Ser Ser Gln Ser Val Leu Thr Gln
115 120 125

Pro Pro Ser Val Ser Val Ala Pro Gly Gln Thr Ala Arg Ile Thr Cys
130 135 140

Gly Gly Asn Asn Ile Gly Thr Lys Ser Val His Trp Tyr Gln Gln Lys
145 150 155 160

Pro Gly Gln Ala Pro Val Leu Val Leu Tyr Asp Glu Ser Asp Arg Pro
165 170 175

Ser Gly Ile Pro Glu Arg Phe Ser Gly Ser Xaa Ser Gly Asn Thr Ala
180 185 190

Thr Leu Thr Ile Ser Arg Val Glu Ala Gly Asp Glu Ala Asp Xaa Leu

```
        195                 200                 205

Leu Gln Val Trp Asp Ser Ser Ser Asp His Tyr Val Phe Gly Ser Gly
    210                 215                 220

Thr Lys Leu Thr Val Leu
225                 230
```

```
<210> SEQ ID NO 253
<211> LENGTH: 210
<212> TYPE: PRT
<213> ORGANISM: Homo sapiens
<220> FEATURE:
<223> OTHER INFORMATION: Clone 16 scFv
<220> FEATURE:
<221> NAME/KEY: VARIANT
<222> LOCATION: 4, 11
<223> OTHER INFORMATION: Xaa = any amino acid

<400> SEQUENCE: 253

Arg Ser Pro Xaa Arg Ser Leu Gly Glu Ala Xaa Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Gly Ser Ala Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Gly Arg Trp Ser Tyr Tyr Phe Asp Tyr Trp
            100                 105                 110

Ser Gln Gly Thr Leu Val Thr Val Ser Ser Glu Ile Val Met Thr Gln
        115                 120                 125

Ser Pro Ser Phe Leu Ser Ala Ser Val Gly Asp Arg Val Thr Ile Thr
    130                 135                 140

Cys Arg Ala Ser Gln Gly Ile Ser Ser Tyr Leu Ala Trp Tyr Gln Gln
145                 150                 155                 160

Lys Pro Gly Lys Ala Pro Lys Leu Leu Ile Tyr Ala Ala Ser Thr Leu
                165                 170                 175

Gln Ser Gly Ser His Gln Gly Phe Ser Gly Ser Gly Ser Gly Thr Glu
            180                 185                 190

Phe Thr Leu Thr Ile Ser Ser Leu Gln Pro Glu Asp Phe Ala Thr Tyr
        195                 200                 205

Tyr Cys
    210
```

```
<210> SEQ ID NO 254
<211> LENGTH: 209
<212> TYPE: PRT
<213> ORGANISM: Homo sapiens
<220> FEATURE:
<223> OTHER INFORMATION: Clone 65 scFv
<220> FEATURE:
<221> NAME/KEY: VARIANT
<222> LOCATION: 31, 209
<223> OTHER INFORMATION: Xaa = any amino acid

<400> SEQUENCE: 254

Gln Val Thr Leu Lys Glu Ser Gly Gly Gly Leu Val Lys Pro Gly Gly
```

```
1               5                   10                  15

Ser Leu Arg Leu Ser Cys Ala Ala Ser Gly Phe Thr Phe Gln Xaa Arg
            20                  25                  30

Leu Asp Glu Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Gly Arg Trp Ser Tyr Tyr Phe Asp Tyr Trp
            100                 105                 110

Ser Gln Gly Thr Leu Val Thr Val Ser Ser Gln Ser Ala Leu Thr Gln
        115                 120                 125

Asp Pro Ala Val Ser Val Ala Leu Gly Thr Asp Ser Gln Asp His Met
    130                 135                 140

Pro Arg Arg Gln Pro Gln Lys Thr Ile Met Gln Trp Tyr Gln Gln Lys
145                 150                 155                 160

Pro Gly Gln Ala Pro Ala Leu Val Ile Tyr Gly Lys Asn Asp Arg Pro
                165                 170                 175

Ser Gly Ile Pro Asp Arg Phe Ser Gly Ser Thr Ser Gly Asn Thr Ala
            180                 185                 190

Ser Leu Thr Ile Thr Gly Ala Gln Ala Glu Asp Glu Ala Asp Tyr Tyr
        195                 200                 205

Xaa
```

<210> SEQ ID NO 255
<211> LENGTH: 228
<212> TYPE: PRT
<213> ORGANISM: Homo sapiens
<220> FEATURE:
<223> OTHER INFORMATION: Clone V18 scFv

<400> SEQUENCE: 255

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Gly Arg Trp Ser Tyr Tyr Phe Asp Tyr Trp
            100                 105                 110

Gly Gln Gly Thr Leu Val Thr Val Ser Ser Val Leu Thr Gln Pro Pro
        115                 120                 125

Ser Val Ser Val Ala Pro Gly Lys Thr Ala Arg Ile Thr Cys Gly Gly
    130                 135                 140

Asn Asn Leu Gly Ser Lys Asn Val His Trp Tyr Gln Gln Lys Pro Gly
145                 150                 155                 160
```

```
Gln Ala Pro Val Leu Val Ile Tyr Asp Asp Asp Asn Arg Pro Ser Gly
                165                 170                 175

Ile Pro Glu Arg Phe Ser Gly Ser Asn Ser Gly Asn Thr Ala Thr Leu
            180                 185                 190

Thr Ile Ser Arg Val Glu Ala Gly Asp Glu Ala Asp Tyr Tyr Cys Gln
        195                 200                 205

Val Trp Asp Ser Ser Ser Arg His Val Val Phe Gly Gly Gly Thr Lys
    210                 215                 220

Leu Thr Val Leu
225
```

<210> SEQ ID NO 256
<211> LENGTH: 232
<212> TYPE: PRT
<213> ORGANISM: Homo sapiens
<220> FEATURE:
<223> OTHER INFORMATION: Clone 40 scFv

<400> SEQUENCE: 256

```
Gln Val Thr Leu Lys Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Arg Thr Glu Asp Thr Ala Val Tyr
                85                  90                  95

Tyr Cys Ala Arg Asp Phe Gly Arg Trp Ser Tyr Tyr Phe Asp Tyr Trp
            100                 105                 110

Ser Gln Gly Thr Leu Val Thr Val Ser Ser Gln Pro Val Leu Thr Gln
        115                 120                 125

Pro His Ser Val Ser Glu Ser Pro Gly Lys Thr Val Thr Ile Ser Cys
    130                 135                 140

Thr Arg Ser Ser Gly Asn Ile Ala Ser Asn Phe Val Gln Trp Tyr Gln
145                 150                 155                 160

Arg Arg Pro Asp Gly Ala Thr Thr Asn Val Ile Tyr Glu Asp Thr Gln
                165                 170                 175

Arg Pro Ser Gly Val Ser Gly Arg Phe Ser Gly Ser Ile Asp Arg Ser
            180                 185                 190

Ser Asn Ser Ala Ser Leu Thr Ile Ser Gly Leu Arg Ala Glu Asp Glu
        195                 200                 205

Ala Asp Tyr Tyr Cys Gln Ser Tyr Asp Gly Arg Asn Leu Met Phe Gly
    210                 215                 220

Gly Gly Thr Lys Val Thr Val Leu
225                 230
```

<210> SEQ ID NO 257
<211> LENGTH: 232
<212> TYPE: PRT
<213> ORGANISM: Homo sapiens
<220> FEATURE:
<223> OTHER INFORMATION: Clone 40 scFv

<400> SEQUENCE: 257

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Arg Thr Glu Asp Thr Ala Val Tyr
                85                  90                  95

Tyr Cys Ala Arg Asp Phe Gly Arg Trp Ser Tyr Tyr Phe Asp Tyr Trp
            100                 105                 110

Ser Gln Gly Thr Leu Val Thr Val Ser Ser Gln Pro Val Leu Thr Gln
        115                 120                 125

Pro His Ser Val Ser Glu Ser Pro Gly Lys Thr Val Thr Ile Ser Cys
    130                 135                 140

Thr Arg Ser Ser Gly Asn Ile Ala Ser Asn Phe Val Gln Trp Tyr Gln
145                 150                 155                 160

Arg Arg Pro Asp Gly Ala Thr Thr Asn Val Ile Tyr Glu Asp Thr Gln
                165                 170                 175

Arg Pro Ser Gly Val Ser Gly Arg Phe Ser Gly Ser Ile Asp Arg Ser
            180                 185                 190

Ser Asn Ser Ala Ser Leu Thr Ile Ser Gly Leu Arg Ala Glu Asp Glu
        195                 200                 205

Ala Asp Tyr Tyr Cys Gln Ser Tyr Asp Gly Arg Asn Leu Met Phe Gly
    210                 215                 220

Gly Gly Thr Lys Val Thr Val Leu
225                 230

<210> SEQ ID NO 258
<211> LENGTH: 229
<212> TYPE: PRT
<213> ORGANISM: Homo sapiens
<220> FEATURE:
<223> OTHER INFORMATION: Clone 350 scFv

<400> SEQUENCE: 258

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Arg Ser Thr Asp His Ala Asp Tyr Val
    50                  55                  60

Lys Gly Arg Phe Thr Ile Ser Arg Asp Asn Ser Lys Asn Thr Val Tyr
65                  70                  75                  80

Leu Gln Met Asn Arg Leu Arg Ala Glu Asp Thr Ala Val Tyr Tyr Cys
                85                  90                  95

Ala Lys Val Ser Asn Tyr Glu Tyr Tyr Phe Asp Tyr Trp Ala Gln Gly
            100                 105                 110

Thr Leu Val Thr Val Ser Ser Gln Pro Val Leu Thr Gln Pro His Ser

```
        115                 120                 125

Val Ser Glu Ser Pro Gly Lys Thr Val Thr Ile Ser Cys Thr Arg Ser
    130                 135                 140

Ser Gly Ser Ile Ala Ser Asn Tyr Val Gln Trp Tyr Gln Gln Arg Pro
145                 150                 155                 160

Gly Ser Ala Pro Thr Thr Val Ile Tyr Glu Asp Asn Gln Arg Pro Ser
                165                 170                 175

Gly Val Pro Asp Arg Phe Ser Gly Ser Ile Asp Ser Ser Ser Asn Ser
            180                 185                 190

Ala Ser Leu Thr Ile Ser Gly Leu Lys Thr Glu Asp Glu Ala Asp Tyr
        195                 200                 205

Tyr Cys Gln Ser Tyr Asp Ser Ser Asn His Val Phe Gly Thr Gly Thr
    210                 215                 220

Lys Leu Thr Val Leu
225


<210> SEQ ID NO 259
<211> LENGTH: 229
<212> TYPE: PRT
<213> ORGANISM: Homo sapiens
<220> FEATURE:
<223> OTHER INFORMATION: Clone 20 scFv

<400> SEQUENCE: 259

Gln Val Thr Leu Lys Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Gly Arg Trp Ser Tyr Tyr Phe Asp Tyr Trp
            100                 105                 110

Ser Gln Gly Thr Leu Val Thr Val Ser Ser Asn Ile Gln Met Thr Gln
        115                 120                 125

Ser Pro Ser Ser Leu Ser Ala Ser Val Gly Asp Arg Val Thr Ile Thr
    130                 135                 140

Cys Arg Ala Ser Gln Ser Ile Asn Lys Trp Leu Ala Trp Tyr Gln Gln
145                 150                 155                 160

Lys Pro Gly Lys Ala Pro Lys Leu Leu Ile His Asp Ala Ser Thr Leu
                165                 170                 175

Glu Ser Gly Val Pro Ser Arg Phe Ser Gly Ser Gly Ser Gly Thr Glu
            180                 185                 190

Phe Thr Leu Thr Ile Ser Ser Leu His Pro Asp Asp Ser Ala Thr Tyr
        195                 200                 205

Tyr Cys Gln Gln Leu Lys Ser Pro Pro Ala Gln Phe Gly Glu Gly Thr
    210                 215                 220

Lys Leu Glu Ile Lys
225
```

<210> SEQ ID NO 260
<211> LENGTH: 229
<212> TYPE: PRT
<213> ORGANISM: Homo sapiens
<220> FEATURE:
<223> OTHER INFORMATION: Clone 20 scFv

<400> SEQUENCE: 260

```
Gln Val Thr Leu Lys Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Gly Arg Trp Ser Tyr Tyr Phe Asp Tyr Trp
            100                 105                 110

Ser Gln Gly Thr Leu Val Thr Val Ser Ser Asn Ile Gln Met Thr Gln
        115                 120                 125

Ser Pro Ser Ser Leu Ser Ala Ser Val Gly Asp Arg Val Thr Ile Thr
    130                 135                 140

Cys Arg Ala Ser Gln Ser Ile Asn Lys Trp Leu Ala Trp Tyr Gln Gln
145                 150                 155                 160

Lys Pro Gly Lys Ala Pro Lys Leu Leu Ile His Asp Ala Ser Thr Leu
                165                 170                 175

Glu Ser Gly Val Pro Ser Arg Phe Ser Gly Ser Gly Ser Gly Thr Glu
            180                 185                 190

Phe Thr Leu Thr Ile Ser Ser Leu His Pro Asp Asp Ser Ala Thr Tyr
        195                 200                 205

Tyr Cys Gln Gln Leu Lys Ser Arg Pro Leu Ser Phe Gly Glu Gly Thr
    210                 215                 220

Lys Leu Glu Ile Lys
225
```

<210> SEQ ID NO 261
<211> LENGTH: 229
<212> TYPE: PRT
<213> ORGANISM: Homo sapiens
<220> FEATURE:
<223> OTHER INFORMATION: Clone 20 scFv

<400> SEQUENCE: 261

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80
```

```
Leu Tyr Leu Gln Met Asn Ser Leu Lys Thr Glu Asp Thr Ala Val Tyr
                85                  90                  95

Tyr Cys Ala Arg Asp Phe Gly Arg Trp Ser Tyr Tyr Phe Asp Tyr Trp
            100                 105                 110

Ser Gln Gly Thr Leu Val Thr Val Ser Ser Asn Ile Gln Met Thr Gln
        115                 120                 125

Ser Pro Ser Ser Leu Ser Ala Ser Val Gly Asp Arg Val Thr Ile Thr
    130                 135                 140

Cys Arg Ala Ser Gln Ser Ile Asn Lys Trp Leu Ala Trp Tyr Gln Gln
145                 150                 155                 160

Lys Pro Gly Lys Ala Pro Lys Leu Leu Ile His Asp Ala Ser Thr Leu
                165                 170                 175

Glu Ser Gly Val Pro Ser Arg Phe Ser Gly Ser Gly Ser Gly Thr Glu
            180                 185                 190

Phe Thr Leu Thr Ile Ser Ser Leu His Pro Asp Asp Ser Ala Thr Tyr
        195                 200                 205

Tyr Cys Gln Gln Leu Lys Ser Pro Pro Ala Gln Phe Gly Glu Gly Thr
    210                 215                 220

Lys Leu Glu Ile Lys
225


<210> SEQ ID NO 262
<211> LENGTH: 229
<212> TYPE: PRT
<213> ORGANISM: Homo sapiens
<220> FEATURE:
<223> OTHER INFORMATION: Clone 20 scFv

<400> SEQUENCE: 262

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Gly Arg Trp Ser Tyr Tyr Phe Asp Tyr Trp
            100                 105                 110

Ser Gln Gly Thr Leu Val Thr Val Ser Ser Asn Ile Gln Met Thr Gln
        115                 120                 125

Ser Pro Ser Ser Leu Ser Ala Ser Val Gly Asp Arg Val Thr Ile Thr
    130                 135                 140

Cys Arg Ala Ser Gln Ser Ile Asn Lys Trp Leu Ala Trp Tyr Gln Gln
145                 150                 155                 160

Lys Pro Gly Lys Ala Pro Lys Leu Leu Ile His Asp Ala Ser Thr Leu
                165                 170                 175

Glu Ser Gly Val Pro Ser Arg Phe Ser Gly Ser Gly Ser Gly Thr Glu
            180                 185                 190

Phe Thr Leu Thr Ile Ser Ser Leu His Pro Asp Asp Ser Ala Thr Tyr
        195                 200                 205
```

```
Tyr Cys Gln Gln Leu Lys Ser Arg Pro Leu Ser Phe Gly Glu Gly Thr
    210                 215                 220

Lys Leu Glu Ile Lys
225
```

<210> SEQ ID NO 263
<211> LENGTH: 232
<212> TYPE: PRT
<213> ORGANISM: Homo sapiens
<220> FEATURE:
<223> OTHER INFORMATION: Clone 43 scFv

<400> SEQUENCE: 263

```
Gln Val Thr Leu Lys Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Phe Gly Arg Trp Ser Tyr Tyr Phe Asp Tyr Trp
            100                 105                 110

Ser Gln Gly Thr Leu Val Thr Val Ser Ser Gln Ser Val Leu Thr Gln
        115                 120                 125

Pro Ser Ser Val Ser Gly Thr Pro Gly Gln Arg Val Thr Ile Ser Cys
    130                 135                 140

Ser Gly Ser Ser Ser Asn Ile Gly Ser Asn Tyr Val Tyr Trp Tyr Gln
145                 150                 155                 160

Gln Leu Pro Gly Thr Ala Pro Lys Leu Leu Ile Tyr Arg Asn Asn Gln
                165                 170                 175

Arg Pro Ser Gly Val Pro Asp Arg Phe Ser Gly Ser Lys Ser Gly Thr
            180                 185                 190

Ser Ala Ser Leu Gly His Gln Trp Ala Pro Gly Pro Arg Met Arg Leu
        195                 200                 205

Ile Ile Thr Ala Ala Trp Asp Asp Ser Leu Ser Gly Val Val Phe Gly
    210                 215                 220

Gly Gly Thr Lys Leu Thr Val Leu
225                 230
```

<210> SEQ ID NO 264
<211> LENGTH: 232
<212> TYPE: PRT
<213> ORGANISM: Homo sapiens
<220> FEATURE:
<223> OTHER INFORMATION: Clone 43 scFv

<400> SEQUENCE: 264

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45
```

-continued

Gly Arg Ile Lys Ser Lys Thr Asp Gly Gly Thr Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asn Ser Leu Lys Thr Glu Asp Thr Ala Val Tyr
85 90 95

Tyr Cys Ala Arg Asp Phe Gly Arg Trp Ser Tyr Tyr Phe Asp Tyr Trp
100 105 110

Ser Gln Gly Thr Leu Val Thr Val Ser Ser Gln Ser Val Leu Thr Gln
115 120 125

Pro Ser Ser Val Ser Gly Thr Pro Gly Gln Arg Val Thr Ile Ser Cys
130 135 140

Ser Gly Ser Ser Ser Asn Ile Gly Ser Asn Tyr Val Tyr Trp Tyr Gln
145 150 155 160

Gln Leu Pro Gly Thr Ala Pro Lys Leu Leu Ile Tyr Arg Asn Asn Gln
165 170 175

Arg Pro Ser Gly Val Pro Asp Arg Phe Ser Gly Ser Lys Ser Gly Thr
180 185 190

Ser Ala Ser Leu Gly His Gln Trp Ala Pro Gly Pro Arg Met Arg Leu
195 200 205

Ile Ile Thr Ala Ala Trp Asp Asp Ser Leu Ser Gly Val Val Phe Gly
210 215 220

Gly Gly Thr Lys Leu Thr Val Leu
225 230

<210> SEQ ID NO 265
<211> LENGTH: 227
<212> TYPE: PRT
<213> ORGANISM: Homo sapiens
<220> FEATURE:
<223> OTHER INFORMATION: Clone 305 scFv

<400> SEQUENCE: 265

Glu Val Gln Leu Val Glu Ser Gly Gly Gly Leu Val Gln Pro Gly Arg
1 5 10 15

Ser Leu Arg Leu Ser Cys Thr Ala Ser Gly Phe Thr Phe Gly Asp Tyr
20 25 30

Ala Met Ser Trp Val Arg Gln Ala Pro Gly Lys Gly Leu Glu Trp Val
35 40 45

Ser Ser Ile Ser Gly Ser Gly Arg Ser Thr Asp His Ala Asp Tyr Val
50 55 60

Lys Gly Arg Phe Thr Ile Ser Arg Asp Asn Ser Lys Asn Thr Val Tyr
65 70 75 80

Leu Gln Met Asn Arg Leu Arg Ala Glu Asp Thr Ala Val Tyr Tyr Cys
85 90 95

Ala Lys Val Ser Asn Tyr Glu Tyr Tyr Phe Asp Tyr Trp Ala Gln Gly
100 105 110

Thr Leu Val Thr Val Ser Ser Gln Ser Val Leu Thr Gln Pro Pro Ser
115 120 125

Val Ser Val Ala Pro Gly Gln Thr Ala Arg Ile Thr Cys Gly Gly Asn
130 135 140

Asn Ile Gly Ser Thr Ser Val His Trp Phe Gln Gln Lys Pro Gly Gln
145 150 155 160

Ala Pro Val Leu Val Val Tyr Asp Asp Ser Asp Arg Pro Ser Gly Ile
165 170 175

-continued

```
Pro Glu Arg Phe Ser Gly Ser Asn Ser Gly Asn Thr Ala Thr Leu Thr
            180                 185                 190

Ile Ser Arg Val Glu Ala Gly Asp Glu Ala Asp Tyr Tyr Cys Gln Val
        195                 200                 205

Trp Asp Asn Asp Ser Asp His Arg Val Phe Gly Gly Gly Thr Lys Leu
    210                 215                 220

Thr Val Leu
225


<210> SEQ ID NO 266
<211> LENGTH: 229
<212> TYPE: PRT
<213> ORGANISM: Homo sapiens
<220> FEATURE:
<223> OTHER INFORMATION: Clone 366 scFv

<400> SEQUENCE: 266

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Arg Ser Thr Asp His Ala Asp Tyr Val
    50                  55                  60

Lys Gly Arg Phe Thr Ile Ser Arg Asp Asn Ser Lys Asn Thr Val Tyr
65                  70                  75                  80

Leu Gln Met Asn Arg Leu Arg Ala Glu Asp Thr Ala Val Tyr Tyr Cys
                85                  90                  95

Ala Lys Val Ser Asn Tyr Glu Tyr Tyr Phe Asp Tyr Trp Ala Gln Gly
            100                 105                 110

Thr Leu Val Thr Val Ser Ser Gln Ser Val Leu Thr Gln Pro Pro Ser
        115                 120                 125

Val Pro Gly Thr Pro Gly Gln Arg Val Thr Ile Thr Cys Ser Gly Ser
    130                 135                 140

Arg Phe Asn Ile Gly Ser Asn Thr Val Asn Trp Tyr Gln Gln Leu Pro
145                 150                 155                 160

Gly Thr Ala Pro Lys Leu Leu Ile Tyr Ser Asn Asn Gln Arg Pro Ser
                165                 170                 175

Gly Val Pro Asp Arg Phe Ser Gly Ser Lys Ser Gly Thr Ser Ala Ser
            180                 185                 190

Leu Ala Ile Ser Gly Leu Gln Ser Glu Asp Glu Ala Asp Tyr Tyr Cys
        195                 200                 205

Ala Ala Trp Asp Asp Ser Leu Asn Gly Tyr Val Phe Gly Thr Gly Thr
    210                 215                 220

Lys Leu Thr Val Leu
225


<210> SEQ ID NO 267
<211> LENGTH: 232
<212> TYPE: PRT
<213> ORGANISM: Homo sapiens
<220> FEATURE:
<223> OTHER INFORMATION: Clone 461 scFv
<220> FEATURE:
<221> NAME/KEY: VARIANT
<222> LOCATION: 194
<223> OTHER INFORMATION: Xaa = any amino acid
```

<400> SEQUENCE: 267

Gln Val Gln Leu Val Glu Ser Gly Gly Gly Leu Val Lys Pro Gly Arg
1 5 10 15

Ser Leu Arg Leu Ser Cys Thr Ala Ser Gly Phe Thr Phe Gly Asp Tyr
20 25 30

Ala Met Ser Trp Phe Arg Gln Ala Pro Gly Lys Gly Leu Glu Trp Val
35 40 45

Gly Phe Ile Arg Ser Lys Ala Tyr Gly Gly Thr Thr Glu Tyr Ala Ala
50 55 60

Ser Val Lys Gly Arg Phe Thr Ile Ser Arg Asp Asp Ser Lys Ser Ile
65 70 75 80

Ala Tyr Leu Gln Met Asn Ser Leu Lys Thr Glu Asp Thr Ala Val Tyr
85 90 95

Tyr Cys Ala Lys Asp Phe Glu Val Arg Glu Ala His Leu Ser Tyr Phe
100 105 110

Asp Tyr Trp Gly Gln Gly Thr Leu Val Thr Val Ser Ser Gln Ser Val
115 120 125

Leu Thr Gln Pro Pro Ser Val Ser Val Ala Pro Gly Gln Thr Ala Arg
130 135 140

Ile Thr Cys Gly Gly Asn Arg Ile Gly Thr Lys Ala Val His Trp Tyr
145 150 155 160

Gln Gln Lys Ser Gly Gln Ala Pro Val Leu Val Val Arg Asp Asp Thr
165 170 175

Asp Arg Pro Ser Gly Ser Leu Arg Asp Ser Leu Ala Pro Thr Leu Gly
180 185 190

Thr Xaa Ala Thr Leu Thr Ile Ser Gly Val Glu Ala Gly Asp Glu Ala
195 200 205

Asp Tyr Tyr Gln Val Trp Asp Ser Ser Ser Asp His Arg Val Phe Gly
210 215 220

Gly Gly Thr Lys Leu Thr Val Leu
225 230

<210> SEQ ID NO 268
<211> LENGTH: 232
<212> TYPE: PRT
<213> ORGANISM: Homo sapiens
<220> FEATURE:
<223> OTHER INFORMATION: Clone 461 scFv
<220> FEATURE:
<221> NAME/KEY: VARIANT
<222> LOCATION: 194
<223> OTHER INFORMATION: Xaa = any amino acid

<400> SEQUENCE: 268

Glu Val Gln Leu Val Glu Ser Gly Gly Gly Leu Val Lys Pro Gly Arg
1 5 10 15

Ser Leu Arg Leu Ser Cys Thr Ala Ser Gly Phe Thr Phe Gly Asp Tyr
20 25 30

Ala Met Ser Trp Phe Arg Gln Ala Pro Gly Lys Gly Leu Glu Trp Val
35 40 45

Gly Phe Ile Arg Ser Lys Ala Tyr Gly Gly Thr Thr Glu Tyr Ala Ala
50 55 60

Ser Val Lys Gly Arg Phe Thr Ile Ser Arg Asp Asp Ser Lys Ser Ile
65 70 75 80

Ala Tyr Leu Gln Met Asn Ser Leu Lys Thr Glu Asp Thr Ala Val Tyr
85 90 95

```
Tyr Cys Ala Lys Asp Phe Glu Val Arg Glu Ala His Leu Ser Tyr Phe
            100                 105                 110

Asp Tyr Trp Gly Gln Gly Thr Leu Val Thr Val Ser Ser Gln Ser Val
        115                 120                 125

Leu Thr Gln Pro Pro Ser Val Ser Val Ala Pro Gly Gln Thr Ala Arg
    130                 135                 140

Ile Thr Cys Gly Gly Asn Arg Ile Gly Thr Lys Ala Val His Trp Tyr
145                 150                 155                 160

Gln Gln Lys Ser Gly Gln Ala Pro Val Leu Val Val Arg Asp Asp Thr
                165                 170                 175

Asp Arg Pro Ser Gly Ser Leu Arg Asp Ser Leu Ala Pro Thr Leu Gly
            180                 185                 190

Thr Xaa Ala Thr Leu Thr Ile Ser Gly Val Glu Ala Gly Asp Glu Ala
        195                 200                 205

Asp Tyr Tyr Gln Val Trp Asp Ser Ser Ser Asp His Arg Val Phe Gly
    210                 215                 220

Gly Gly Thr Lys Leu Thr Val Leu
225                 230


<210> SEQ ID NO 269
<211> LENGTH: 7
<212> TYPE: PRT
<213> ORGANISM: Homo sapiens
<220> FEATURE:
<223> OTHER INFORMATION: Clone 83, 83B CDR-H1

<400> SEQUENCE: 269

Gly Tyr Thr Phe Thr Ser Tyr
1               5


<210> SEQ ID NO 270
<211> LENGTH: 7
<212> TYPE: PRT
<213> ORGANISM: Homo sapiens
<220> FEATURE:
<223> OTHER INFORMATION: Clone 298, V70, Clone 350, 305, 366, 461, V68,
      V102, V181 CDR-H1

<400> SEQUENCE: 270

Gly Phe Thr Phe Gly Asp Tyr
1               5


<210> SEQ ID NO 271
<211> LENGTH: 7
<212> TYPE: PRT
<213> ORGANISM: Homo sapiens
<220> FEATURE:
<223> OTHER INFORMATION: Clone 48, V353, Clone 7, 81, 16, V18, 40, 20,
      43, V9,  V163, V95, V312, V357, V397 CDR-H1

<400> SEQUENCE: 271

Gly Phe Thr Phe Ser Asn Ala
1               5


<210> SEQ ID NO 272
<211> LENGTH: 7
<212> TYPE: PRT
<213> ORGANISM: Homo sapiens
<220> FEATURE:
<223> OTHER INFORMATION: Clone V71 CDR-H1

<400> SEQUENCE: 272
```

-continued

Gly Phe Thr Phe Ser Thr Ser
1 5

<210> SEQ ID NO 273
<211> LENGTH: 7
<212> TYPE: PRT
<213> ORGANISM: Homo sapiens
<220> FEATURE:
<223> OTHER INFORMATION: Clone V86, V278, V282, V365, V420, V336 CDR-H1

<400> SEQUENCE: 273

Gly Phe Thr Phe Ser Ser Tyr
1 5

<210> SEQ ID NO 274
<211> LENGTH: 7
<212> TYPE: PRT
<213> ORGANISM: Homo sapiens
<220> FEATURE:
<221> NAME/KEY: VARIANT
<222> LOCATION: 6
<223> OTHER INFORMATION: Xaa = any amino acid
<220> FEATURE:
<223> OTHER INFORMATION: Clone 65 CDR-H1

<400> SEQUENCE: 274

Gly Phe Thr Phe Gln Xaa Arg
1 5

<210> SEQ ID NO 275
<211> LENGTH: 7
<212> TYPE: PRT
<213> ORGANISM: Homo sapiens
<220> FEATURE:
<223> OTHER INFORMATION: Clone V128 CDR-H1

<400> SEQUENCE: 275

Gly Phe Thr Phe Asp Thr Phe
1 5

<210> SEQ ID NO 276
<211> LENGTH: 7
<212> TYPE: PRT
<213> ORGANISM: Homo sapiens
<220> FEATURE:
<223> OTHER INFORMATION: Clone V224 CDR-H1

<400> SEQUENCE: 276

Gly Phe Thr Phe Ile Asn Ala
1 5

<210> SEQ ID NO 277
<211> LENGTH: 7
<212> TYPE: PRT
<213> ORGANISM: Homo sapiens
<220> FEATURE:
<223> OTHER INFORMATION: Clone V316 CDR-H1

<400> SEQUENCE: 277

Gly Leu Thr Phe Ser Arg Thr
1 5

<210> SEQ ID NO 278
<211> LENGTH: 7
<212> TYPE: PRT
<213> ORGANISM: Homo sapiens
<220> FEATURE:
<223> OTHER INFORMATION: Clone V331, V345 CDR-H1

<400> SEQUENCE: 278

Gly Gly Ser Phe Ser Gly Tyr
1 5

<210> SEQ ID NO 279
<211> LENGTH: 7
<212> TYPE: PRT
<213> ORGANISM: Homo sapiens
<220> FEATURE:
<223> OTHER INFORMATION: Clone V355 CDR-H1

<400> SEQUENCE: 279

Gly Gly Thr Phe Ser Ser Tyr
1 5

<210> SEQ ID NO 280
<211> LENGTH: 10
<212> TYPE: PRT
<213> ORGANISM: Homo sapiens
<220> FEATURE:
<223> OTHER INFORMATION: Clone 65 CDR-H1
<220> FEATURE:
<221> NAME/KEY: VARIANT
<222> LOCATION: 6
<223> OTHER INFORMATION: Xaa = any amino acid

<400> SEQUENCE: 280

Gly Phe Thr Phe Gln Xaa Arg Leu Asp Glu
1 5 10

<210> SEQ ID NO 281
<211> LENGTH: 10
<212> TYPE: PRT
<213> ORGANISM: Homo sapiens
<220> FEATURE:
<223> OTHER INFORMATION: Clone V71 CDR-H1

<400> SEQUENCE: 281

Gly Phe Thr Phe Ser Thr Ser Ala Met Ser
1 5 10

<210> SEQ ID NO 282
<211> LENGTH: 10
<212> TYPE: PRT
<213> ORGANISM: Homo sapiens
<220> FEATURE:
<223> OTHER INFORMATION: Clone 86, V278, V365 CDR-H1

<400> SEQUENCE: 282

Gly Phe Thr Phe Ser Ser Tyr Ala Met Ser
1 5 10

<210> SEQ ID NO 283
<211> LENGTH: 10
<212> TYPE: PRT
<213> ORGANISM: Homo sapiens
<220> FEATURE:
<223> OTHER INFORMATION: Clone V128 CDR-H1

<400> SEQUENCE: 283

Gly Phe Thr Phe Asp Thr Phe Trp Met Ser
1 5 10

<210> SEQ ID NO 284
<211> LENGTH: 10
<212> TYPE: PRT

<213> ORGANISM: Homo sapiens
<220> FEATURE:
<223> OTHER INFORMATION: Clone V224 CDR-H1

<400> SEQUENCE: 284

Gly Phe Thr Phe Ile Asn Ala Trp Met Ser
1 5 10

<210> SEQ ID NO 285
<211> LENGTH: 10
<212> TYPE: PRT
<213> ORGANISM: Homo sapiens
<220> FEATURE:
<223> OTHER INFORMATION: Clone V316 CDR-H1

<400> SEQUENCE: 285

Gly Leu Thr Phe Ser Arg Thr Trp Met Ser
1 5 10

<210> SEQ ID NO 286
<211> LENGTH: 10
<212> TYPE: PRT
<213> ORGANISM: Homo sapiens
<220> FEATURE:
<223> OTHER INFORMATION: Clone V331 CDR-H1

<400> SEQUENCE: 286

Gly Gly Ser Phe Ser Gly Tyr Tyr Trp Ser
1 5 10

<210> SEQ ID NO 287
<211> LENGTH: 10
<212> TYPE: PRT
<213> ORGANISM: Homo sapiens
<220> FEATURE:
<223> OTHER INFORMATION: Clone V355 CDR-H1

<400> SEQUENCE: 287

Gly Gly Thr Phe Ser Ser Tyr Ala Ile Ser
1 5 10

<210> SEQ ID NO 288
<211> LENGTH: 10
<212> TYPE: PRT
<213> ORGANISM: Homo sapiens
<220> FEATURE:
<223> OTHER INFORMATION: Clone V282, V420 CDR-H1

<400> SEQUENCE: 288

Gly Phe Thr Phe Ser Ser Tyr Trp Met Ser
1 5 10

<210> SEQ ID NO 289
<211> LENGTH: 10
<212> TYPE: PRT
<213> ORGANISM: Homo sapiens
<220> FEATURE:
<223> OTHER INFORMATION: Clone V345 CDR-H1

<400> SEQUENCE: 289

Gly Gly Ser Phe Ser Gly Tyr Tyr Trp Ser
1 5 10

<210> SEQ ID NO 290
<211> LENGTH: 10
<212> TYPE: PRT
<213> ORGANISM: Homo sapiens
<220> FEATURE:
<223> OTHER INFORMATION: Clone V336 CDR-H1

<400> SEQUENCE: 290

Gly Phe Thr Phe Ser Ser Tyr Ala Met His
1 5 10

<210> SEQ ID NO 291
<211> LENGTH: 8
<212> TYPE: PRT
<213> ORGANISM: Homo sapiens
<220> FEATURE:
<223> OTHER INFORMATION: Clone V353, V48, V81, V16, V65, V18, V40, V20,
V43, V224, V163, V95, V312, V357, V397 CDR-H2

<400> SEQUENCE: 291

Lys Ser Lys Thr Asp Gly Gly Thr
1 5

<210> SEQ ID NO 292
<211> LENGTH: 6
<212> TYPE: PRT
<213> ORGANISM: Homo sapiens
<220> FEATURE:
<223> OTHER INFORMATION: Clone V298, V350, V305, V366 CDR-H2

<400> SEQUENCE: 292

Ser Gly Ser Gly Arg Ser
1 5

<210> SEQ ID NO 293
<211> LENGTH: 6
<212> TYPE: PRT
<213> ORGANISM: Homo sapiens
<220> FEATURE:
<223> OTHER INFORMATION: Clone V83 CDR-H2

<400> SEQUENCE: 293

Asn Pro Ser Gly Gly Ser
1 5

<210> SEQ ID NO 294
<211> LENGTH: 6
<212> TYPE: PRT
<213> ORGANISM: Homo sapiens
<220> FEATURE:
<223> OTHER INFORMATION: Clone V83B CDR-H2

<400> SEQUENCE: 294

Asn Pro Asn Gly Gly Ser
1 5

<210> SEQ ID NO 295
<211> LENGTH: 8
<212> TYPE: PRT
<213> ORGANISM: Homo sapiens
<220> FEATURE:
<223> OTHER INFORMATION: Clone 7 CDR-H2

<400> SEQUENCE: 295

Arg Ser Lys Thr Asp Gly Gly Thr
1 5

<210> SEQ ID NO 296
<211> LENGTH: 8
<212> TYPE: PRT
<213> ORGANISM: Homo sapiens -continued
<220> FEATURE:
<223> OTHER INFORMATION: Clone V68, V102 CDR-H2

<400> SEQUENCE: 296

Arg Ser Lys Ala Tyr Gly Gly Thr
1               5

<210> SEQ ID NO 297
<211> LENGTH: 6
<212> TYPE: PRT
<213> ORGANISM: Homo sapiens
<220> FEATURE:
<223> OTHER INFORMATION: Clone V71 CDR-H2

<400> SEQUENCE: 297

Ser Thr Asp Gly Ala Thr
1               5

<210> SEQ ID NO 298
<211> LENGTH: 6
<212> TYPE: PRT
<213> ORGANISM: Homo sapiens
<220> FEATURE:
<223> OTHER INFORMATION: Clone V86, V278, V365 CDR-H2

<400> SEQUENCE: 298

Ser Gly Ser Gly Gly Ser
1               5

<210> SEQ ID NO 299
<211> LENGTH: 6
<212> TYPE: PRT
<213> ORGANISM: Homo sapiens
<220> FEATURE:
<223> OTHER INFORMATION: Clone V316 CDR-H2

<400> SEQUENCE: 299

Asn Asp Asp Gly Ser Glu
1               5

<210> SEQ ID NO 300
<211> LENGTH: 5
<212> TYPE: PRT
<213> ORGANISM: Homo sapiens
<220> FEATURE:
<223> OTHER INFORMATION: Clone V331, V345 CDR-H2

<400> SEQUENCE: 300

Asn His Ser Gly Ser
1               5

<210> SEQ ID NO 301
<211> LENGTH: 6
<212> TYPE: PRT
<213> ORGANISM: Homo sapiens
<220> FEATURE:
<223> OTHER INFORMATION: Clone V355  CDR-H2

<400> SEQUENCE: 301

Ile Pro Ile Phe Gly Thr
1               5

<210> SEQ ID NO 302
<211> LENGTH: 6
<212> TYPE: PRT
<213> ORGANISM: Homo sapiens
<220> FEATURE:

<223> OTHER INFORMATION: Clone V282, V420 CDR-H2

<400> SEQUENCE: 302

Lys Gln Asp Gly Ser Glu
1 5

<210> SEQ ID NO 303
<211> LENGTH: 5
<212> TYPE: PRT
<213> ORGANISM: Homo sapiens
<220> FEATURE:
<223> OTHER INFORMATION: Clone V336 CDR-H2

<400> SEQUENCE: 303

Ser Tyr Asp Gly Ser
1 5

<210> SEQ ID NO 304
<211> LENGTH: 12
<212> TYPE: PRT
<213> ORGANISM: Homo sapiens
<220> FEATURE:
<223> OTHER INFORMATION: Clone V353, V48, V81, V16, V65, V18, V40, V20, V43, V224, V163, V95, V312, V357, V397 CDR-H2

<400> SEQUENCE: 304

Arg Ile Lys Ser Lys Thr Asp Gly Gly Thr Thr Asp
1 5 10

<210> SEQ ID NO 305
<211> LENGTH: 10
<212> TYPE: PRT
<213> ORGANISM: Homo sapiens
<220> FEATURE:
<223> OTHER INFORMATION: Clone 298, V350, V305, V366 CDR-H2

<400> SEQUENCE: 305

Ser Ile Ser Gly Ser Gly Arg Ser Thr Asp
1 5 10

<210> SEQ ID NO 306
<211> LENGTH: 10
<212> TYPE: PRT
<213> ORGANISM: Homo sapiens
<220> FEATURE:
<223> OTHER INFORMATION: Clone V83 CDR-H2

<400> SEQUENCE: 306

Ile Ile Asn Pro Ser Gly Gly Ser Thr Ser
1 5 10

<210> SEQ ID NO 307
<211> LENGTH: 10
<212> TYPE: PRT
<213> ORGANISM: Homo sapiens
<220> FEATURE:
<223> OTHER INFORMATION: Clone V83B CDR-H2

<400> SEQUENCE: 307

Ile Ile Asn Pro Asn Gly Gly Ser Thr Ser
1 5 10

<210> SEQ ID NO 308
<211> LENGTH: 12
<212> TYPE: PRT
<213> ORGANISM: Homo sapiens
<220> FEATURE:

<223> OTHER INFORMATION: Clone 7 CDR-H2

<400> SEQUENCE: 308

Arg Ile Arg Ser Lys Thr Asp Gly Gly Thr Thr Asp
1 5 10

<210> SEQ ID NO 309
<211> LENGTH: 12
<212> TYPE: PRT
<213> ORGANISM: Homo sapiens
<220> FEATURE:
<223> OTHER INFORMATION: Clone V68, V102, V181 CDR-H2

<400> SEQUENCE: 309

Phe Ile Arg Ser Lys Ala Tyr Gly Gly Thr Thr Glu
1 5 10

<210> SEQ ID NO 310
<211> LENGTH: 10
<212> TYPE: PRT
<213> ORGANISM: Homo sapiens
<220> FEATURE:
<223> OTHER INFORMATION: Clone V71 CDR-H2

<400> SEQUENCE: 310

Thr Ile Ser Thr Asp Gly Ala Thr Thr Trp
1 5 10

<210> SEQ ID NO 311
<211> LENGTH: 10
<212> TYPE: PRT
<213> ORGANISM: Homo sapiens
<220> FEATURE:
<223> OTHER INFORMATION: Clone V86, V278, V365 CDR-H2

<400> SEQUENCE: 311

Ala Ile Ser Gly Ser Gly Gly Ser Thr Tyr
1 5 10

<210> SEQ ID NO 312
<211> LENGTH: 10
<212> TYPE: PRT
<213> ORGANISM: Homo sapiens
<220> FEATURE:
<223> OTHER INFORMATION: Clone V316 CDR-H2

<400> SEQUENCE: 312

Ser Ile Asn Asp Asp Gly Ser Glu Lys Tyr
1 5 10

<210> SEQ ID NO 313
<211> LENGTH: 9
<212> TYPE: PRT
<213> ORGANISM: Homo sapiens
<220> FEATURE:
<223> OTHER INFORMATION: Clone V331 CDR-H2

<400> SEQUENCE: 313

Lys Ile Asn His Ser Gly Ser Thr Asn
1 5

<210> SEQ ID NO 314
<211> LENGTH: 10
<212> TYPE: PRT
<213> ORGANISM: Homo sapiens
<220> FEATURE:
<223> OTHER INFORMATION: Clone V355 CDR-H2

-continued

```
<400> SEQUENCE: 314

Gly Ile Ile Pro Ile Phe Gly Thr Ala Asn
1               5                   10


<210> SEQ ID NO 315
<211> LENGTH: 10
<212> TYPE: PRT
<213> ORGANISM: Homo sapiens
<220> FEATURE:
<223> OTHER INFORMATION: Clone V282, V420 CDR-H2

<400> SEQUENCE: 315

Asn Ile Lys Gln Asp Gly Ser Glu Lys Tyr
1               5                   10


<210> SEQ ID NO 316
<211> LENGTH: 9
<212> TYPE: PRT
<213> ORGANISM: Homo sapiens
<220> FEATURE:
<223> OTHER INFORMATION: Clone V345 CDR-H2

<400> SEQUENCE: 316

Glu Ile Asn His Ser Gly Ser Thr Asn
1               5


<210> SEQ ID NO 317
<211> LENGTH: 9
<212> TYPE: PRT
<213> ORGANISM: Homo sapiens
<220> FEATURE:
<223> OTHER INFORMATION: Clone V336 CDR-H2

<400> SEQUENCE: 317

Val Ile Ser Tyr Asp Gly Ser Thr Asn
1               5


<210> SEQ ID NO 318
<211> LENGTH: 19
<212> TYPE: PRT
<213> ORGANISM: Homo sapiens
<220> FEATURE:
<223> OTHER INFORMATION: Clone 7 CDR-H2

<400> SEQUENCE: 318

Arg Ile Arg Ser Lys Thr Asp Gly Gly Thr Thr Asp Tyr Ala Ala Leu
1               5                   10                  15

Val Lys Gly
```

ANTIBODIES AND CHIMERIC ANTIGEN RECEPTORS SPECIFIC FOR ROR1

CROSS-REFERENCE TO RELATED APPLICATIONS

This application is a divisional of U.S. patent application Ser. No. 15/997,635, filed Jun. 4, 2018, entitled, "ANTIBODIES AND CHIMERIC ANTIGEN RECEPTORS SPECIFIC FOR ROR1," now U.S. Pat. No. 10,889,652, issued Jan. 12, 2021, which is a continuation of U.S. patent application Ser. No. 14/997,991, filed Jan. 18, 2016, entitled "ANTIBODIES AND CHIMERIC ANTIGEN RECEPTORS SPECIFIC FOR ROR1," which claims priority from U.S. provisional application No. 62/104,664 filed Jan. 16, 2015, entitled "ANTIBODIES AND CHIMERIC ANTIGEN RECEPTORS SPECIFIC FOR ROR1," the contents of which are incorporated by reference in their entirety.

INCORPORATION BY REFERENCE OF SEQUENCE LISTING

The present application is being filed with a Sequence Listing in electronic format. The Sequence Listing is provided as a file entitled 735042001710SeqList.txt, created Dec. 9, 2020, which is 215,728 bytes in size. The information in electronic format of the Sequence Listing is incorporated by reference in its entirety.

FIELD

The present disclosure relates in some aspects to ROR1 binding molecules, in particular, to anti-ROR1 antibodies, including antibody fragments. The present disclosure further relates to recombinant receptors containing such antibodies, including chimeric antigen receptors (CARs), which contain such antibodies. The disclosure further relates to genetically engineered cells expressing such receptors and antibodies, and use thereof in adoptive cell therapy.

BACKGROUND

Receptor tyrosine kinase-like orphan receptor 1 (ROR1) is a transmembrane receptor that is expressed during embryogenesis, but generally is not expressed on normal adult cells. ROR1, however, is expressed in the context of a variety of different cancers, where it is involved in cell signaling to promote tumor cell survival. Because ROR1 is generally not expressed on normal cells, ROR1 is a tumor-specific and/or tumor-associated target for therapy. Various ROR1-binding molecules, including anti-ROR1 antibodies are available. Chimeric antigen receptors containing anti-ROR1 antibody portions, and cells expressing such chimeric receptors, also are available. Improved ROR1-binding molecules and engineered ROR1-targeting cells are needed. For example, there is a need for molecules and cells with reduced immunogenicity and fully human antibodies, including antibody fragments, that specifically bind to ROR1, and chimeric receptors expressing such human antibodies for use in adoptive cell therapy. Provided are embodiments that meet such needs.

SUMMARY

Provided are ROR1-binding molecules, including polypeptides, such as anti-ROR1 antibodies, including antigen-binding antibody fragments such as single domain antibodies (e.g. $V_H$ alone), single-chain fragments including scFv fragments, and polypeptides containing such antibodies, including fusion proteins, receptors, e.g., recombinant receptors, including chimeric receptors such as chimeric antigen receptors (CARs) containing the antibody as an antigen-recognition component. In particular embodiments, the antibodies are human antibodies, such as human single-chain fragments including scFvs.

Provided are antibodies or antigen-binding fragments thereof, including those that specifically bind to ROR1, such as specifically bind to human ROR1. In some embodiments, the antibodies contain particular complementarity determining regions (CDRs), including heavy chain CDRs (CDR-Hs) and light chain CDRs (CDR-Ls), such as any described. In some embodiments, the antibody or antigen-binding fragment thereof includes a heavy chain variable ($V_H$) region. In some embodiments, the antibody or antigen-binding fragment thereof includes a VH region and a light chain variable ($V_L$) region.

In some embodiments, provided are antibodies or antigen-binding fragments thereof that include a heavy chain variable (VH) region containing a heavy chain complementarity determining region 3 (CDR-H3) having the amino acid sequence set forth in SEQ ID NO: 22, 29, 35, 45, 50, 51, 52, 53, 54, 55, 56, 57, 58, 59, 60, 61, 62, 63, 64, 65, 66, 67, 68, 69, 70, 71 or 174 and/or a CDR-H3 contained within the heavy chain variable ($V_H$) sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209.

Provided are antibody or antigen-binding fragments thereof that include a heavy chain variable ($V_H$) region comprising at least 90% sequence identity to the $V_H$ region amino acid sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209. In some embodiments, provided are antibodies or antigen-binding fragments thereof that include a heavy chain variable ($V_H$) region having at least 90% sequence identity to the $V_H$ region amino acid sequence set forth in SEQ ID NO: 8, 10, 13, 15, 17, or 19, such as at least 91%, 92%, 93%, 94%, 95%, 96%, 97%, 98%, or 99% sequence identity thereto.

In some of any such embodiments, the $V_H$ region comprises a heavy chain complementarity determining region 3 (CDR-H3) comprising the amino acid sequence set forth in SEQ ID NO: 22, 29, 35, 45, 50, 51, 52, 53, 54, 55, 56, 57, 58, 59, 60, 61, 62, 63, 64, 65, 66, 67, 68, 69, 70, 71 or 174; or a CDR-H3 contained within the VH sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209. In some of any such embodiments, the $V_H$ region includes a heavy chain complementarity determining region 3 (CDR-H3) having the amino acid sequence set forth in SEQ ID NO: 22, 29, 35, 45, 50, 51, 52, 53, 54, 55, 56, 57, 58, 59, 60, 61, 62, 63, 64, 65, 66, 67, 68, 69, 70, 71 or 174 and/or a CDR-H3 contained within the $V_H$ sequence set forth in SEQ ID NO: 8, 10, 13, 15, 17, or 19. In some embodiments, the $V_H$ region includes a heavy chain complementarity determining region 3 (CDR-H3) having the amino acid sequence set forth in SEQ ID NO: 72 and/or a CDR-H3 contained within the $V_H$ sequence set forth in SEQ ID NO: 85.

In some of any such embodiments, the $V_H$ region includes a heavy chain complementarity determining region 1 (CDR-H1) comprising the amino acid sequence set forth in SEQ ID NO: 20, 27, 33, 155, 156, 157, 158, 159, 160, 161, 162 or 163, and/or comprising the amino acid sequence set forth in SEQ ID NO: 269, 270, 271, 272, 273, 274, 275, 276, 278 or 279 and/or comprising the amino acid sequence set forth in SEQ ID NO: 75, 77, 79, 280, 281, 282, 283, 284, 285, 286, 287, 288 or 289 and/or a CDR-H1 contained within the $V_H$ sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209; and/or a heavy chain complementarity determining region 2 (CDR-H2) comprising the amino acid sequence set forth in SEQ ID NO: 21, 26, 28, 34, 164, 165, 166, 167, 168, 169, 170, 171, 172, 173 or 318 and/or comprising the amino acid sequence set forth in SEQ ID NO: 291, 292, 293, 294, 295, 296, 297, 298, 299, 300, 301, 302 or 303 and/or comprising the amino acid sequence set forth in SEQ ID NO: 304, 305, 306, 307, 308, 309, 310, 311, 312, 313, 314, 315, 316 or 317 and/or a CDR-H2 contained within the $V_H$ sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209. In some of any such embodiments, the $V_H$ region includes a heavy chain complementarity determining region 1 (CDR-H1) having the amino acid sequence set forth in SEQ ID NO: 20, 27, or 33 and/or a CDR-H1 contained within the $V_H$ sequence set forth in SEQ ID NO: 8, 10, 13, 15, 17, or 19; and/or a heavy chain complementarity determining region 2 (CDR-H2) having the amino acid sequence set forth in SEQ ID NO: 21, 26, 28, or 34 and/or a CDR-H2 contained within the $V_H$ sequence set forth in SEQ ID NO: 8, 10, 13, 15, 17, or 19.

Provided are antibodies or antigen-binding fragments thereof that include a heavy chain variable (VH) region comprising a heavy chain complementarity determining region 1 (CDR-H1), CDR-H2, and CDR-H3, wherein the CDR-H1 comprises the amino acid sequence set forth in SEQ ID NO: 20, 27, 33, 74, 75, 76, 77, 78, 79, 155, 156, 157, 158, 159, 160, 161, 162 or 163; the CDR-H2 comprises the amino acid sequence set forth in SEQ ID NO: 21, 26, 28, 34, 80, 81, 82, 83, 164, 165, 166, 167, 168, 169, 170, 171, 172, 173, or 318; and/or the CDR-H3 comprises the amino acid sequence set forth in SEQ ID NO: 22, 29, 35, 45, 50, 51, 52, 53, 54, 55, 56, 57, 58, 59, 60, 61, 62, 63, 64, 65, 66, 67, 68, 69, 70, 71 or 174. In some embodiments, provided are antibodies or antigen-binding fragments thereof that include a CDR-H1 having the amino acid sequence set forth in SEQ ID NO: 20, 27, or 33; a CDR-H2 having the amino acid sequence set forth in SEQ ID NO: 21, 26, 28, or 34; and a CDR-H3 having the amino acid sequence set forth in SEQ ID NO: 22, 29, 35, 45, 50, 51, 52, 53, 54, 55, 56, 57, 58, 59, 60, 61, 62, 63, 64, 65, 66, 67, 68, 69, 70, 71 or 174.

In some of any of such embodiments, the antibody includes a CDR-H3 that has the amino acid sequence VSNYEYYFDY (SEQ ID NO: 29), DFGRWGYYFDY (SEQ ID NO: 52), DFGRWSYYFDY (SEQ ID NO: 35) or DSSYDAFDI (SEQ ID NO: 22).

In some of any of such embodiments, the antibody includes a $V_H$ region that includes the CDR-H1, CDR-H2, and CDR-H3 having the sequences of SEQ ID NOs: 20, 21, and 22, respectively; the CDR-H1, CDR-H2, and CDR-H3 having the sequences of SEQ ID NOs: 20, 26, and 22, respectively; the CDR-H1, CDR-H2, and CDR-H3 having the sequences of SEQ ID NOs: 27, 28, and 29, respectively; the CDR-H1, CDR-H2, and CDR-H3 having the sequences of SEQ ID NOs: 33, 34, and 35, respectively; the CDR-H1, CDR-H2, and CDR-H3 having the sequences of SEQ ID NOs: 33, 34, and 52, respectively; the CDR-H1, CDR-H2, and CDR-H3 comprise the sequences of SEQ ID NOs: 27, 164 and 45, respectively; the CDR-H1, CDR-H2, and CDR-H3 comprise the sequences of SEQ ID NOs: 27, 164 and 68, respectively; the CDR-H1, CDR-H2, and CDR-H3 comprise the sequences of SEQ ID NOs: 27, 164 and 64, respectively; the CDR-H1, CDR-H2, and CDR-H3 comprise the sequences of SEQ ID NOs: 27, 164 and 66, respectively; the CDR-H1, CDR-H2, and CDR-H3 having the sequences of SEQ ID NOs: 33, 318, and 35, respectively; the CDR-H1, CDR-H2, and CDR-H3 comprise the sequences of SEQ ID NOs: 33, 34 and 70, respectively; the CDR-H1, CDR-H2, and CDR-H3 comprise the sequences of SEQ ID NOs: 33, 34 and 55, respectively; the CDR-H1, CDR-H2, and CDR-H3 comprise the sequences of SEQ ID NOs: 33, 34 and 53, respectively; the CDR-H1, CDR-H2, and CDR-H3 comprise the sequences of SEQ ID NOs: 33, 34 and 56, respectively; the CDR-H1, CDR-H2, and CDR-H3 comprise the sequences of SEQ ID NOs: 33, 34 and 61, respectively; the CDR-H1, CDR-H2, and CDR-H3 comprise the sequences of SEQ ID NOs: 33, 34 and 59, respectively; the CDR-H1, CDR-H2, and CDR-H3 comprise the sequences of SEQ ID NOs: 33, 171 and 60, respectively; the CDR-H1, CDR-H2, and CDR-H3 comprise the sequences of SEQ ID NOs: 155, 34 and 35, respectively; the CDR-H1, CDR-H2, and CDR-H3 comprise the sequences of SEQ ID NOs: 156, 34 and 35, respectively; the CDR-H1, CDR-H2, and CDR-H3 comprise the sequences of SEQ ID NOs: 162, 170 and 50, respectively; the CDR-H1, CDR-H2, and CDR-H3 comprise the sequences of SEQ ID NOs: 162, 170 and 51, respectively; the CDR-H1, CDR-H2, and CDR-H3 comprise the sequences of SEQ ID NOs: 161, 169 and 54, respectively; the CDR-H1, CDR-H2, and CDR-H3 comprise the sequences of SEQ ID NOs:159, 167 and 57, respectively; the CDR-H1, CDR-H2, and CDR-H3 comprise the sequences of SEQ ID NOs: 160, 168 and 58, respectively; the CDR-H1, CDR-H2, and CDR-H3 comprise the sequences of SEQ ID NOs: 158, 166 and 62, respectively; the CDR-H1, CDR-H2, and CDR-H3 comprise the sequences of SEQ ID NOs: 158, 166 and 63, respectively; the CDR-H1, CDR-H2, and CDR-H3 comprise the sequences of SEQ ID NOs: 158, 166 and 65, respectively; the CDR-H1, CDR-H2, and CDR-H3 comprise the sequences of SEQ ID NOs: 157, 165 and 67, respectively; the CDR-H1, CDR-H2, and CDR-H3 comprise the sequences of SEQ ID NOs: 163, 173 and 69, respectively; the CDR-H1, CDR-H2, and CDR-H3 comprise the sequences of SEQ ID NOs: 160, 172, 71, respectively; or the CDR-H1, CDR-H2, and CDR-H3 comprise the sequences of SEQ ID NOs: 160, 172, 174, respectively. In some embodiments, any of the above provided antibodies or fragments can contain the corresponding CDR (e.g. CDR-H1 or CDR-H2) in accord with an alternative numbering scheme as is described and known to a skilled artisan.

In some of any of such embodiments, the antibody includes a $V_H$ region that includes the CDR-H1, CDR-H2, and CDR-H3 having the sequences of SEQ ID NOs: 20, 21, and 22, respectively; the CDR-H1, CDR-H2, and CDR-H3 having the sequences of SEQ ID NOs: 20, 26, and 22, respectively; the CDR-H1, CDR-H2, and CDR-H3 having the sequences of SEQ ID NOs: 27, 28, and 29, respectively; the CDR-H1, CDR-H2, and CDR-H3 having the sequences of SEQ ID NOs: 33, 34, and 35, respectively; or the CDR-H1, CDR-H2, and CDR-H3 having the sequences of SEQ ID NOs: 33, 34, and 52, respectively. In some embodiments, the antibody includes a $V_H$ region that includes the CDR-H1, CDR-H2, and CDR-H3 having the sequences of SEQ ID NOs: 27, 28, and 29, respectively; or the CDR-H1, CDR-H2, and CDR-H3 comprise the sequences of SEQ ID NOs: 33, 34, and 52, respectively. In some embodiments, the antibody includes a $V_H$ region that includes the CDR-H1, CDR-H2, and CDR-H3 having the sequences of SEQ ID NOs: 20, 21, and 22, respectively; the CDR-H1, CDR-H2, and CDR-H3 having the sequences of SEQ ID NOs: 20, 26, and 22, respectively; the CDR-H1, CDR-H2, and CDR-H3 having the sequences of SEQ ID NOs: 27, 28, and 29, respectively; the CDR-H1, CDR-H2, and CDR-H3 having the sequences of SEQ ID NOs: 33, 34, and 35, respectively.

Provided are antibodies or antigen-binding fragments thereof that includes a heavy chain complementarity determining region 1 (CDR-H1), a CDR-H2, and a CDR-H3, respectively, comprising the amino acid sequences of a CDR-H1, a CDR-H2, and a CDR-H3 contained within the $V_H$ region amino acid sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209. In some embodiments, provided are antibodies or antigen-binding fragments thereof includes a $V_H$ region that includes a heavy chain CDR-H1, a CDR-H2, and a CDR-H3, respectively having the amino acid sequences of a CDR-H1, a CDR-H2, and a CDR-H3 contained within the $V_H$ region amino acid sequence set forth in SEQ ID NO: 8, 10, 13, 15, 17, or 19. In some embodiments, the antibody includes a $V_H$ region that includes a heavy chain CDR-H1, a CDR-H2, and a CDR-H3, respectively having the amino acid sequences of a CDR-H1, a CDR-H2, and a CDR-H3 contained within the $V_H$ region amino acid sequence set forth in SEQ ID NO: 8 or 10. In some embodiments, the antibody includes a $V_H$ region that includes a heavy chain CDR-H1, a CDR-H2, and a CDR-H3, respectively having the amino acid sequences of a CDR-H1, a CDR-H2, and a CDR-H3 contained within the $V_H$ region amino acid sequence set forth in SEQ ID NO: 13, 15, 17, or 19.

In some of any such embodiments, the $V_H$ region contains a framework region 1 (FR1), a FR2, a FR3, and/or a FR4 comprising at least 90% sequence identity, respectively, to a FR1, FR2, FR3, and/or FR4 of the amino acid sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209. In some of any such embodiments, the $V_H$ region contains a framework region 1 (FR1), a FR2, a FR3, and/or a FR4 sequence having at least 90% sequence identity, respectively, to a FR1, FR2, FR3, and/or FR4 of the amino acid sequence set forth in SEQ ID NO: 8, 10, 13, 15, 17 or 19. In some embodiments, the $V_H$ region contains a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 8, 10, 13, 15, 17 or 19. In some embodiments, the $V_H$ region contains a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 8, 10, 13, 15, 17 or 19.

In some of any of such embodiments, the $V_H$ region has the sequence of amino acids set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209. In some of any such embodiments, the $V_H$ region has the sequence of amino acids set forth in SEQ ID NO: 8, 10, 13, 15, 17, or 19. In some embodiments, the $V_H$ region has the sequence of amino acids set forth in SEQ ID NO: 8 or 10. In some embodiments, the $V_H$ region has the sequence of amino acids set forth in SEQ ID NO: 13, 15, 17, or 19.

In some of any of such embodiments, the $V_H$ region comprises the CDR-H1, CDR-H2, and CDR-H3 set forth in SEQ ID NOS: 20, 26, and 22, respectively, and/or the $V_H$ region comprises the sequence of amino acids set forth in SEQ ID NO: 19. In some of any of such embodiments, the $V_H$ region comprises the CDR-H1, CDR-H2, and CDR-H3 set forth in SEQ ID NOS: 33, 34, and 52, respectively, and/or the $V_H$ region comprises the sequence of amino acids set forth in SEQ ID NO: 10. In some of any of such embodiments, the $V_H$ region comprises the CDR-H1, CDR-H2, and CDR-H3 set forth in SEQ ID NOS: 33, 34, and 35, respectively, and/or the $V_H$ region comprises the sequence of amino acids set forth in SEQ ID NO: 13. In some of any of such embodiments, the $V_H$ region comprises the CDR-H1, CDR-H2, and CDR-H3 set forth in SEQ ID NOS: 27, 28, and 29, respectively, and/or the $V_H$ region comprises the sequence of amino acids set forth in SEQ ID NO: 15.

In any of such provided embodiments, the antibody or antigen-binding fragment is a heavy chain only, a VH-only, and/or does not include a VL or antigen-binding portion thereof and/or the antigen-binding site of the antibody or fragment includes residues from the heavy chain only and/or does not include residues from a light chain.

In some of any such embodiments, the antibody or fragment does not contain a light chain variable ($V_L$) region, does not contain a CDR-L1, CDR-L2, and/or CDR-L3, and/or is a single-domain antibody (sdAb) containing only the $V_H$ region. In some embodiments, the antibody or fragment is an sdAb that only contains a VH region from any as described.

In some embodiments of any of the antibodies or fragments containing any of the above VH region sequences, the antibody or fragment further contains a light chain variable ($V_L$) region. In some such embodiments, the $V_L$ region has at least 90% sequence identity to the $V_L$ region amino acid sequence set forth in SEQ ID NO: 14, 16, 18, 234, 235, 236, 237, 238, 239, 240, 241, 242, 243, 244, 245, 246, 247 or 248, such as at least 91%, 92%, 93%, 94%, 95%, 96%, 97%, 98%, 99% sequence identity to the $V_L$ region amino acid sequence set forth in SEQ ID NO: 14, 16, 18, 234, 235, 236, 237, 238, 239, 240, 241, 242, 243, 244, 245, 246, 247 or 248. In some such embodiments, the $V_L$ region has at least 90% sequence identity to the $V_L$ region amino acid sequence set forth in SEQ ID NO: 14, 16, or 18, such as at least 91%, 92%, 93%, 94%, 95%, 96%, 97%, 98%, 99% sequence identity to the $V_L$ region amino acid sequence set forth in SEQ ID NO: 14, 16, or 18.

In some of any such embodiments, he $V_L$ region comprises a light chain complementarity determining region 3 (CDR-L3) comprising the amino acid sequence set forth in SEQ ID NO: 25, 32, 38, 39, 40, 41, 42, 43, 44, 46, 47, 48, 49, 232 or 233. In some of any such embodiments, the $V_L$ region contains a light chain complementarity determining region 3 (CDR-L3) having the amino acid sequence set forth in SEQ ID NO: 25, 32, 38, 39, 40, 41, 42, 43, 44, 46, 47, 48 or 49.

In some of any such embodiments, he $V_L$ region contains a light chain complementarity determining region 1 (CDR-L1) comprising the amino acid sequence set forth in SEQ ID NO: 23, 30, 36, 210, 211, 212, 213, 214, 215, 217, 216, 218, 219 or 220 and/or a CDR-L1 contained within the $V_L$ sequence set forth in SEQ ID NO: 14, 16, 18, 234, 235, 236, 237, 238, 239, 240, 241, 242, 243, 244, 245, 246, 247 or 248; and/or a light chain complementarity determining region 2 (CDR-L2) comprising the amino acid sequence set forth in SEQ ID NO: 24, 31, 37, 221, 222, 223, 224, 225, 226, 227, 228, 229, 230 or 231 and/or a CDR-L2 contained within the $V_L$ sequence set forth in SEQ ID NO: 14, 16, 18, 234, 235, 236, 237, 238, 239, 240, 241, 242, 243, 244, 245, 246, 247 or 248. In some of any such embodiments, the $V_L$ region contains a light chain complementarity determining region 1 (CDR-L1) having the amino acid sequence set forth in SEQ ID NO: 23, 30, or 36 and/or a CDR-L1 contained within the $V_L$ sequence set forth in SEQ ID NO: 14, 16, or 18; and/or a light chain complementarity determining region 2 (CDR-L2) having the amino acid sequence set forth in SEQ ID NO: 24, 31, or 37 and/or a CDR-L2 contained within the $V_L$ sequence set forth in SEQ ID NO: 14, 16, or 18.

In some of any such embodiments, the $V_L$ region contains a CDR-L1 containing the amino acid sequence set forth in SEQ ID NO: 23, 30, 36, 210, 211, 212, 213, 214, 215, 217, 216, 218, 219 or 220; a CDR-L2 containing the amino acid sequence set forth in SEQ ID NO: 24, 31, 37, 221, 222, 223, 224, 225, 226, 227, 228, 229, 230 or 231; and a CDR-L3 containing the amino acid sequence set forth in SEQ ID NO: 25, 32, 38, 39, 40, 41, 42, 43, 44, 46, 47, 48, 49, 232 or 233. In some of any such embodiments, the $V_L$ region contains a CDR-L1 having the amino acid sequence set forth in SEQ ID NO: 23, 30, or 36; a CDR-L2 having the amino acid sequence set forth in SEQ ID NO: 24, 31, or 37; and a CDR-L3 having the amino acid sequence set forth in SEQ ID NO: 25, 32, 38, 39, 40, 41, 42, 43, 44, 46, 47, 48, or 49.

In some of any such embodiments, the CDR-L3 has the amino acid sequence set forth in SEQ ID NO: 25, 32 or 38.

In some of any such embodiments, the antibody includes a $V_L$ region that includes the CDR-L1, CDR-L2, and CDR-L3 comprising the sequences of SEQ ID NOs: 23, 24, and 25, respectively; the CDR-L1, CDR-L2, and CDR-L3 comprising the sequences of SEQ ID NOs: 30, 31, and 32, respectively; the CDR-L1, CDR-L2, and CDR-L3 comprising the sequences of SEQ ID NOs: 36, 37, and 38, respectively; the CDR-L1, CDR-L2 and CDR-L3 comprising the sequences of SEQ ID NOs: 216, 227, and 40, respectively; the CDR-L1, CDR-L2 and CDR-L3 comprising the sequences of SEQ ID NOs: 218, 229, and 39, respectively; the CDR-L1, CDR-L2 and CDR-L3 comprising the sequences of SEQ ID NOs: 219, 230, and 43, respectively; the CDR-L1, CDR-L2 and CDR-L3 comprising the sequences of SEQ ID NOs: 220, 231, and 46, respectively; the CDR-L1, CDR-L2 and CDR-L3 comprising the sequences of SEQ ID NOs: 210, 221, and 49, respectively; the CDR-L1, CDR-L2 and CDR-L3 comprising the sequences of SEQ ID NOs: 210, 221, and 233, respectively; the CDR-L1, CDR-L2 and CDR-L3 comprising the sequences of SEQ ID NOs: 211, 222, and 48, respectively; the CDR-L1, CDR-L2 and CDR-L3 comprising the sequences of SEQ ID NOs: 212, 223, and 42, respectively; the CDR-L1, CDR-L2 and CDR-L3 comprising the sequences of SEQ ID NOs: 214, 225, and 232, respectively; the CDR-L1, CDR-L2 and CDR-L3 comprising the sequences of SEQ ID NOs: 215, 226, and 44, respectively; the CDR-L1, CDR-L2 and CDR-L3 comprising the sequences of SEQ ID NOs: 217, 228, and 41, respectively; the CDR-L1, CDR-L2 and CDR-L3 comprising the sequences of SEQ ID NOs: 36, 37, and 38, respectively; or the CDR-L1, CDR-L2 and CDR-L3 comprising the sequences of SEQ ID NOs: 213, 224, and 47, respectively. In some of any such embodiments, the antibody or fragment includes a $V_L$ region that includes the CDR-L1, CDR-L2, and CDR-L3 comprising the sequences of SEQ ID NOs: 23, 24, and 25, respectively; the CDR-L1, CDR-L2, and CDR-L3 comprising the sequences of SEQ ID NOs: 30, 31, and 32, respectively; or the CDR-L1, CDR-L2, and CDR-L3 comprising the sequences of SEQ ID NOs: 36, 37, and 38, respectively.

In some of any such embodiments, the $V_L$ region contains the CDR-L1, CDR-L2, and CDR-L3, respectively, contained within the $V_L$ region amino acid sequence set forth in SEQ ID NO: 14, 16, 18, 234, 235, 236, 237, 238, 239, 240, 241, 242, 243, 244, 245, 246, 247 or 248. In some of any such embodiments, the $V_L$ region contains the CDR-L1, CDR-L2, and CDR-L3, respectively, contained within the $V_L$ region amino acid sequence set forth in SEQ ID NO: 14, 16, or 18.

In some of any such embodiments, the $V_L$ region contains a framework region 1 (FR1), a FR2, a FR3, and/or a FR4 having at least 90% sequence identity, respectively, to the FR1, FR2, FR3, and/or FR4 of the amino acid sequence set forth in SEQ ID NO: 14, 16, or 18. In some embodiments, the $V_L$ region contains a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 14, 16, or 18. In some embodiments, the $V_L$ region contains a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 14, 16, or 18.

In some of any such embodiments, the $V_L$ region has the amino acid sequence set forth in SEQ ID NO: 14, 16, 18, 234, 235, 236, 237, 238, 239, 240, 241, 242, 243, 244, 245, 246, 247 or 248. In some of any such embodiments, the $V_L$ region has the amino acid sequence set forth in SEQ ID NO: 14, 16, or 18.

Provided are antibodies or antigen-binding fragments thereof that contain the amino acid sequences of CDR-H1, CDR-H2, and CDR-H3 sequences contained within the $V_H$ region amino acid sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209; and/or contain the amino acid sequences of CDR-L1, CDR-L2, and CDR-L3 sequences contained within the light chain variable (VL) region amino acid sequence set forth in SEQ ID NO: 14, 16, 18, 234, 235, 236, 237, 238, 239, 240, 241, 242, 243, 244, 245, 246, 247 or 248. In some embodiments, provided are antibodies or antigen-binding fragments thereof that contain the amino acid sequences of CDR-H1, CDR-H2, and CDR-H3 sequences contained within the $V_H$ region amino acid sequence set forth in SEQ ID NO: 8, 10, 13, 15, 17, or 19; and/or contain the amino acid sequences of CDR-L1, CDR-L2, and CDR-L3 sequences contained within the light chain variable (VL) region amino acid sequence set forth in SEQ ID NO: 14, 16, or 18.

Provided are antibodies or antigen-binding fragments thereof that include the $V_H$ and $V_L$ regions having amino acid sequences having at least 90%, 91%, 92%, 93%, 94%, 95%, 96%, 97%, 98% or 99% identity to SEQ ID NOs: 19 and 18, respectively; $V_H$ and $V_L$ regions having amino acid sequences having at least 90%, 91%, 92%, 93%, 94%, 95%, 96%, 97%, 98% or 99% identity to SEQ ID NOs: 17 and 18, respectively; $V_H$ and $V_L$ regions having amino acid sequences having at least 90%, 91%, 92%, 93%, 94%, 95%, 96%, 97%, 98% or 99% identity to SEQ ID NOs: 15 and 16, respectively; $V_H$ and $V_L$ regions having amino acid sequences having at least 90%, 91%, 92%, 93%, 94%, 95%, 96%, 97%, 98% or 99% identity to SEQ ID NOs: 13 and 14, respectively; a $V_H$ and $V_L$ regions comprising amino acid sequences having at least 90%, 91%, 92%, 93%, 94%, 95%, 96%, 97%, 98% or 99% identity to SEQ ID NOs: 182 and 242 respectively; a $V_H$ and $V_L$ regions comprising amino acid sequences having at least 90%, 91%, 92%, 93%, 94%, 95%, 96%, 97%, 98% or 99% identity to SEQ ID NOs: 182 and 246, respectively; a $V_H$ and $V_L$ regions comprising amino acid sequences having at least 90%, 91%, 92%, 93%, 94%, 95%, 96%, 97%, 98% or 99% identity to SEQ ID NOs: 182 and 247, respectively; a $V_H$ and $V_L$ regions comprising amino acid sequences having at least 90%, 91%, 92%, 93%, 94%, 95%, 96%, 97%, 98% or 99% identity to SEQ ID NOs: 185 and 248, respectively; a $V_H$ and $V_L$ regions comprising amino acid sequences having at least 90%, 91%, 92%, 93%, 94%, 95%, 96%, 97%, 98% or 99% identity to SEQ ID NOs: 186 and 248, respectively; a $V_H$ and $V_L$ regions comprising amino acid sequences having at least 90%, 91%, 92%, 93%, 94%, 95%, 96%, 97%, 98% or 99% identity to SEQ ID NOs: 175 and 234, respectively; a $V_H$ and $V_L$ regions comprising amino acid sequences having at least 90%, 91%, 92%, 93%, 94%, 95%, 96%, 97%, 98% or 99% identity to SEQ ID NOs: 175 and 235, respectively; a $V_H$ and $V_L$ regions comprising amino acid sequences having at least 90%, 91%, 92%, 93%, 94%, 95%, 96%, 97%, 98% or 99% identity to SEQ ID NOs: 176 and 236, respectively; a $V_H$ and $V_L$ regions comprising amino acid sequences having at least 90%, 91%, 92%, 93%, 94%, 95%, 96%, 97%, 98% or 99% identity to SEQ ID NOs: 176 and 237, respectively; a $V_H$ and $V_L$ regions comprising amino acid sequences having at least 90%, 91%, 92%, 93%, 94%, 95%, 96%, 97%, 98% or 99% identity to SEQ ID NOs: 177 and 238, respectively; a $V_H$ and $V_L$ regions comprising amino acid sequences having at least 90%, 91%, 92%, 93%, 94%, 95%, 96%, 97%, 98% or 99% identity to SEQ ID NOs: 179 and 240 respectively; a $V_H$ and $V_L$ regions comprising amino acid sequences having at least 90%, 91%, 92%, 93%, 94%, 95%, 96%, 97%, 98% or 99% identity to SEQ ID NOs: 180 and 241, respectively; a $V_H$ and $V_L$ regions comprising amino acid sequences having at least 90%, 91%, 92%, 93%, 94%, 95%, 96%, 97%, 98% or 99% identity to SEQ ID NOs: 181 and 241, respectively; a $V_H$ and $V_L$ regions comprising amino acid sequences having at least 90%, 91%, 92%, 93%, 94%, 95%, 96%, 97%, 98% or 99% identity to SEQ ID NOs: 183 and 243 respectively; a $V_H$ and $V_L$ regions comprising amino acid sequences having at least 90%, 91%, 92%, 93%, 94%, 95%, 96%, 97%, 98% or 99% identity to SEQ ID NOs: 183 and 244 respectively; a $V_H$ and $V_L$ regions comprising amino acid sequences having at least 90%, 91%, 92%, 93%, 94%, 95%, 96%, 97%, 98% or 99% identity to SEQ ID NOs: 184 and 243, respectively; a $V_H$ and $V_L$ regions comprising amino acid sequences having at least 90%, 91%, 92%, 93%, 94%, 95%, 96%, 97%, 98% or 99% identity to SEQ ID NOs: 184 and 244 respectively; a $V_H$ and $V_L$ regions comprising amino acid sequences having at least 90%, 91%, 92%, 93%, 94%, 95%, 96%, 97%, 98% or 99% identity to SEQ ID NOs: 183 and 245, respectively; a $V_H$ and $V_L$ regions comprising amino acid sequences having at least 90%, 91%, 92%, 93%, 94%, 95%, 96%, 97%, 98% or 99% identity to SEQ ID NOs: 184 and 245, respectively; or a $V_H$ and $V_L$ regions comprising amino acid sequences having at least 90%, 91%, 92%, 93%, 94%, 95%, 96%, 97%, 98% or 99% identity to SEQ ID NOs: 178 and 239, respectively.

In some embodiments, provided are antibodies or antigen-binding fragments thereof that include the $V_H$ and $V_L$ regions having amino acid sequences set forth in SEQ ID NOs: 19 and 18, respectively; $V_H$ and $V_L$ regions having amino acid sequences set forth in SEQ ID NOs: 17 and 18, respectively; $V_H$ and $V_L$ regions having amino acid sequences set forth in SEQ ID NOs: 15 and 16, respectively; $V_H$ and $V_L$ regions having amino acid sequences set forth in SEQ ID NOs: 13 and 14, respectively; a $V_H$ and $V_L$ regions comprising amino acid sequences set forth in SEQ ID NOs: 182 and 242 respectively; a $V_H$ and $V_L$ regions comprising amino acid sequences set forth in SEQ ID NOs: 182 and 246, respectively; a $V_H$ and $V_L$ regions comprising amino acid sequences set forth in SEQ ID NOs: 182 and 247, respectively; a $V_H$ and $V_L$ regions comprising amino acid sequences set forth in SEQ ID NOs: 185 and 248, respectively; a $V_H$ and $V_L$ regions comprising amino acid sequences set forth in SEQ ID NOs: 186 and 248, respectively; a $V_H$ and $V_L$ regions comprising amino acid sequences set forth in SEQ ID NOs: 175 and 234, respectively; a $V_H$ and $V_L$ regions comprising amino acid sequences set forth in SEQ ID NOs: 175 and 235, respectively; a $V_H$ and $V_L$ regions comprising amino acid sequences set forth in SEQ ID NOs: 176 and 236, respectively; a $V_H$ and $V_L$ regions comprising amino acid sequences set forth in SEQ ID NOs: 176 and 237, respectively; a $V_H$ and $V_L$ regions comprising amino acid sequences set forth in SEQ ID NOs: 177 and 238, respectively; a $V_H$ and $V_L$ regions comprising amino acid sequences set forth in SEQ ID NOs: 179 and 240 respectively; a $V_H$ and $V_L$ regions comprising amino acid sequences set forth in SEQ ID NOs: 180 and 241, respectively; a $V_H$ and $V_L$ regions comprising amino acid sequences set forth in SEQ ID NOs: 181 and 241, respectively; a $V_H$ and $V_L$ regions comprising amino acid sequences set forth in SEQ ID NOs: 183 and 243 respectively; a $V_H$ and $V_L$ regions comprising amino acid sequences set forth in SEQ ID NOs: 183 and 244 respectively; a $V_H$ and $V_L$ regions comprising amino acid sequences set forth in SEQ ID NOs: 184 and 243, respectively; a $V_H$ and $V_L$ regions comprising amino acid sequences set forth in SEQ ID NOs: 184 and 244 respectively; a $V_H$ and $V_L$ regions comprising amino acid sequences set forth in SEQ ID NOs: 183 and 245, respectively; a $V_H$ and $V_L$ regions comprising amino acid sequences set forth in SEQ ID NOs: 184 and 245, respectively; or a $V_H$ and $V_L$ regions comprising amino acid sequences set forth in SEQ ID NOs: 178 and 239, respectively.

In some of any such embodiments, the $V_H$ and $V_L$ regions include the amino acid sequences of SEQ ID NOs: 19 and 18, respectively; the $V_H$ and $V_L$ regions include the amino acid sequences of SEQ ID NOs: 17 and 18, respectively; the $V_H$ and $V_L$ regions include the amino acid sequences of SEQ ID NOs: 15 and 16 respectively; or the $V_H$ and $V_L$ regions include the amino acid sequences of SEQ ID NOs: 13 and 14 respectively.

In some of any such embodiments, the antibody or fragment specifically binds to a ROR1 protein. In some embodiments, the antibody or fragment has a binding affinity for a ROR1 protein with an EC50 that is from or from about 0.1 nM to 100 nM, 0.5 nM to 50 nM or 1 nM to 10 nM. In some embodiments, the antibody or fragment has a binding affinity for a ROR1 protein with an EC50 that is less than or less than about 100 nM, less than or less than about 50 nM, less than or less than about 10 nM or less than or less than about 1 nM.

In some of any such embodiments, the antibody or fragment has a binding affinity for a ROR1 protein, such as a human ROR1 protein, that is at least as high or substantially as high as the binding affinity for the same ROR1 protein of the corresponding form of the anti-ROR1 antibody R12 or antigen-binding fragment thereof, which is optionally an scFv fragment of R12.

In some of any such embodiments, the antibody or fragment specifically binds to the same or an overlapping epitope of a ROR1 protein, such as a human ROR1 protein, as the epitope specifically bound by the anti-ROR1 antibody R12 or an antigen-binding fragment thereof, which is optionally an scFv fragment of R12. In some embodiments, the antibody or fragment inhibits the binding of the anti-ROR1 antibody R12 or an antigen-binding fragment thereof, which is optionally an scFv fragment of R12, to a ROR1 protein, such as a human ROR1 protein, by greater than or greater than about 80%, 81%, 82%, 83%, 84%, 85%, 86%, 87%, 88%, 89%, 90%, 91%, 92%, 93%, 94%, 95%, 96%, 97%, 98%, or 99%, such as greater than or greater than about 80% or greater than or greater than about 90%.

In some of any such embodiments, the ROR1 protein is a human ROR1 protein and the antibody or fragment binds to a human ROR1 protein. In some embodiments, the human ROR1 protein has the amino acid sequence set forth in SEQ ID NO: 103. In some embodiments, provided are anti-human ROR1 antibodies.

In some of any such embodiments, the antibody or fragment binds an epitope within an extracellular portion of the ROR1 protein, such as a human ROR1 protein. In some embodiments, the extracellular portion of ROR1 contains the amino acids 1-377 of SEQ ID NO: 103. In some of any such embodiments, the antibody or fragment binds to an epitope of a ROR1 protein, such as a human ROR1 protein, containing residues within the fz domain or the Ig domain of the ROR1 protein. In some embodiments, the epitope contains a residue within the fz domain of the ROR1 protein and a residue within the Ig domain of the ROR1 protein. In some embodiments, the Ig domain is one that contains residues 13-118 of the amino acid sequence set forth in SEQ ID NO: 103; and/or the fz domain contains residues 136-270 of the amino acid sequence set forth in SEQ ID NO:103.

In some embodiments, the ROR1 protein is a mouse ROR1 protein and the antibody or fragment binds to a mouse ROR1 protein. In some embodiments, the mouse ROR1 protein has the amino acid sequence set forth in SEQ ID NO:106. In some embodiments, the antibody or fragment binds to an overlapping epitope of a human ROR1 protein as the epitope specifically bound by the anti-ROR1 antibody R12 or an antigen-binding fragment thereof, which is optionally an scFv fragment of R12 and the antibody or fragment also binds to mouse ROR1.

In some of any such embodiments, the antibody or fragment does not specifically bind to a mouse ROR1 protein or does not specifically bind to a protein having the amino acid sequence set forth in SEQ ID NO: 106.

In some of any such embodiments, the antibody or fragment does not contain the CDR-H1, CDR-H2, CDR-H3 and/or CDR-L1, CDR-L2, CDR-L3 sequences of the anti-ROR1 antibody, R12, and/or of the anti-ROR1 antibody 2A2. In some embodiments, the antibody or fragment does not contain a CDR-H1, CDR-H2, CDR-H3, CDR-L1, CDR-L2 and/or CDR-L3 sequences having at least 90%, 91%, 92%, 93%, 94%, 95%, 96%, 97%, 98% or 99% identity to the CDR-H1, CDR-H2, CDR-H3 and/or CDR-L1, CDR-L2, CDR-L3 sequences of the anti-ROR1 antibody, R12, and/or of the anti-ROR1 antibody 2A2.

In some of any such embodiments, the antibody or fragment is human.

Provided are human antibodies or antigen-binding fragments thereof that specifically bind to the same or an overlapping epitope of a ROR1 protein, such as a human ROR1 protein, as the epitope specifically bound by any of the above provided antibodies or antigen-binding fragments thereof or by the anti-ROR1 antibody designated R12 or an antigen-binding fragment thereof. Also provided are human antibodies or antigen-binding fragments thereof that specifically bind to ROR1 and competes for binding to ROR1, such as a human ROR1 protein, with any of the above provided antibodies or antigen-binding fragments thereof or by the anti-ROR1 antibody designated R12 or antigen-binding fragment thereof. In some such embodiments, the human antibody or fragment contains a CDR-H1, CDR-H2, CDR-H3, CDR-L1, CDR-L2 and/or CDR-L3 that is distinct from a corresponding CDR-H1, CDR-H2, CDR-H3, CDR-L1, CDR-L2 and/or CDR-L3 present in an antibody designated R12 and/or 2A2.

In some of any such embodiments, the human antibody or fragment contains a $V_H$ region with a portion having at least 95%, 96%, 97%, 98%, 99%, or 100% sequence identity to an amino acid sequence encoded by a germline nucleotide human heavy chain V segment, a portion with at least 95%, 96%, 97%, 98%, 99%, or 100% sequence identity to an amino acid sequence encoded by a germline nucleotide human heavy chain D segment, and/or a portion having at least 95%, 96%, 97%, 98%, 99%, or 100% sequence identity to an amino acid sequence encoded by a germline nucleotide human heavy chain J segment. In some of any such embodiments, the human antibody or fragment contains vale region with a portion with at least 95%, 96%, 97%, 98%, 99%, or 100% sequence identity to an amino acid sequence encoded by a germline nucleotide human kappa or lambda chain V segment, and/or a portion with at least 95%, 96%, 97%, 98%, 99%, or 100% sequence identity to an amino acid sequence encoded by a germline nucleotide human kappa or lambda chain J segment.

In some of any such embodiments, the human antibody or fragment contains a CDR-H1 and/or CDR-H2 that has a sequence 100% identical or with no more than one amino acid difference as compared to an amino acid sequence of a CDR-H1 and/or CDR-H2, respectively, within a sequence encoded by a germline nucleotide human heavy chain V segment; and/or contains a CDR-L1 and/or CDR-L2 that has a sequence 100% identical or with no more than one amino acid difference as compared to an amino acid sequence of a CDR-L1 and/or CDR-L2, respectively, within a sequence encoded by a germline nucleotide human kappa or lambda v segment.

In some of any such embodiments, the antibody or fragment is recombinant. In some of any such embodiments, the antibody or fragment is monoclonal.

In some of any such embodiments, the antibody or fragment is an antigen-binding fragment. In some embodiments, the antibody is a single chain fragment. In some embodiments, the antibody is a single domain antibody, such as a single domain antibody containing only a $V_H$ region. In some embodiments, the antibody contains both a $V_H$ region and a $V_L$ region and is a fragment in which the antibody variable regions are joined by a flexible linker.

In some of any such embodiments, the fragment is an scFv. In some embodiments, the scFv contains a linker having the sequence set forth SEQ ID NO: 91. In some embodiments, the scFv contains the amino acid sequence set forth in SEQ ID NO: 2, 4, 6, 12, 249, 250, 251, 252, 253, 254, 255, 256, 257, 258, 259, 260, 261, 262, 263, 264, 265, 266, 267 or 268, or a sequence of amino acids that exhibits at least 90%, 91%, 92%, 93%, 94%, 95%, 96%, 97%, 98% or 99% sequence identity to the amino acid sequence set forth in SEQ ID NO: 2, 4, 6, 12, 249, 250, 251, 252, 253, 254, 255, 256, 257, 258, 259, 260, 261, 262, 263, 264, 265, 266, 267 or 268. In some embodiments, the scFv contains the amino acid sequence set forth in SEQ ID NO: 2, 4, 6, or 12, or a sequence of amino acids that exhibits at least 90%, 91%, 92%, 93%, 94%, 95%, 96%, 97%, 98% or 99% sequence identity to the amino acid sequence set forth in SEQ ID NO: 2, 4, 6, or 12. In some embodiments, the scFv contains the amino acid sequence set forth in SEQ ID NO: 2, 4, 6, or 12.

In some aspects, the scFv contains the $V_H$, linker and $V_L$ as set forth in SEQ ID NO: 2, 4, 6, 12, 249, 250, 251, 252, 253, 254, 255, 256, 257, 258, 259, 260, 261, 262, 263, 264, 265, 266, 267 or 268, or a sequence at least at or about 90%, 91%, 92%, 93%, 94%, 95%, 96%, 97%, 98%, or 99% identical to such a sequence, but in which the $V_H$ and $V_L$ are configured in the opposite orientation, i.e. $V_L$-$V_H$, as compared to such sequence.

In some embodiments, the antibody or fragment comprises the $V_H$ region set forth in SEQ ID NO: 19 and the $V_L$ region set forth in SEQ ID NO: 18, and/or the antibody or fragment comprises the sequence of amino acids set forth in SEQ ID NO: 12. In some embodiments, the antibody or fragment comprises the $V_H$ region set forth in SEQ ID NO: 13 and the $V_L$ region set forth in SEQ ID NO: 14, and/or the antibody or fragment comprises the sequence of amino acids set forth in SEQ ID NO: 6. In some embodiments, the antibody or fragment comprises the $V_H$ region set forth in SEQ ID NO: 15 and the $V_L$ region set forth in SEQ ID NO: 16, and/or the antibody or fragment comprises the sequence of amino acids set forth in SEQ ID NO: 4. In some embodiments, the antibody or fragment comprises the $V_H$ region set forth in SEQ ID NO: 17 and the $V_L$ region set forth in SEQ ID NO: 18, and/or the antibody or fragment comprises the sequence of amino acids set forth in SEQ ID NO: 2.

Provided is a single chain cell-surface protein containing any of the provided single chain antibody fragment. In some embodiments, the single chain cell surface protein contains any of the provided single domain antibodies. In some embodiments, the single chain cell surface protein contains the $V_H$ sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209. In some embodiment, the single chain cell surface protein contains the $V_H$ region sequence having the sequence set forth in SEQ ID NO: 8, 10, 13, 15, 17, or 19. In some embodiments, the single chain cell surface protein contains any of the provided scFv antibody fragments. In some embodiments, the single chain cell surface protein contains the scFv sequence of SEQ ID NO: 2, 4, 6, 12, 249, 250, 251, 252, 253, 254, 255, 256, 257, 258, 259, 260, 261, 262, 263, 264, 265, 266, 267 or 268. In some embodiment, the single chain cell surface protein contains the scFv sequence of SEQ ID NO: 2, 4, 6 or 12. In some embodiments, the single chain cell surface protein contains the scFv sequence of SEQ ID NO: 2, 4, 6, 12, 249, 250, 251, 252, 253, 254, 255, 256, 257, 258, 259, 260, 261, 262, 263, 264, 265, 266, 267 or 268, but in which the VH and VL are configured in the opposite orientation, i.e. VL-VH, as compared to such sequence.

In some of any such embodiments, the antibody or fragment further contains at least a portion of an immunoglobulin constant region. In some embodiments, the antibody or fragment further contains a spacer. In some embodiments, the antibody or fragment contains a spacer set forth in SEQ ID NO: 108. In some embodiments, the antibody or fragment contains a spacer set forth in SEQ ID NO: 142. In some embodiments, the antibody or fragment contains a spacer set forth in SEQ ID NO: 143. In some embodiments, the antibody or fragment contains an immunoglobulin constant region containing an Fc region. In some embodiments, the Fc region is an Fc region of a human IgG.

Also provided is a conjugate containing any of the provided antibodies or fragments. Also provided is a conjugate containing any of the provided single chain cell-surface proteins. In some embodiments, the conjugate contains a heterologous moiety that is linked directly or indirectly to the antibody or antigen-binding fragment. In some embodiments, the conjugate can be a fusion protein or chimeric molecule. In some embodiments, the heterologous moiety is an effect domain.

In some embodiments, provided is a conjugate, fusion protein or chimeric molecule containing a) any of the provided antibodies or antigen-binding fragments and b) an effector domain. In some embodiments, the effector domain is not naturally associated in a single polypeptide chain with the antibody or antigen-binding fragment thereof. In some embodiments, the effector domain is a chemotherapeutic agent or toxin. In some embodiments, the effector domain contains a signaling domain that is capable of delivering a signal to a cell, such as an immune cell, such as a lymphocyte, for example, an activating signal, a costimulatory signal, a suppressive signal and/or an inhibitory signal.

Also provided is a chimeric antigen receptor (CAR) including an extracellular portion containing any of the provided antibodies or antigen-binding fragments and an intracellular signaling domain. In some embodiments, the antibody or fragment is an scFv and the intracellular signaling domain contains an ITAM. In some embodiments, the intracellular signaling domain contains a signaling domain of a zeta chain of a CD3-zeta (CD3ζ) chain.

In some of any such embodiments, the CAR also contains a transmembrane domain linking the extracellular domain and the intracellular signaling domain. In some embodiments, the transmembrane domain contains a transmembrane portion of a costimulatory molecule, such as a T cell costimulatory molecule, e.g., CD28 and/or 41BB. In some embodiments, the T cell costimulatory molecule is CD28 or 41BB. In some embodiments, the intracellular signaling domain also includes an intracellular domain of a T cell costimulatory molecule. In some aspects, the T cell costimulatory molecule is CD28 or 41BB.

In some embodiments of any of the provided CARs, the CAR contains an antibody or antigen-binding fragment as provided herein, a transmembrane domain that is a portion of CD28 or variant thereof, and an intracellular signaling domain containing a signaling portion of CD28 or functional variant thereof and a signaling portion of CD3 zeta or functional variant thereof. In some such embodiments, the receptor further includes a spacer containing an Ig hinge, e.g., an IgG4 hinge, such as a hinge-only spacer, between the antibody or antigen-binding fragment and the transmembrane domain.

In some embodiments of any of the provided CARs, the CAR contains an antibody or antigen-binding fragment as provided herein, a transmembrane domain that is a portion of CD28 or variant thereof, and an intracellular signaling domain containing a signaling portion of a 4-1BB or functional variant thereof and a signaling portion of CD3 zeta or functional variant thereof. In some such embodiments, the receptor further includes a spacer containing an Ig hinge, e.g., an IgG4 hinge, such as a hinge-only spacer, between the antibody or antigen-binding fragment and the transmembrane domain.

Provided are nucleic acids encoding any of the provided antibodies or fragments thereof, any of the provided single chain cell-surface proteins, any of the provided conjugates, or any of the provided CARs. In some embodiments, the nucleic acid molecule encoding an antibody or antigen-binding fragment comprises the sequence of nucleotides set forth in SEQ ID NO:7 or 9 or a sequence of nucleotides that exhibits at least 90%, 91%, 92%, 93%, 94%, 95%, 96%, 97%, 98%, 99% or more sequence identity to the sequence set forth in SEQ ID NO:7 or 9. In some embodiments, the nucleic acid molecule encoding an antibody or antigen-binding fragment comprises the sequence of nucleotides set forth in SEQ ID NO: 1, 3, 5 or 11 or a sequence of nucleotides that exhibits at least 90%, 91%, 92%, 93%, 94%, 95%, 96%, 97%, 98%, 99% or more sequence identity to the sequence set forth in SEQ ID NO: 1, 3, 5 or 11.

Also provided are cells that contain any of the provided antibodies or fragments, any of the provided single chain cell-surface proteins, any of the provided conjugates, or any of the provided CARs. In some embodiments, the cell is an engineered cell expressing a receptor and contains any of the provided antibodies or fragments, any of the single chain cell-surface proteins, any of the provided conjugates, or any of the provided CARs. In some embodiments, the cell or engineered cell is a T cell.

Provided are compositions or pharmaceutical compositions containing any of the provided antibodies or fragments, any of the provided single chain cell-surface proteins, any of the provided conjugates, any of the provided CARs or any of the provided cells. In some embodiments, the composition or pharmaceutical composition contains a pharmaceutically acceptable excipient.

Provided are methods of treatments that include administering any of the provided compositions or pharmaceutical compositions to a subject having a disease or disorder associated with ROR1. Provided are methods of treatment that include administering any of the provided antibodies or fragments, any of the provided single chain cell-surface proteins, any of the provided conjugates, any of the provided CARs or any of the provided cell to a subject having a disease or disorder associated with ROR1.

Provided are any of the provided compositions or pharmaceutical compositions for use in treating a disease or disorder associated with ROR1. Provided is use of any of the provided compositions or pharmaceutical compositions for the manufacture of a medicament for treating a disease or disorder associated with ROR1.

In some of any such embodiments, the disease or disorder is a ROR-1-expressing cancer. In some embodiments, the ROR-1-expressing cancer is a B cell leukemia, lymphoma, B cell chronic lymphocytic leukemia (CLL), AML, acute myeloid leukemia (AML), acute lymphocytic leukemia (ALL), Burkett's Lymphoma, mantle cell lymphoma (MCL), non-small cell lung cancer (NSCLC), neuroblastoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, uterine cancer, adrenal cancer or head and neck cancer.

In some embodiments, administration of the antibody or receptor, or conjugate or cell containing the same, is associated with a lower degree of immunogenicity as compared to administration of a reference antibody (or receptor containing the reference antibody) that competes for binding with the antibody or binds to an overlapping epitope. In some aspects, the reference antibody is a humanized, chimeric, or non-human antibody.

DETAILED DESCRIPTION

Figure 1A:
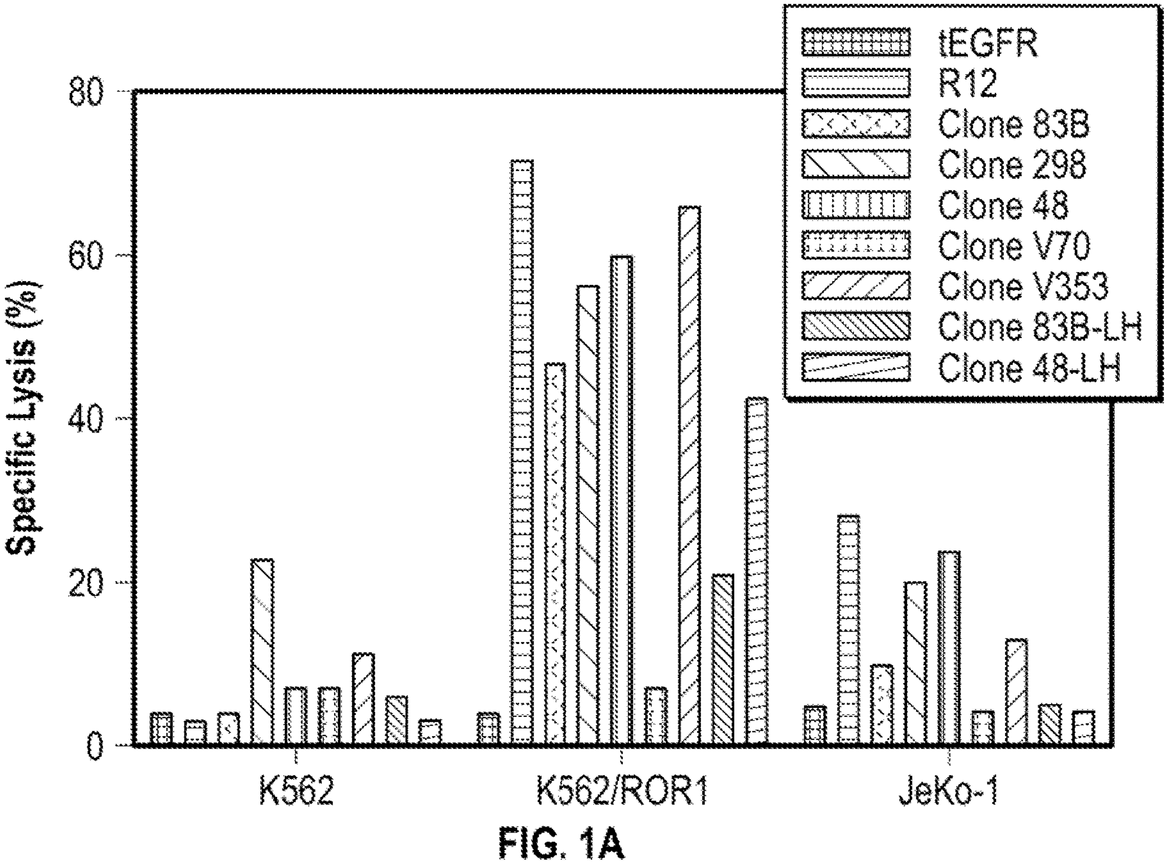
FIG. 1A shows cytolytic activity of primary human CD8+ T cells expressing various anti-ROR1 specific CARs against ROR1-expressing cells. tEGFR alone is a negative control; R12 is R12 scFv CAR.

Provided are ROR1-binding molecules, including antibodies (including antigen-binding antibody fragments, such as heavy chain variable (VH) regions and single chain fragments, including scFvs) and recombinant receptors, including chimeric receptors containing such antibodies and fragments, nucleic acids encoding such antibodies and fragments, and cells, such as recombinant cells, expressing and for production of these antibodies and fragments. The invention also provides methods of making and using the antibodies and fragments as well as cells expressing or containing the antibodies and fragments.

I. ROR1 BINDING MOLECULES

Provided in some aspects are ROR1 binding molecules, such as ROR1-binding polypeptides. Such binding molecules include antibodies (including antigen-binding fragments) that specifically bind to ROR1 proteins, such as human ROR1 protein. Also among the binding molecules are polypeptides containing such antibodies, including single chain cell surface proteins, e.g., recombinant receptors such as chimeric antigen receptors, containing such antibodies.

A. ROR1 Antibodies

Provided are anti-ROR1 antibodies, including functional antibody fragments. In some embodiments, the antibodies include those that are single domain antibodies, containing a variable heavy chain that without pairing with a light chain antigen-binding site and/or without any additional antibody domain or binding site are capable of specifically binding to ROR1. Also among the antibodies are multi-domain antibodies, such as those containing $V_H$ and $V_L$ domains, comprised of the $V_H$ domain or antigen-binding site thereof of the single-domain antibody. In some embodiments, the antibodies include a variable heavy chain and a variable light chain, such as scFvs. The antibodies include antibodies that specifically bind to ROR1, e.g., human ROR1. Among the provided anti-ROR1 antibodies are human antibodies.

The antibodies include isolated antibodies. The molecules include isolated molecules. Also provided are molecules containing such antibodies, e.g., single-chain proteins, fusion proteins, and/or recombinant receptors such as chimeric receptors, including antigen receptors.

The term "antibody" herein is used in the broadest sense and includes polyclonal and monoclonal antibodies, including intact antibodies and functional (antigen-binding) antibody fragments, including fragment antigen binding (Fab) fragments, F(ab')2 fragments, Fab' fragments, Fv fragments, recombinant IgG (rIgG) fragments, variable heavy chain ($V_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and subclasses thereof, IgM, IgE, IgA, and IgD.

The terms "complementarity determining region," and "CDR," synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273,927-948 ("Chothia" numbering scheme), MacCallum et al., J. Mol. Biol. 262: 732-745 (1996), "Antibody-antigen interactions: Contact analysis and binding site topography," J. Mol. Biol. 262, 732-745," ("Contact" numbering scheme), Martin et al., Proc. Natl. Acad. Sci., 86:9268-9272 (1989) ("AbM" numbering scheme), Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme), and Honegger A and Plückthun A, "Yet another numbering scheme for immunoglobulin variable domains: an automatic modeling and analysis tool," J Mol Biol, 2001 Jun. 8; 309(3):657-70, ("Aho" numbering scheme).

The boundaries of a given CDR or FR may vary depending on the scheme used for identification. For example, the Kabat scheme is based structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

Table 1, below, lists exemplary position boundaries of CDR-L1, CDR-L2, CDR-L3 and CDR-H1, CDR-H2, CDR-H3 as identified by Kabat, Chothia, and Contact schemes, respectively. For CDR-H1, residue numbering is listed using both the Kabat and Chothia numbering schemes. FRs are located between CDRs, for example, with FR-L1 located between CDR-L1 and CDR-L2, and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

TABLE 1

| CDR | Kabat | Chothia | AbM | Contact |
|---|---|---|---|---|
| CDR-L1 | L24-L34 | L24-L34 | L24-L34 | L30-L36 |
| CDR-L2 | L50-L56 | L50-L56 | L50-L56 | L46-L55 |
| CDR-L3 | L89-L97 | L89-L97 | L89-L97 | L89-L96 |
| CDR-H1 Kabat Numbering[1]) | H31-H35B | H26-H32 . . . 34 | H26-H35B | H30-H35B |
| CDR-H1 (Chothia Numbering[2]) | H31-H35 | H26-H32 | H26-H35 | H30-H35 |
| CDR-H2 | H50-H65 | H52-H56 | H50-H58 | H47-H58 |
| CDR-H3 | H95-H102 | H95-H102 | H95-H102 | H93-H101 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273,927-948

Thus, unless otherwise specified, a "CDR" or "complementary determining region," or individual specified CDRs (e.g., "CDR-H1, CDR-H2), of a given antibody or region thereof, such as a variable region thereof, should be understood to encompass a (or the specific) complementary determining region as defined by any of the aforementioned schemes. For example, where it is stated that a particular CDR (e.g., a CDR-H3) contains the amino acid sequence of a corresponding CDR in a given $V_H$ or $V_L$ amino acid sequence, it is understood that such a CDR has a sequence of the corresponding CDR (e.g., CDR-H3) within the variable region, as defined by any of the aforementioned schemes. In some embodiments, specific CDR sequences are specified.

Likewise, unless otherwise specified, a FR or individual specified FR(s) (e.g., FR-H1, FR-H2), of a given antibody or region thereof, such as a variable region thereof, should be understood to encompass a (or the specific) framework region as defined by any of the known schemes. In some instances, the scheme for identification of a particular CDR, FR, or FRs or CDRs is specified, such as the CDR as defined by the Kabat, Chothia, or Contact method. In other cases, the particular amino acid sequence of a CDR or FR is given.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; variable heavy chain ($V_H$) regions, single-chain antibody molecules such as scFvs and single-domain $V_H$ single antibodies; and multispecific antibodies formed from antibody fragments. In particular embodiments, the antibodies are single-chain antibody fragments comprising a variable heavy chain region and/or a variable light chain region, such as scFvs.

Single-domain antibodies are antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some aspects, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Among the provided anti-ROR1 antibodies are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human. The term includes antigen-binding fragments of human antibodies.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived from human antibody libraries, including phage display and cell-free libraries, containing antibody-encoding sequences derived from a human repertoire.

Among the provided antibodies are monoclonal antibodies, including monoclonal antibody fragments. The term "monoclonal antibody" as used herein refers to an antibody obtained from or within a population of substantially homogeneous antibodies, i.e., the individual antibodies comprising the population are identical, except for possible variants containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. The term is not to be construed as requiring production of the antibody by any particular method. A monoclonal antibody may be made by a variety of techniques, including but not limited to generation from a hybridoma, recombinant DNA methods, phage-display and other antibody display methods.

The terms "polypeptide" and "protein" are used interchangeably to refer to a polymer of amino acid residues, and are not limited to a minimum length. Polypeptides, including the provided antibodies and antibody chains and other peptides, e.g., linkers and ROR1-binding peptides, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

Exemplary Antibodies

In some embodiments, the antibody, e.g., the anti-ROR1 antibody, e.g., antigen-binding antibody fragment, contains a heavy and/or light chain variable ($V_H$ or $V_L$) region sequence as described, or a sufficient antigen-binding portion thereof. In some embodiments, the anti-ROR1 antibody, e.g., antigen-binding antibody fragment, contains a $V_H$ region sequence or sufficient antigen-binding portion thereof that contains a CDR-H1, CDR-H2 and/or CDR-H3 as described. In some embodiments, the anti-ROR1 antibody, e.g., antigen-binding antibody fragment, contains a $V_L$ region sequence or sufficient antigen-binding portion that contains a CDR-L1, CDR-L2 and/or CDR-L2 as described. In some embodiments, the anti-ROR1 antibody, e.g., antigen-binding antibody fragment, contains a $V_H$ region sequence that contains a CDR-H1, CDR-H2 and/or CDR-H3 as described and contains a $V_L$ region sequence that contains a CDR-L1, CDR-L2 and/or CDR-L2 as described. Also among the provided antibodies are those having sequences at least at or about 90, 91, 92, 93, 94, 95, 96, 97, 98, or 99% identical to such a sequence.

In some embodiments, the antibody, e.g., antigen-binding fragment thereof, has a heavy chain variable ($V_H$) region having the amino acid sequence set forth in SEQ ID NO: 8, 10, 13, 15, 17 or 19, or an amino acid sequence that has at least 90%, 91%, 92%, 93%, 94%, 95%, 96%, 97%, 98%, or 99% sequence identity to the $V_H$ region amino acid sequence set forth in SEQ ID NO: 8, 10, 13, 15, 17, or 19, or contains a CDR-H1, CDR-H2, and/or CDR-H3 present in such a $V_H$ sequence.

In some embodiments, the $V_H$ region of the anti-ROR1 antibody is one that includes a heavy chain complementarity determining region 3 (CDR-H3) that contains the amino acid sequence: $X_1X_2X_3X_4X_5X_6X_7X_8X_9X_{10}X_{11}X_{12}X_{13}X_{14}X_{15}X_{16}$ (SEQ ID NO: 92), wherein $X_1$ is D, V, Q, I, T, G, A, or E; $X_2$ is S, F, N, R, G, T, Y, D, Q, M, K, I, L, or P; $X_3$ is S, N, G, E, D, P, I, V, R, F, N, or L; $X_4$ is Y, R, V, G, S, P, E, A, or L; $X_5$ is D, E, W, R, S, L, A, V, G, or P; $X_6$ is A, W, S, E, G, Y, R, F, H, V, D, S, or Q; $X_7$ is F, Y, A, W, L, G, D, V, N, S, K, or R; $X_8$ is F, Y, H, E, L, W, V, N, I, D, or null; $X_9$ is F, L, V, S, E, W, G, P, Y, or null; $X_{10}$ is S, E, L, Y, W, F, N, G, P, or null; $X_{11}$ is Y, V, L, F, I, W, N, or null; $X_{12}$ is F, Y, W, or null; $X_{13}$ is Y, F, T, or null; $X_{14}$ is F or null; $X_{15}$ is D or Q; and $X_{16}$ is I, Y, or P. In some such embodiments, in said CDR-H3, $X_1$ is D or V; $X_2$ is S or F; $X_3$ is S, N, G, or E; $X_4$ is Y, R, or V; $X_5$ is D, E, W, or R; $X_6$ is A, Y, S, or E; $X_7$ is F, Y, or A; $X_8$ is F, Y, H, or null; $X_9$ is F, L, or null; $X_{10}$ is S or null; $X_{11}$ is Y or null; $X_{12}$ is F or null; $X_{13}$ is null; $X_{14}$ is null; $X_{15}$ is D; and $X_{16}$ is I or Y. In some such embodiments, in said CDR-H3, $X_1$ is V or D; $X_2$ is S or F; $X_3$ is N or G; $X_4$ is Y or R; $X_5$ is E or W; $X_6$ is Y or G; $X_7$ is Y; $X_8$ is F or Y; $X_9$ is F or null; $X_{10}$ is null; $X_{11}$ is null; $X_{12}$ is null; $X_{13}$ is null; $X_{14}$ is null; $X_{15}$ is D; and $X_{16}$ is Y.

In some embodiments, the $V_H$ region of the anti-ROR1 antibody is one that includes a CDR-H3 that contains the amino acid sequence: $X_1X_2X_3X_4X_5X_6X_7X_8X_9X_{10}X_{11}X_{12}DX_{14}$ (SEQ ID NO: 93), wherein $X_1$ is D or V; $X_2$ is S or F; $X_3$ is S, N, G, or E; $X_4$ is Y, R, or V; $X_5$ is D, E, W, or R; $X_6$ is A, Y, S, or E; $X_7$ is F, Y, or A; $X_8$ is F, Y, H, or null; $X_9$ is F, L, or null; $X_{10}$ is S or null; $X_{11}$ is Y or null; $X_{12}$ is F or null; and $X_{14}$ is I or Y.

In some embodiments, the $V_H$ region of the anti-ROR1 antibody is one that includes a CDR-H3 that contains the amino acid sequence: $X_1X_2X_3X_4X_5X_6YX_8X_9DY$ (SEQ ID NO: 94), wherein $X_1$ is V or D; $X_2$ is S or F; $X_3$ is N or G; $X_4$ is Y or R; $X_5$ is E or W; $X_6$ is Y or G; $X_8$ is F or Y; and $X_9$ is F or null.

In some embodiments, the $V_H$ region of the anti-ROR1 antibody is one that includes a CDR-H3 that contains the amino acid sequence: $X_1SX_3YX_5X_6$ $X_7X_8DX_{10}$ (SEQ ID NO: 109), wherein $X_1$ is V or D; $X_3$ is S or N; $X_5$ is D or E; $X_6$ is Y or A; $X_7$ is F or Y; $X_8$ is F or null; and $X_{10}$ is I or Y.

In some embodiments, the $V_H$ region of the anti-ROR1 antibody is one that includes a CDR-H3 that contains the amino acid sequence: $VX_2X_3X_4EYYFDY$ (SEQ ID NO: 110), wherein $X_2$ is S or N or R; $X_3$ is N or G; $X_4$ is Y or G or S.

In some embodiments, the provided antibody contains a CDR-H3 having the amino acid sequence set forth in SEQ ID NO: 22, 29, 35, 45, 50, 51, 52, 53, 54, 55, 56, 57, 58, 59, 60, 61, 62, 63, 64, 65, 66, 67, 68, 69, 70, 71 or 174. In any of such examples, the provided antibody can contain a $V_H$ region sequence set forth in any of SEQ ID NOs: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209 in which the corresponding CDR-H3 sequence contained therein (e.g. corresponding to amino acid residues H95-H102 by Kabat numbering) is replaced by the CDR-H3 sequence set forth in SEQ ID NO: 22, 29, 35, 45, 50, 51, 52, 53, 54, 55, 56, 57, 58, 59, 60, 61, 62, 63, 64, 65, 66, 67, 68, 69, 70, 71 or 174.

In some embodiments, the provided antibody contains a CDR-H3 having the amino acid sequence set forth in SEQ ID NO: 22, 29, 35, 45, or 52. In some embodiments, the provided antibody contains a CDR-H3 set forth in SEQ ID NO: 22, 29 or 35. In some embodiments, the provided antibody contains a CDR-H3 set forth in SEQ ID NO: 29 or 35. In some embodiments, the provided antibody contains a CDR-H3 having the amino acid sequence set forth in SEQ ID NO: 29 or 52. In some embodiments, the provided antibody contains a CDR-H3 contained within the CDR-H3 of the $V_H$ region amino acid sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209. In some embodiments, the provided antibody contains a CDR-H3 contained within the CDR-H3 of the $V_H$ region amino acid sequence set forth in SEQ ID NO: 8 or 10. In some embodiments, the provided antibody contains a CDR-H3 contained within the CDR-H3 of the $V_H$ region amino acid sequence set forth in SEQ ID NO: 10, 13, 15, 17 or 19. In some embodiments, the provided antibody contains a CDR-H3 contained within the CDR-H3 of the $V_H$ region amino acid sequence set forth in SEQ ID NO: 13, 15 or 19. In some embodiments, the provided antibody contains a CDR-H3 contained within the CDR-H3 of the $V_H$ region amino acid sequence set forth in SEQ ID NO: 13 or 15.

In some embodiments, the $V_H$ region of the anti-ROR1 antibody is one that includes a heavy chain complementarity determining region 1 (CDR-H1) that contains the amino acid sequence: $X_1X_2X_3MX_5$ (SEQ ID NO: 95), wherein $X_1$ is S, D, or N; $X_2$ is Y or A; $X_3$ is Y, A, or W; and $X_5$ is H or S. In some embodiments, in said CDR-H1, $X_1$ is D or N; $X_2$ is Y or A; $X_3$ is A or W; and $X_5$ is S.

In some embodiments, the $V_H$ region of the anti-ROR1 antibody is one that includes a CDR-H1 that contains the amino acid sequence: $X_1X_2X_3MS$ (SEQ ID NO: 97), wherein $X_1$ is D or N; $X_2$ is Y or A; and $X_3$ is A or W.

In some embodiments, the provided antibody contains a CDR-H1 having the amino acid sequence set forth in SEQ ID NO: 20, 27, 33, 155, 156, 157, 158, 159, 160, 161, 162 or 163. In some embodiments, the provided antibody contains a CDR-H1 having the amino acid sequence set forth in SEQ ID NO: 269, 270, 271, 272, 273, 274, 275, 276, 277, 278 or 279. In some embodiments, the provided antibody contains a CDR-H1 having the amino acid sequence set forth in SEQ ID NO: 75, 77, 79, 280, 281, 282, 283, 284, 285, 286, 287, 288, 289 or 290. In some embodiments, the provided antibody contains a CDR-H1 having the amino acid sequence set forth in SEQ ID NO: 20, 27, 33, 75, 77, 79, 269, 270 or 271. In some embodiments, the provided antibody contains a CDR-H1 having the amino acid sequence set forth in SEQ ID NO: 27, 33, 77, 79, 270 or 271. In some embodiments, the provided antibody contains a CDR-H1 having the amino acid sequence set forth in SEQ ID NO: 74, 76 or 78. In some embodiments, the provided antibody contains a CDR-H1 contained within the CDR-H1 of the $V_H$ region amino acid sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209. In some embodiments, the provided antibody contains a CDR-H1 contained within the CDR-H1 of the $V_H$ region amino acid sequence set forth in SEQ ID NO: 8 or 10. In some embodiments, the provided antibody contains a CDR-H1 contained within the CDR-H1 of the $V_H$ region amino acid sequence set forth in SEQ ID NO: 10, 13, 15, 17 or 19. In some embodiments, the provided antibody contains a CDR-H1 contained within the CDR-H1 of the $V_H$ region amino acid sequence set forth in SEQ ID NO: 13, 15 or 19. In some embodiments, the provided antibody contains a CDR-H1 contained within the CDR-H1 of the $V_H$ region amino acid sequence set forth in SEQ ID NO: 13 or 15.

In some embodiments, the $V_H$ region of the anti-ROR1 antibody is one that includes a heavy chain complementarity determining region 2 (CDR-H2) that contains the amino acid sequence: $X_1IX_3X_4X_5X_6X_7GX_9X_{10}TX_{12}X_{13}AX_{15}X_{16}X_{17}X_{18}G$ (SEQ ID NO: 96), wherein $X_1$ is I, S, or R; $X_3$ is N, S, or K; $X_4$ is P, G, or S; $X_5$ is K or null; $X_6$ is T or null; $X_7$ is S, D, or N; $X_9$ is G or R; $X_{10}$ is S or T; $X_{12}$ is S or D; $X_{13}$ is Y or H; $X_{15}$ is Q, D, or A; $X_{16}$ is K, Y, or P; $X_{17}$ is F or V; and $X_{18}$ is Q or K. In some embodiments in said CDR-H2, $X_1$ is S or R; $X_3$ is S or K; $X_4$ is G or S; $X_5$ is K or null; $X_6$ is T or null; $X_7$ is S or D; $X_9$ is G or R; $X_{10}$ is S or T; $X_{12}$ is D; $X_{13}$ is Y or H; $X_{15}$ is D or A; $X_{16}$ is Y or P; $X_{17}$ is F; and $X_{18}$ is K In some embodiments, the $V_H$ region of the anti-ROR1 antibody is one that includes a CDR-H2 that contains the amino acid sequence: $X_1IX_3X_4X_5X_6X_7GX_9X_{10}TX_{12}X_{13}AX_{15}X_{16}X_{17}X_{18}G$ (SEQ ID NO: 98), wherein $X_1$ is I, S, or R; $X_3$ is N, S, or K; $X_4$ is P, G, or S; $X_5$ is K or null; $X_6$ is T or null; $X_7$ is S, D, or N; $X_9$ is G or R; $X_{10}$ is S or T; $X_{12}$ is S or D; $X_{13}$ is Y or H; $X_{15}$ is Q, D, or A; $X_{16}$ is K, Y, or P; $X_{17}$ is F or V; and $X_{18}$ is Q or K.

In some embodiments, the provided antibody contains a CDR-H2 having the amino acid sequence set forth in SEQ ID NO: 21, 26, 28, 34, 164, 165, 166, 167, 168, 169, 170, 171, 172, 173 or 318. In some embodiments, the provided antibody contains a CDR-H2 having the amino acid sequence set forth in SEQ ID NO: 291, 292, 293, 294, 295, 296, 297, 298, 299, 300, 301, 302 or 303. In some embodiments, the provided antibody contains a CDR-H2 having the amino acid sequence set forth in SEQ ID NO: 304, 305, 306, 307, 308, 309, 310, 311, 312, 313, 314, 315, 316 or 317. In some embodiments, the provided antibody contains a CDR-H2 having the amino acid sequence set forth in SEQ ID NO: 21, 26, 28, 34, 291, 292, 293, 294, 304, 305, 306, 307. In some embodiments, the provided antibody contains a CDR-H2 having the amino acid sequence set forth in SEQ ID NO: 26, 28, 34, 291, 292, 294, 304, 305 or 307. In some embodiments, the provided antibody contains a CDR-H2 having the amino acid sequence set forth in SEQ ID NO: 28, 34, 291, 292, 304 or 305. In some embodiments, the provided antibody contains a CDR-H2 having the amino acid sequence set forth in SEQ ID NO: 80, 81, 82 or 83. In some embodiments, the provided antibody contains a CDR-H2 contained within the CDR-H2 of the $V_H$ region amino acid sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209. In some embodiments, the provided antibody contains a CDR-H2 contained within the CDR-H2 of the $V_H$ region amino acid sequence set forth in SEQ ID NO:8 or 10. In some embodiments, the provided antibody contains a CDR-H2 contained within the CDR-H2 of the $V_H$ region amino acid sequence set forth in SEQ ID NO: 10, 13, 15, 17 or 19. In some embodiments, the provided antibody contains a CDR-H2 contained within the CDR-H2 of the $V_H$ region amino acid sequence set forth in SEQ ID NO: 13, 15 or 19. In some embodiments, the provided antibody contains a CDR-H2 contained within the CDR-H2 of the $V_H$ region amino acid sequence set forth in SEQ ID NO: 13 or 15.

In some embodiments, the provided antibody contains a CDR-H1 having the amino acid sequence set forth in SEQ ID NO: 20, 27, 33, 155, 156, 157, 158, 159, 160, 161, 162 or 163; a CDR-H2 having the amino acid sequence set forth in SEQ ID NO: 21, 26, 28, 34, 164, 165, 166, 167, 168, 169, 170, 171, 172, 173 or 318; and a CDR-H3 having the amino acid sequence set forth in SEQ ID NO: 22, 29, 35, 45, 50, 51, 52, 53, 54, 55, 56, 57, 58, 59, 60, 61, 62, 63, 64, 65, 66, 67, 68, 69, 70, 71 or 174. In some embodiments, the provided antibody contains a CDR-H1 having the amino acid sequence set forth in SEQ ID NO: 269, 270, 271, 272, 273, 274, 275, 276, 277, 278 or 279; a CDR-H2 having the amino acid sequence set forth in SEQ ID NO: 291, 292, 293, 294, 295, 296, 297, 298, 299, 300, 301, 302 or 303; and a CDR-H3 having the amino acid sequence set forth in SEQ ID NO: 22, 29, 35, 45, 50, 51, 52, 53, 54, 55, 56, 57, 58, 59, 60, 61, 62, 63, 64, 65, 66, 67, 68, 69, 70, 71 or 174. In some embodiments, the provided antibody contains a CDR-H1 having the amino acid sequence set forth in SEQ ID NO: 75, 77, 79, 280, 281, 282, 283, 284, 285, 286, 287, 288 or 289; a CDR-H2 having the amino acid sequence set forth in SEQ ID NO: 304, 305, 306, 307, 308, 309, 310, 311, 312, 313, 314, 315, 316 or 317; and a CDR-H3 having the amino acid sequence set forth in SEQ ID NO: 22, 29, 35, 45, 50, 51, 52, 53, 54, 55, 56, 57, 58, 59, 60, 61, 62, 63, 64, 65, 66, 67, 68, 69, 70, 71 or 174.

In some embodiments, the provided antibody contains a CDR-H1 having the amino acid sequence set forth in SEQ ID NO: 20, 27, 33, 75, 77, 79, 269, 270, or 271, a CDR-H2 having the amino acid sequence set forth in SEQ ID NO: 21, 26, 28, 34, 291, 292, 293, 294, 304, 305 306 or 307; and a CDR-H3 having the amino acid sequence set forth in SEQ ID NO: 22, 29, 35, 45, 50, 51, 52, 53, 54, 55, 56, 57, 58, 59, 60, 61, 62, 63, 64, 65, 66, 67, 68, 69, 70, 71 or 174. In some embodiments, the provided antibody contains a CDR-H1 having the amino acid sequence set forth in SEQ ID NO: 20, 27, 33, 75, 77, 79, 269, 270, or 271; a CDR-H2 having the amino acid sequence set forth in SEQ ID NO: 21, 26, 28, 34, 291, 292, 293, 294, 304, 305 306 or 307; and a CDR-H3 having the amino acid sequence set forth in SEQ ID NO: 22, 29, 35 or 52. In some embodiments, the provided antibody contains a CDR-H1 having the amino acid sequence set forth in SEQ ID NO: 27, 33, 77, 79, 269, 271; a CDR-H2 having the amino acid sequence set forth in SEQ ID NO: 28, 34, 291, 292, 304 or 305; and a CDR-H3 having the amino acid sequence set forth in SEQ ID NO: 29 or 352.

In some embodiments, the CDR-H1, CDR-H2 and CDR-H3 contain the sequences of SEQ ID NOS: 20, 21, and 22, respectively; the CDR-H1, CDR-H2, and CDR-H3 contain the sequences of SEQ ID NOs: 20, 26, and 22, respectively; the CDR-H1, CDR-H2, and CDR-H3 contain the sequences of SEQ ID NOs: 27, 28, and 29, respectively; the CDR-H1, CDR-H2, and CDR-H3 contain the sequences of SEQ ID NOs: 33, 34, and 35, respectively; the CDR-H1, CDR-H2, and CDR-H3 contain the sequences of SEQ ID NOs: 33, 34, and 52, respectively; the CDR-H1, CDR-H2, and CDR-H3 contain the sequences of SEQ ID NOs: 27, 164 and 45, respectively; the CDR-H1, CDR-H2, and CDR-H3 contain the sequences of SEQ ID NOs: 27, 164 and 68, respectively; the CDR-H1, CDR-H2, and CDR-H3 contain the sequences of SEQ ID NOs: 27, 164 and 64, respectively; the CDR-H1, CDR-H2, and CDR-H3 contain the sequences of SEQ ID NOs: 27, 164 and 66, respectively; the CDR-H1, CDR-H2, and CDR-H3 having the sequences of SEQ ID NOs: 33, 318, and 35, respectively; the CDR-H1, CDR-H2, and CDR-H3 contain the sequences of SEQ ID NOs: 33, 34 and 70, respectively; the CDR-H1, CDR-H2, and CDR-H3 contain the sequences of SEQ ID NOs: 33, 34 and 55, respectively; the CDR-H1, CDR-H2, and CDR-H3 contain the sequences of SEQ ID NOs: 33, 34 and 53, respectively; the CDR-H1, CDR-H2, and CDR-H3 contain the sequences of SEQ ID NOs: 33, 34 and 56, respectively; the CDR-H1, CDR-H2, and CDR-H3 contain the sequences of SEQ ID NOs: 33, 34 and 61, respectively; the CDR-H1, CDR-H2, and CDR-H3 contain the sequences of SEQ ID NOs: 33, 34 and 59, respectively; the CDR-H1, CDR-H2, and CDR-H3 contain the sequences of SEQ ID NOs: 33, 171 and 60, respectively; the CDR-H1, CDR-H2, and CDR-H3 contain the sequences of SEQ ID NOs: 155, 34 and 35, respectively; the CDR-H1, CDR-H2, and CDR-H3 contain the sequences of SEQ ID NOs: 156, 34 and 35, respectively; the CDR-H1, CDR-H2, and CDR-H3 contain the sequences of SEQ ID NOs: 162, 170 and 50, respectively; the CDR-H1, CDR-H2, and CDR-H3 contain the sequences of SEQ ID NOs: 162, 170 and 51, respectively; the CDR-H1, CDR-H2, and CDR-H3 contain the sequences of SEQ ID NOs: 161, 169 and 54, respectively; the CDR-H1, CDR-H2, and CDR-H3 contain the sequences of SEQ ID NOs:159, 167 and 57, respectively; the CDR-H1, CDR-H2, and CDR-H3 contain the sequences of SEQ ID NOs: 160, 168 and 58, respectively; the CDR-H1, CDR-H2, and CDR-H3 contain the sequences of SEQ ID NOs: 158, 166 and 62, respectively; the CDR-H1, CDR-H2, and CDR-H3 contain the sequences of SEQ ID NOs: 158, 166 and 63, respectively; the CDR-H1, CDR-H2, and CDR-H3 contain the sequences of SEQ ID NOs: 158, 166 and 65, respectively; the CDR-H1, CDR-H2, and CDR-H3 contain the sequences of SEQ ID NOs: 157, 165 and 67, respectively; the CDR-H1, CDR-H2, and CDR-H3 contain the sequences of SEQ ID NOs: 163, 173 and 69, respectively; the CDR-H1, CDR-H2, and CDR-H3 contain the sequences of SEQ ID NOs: 160, 172, 71, respectively; or the CDR-H1, CDR-H2, and CDR-H3 contain the sequences of SEQ ID NOs: 160, 172, 174, respectively.

In some embodiments, the CDR-H1, CDR-H2 and CDR-H3 contain the sequences of SEQ ID NOS: 269, 293, and 22, respectively; the CDR-H1, CDR-H2, and CDR-H3 contain the sequences of SEQ ID NOs: 269, 294, and 22, respectively; the CDR-H1, CDR-H2, and CDR-H3 contain the sequences of SEQ ID NOs: 270, 292, and 29, respectively; the CDR-H1, CDR-H2, and CDR-H3 contain the sequences of SEQ ID NOs: 271, 291, and 35, respectively; the CDR-H1, CDR-H2, and CDR-H3 contain the sequences of SEQ ID NOs: 276, 291, and 35, respectively; the CDR-H1, CDR-H2, and CDR-H3 contain the sequences of SEQ ID NOs: 271, 291, and 52, respectively; the CDR-H1, CDR-H2, and CDR-H3 contain the sequences of SEQ ID NOs: 276, 291, and 52, respectively; the CDR-H1, CDR-H2, and CDR-H3 contain the sequences of SEQ ID NOs: 270, 296 and 45, respectively; the CDR-H1, CDR-H2, and CDR-H3 contain the sequences of SEQ ID NOs: 270, 296 and 68, respectively; the CDR-H1, CDR-H2, and CDR-H3 contain the sequences of SEQ ID NOs: 270, 296 and 64, respectively; the CDR-H1, CDR-H2, and CDR-H3 contain the sequences of SEQ ID NOs: 270, 296 and 66, respectively; the CDR-H1, CDR-H2, and CDR-H3 having the sequences of SEQ ID NOs: 271, 295, and 35, respectively; the CDR-H1, CDR-H2, and CDR-H3 having the sequences of SEQ ID NOs: 276, 295, and 35, respectively; the CDR-H1, CDR-H2, and CDR-H3 contain the sequences of SEQ ID NOs: 271, 291 and 70, respectively; the CDR-H1, CDR-H2, and CDR-H3 contain the sequences of SEQ ID NOs: 276, 291 and 70, respectively; the CDR-H1, CDR-H2, and CDR-H3 contain the sequences of SEQ ID NOs: 271, 291 and 55, respectively; the CDR-H1, CDR-H2, and CDR-H3 contain the sequences of SEQ ID NOs: 276, 291 and 55, respectively; the CDR-H1, CDR-H2, and CDR-H3 contain the sequences of SEQ ID NOs: 271, 291 and 53, respectively; the CDR-H1, CDR-H2, and CDR-H3 contain the sequences of SEQ ID NOs: 276, 291 and 53, respectively; the CDR-H1, CDR-H2, and CDR-H3 contain the sequences of SEQ ID NOs: 271, 291 and 56, respectively; the CDR-H1, CDR-H2, and CDR-H3 contain the sequences of SEQ ID NOs: 276, 291 and 56, respectively; the CDR-H1, CDR-H2, and CDR-H3 contain the sequences of SEQ ID NOs: 271, 291 and 61, respectively; the CDR-H1, CDR-H2, and CDR-H3 contain the sequences of SEQ ID NOs: 276, 291 and 61, respectively; the CDR-H1, CDR-H2, and CDR-H3 contain the sequences of SEQ ID NOs: 271, 291 and 59, respectively; the CDR-H1, CDR-H2, and CDR-H3 contain the sequences of SEQ ID NOs: 276, 291 and 59, respectively; the CDR-H1, CDR-H2, and CDR-H3 contain the sequences of SEQ ID NOs: 271, 291 and 60, respectively; the CDR-H1, CDR-H2, and CDR-H3 contain the sequences of SEQ ID NOs: 276, 291 and 60, respectively; the CDR-H1, CDR-H2, and CDR-H3 contain the sequences of SEQ ID NOs: 274, 291 and 35, respectively; the CDR-H1, CDR-H2, and CDR-H3 contain the sequences of SEQ ID NOs: 275, 291 and 35, respectively; the CDR-H1, CDR-H2, and CDR-H3 contain the sequences of SEQ ID NOs: 273, 302 and 50, respectively; the CDR-H1, CDR-H2, and CDR-H3 contain the sequences of SEQ ID NOs: 273, 302 and 51, respectively; the CDR-H1, CDR-H2, and CDR-H3 contain the sequences of SEQ ID NOs: 279, 301 and 54, respectively; the CDR-H1, CDR-H2, and CDR-H3 contain the sequences of SEQ ID NOs:277, 299 and 57, respectively; the CDR-H1, CDR-H2, and CDR-H3 contain the sequences of SEQ ID NOs: 278, 300 and 58, respectively; the CDR-H1, CDR-H2, and CDR-H3 contain the sequences of SEQ ID NOs: 273, 298 and 62, respectively; the CDR-H1, CDR-H2, and CDR-H3 contain the sequences of SEQ ID NOs: 273, 298 and 63, respectively; the CDR-H1, CDR-H2, and CDR-H3 contain the sequences of SEQ ID NOs: 273, 298 and 65, respectively; the CDR-H1, CDR-H2, and CDR-H3 contain the sequences of SEQ ID NOs: 272, 297 and 67, respectively; the CDR-H1, CDR-H2, and CDR-H3 contain the sequences of SEQ ID NOs: 273, 303 and 69, respectively; the CDR-H1, CDR-H2, and CDR-H3 contain the sequences of SEQ ID NOs: 278, 300, 71, respectively; or the CDR-H1, CDR-H2, and CDR-H3 contain the sequences of SEQ ID NOs: 278, 300, 174, respectively.

In some embodiments, the CDR-H1, CDR-H2 and CDR-H3 contain the sequences of SEQ ID NOS: 75, 306, and 22, respectively; the CDR-H1, CDR-H2, and CDR-H3 contain the sequences of SEQ ID NOs: 75, 307, and 22, respectively; the CDR-H1, CDR-H2, and CDR-H3 contain the sequences of SEQ ID NOs: 77, 305, and 29, respectively; the CDR-H1, CDR-H2, and CDR-H3 contain the sequences of SEQ ID NOs: 79, 304, and 35, respectively; the CDR-H1, CDR-H2, and CDR-H3 contain the sequences of SEQ ID NOs: 79, 304, and 52, respectively; the CDR-H1, CDR-H2, and CDR-H3 contain the sequences of SEQ ID NOs: 77, 309 and 45, respectively; the CDR-H1, CDR-H2, and CDR-H3 contain the sequences of SEQ ID NOs: 77, 309 and 68, respectively; the CDR-H1, CDR-H2, and CDR-H3 contain the sequences of SEQ ID NOs: 77, 309 and 64, respectively; the CDR-H1, CDR-H2, and CDR-H3 contain the sequences of SEQ ID NOs: 77, 309 and 66, respectively; the CDR-H1, CDR-H2, and CDR-H3 having the sequences of SEQ ID NOs: 79, 308, and 35, respectively; the CDR-H1, CDR-H2, and CDR-H3 contain the sequences of SEQ ID NOs: 79, 304 and 70, respectively; the CDR-H1, CDR-H2, and CDR-H3 contain the sequences of SEQ ID NOs: 79, 304 and 55, respectively; the CDR-H1, CDR-H2, and CDR-H3 contain the sequences of SEQ ID NOs: 284, 304 and 55, respectively; the CDR-H1, CDR-H2, and CDR-H3 contain the sequences of SEQ ID NOs: 79, 304 and 53, respectively; the CDR-H1, CDR-H2, and CDR-H3 contain the sequences of SEQ ID NOs: 79, 304 and 56, respectively; the CDR-H1, CDR-H2, and CDR-H3 contain the sequences of SEQ ID NOs: 79, 304 and 61, respectively; the CDR-H1, CDR-H2, and CDR-H3 contain the sequences of SEQ ID NOs: 79, 304 and 59, respectively; the CDR-H1, CDR-H2, and CDR-H3 contain the sequences of SEQ ID NOs: 79, 304 and 60, respectively; the CDR-H1, CDR-H2, and CDR-H3 contain the sequences of SEQ ID NOs: 280, 304 and 35, respectively; the CDR-H1, CDR-H2, and CDR-H3 contain the sequences of SEQ ID NOs: 283, 304 and 35, respectively; the CDR-H1, CDR-H2, and CDR-H3 contain the sequences of SEQ ID NOs: 288, 315 and 50, respectively; the CDR-H1, CDR-H2, and CDR-H3 contain the sequences of SEQ ID NOs: 288, 315 and 51, respectively; the CDR-H1, CDR-H2, and CDR-H3 contain the sequences of SEQ ID NOs: 287, 314 and 54, respectively; the CDR-H1, CDR-H2, and CDR-H3 contain the sequences of SEQ ID NOs:285, 312 and 57, respectively; the CDR-H1, CDR-H2, and CDR-H3 contain the sequences of SEQ ID NOs: 286 or 289, 313 and 58, respectively; the CDR-H1, CDR-H2, and CDR-H3 contain the sequences of SEQ ID NOs: 282, 311 and 62, respectively; the CDR-H1, CDR-H2, and CDR-H3 contain the sequences of SEQ ID NOs: 282, 311 and 63, respectively; the CDR-H1, CDR-H2, and CDR-H3 contain the sequences of SEQ ID NOs: 282, 311 and 65, respectively; the CDR-H1, CDR-H2, and CDR-H3 contain the sequences of SEQ ID NOs: 281, 310 and 67, respectively; the CDR-H1, CDR-H2, and CDR-H3 contain the sequences of SEQ ID NOs: 290, 317 and 69, respectively; the CDR-H1, CDR-H2, and CDR-H3 contain the sequences of SEQ ID NOs: 286 or 289, 316, 71, respectively; or the CDR-H1, CDR-H2, and CDR-H3 contain the sequences of SEQ ID NOs: 286 or 289, 316, 174, respectively.

In some embodiments, the CDR-H1, CDR-H2 and CDR-H3 contain the sequences of SEQ ID NOS: 20, 80, and 22, respectively; the CDR-H1, CDR-H2, and CDR-H3 contain the sequences of SEQ ID NOs: 20, 83, and 22, respectively; the CDR-H1, CDR-H2, and CDR-H3 contain the sequences of SEQ ID NOs: 27, 81, and 29, respectively; the CDR-H1, CDR-H2, and CDR-H3 contain the sequences of SEQ ID NOs: 33, 82, and 35, respectively; or the CDR-H1, CDR-H2, and CDR-H3 contain the sequences of SEQ ID NOs: 33, 82, and 52, respectively.

In some embodiments, the CDR-H1, CDR-H2 and CDR-H3 contain the sequences of SEQ ID NOS: 269, 293, and 22, respectively; the CDR-H1, CDR-H2, and CDR-H3 contain the sequences of SEQ ID NOs: 269, 294, and 22, respectively; the CDR-H1, CDR-H2, and CDR-H3 contain the sequences of SEQ ID NOs: 270, 292, and 29, respectively; the CDR-H1, CDR-H2, and CDR-H3 contain the sequences of SEQ ID NOs: 271, 291, and 35, respectively; or the CDR-H1, CDR-H2, and CDR-H3 contain the sequences of SEQ ID NOs: 271, 291, and 52, respectively.

In some embodiments, the CDR-H1, CDR-H2 and CDR-H3 contain the sequences of SEQ ID NOS: 75, 306, and 22, respectively; the CDR-H1, CDR-H2, and CDR-H3 contain the sequences of SEQ ID NOs: 75, 307, and 22, respectively; the CDR-H1, CDR-H2, and CDR-H3 contain the sequences of SEQ ID NOs: 77, 305, and 29, respectively; the CDR-H1, CDR-H2, and CDR-H3 contain the sequences of SEQ ID NOs: 79, 304, and 35, respectively; or the CDR-H1, CDR-H2, and CDR-H3 contain the sequences of SEQ ID NOs: 79, 304, and 52, respectively.

In some embodiments, the provided antibody contains a CDR-H1, CDR-H2 and CDR-H3, respectively, contained within the $V_H$ region amino acid sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209. In some embodiments, the provided antibody contains a CDR-H1, CDR-H2 and CDR-H3, respectively, contained within the $V_H$ region amino acid sequence set forth in SEQ ID NO: 8, 10, 13, 15, 17, or 19. In some embodiments, the provided antibody contains a CDR-H1, CDR-H2 and CDR-H3, respectively, contained within the $V_H$ region amino acid sequence set forth in SEQ ID NO: 8 or 10. In some embodiments, the provided antibody contains a CDR-H1, CDR-H2 and CDR-H3, respectively, contained within the $V_H$ region amino acid sequence set forth in SEQ ID NO: 10, 13, 15, 17 or 19. In some embodiments, the provided antibody contains a CDR-H1, CDR-H2 and CDR-H3, respectively, contained within the $V_H$ region amino acid sequence set forth in SEQ ID NO: 13, 15 or 19. In some embodiments, the provided antibody contains a CDR-H1, CDR-H2 and CDR-H3, respectively, contained within the $V_H$ region amino acid sequence set forth in SEQ ID NO: 13 or 15.

In some embodiments, the $V_H$ region contains any of the CDR-H1, CDR-H2 and CDR-H3 as described and contains a framework region that contains at least 90%, 91%, 92%, 93%, 94%, 95%, 96%, 97%, 98%, 99% sequence identity to the framework region set forth in the $V_H$ region amino acid sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209. In some embodiments, the anti-ROR1 antibody can contain a CDR-H1, CDR-H2 and CDR-H3, respectively, contained within the $V_H$ region amino acid sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209, and a frame work region that contains at least 90%, 91%, 92%, 93%, 94%, 95%, 96%, 97%, 98%, 99% sequence identity to the framework region of the amino acid sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209.

In some embodiments, the $V_H$ region contains any of the CDR-H1, CDR-H2 and CDR-H3 as described and contains a framework region that contains at least 90%, 91%, 92%, 93%, 94%, 95%, 96%, 97%, 98%, 99% sequence identity to the framework region set forth in the $V_H$ region amino acid sequence set forth in SEQ ID NO: 8, 10, 13, 15, 17, or 19. For example, the anti-ROR1 antibody can contain a CDR-H1, CDR-H2 and CDR-H3, respectively, contained within the $V_H$ region amino acid sequence set forth in SEQ ID NO: 8, 10, 13, 15, 17, or 19, and a frame work region that contains at least 90%, 91%, 92%, 93%, 94%, 95%, 96%, 97%, 98%, 99% sequence identity to the framework region of the amino acid sequence set forth in SEQ ID NO: 8, 10, 13, 15, 17, or 19.

In some embodiments, the provided antibody contains a $V_H$ region that has the sequence of amino acids set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209. In some embodiments, the provided antibody contains a $V_H$ region that has the sequence of amino acids set forth in SEQ ID NO: 8, 10, 13, 15, 17 or 19. In some embodiments, the provided antibody contains a $V_H$ region that has the sequence of amino acids set forth in SEQ ID NO: 10, 13, 15 or 19. In some embodiments, the provided antibody contains a $V_H$ region that has the sequence of amino acids set forth in SEQ ID NO: 13, 15 or 19. In some embodiments, the provided antibody contains a $V_H$ region that has the sequence of amino acids set forth in SEQ ID NO: 13 or 15.

Also provided are antibodies having sequences at least at or about at least 90%, 91%, 92%, 93%, 94%, 95%, 96%, 97%, 98%, or 99% identical to such sequences.

In some embodiments, the antibody is a single domain antibody (sdAb) containing only the $V_H$ region sequence, such as any of the above described $V_H$ region sequences, or a sufficient antigen-binding portion thereof.

In some embodiments, the anti-ROR1 antibody containing a $V_H$ region further contains a light chain or a sufficient antigen binding portion thereof. For example, in some embodiments, the antibody contains a $V_H$ region and a $V_L$ region, or a sufficient antigen-binding portion of a $V_H$ and $V_L$ region. In such embodiments, a $V_H$ region sequence can be any of the above described $V_H$ sequence. In some such embodiments, the antibody is an antigen-binding fragment, such as a Fab or a scFv. In some such embodiments, the antibody is a full-length or intact antibody that also contains a constant region.

In some embodiments, the antibody, e.g., antigen-binding fragment thereof, has a light chain variable ($V_L$) region having the amino acid sequence set forth in SEQ ID NO: 14, 16, 18, 234, 235, 236, 237, 238, 239, 240, 241, 242, 243, 244, 245, 246, 247 or 248, or an amino acid sequence that has at least 90%, 91%, 92%, 93%, 94%, 95%, 96%, 97%, 98%, or 99% sequence identity to the $V_H$ region amino acid sequence set forth in SEQ ID NO: 14, 16, 18, 234, 235, 236, 237, 238, 239, 240, 241, 242, 243, 244, 245, 246, 247 or 248. In some embodiments, the antibody, e.g., antigen-binding fragment thereof, has a light chain variable ($V_L$) region having the amino acid sequence set forth in SEQ ID NO: 14, 16, or 18, or an amino acid sequence that has at least 90%, 91%, 92%, 93%, 94%, 95%, 96%, 97%, 98%, or 99% sequence identity to the $V_H$ region amino acid sequence set forth in SEQ ID NO: 14, 16, or 18.

In some embodiments, the $V_L$ region of the anti-ROR1 antibody is one that includes a light chain complementarity determining region 3 (CDR-L3) that contains the amino acid sequence: $X_1X_2X_3X_4X_5X_6X_7X_8X_9X_{10}X_{11}X_{12}X_{13}X_{14}$ (SEQ ID NO: 99), wherein $X_1$ is Q, A, or K; $X_2$ is Q, V, A, or S; $X_3$ is Y, W, or L; $X_4$ is E, D, K, or N; $X_5$ is S, D, N, or G; $X_6$ is L, T, S, D, R, or Y; $X_7$ is P, G, L, S, N, or T; $X_8$ is D, S, N, or null; $X_9$ is H, G, L, or null; $X_{10}$ is Y, P, V, R, H, or L; and $X_{11}$ is T, V, S, or M. In some embodiments, in said CDR-L3, $X_1$ is Q or A; $X_2$ is Q, V, or A; $X_3$ is Y or W; $X_4$ is E or D; $X_5$ is S or D; $X_6$ is L, T, or S; $X_7$ is P, G, or L; $X_8$ is D, S, or null; $X_9$ is H, G, or null; $X_{10}$ is Y, P, or V; and $X_{11}$ is T or V.

In some embodiments, the $V_L$ region of the anti-ROR1 antibody is one that includes a light chain complementarity determining region 3 (CDR-L3) that contains the amino acid sequence: $X_1X_2X_3X_4X_5X_6X_7X_8X_9X_{10}X_{11}X_{12}X_{13}X_{14}$ (SEQ ID NO: 100), wherein $X_1$ is Q or A; $X_2$ is Q, V, or A; $X_3$ is Y or W; $X_4$ is E or D; $X_5$ is S or D; $X_6$ is L, T, or S; $X_7$ is P, G, or L; $X_8$ is D, S, or null; $X_9$ is H, G, or null; $X_{10}$ is Y, P, or V; and $X_{11}$ is T or V.

In some embodiments, the provided antibody contains a CDR-L3 having the amino acid sequence set forth in SEQ ID NO: 25, 32, 38, 39, 40, 41, 42, 43, 44, 46, 47, 48, 49, 232 or 233. In some embodiments, the provided antibody can contain a $V_L$ region sequence set forth in SEQ ID NO: 14, 16, 18, 234, 235, 236, 237, 238, 239, 240, 241, 242, 243, 244, 245, 246, 247 or 248 in which the corresponding CDR-L3 sequence contained therein (e.g. corresponding to amino acid residues L89 to L97 by Kabat numbering) is replaced by the CDR-L3 sequence set forth in SEQ ID NO: 25, 32, 38, 39, 40, 41, 42, 43, 44, 46, 47, 48, 49, 232 or 233. In some embodiments, the provided antibody can contain a $V_L$ region sequence set forth in SEQ ID NO: 14, 16, or 18 in which the corresponding CDR-L3 sequence contained therein (e.g. corresponding to amino acid residues L89 to L97 by Kabat numbering) is replaced by the CDR-L3 sequence set forth in SEQ ID NO: 25, 32, 38, 39, 40, 41, 42, 43, 44, 46, 47, 48, and 49.

In some embodiments, the provided antibody contains a CDR-L3 having the amino acid sequence set forth in SEQ ID NO: 25, 32, or 38. In some embodiments, the provided antibody contains a CDR-L3 contained within the CDR-L3 of the $V_L$ region amino acid sequence set forth in SEQ ID NO: 14, 16, or 18. In some embodiments, the provided antibody contains a CDR-L3 having the amino acid sequence set forth in SEQ ID NO: 32, or 38. In some embodiments, the provided antibody contains a CDR-L3 contained within the CDR-L3 of the $V_L$ region amino acid sequence set forth in SEQ ID NO: 14 or 16.

In some embodiments, the $V_L$ region of the anti-ROR1 antibody is one that includes a light chain complementarity determining region 1 (CDR-L1) that contains the amino acid sequence: $X_1X_2SX_4X_5X_6X_7X_8SX_{10}X_{11}X_{12}X_{13}$ (SEQ ID NO: 101), wherein $X_1$ is Q, G, or S; $X_2$ is A or G; $X_4$ is Q, N, or S; $X_5$ is S or null; $X_6$ is N or null; $X_7$ is D or I; $X_8$ is I or G; $X_{10}$ is N or E; $X_{11}$ is Y or S; $X_{12}$ is L or V; and $X_{13}$ is N or Y.

In some embodiments, the provided antibody contains a CDR-L1 having the amino acid sequence set forth in SEQ ID NO: 23, 30, 36, 210, 211, 212, 213, 214, 215, 217, 216, 218, 219 or 220. In some embodiments, the provided antibody contains a CDR-L1 contained within the CDR-L1 of the $V_L$ region amino acid sequence set forth in SEQ ID NO: 234, 235, 236, 237, 238, 239, 240, 241, 242, 243, 244, 245, 246, 247 or 248. In some embodiments, the provided antibody contains a CDR-L1 having the amino acid sequence set forth in SEQ ID NO: 23, 30, or 36. In some embodiments, the provided antibody contains a CDR-L1 contained within the CDR-L1 of the $V_L$ region amino acid sequence set forth in SEQ ID NO: 14, 16, or 18.

In some embodiments, the $V_L$ region of the anti-ROR1 antibody is one that includes a light chain complementarity determining region 2 (CDR-L2) that contains the amino acid sequence of $X_1X_2X_3X_4X_5X_6X_7$ (SEQ ID NO: 102), wherein $X_1$ is D or R; $X_2$ is A, T, or N; $X_3$ is S, T, or N; $X_4$ is Y, D, or Q; $X_5$ is L or R; $X_6$ is E or P; and $X_7$ is T or S.

In some embodiments, the provided antibody contains a CDR-L2 having the amino acid sequence set forth in SEQ ID NO: 24, 31, 37, 221, 222, 223, 224, 225, 226, 227, 228, 229, 230 or 231. In some embodiments, the provided antibody contains a CDR-L2 contained within the CDR-L2 of the $V_L$ region amino acid sequence set forth in SEQ ID NO: 234, 235, 236, 237, 238, 239, 240, 241, 242, 243, 244, 245, 246, 247 or 248. In some embodiments, the provided antibody contains a CDR-L2 having the amino acid sequence set forth in SEQ ID NO: 24, 31, or 37. In some embodiments, the provided antibody contains a CDR-L2 contained within the CDR-L2 of the $V_L$ region amino acid sequence set forth in SEQ ID NO: 14, 16, or 18.

In some embodiments, the provided antibody contains a CDR-L1 having the amino acid sequence set forth in SEQ ID NO: 23, 30, 36, 210, 211, 212, 213, 214, 215, 216, 217, 218, 219 or 220; a CDR-L2 having the amino acid sequence set forth in SEQ ID NO: 24, 31, 37, 221, 222, 223, 224, 225, 226, 227, 228, 229, 230 or 231; and a CDR-L3 having the amino acid sequence set forth in SEQ ID NO: 25, 32, 38, 39, 40, 41, 42, 43, 44, 46, 47, 48, 49 or 233. In some embodiments, the provided antibody contains a CDR-L1 having the amino acid sequence set forth in SEQ ID NO: 23, 30, or 36; a CDR-L2 having the amino acid sequence set forth in SEQ ID NO: 24, 31, or 37; and a CDR-L3 having the amino acid sequence set forth in SEQ ID NO: 25, 32, 38, 39, 40, 41, 42, 43, 44, 46, 47, 48 49 or 233. In some embodiments, the provided antibody contains a CDR-L1 having the amino acid sequence set forth in SEQ ID NO: 23, 30, or 36; a CDR-L2 having the amino acid sequence set forth in SEQ ID NO: 24, 31, or 37; and a CDR-L3 having the amino acid sequence set forth in SEQ ID NO: 25, 32 or 38.

In some embodiments, the CDR-L1, CDR-L2 and CDR-L3 contain the sequences of SEQ ID NOs: 23, 24, and 25, respectively; the CDR-L1, CDR-L2, and CDR-L3 contain the sequences of SEQ ID NOs: 30, 31, and 22, respectively; the CDR-L1, CDR-L2, and CDR-L3 comprising the sequences of SEQ ID NOs: 36, 37, and 38, respectively; the CDR-L1, CDR-L2 and CDR-L3 contain the sequences of SEQ ID NOs: 216, 227, and 40, respectively; the CDR-L1, CDR-L2 and CDR-L3 contain the sequences of SEQ ID NOs: 218, 229, and 39, respectively; the CDR-L1, CDR-L2 and CDR-L3 contain the sequences of SEQ ID NOs: 219, 230, and 43, respectively; the CDR-L1, CDR-L2 and CDR-L3 contain the sequences of SEQ ID NOs: 220, 231, and 46, respectively; the CDR-L1, CDR-L2 and CDR-L3 contain the sequences of SEQ ID NOs: 210, 221, and 49, respectively; the CDR-L1, CDR-L2 and CDR-L3 contain the sequences of SEQ ID NOs: 210, 221, and 233, respectively; the CDR-L1, CDR-L2 and CDR-L3 contain the sequences of SEQ ID NOs: 211, 222, and 48, respectively; the CDR-L1, CDR-L2 and CDR-L3 contain the sequences of SEQ ID NOs: 212, 223, and 42, respectively; the CDR-L1, CDR-L2 and CDR-L3 contain the sequences of SEQ ID NOs: 214, 225, and 232, respectively; the CDR-L1, CDR-L2 and CDR-L3 contain the sequences of SEQ ID NOs: 215, 226, and 44, respectively; the CDR-L1, CDR-L2 and CDR-L3 contain the sequences of SEQ ID NOs: 217, 228, and 41, respectively; the CDR-L1, CDR-L2 and CDR-L3 contain the sequences of SEQ ID NOs: 36, 37, and 38, respectively; or the CDR-L1, CDR-L2 and CDR-L3 contain the sequences of SEQ ID NOs: 213, 224, and 47, respectively.

In some embodiments, the provided antibody contains a CDR-L1, CDR-L2, and CDR-L3, respectively, contained within the $V_L$ region amino acid sequence set forth in SEQ ID NO: 14, 16, 18, 234, 235, 236, 237, 238, 239, 240, 241, 242, 243, 244, 245 246, 247 or 248. In some embodiments, the provided antibody contains a CDR-L1, CDR-L2, and CDR-L3, respectively, contained within the $V_L$ region amino acid sequence set forth in SEQ ID NO: 14, 16, or 18. In some embodiments, the provided antibody contains a CDR-L1, CDR-L2, and CDR-L3, respectively, contained within the $V_L$ region amino acid sequence set forth in SEQ ID NO: 14 or 16.

In some embodiments, the $V_L$ region contains any of the CDR-L1, CDR-L2 and CDR-L3 as described and contains a framework region that contains at least 90%, 91%, 92%, 93%, 94%, 95%, 96%, 97%, 98%, 99% sequence identity to the framework region of the amino acid sequence set forth in SEQ ID NO: 14, 16, 18, 234, 235, 236, 237, 238, 239, 240, 241, 242, 243, 244, 245 246, 247 or 248. For example, the anti-ROR1 antibody can contain a CDR-L1, CDR-L2 and CDR-L3, respectively, contained within the $V_L$ region amino acid sequence set forth in SEQ ID NO: 14, 16, 18, 234, 235, 236, 237, 238, 239, 240, 241, 242, 243, 244, 245 246, 247 or 248, and a frame work region that contains at least 90%, 91%, 92%, 93%, 94%, 95%, 96%, 97%, 98%, 99% sequence identity to the framework region of the amino acid sequence set forth in SEQ ID NO: 14, 16, 18, 234, 235, 236, 237, 238, 239, 240, 241, 242, 243, 244, 245 246, 247 or 248.

In some embodiments, the $V_L$ region contains any of the CDR-L1, CDR-L2 and CDR-L3 as described and contains a framework region that contains at least 90%, 91%, 92%, 93%, 94%, 95%, 96%, 97%, 98%, 99% sequence identity to the framework region of the amino acid sequence set forth in SEQ ID NO: 14, 16, or 18. For example, the anti-ROR1 antibody can contain a CDR-L1, CDR-L2 and CDR-L3, respectively, contained within the $V_L$ region amino acid sequence set forth in SEQ ID NO: 14, 16, or 18, and a frame work region that contains at least 90%, 91%, 92%, 93%, 94%, 95%, 96%, 97%, 98%, 99% sequence identity to the framework region of the amino acid sequence set forth in SEQ ID NO: 14, 16, or 18.

In some embodiments, the provided antibody contains a $V_L$ region that has the sequence of amino acids set forth in SEQ ID NO: 14, 16, 18, 234, 235, 236, 237, 238, 239, 240, 241, 242, 243, 244, 245 246, 247 or 248. In some embodiments, the provided antibody contains a $V_L$ region that has the sequence of amino acids set forth in SEQ ID NO: 14, 16, or 18. In some embodiments, the provided antibody contains a $V_L$ region that has the sequence of amino acids set forth in SEQ ID NO: 14 or 16.

Also provided are antibodies having sequences at least at or about at least 90%, 91%, 92%, 93%, 94%, 95%, 96%, 97%, 98%, or 99% identical to such sequences.

In some embodiments, the $V_H$ region of the antibody or fragment comprises the amino acid sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209 and the $V_L$ region of the antibody or fragment comprises the amino acid sequence set forth in SEQ ID NO: 14, 16, 18, 234, 235, 236, 237, 238, 239, 240, 241, 242, 243, 244, 245 246, 247 or 248. In some embodiments, the $V_H$ region of the antibody or fragment comprises the amino acid sequence set forth in SEQ ID NO: 8, 10, 13, 15, 17 or 19 and the $V_L$ region of the antibody or fragment comprises the amino acid sequence set forth in SEQ ID NO: 14, 16, or 18. In some embodiments, the $V_H$ region of the antibody or fragment comprises the amino acid sequence set forth in SEQ ID NO: 10, 13, 15 or 19 and the $V_L$ region of the antibody or fragment comprises the amino acid sequence set forth in SEQ ID NO: 14, 16, or 18. In some embodiments, the $V_H$ region of the antibody or fragment comprises the amino acid sequence set forth in SEQ ID NO: 13, 15 or 19 and the $V_L$ region of the antibody or fragment comprises the amino acid sequence set forth in SEQ ID NO: 14, 16, or 18. In some embodiments, the $V_H$ region of the antibody or fragment comprises the amino acid sequence set forth in SEQ ID NO: 13 or 15 and the $V_L$ region of the antibody or fragment comprises the amino acid sequence set forth in SEQ ID NO: 14 or 16.

Also provided are antibodies having sequences at least at or about at least 90%, 91%, 92%, 93%, 94%, 95%, 96%, 97%, 98%, or 99% identical to such sequences.

In some embodiments, the $V_H$ region of the antibody contains the CDR-H1, CDR-H2, and CDR-H3, respectively contained within the $V_H$ region amino acid sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209; and contains the CDR-L1, CDR-L2, and CDR-L3 sequences contained within the light chain variable ($V_L$) region amino acid sequence set forth in SEQ ID NO: 14, 16, 18, 234, 235, 236, 237, 238, 239, 240, 241, 242, 243, 244, 245 246, 247 or 248. In some embodiments, the $V_H$ region of the antibody contains the CDR-H1, CDR-H2, and CDR-H3, respectively contained within the $V_H$ region amino acid sequence set forth in SEQ ID NO: 8, 10, 13, 15, 17, or 19; and contains the CDR-L1, CDR-L2, and CDR-L3 sequences contained within the light chain variable ($V_L$) region amino acid sequence set forth in SEQ ID NO: 14, 16, or 18. In some embodiments, the $V_H$ region of the antibody contains the CDR-H1, CDR-H2, and CDR-H3, respectively contained within the $V_H$ region amino acid sequence set forth in SEQ ID NO: 10, 13, 15, 17, or 19; and contains the CDR-L1, CDR-L2, and CDR-L3 sequences contained within the light chain variable (VL) region amino acid sequence set forth in SEQ ID NO: 14, 16, or 18. In some embodiments, the $V_H$ region of the antibody contains the CDR-H1, CDR-H2, and CDR-H3, respectively contained within the $V_H$ region amino acid sequence set forth in SEQ ID NO: 13, 15 or 19; and contains the CDR-L1, CDR-L2, and CDR-L3 sequences contained within the light chain variable (VL) region amino acid sequence set forth in SEQ ID NO: 14, 16, or 18. In some embodiments, the $V_H$ region of the antibody contains the CDR-H1, CDR-H2, and CDR-H3, respectively contained within the $V_H$ region amino acid sequence set forth in SEQ ID NO: 13 or 15; and contains the CDR-L1, CDR-L2, and CDR-L3 sequences contained within the light chain variable (VL) region amino acid sequence set forth in SEQ ID NO: 14 or 16.

In some embodiments, the $V_H$ and $V_L$ regions of the antibody or fragment comprise the amino acid sequences of SEQ ID NOs: 19 and 18, respectively; the $V_H$ and $V_L$ regions of the antibody or fragment comprise the amino acid sequences of SEQ ID NOs: 17 and 18, respectively; the $V_H$ and $V_L$ regions of the antibody or fragment comprise the amino acid sequences of SEQ ID NOs: 15 and 16 respectively; the $V_H$ and $V_L$ regions of the antibody or fragment comprise the amino acid sequences of SEQ ID NOs: 13 and 14, respectively; the $V_H$ and $V_L$ regions of the antibody or fragment comprise the amino acid sequences of SEQ ID NOs: 182 and 242 respectively; the $V_H$ and $V_L$ regions of the antibody or fragment comprise the amino acid sequences of SEQ ID NOs: 182 and 246, respectively; the $V_H$ and $V_L$ regions of the antibody or fragment comprise the amino acid sequences of SEQ ID NOs: 182 and 247, respectively; the $V_H$ and $V_L$ regions of the antibody or fragment comprise the amino acid sequences of SEQ ID NOs: 185 and 248, respectively; the $V_H$ and $V_L$ regions of the antibody or fragment comprise the amino acid sequences of SEQ ID NOs: 186 and 248, respectively; the $V_H$ and $V_L$ regions of the antibody or fragment comprise the amino acid sequences of SEQ ID NOs: 175 and 234, respectively; the $V_H$ and $V_L$ regions of the antibody or fragment comprise the amino acid sequences of SEQ ID NOs: 175 and 235, respectively; the $V_H$ and $V_L$ regions of the antibody or fragment comprise the amino acid sequences of SEQ ID NOs: 176 and 236, respectively; the $V_H$ and $V_L$ regions of the antibody or fragment comprise the amino acid sequences of SEQ ID NOs: 176 and 237, respectively; the $V_H$ and $V_L$ regions of the antibody or fragment comprise the amino acid sequences of SEQ ID NOs: 177 and 238, respectively; the $V_H$ and $V_L$ regions of the antibody or fragment comprise the amino acid sequences of SEQ ID NOs: 179 and 240 respectively; the $V_H$ and $V_L$ regions of the antibody or fragment comprise the amino acid sequences of SEQ ID NOs: 180 and 241, respectively; the $V_H$ and $V_L$ regions of the antibody or fragment comprise the amino acid sequences of SEQ ID NOs: 181 and 241, respectively; the $V_H$ and $V_L$ regions of the antibody or fragment comprise the amino acid sequences of SEQ ID NOs: 183 and 243 respectively; the $V_H$ and $V_L$ regions of the antibody or fragment comprise the amino acid sequences of SEQ ID NOs: 183 and 244 respectively; the $V_H$ and $V_L$ regions of the antibody or fragment comprise the amino acid sequences of SEQ ID NOs: 184 and 243, respectively; the $V_H$ and $V_L$ regions of the antibody or fragment comprise the amino acid sequences of SEQ ID NOs: 184 and 244 respectively; the $V_H$ and $V_L$ regions of the antibody or fragment comprise the amino acid sequences of SEQ ID NOs: 183 and 245, respectively; the $V_H$ and $V_L$ regions of the antibody or fragment comprise the amino acid sequences of SEQ ID NOs: 184 and 245, respectively; or the $V_H$ and $V_L$ regions of the antibody or fragment comprise the amino acid sequences of SEQ ID NOs: 178 and 239, respectively.

Also provided are antibodies having sequences at least at or about 90%, 91%, 92%, 93%, 94%, 95%, 96%, 97%, 98%, or 99% identical to such sequences.

In some embodiments, the antibody is a single-chain antibody fragment, such as an scFv or diabody or a VH-only single domain antibody. In some embodiments, the single-chain antibody includes one or more linkers joining two antibody domains or regions, such as a variable heavy chain (VH) region and a variable light chain ($V_L$). The linker typically is a peptide linker, e.g., a flexible and/or soluble peptide linker. Among the linkers are those rich in glycine and serine and/or in some cases threonine. In some embodiments, the linkers further include charged residues such as lysine and/or glutamate, which can improve solubility. In some embodiments, the linkers further include one or more proline.

Accordingly, the provided anti-ROR1 antibodies include single-chain antibody fragments, such as scFvs and diabodies, particularly human single-chain fragments, typically comprising linker(s) joining two antibody domains or regions, such $V_H$ and $V_L$ domains. The linker typically is a peptide linker, e.g., a flexible and/or soluble peptide linker, such as one rich in glycine and serine.

In some aspects, the linkers rich in glycine and serine (and/or threonine) include at least 80%, 85%, 90%, 91%, 92%, 93%, 94%, 95%, 96%, 97%, 98%, or 99% such amino acid(s). In some embodiments, they include at least at or about 50%, 55%, 60%, 70%, or 75%, glycine, serine, and/or threonine. In some embodiments, the linker is comprised substantially entirely of glycine, serine, and/or threonine. The linkers generally are between about 5 and about 50 amino acids in length, typically between at or about 10 and at or about 30, e.g., 10, 11, 12, 13, 14, 15, 16, 17, 18, 19, 20, 21, 22, 23, 24, 25, 26, 27, 28, 29, or 30, and in some examples between 10 and 25 amino acids in length. Exemplary linkers include linkers having various numbers of repeats of the sequence GGGGS (4GS; SEQ ID NO:111) or GGGS (3GS; SEQ ID NO:112), such as between 2, 3, 4, and 5 repeats of such a sequence. Exemplary linkers include those having or consisting of a sequence set forth in SEQ ID NO: 91 (GGGGSGGGGSGGGGS). Exemplary linkers further include those having or consisting of the sequence set forth in SEQ ID NO: 113 (GSTSGSGKPGSGEGSTKG).

Accordingly, in some embodiments, the provided embodiments include single-chain fragments, e.g., scFvs, comprising one or more of the aforementioned linkers, such as glycine/serine rich linkers, including linkers having repeats of GGGS or GGGGS, such as the linker set forth as SEQ ID NO: 91.

In some embodiments, the linker has an amino acid sequence containing the sequence set forth SEQ ID NO: 91. The fragment, e.g., scFv, may include a $V_H$ region or portion thereof, followed by the linker, followed by a $V_L$ or portions thereof. The fragment, e.g., the scFv, may include the $V_L$, followed by the linker, followed by the VH.

In some embodiments, the scFv has the amino acid sequence set forth in SEQ ID NO: 2, 4, 6, 12, 249, 250, 251, 252, 253, 254, 255, 256, 257, 258, 259, 260, 261, 262, 263, 264, 265, 266, 267 or 268, or has a sequence at least at or about 90%, 91%, 92%, 93%, 94%, 95%, 96%, 97%, 98%, or 99% identical to the amino acid sequence set forth in SEQ ID NO: 2, 4, 6, 12, 249, 250, 251, 252, 253, 254, 255, 256, 257, 258, 259, 260, 261, 262, 263, 264, 265, 266, 267 or 268. In some aspects, the scFv has the amino acid sequence set forth in SEQ ID NO: 2, 4, 6, or 12, or has a sequence at least at or about 90%, 91%, 92%, 93%, 94%, 95%, 96%, 97%, 98%, or 99% identical to the amino acid sequence set forth in SEQ ID NO: 2, 4, 6, or 12. In some aspects, the scFv has the amino acid sequence set forth in SEQ ID NO: 4 or 6, or has a sequence at least at or about 90%, 91%, 92%, 93%, 94%, 95%, 96%, 97%, 98%, or 99% identical to the amino acid sequence set forth in SEQ ID NO: 4 or 6.

In some aspects, the scFv contains the VH, linker and VL as set forth in SEQ ID NO: 2, 4, 6, 12, 249, 250, 251, 252, 253, 254, 255, 256, 257, 258, 259, 260, 261, 262, 263, 264, 265, 266, 267 or 268, or a sequence at least at or about 90%, 91%, 92%, 93%, 94%, 95%, 96%, 97%, 98%, or 99% identical to such a sequence, but in which the VH and VL are configured in the opposite orientation, i.e. VL-VH, as compared to such sequence. In some aspects, the scFv has the amino acid sequence set forth in SEQ ID NO: 2, 4, 6 or 12, or has a sequence at least at or about 90%, 91%, 92%, 93%, 94%, 95%, 96%, 97%, 98%, or 99% identical to the amino acid sequence set forth in SEQ ID NO: 2, 4, 6 or 12, but in which the VH and VL are configured in the opposite orientation, i.e. VL-VH, as compared to such sequence. In some embodiments, the scFv has the amino acid sequence set forth in SEQ ID NO:12, but in which the VH and VL are configured in the opposite orientation, i.e. VL-VH, as compared to such sequence. In some embodiments, the scFv has the amino acid sequence set forth in SEQ ID NO:6, but in which the VH and VL are configured in the opposite orientation, i.e. VL-VH, as compared to such sequence.

Also provided are human anti-ROR1 antibodies, e.g., antigen-binding antibody fragments that specifically bind to the same or an overlapping epitope of a ROR1 protein, such as a human ROR1 protein, as the epitope specifically bound by a reference antibody. Such antibody may be any of the above described antibodies or the anti-ROR1 antibody designated R12 or an antigen-binding fragment thereof.

Also provided are human anti-ROR1 antibodies, e.g., antigen-binding antibody fragments, that specifically bind to a ROR1 protein, such as a human ROR1 protein, and compete for binding to the ROR1 protein with a reference antibody that is any of the above described antibodies or is the anti-ROR1 antibody designated R12 or an antigen-binding fragment thereof.

In some such embodiments, the reference antibody can be an scFv that comprises the amino acid sequence set forth in SEQ ID NO: 2, 4, 6, 12, 249, 250, 251, 252, 253, 254, 255, 256, 257, 258, 259, 260, 261, 262, 263, 264, 265, 266, 267 or 268, or that has a sequence at least at or about 90%, 91%, 92%, 93%, 94%, 95%, 96%, 97%, 98%, or 99% identical to the amino acid sequence set forth in SEQ ID NO: 2, 4, 6, 12, 249, 250, 251, 252, 253, 254, 255, 256, 257, 258, 259, 260, 261, 262, 263, 264, 265, 266, 267 or 268. In some such embodiments, the reference antibody can be an scFv that comprises the amino acid sequence set forth in SEQ ID NO: 2, 4, 6, or 12, or that has a sequence at least at or about 90%, 91%, 92%, 93%, 94%, 95%, 96%, 97%, 98%, or 99% identical to the amino acid sequence set forth in SEQ ID NO: 2, 4, 6, or 12. In some embodiments, the reference antibody can be an antibody that contains the $V_H$ and $V_L$ of an scFv that comprises the amino acid sequence set forth in SEQ ID NO: 2, 4, 6, 12, 249, 250, 251, 252, 253, 254, 255, 256, 257, 258, 259, 260, 261, 262, 263, 264, 265, 266, 267 or 268, such as set forth in SEQ ID NO: 2, 4, 6, or 12.

In some embodiments of a provided human anti-ROR1 antibody, the human antibody contains a $V_H$ region that contains a portion having at least 95%, 96%, 97%, 98%, 99%, or 100% sequence identity to an amino acid sequence encoded by a germline nucleotide human heavy chain V segment, a portion with at least 95%, 96%, 97%, 98%, 99%, or 100% identity to an amino acid sequence encoded by a germline nucleotide human heavy chain D segment, and/or a portion having at least 95%, 96%, 97%, 98%, 99%, or 100% identity to an amino acid sequence encoded by a germline nucleotide human heavy chain J segment; and/or contains a $V_L$ region that contains a portion with at least 95%, 96%, 97%, 98%, 99%, or 100% identity to an amino acid sequence encoded by a germline nucleotide human kappa or lambda chain V segment, and/or a portion with at least 95%, 96%, 97%, 98%, 99%, or 100% identity to an amino acid sequence encoded by a germline nucleotide human kappa or lambda chain J segment. In some embodiments, the portion of the $V_H$ region corresponds to the CDR-H1, CDR-H2 and/or CDR-H3. In some embodiments, the portion of the $V_H$ region corresponds to the framework region 1 (FR1), FR2, FR2 and/or FR4. In some embodiments, the portion of the $V_L$ region corresponds to the CDR-L1, CDR-L2 and/or CDR-L3. In some embodiments, the portion of the $V_L$ region corresponds to the FR1, FR2, FR2 and/or FR4.

In some embodiments, the human antibody contains a CDR-H1 having at least 95%, 96%, 97%, 98%, 99%, or 100% sequence identity to an amino acid sequence of the corresponding CDR-H1 region within a sequence encoded by a germline nucleotide human heavy chain V segment. For example, the human antibody in some embodiments contains a CDR-H1 having a sequence that is 100% identical or with no more than one, two or three amino acid differences as compared to the corresponding CDR-H1 region within a sequence encoded by a germline nucleotide human heavy chain V segment.

In some embodiments, the human antibody contains a CDR-H2 having at least 95%, 96%, 97%, 98%, 99%, or 100% sequence identity to an amino acid sequence of the corresponding CDR-H2 region within a sequence encoded by a germline nucleotide human heavy chain V segment. For example, the human antibody in some embodiments contains a CDR-H2 having a sequence that is 100% identical or with no more than one, two or three amino acid difference as compared to the corresponding CDR-H2 region within a sequence encoded by a germline nucleotide human heavy chain V segment.

In some embodiments, the human antibody contains a CDR-H3 having at least 95%, 96%, 97%, 98%, 99%, or 100% sequence identity to an amino acid sequence of the corresponding CDR-H3 region within a sequence encoded by a germline nucleotide human heavy chain V segment, D segment and J segment. For example, the human antibody in some embodiments contains a CDR-H3 having a sequence that is 100% identical or with no more than one, two or three amino acid differences as compared to the corresponding CDR-H3 region within a sequence encoded by a germline nucleotide human heavy chain V segment, D segment and J segment.

In some embodiments, the human antibody contains a CDR-L1 having at least 95%, 96%, 97%, 98%, 99%, or 100% sequence identity to an amino acid sequence of the corresponding CDR-L1 region within a sequence encoded by a germline nucleotide human light chain V segment. For example, the human antibody in some embodiments contains a CDR-L1 having a sequence that is 100% identical or with no more than one, two or three amino acid differences as compared to the corresponding CDR-L1 region within a sequence encoded by a germline nucleotide human light chain V segment.

In some embodiments, the human antibody contains a CDR-L2 having at least 95%, 96%, 97%, 98%, 99%, or 100% sequence identity to an amino acid sequence of the corresponding CDR-L2 region within a sequence encoded by a germline nucleotide human light chain V segment. For example, the human antibody in some embodiments contains a CDR-L2 having a sequence that is 100% identical or with no more than one, two or three amino acid difference as compared to the corresponding CDR-L2 region within a sequence encoded by a germline nucleotide human light chain V segment.

In some embodiments, the human antibody contains a CDR-L3 having at least 95%, 96%, 97%, 98%, 99%, or 100% sequence identity to an amino acid sequence of the corresponding CDR-L3 region within a sequence encoded by a germline nucleotide human light chain V segment and J segment. For example, the human antibody in some embodiments contains a CDR-L3 having a sequence that is 100% identical or with no more than one, two or three amino acid differences as compared to the corresponding CDR-L3 region within a sequence encoded by a germline nucleotide human light chain V segment and J segment.

In some embodiments, the human antibody contains a framework region that contains human germline gene segment sequences. For example, in some embodiments, the human antibody contains a $V_H$ region in which the framework region, e.g. FR1, FR2, FR3 and FR4, has at least 95%, 96%, 97%, 98%, 99%, or 100% sequence identity to a framework region encoded by a human germline antibody segment, such as a V and/or J segment. In some embodiments, the human antibody contains a $V_L$ region in which the framework region e.g. FR1, FR2, FR3 and FR4, has at least 95%, 96%, 97%, 98%, 99%, or 100% sequence identity to a framework region encoded by a human germline antibody segment, such as a V and/or segment. For example, in some such embodiments, the framework sequence of the $V_H$ and/or $V_L$ sequence differs by no more than 10 amino acids, such as no more than 9, 8, 7, 6, 5, 4, 3, 2 or 1 amino acid, compared to the framework region encoded by a human germline antibody segment.

The antibody, e.g., antibody fragment, may contain at least a portion of an immunoglobulin constant region, such as one or more constant region domain. In some embodiments, the constant regions include a light chain constant region and/or a heavy chain constant region 1 (CH1). In some embodiments, the antibody includes a CH2 and/or CH3 domain, such as an Fc region. In some embodiments, the Fc region is an Fc region of a human IgG, such as an IgG1 or IgG4.

Also provided are nucleic acids encoding the antibodies and/or portions, e.g., chains, thereof. Among the provided nucleic acids are those encoding the anti-ROR antibodies described herein. The nucleic acids may include those encompassing natural and/or non-naturally occurring nucleotides and bases, e.g., including those with backbone modifications. The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

Also provided are vectors containing the nucleic acids, host cells containing the vectors, e.g., for producing the antibodies. Also provided are methods for producing the antibodies. The nucleic acid may encode an amino acid sequence comprising the $V_L$ and/or an amino acid sequence comprising the $V_H$ of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): a vector comprising a nucleic acid that encodes an amino acid sequence comprising the $V_H$ of the antibody. In another such embodiment, a host cell comprises (e.g., has been transformed with): (1) a vector comprising a nucleic acid that encodes an amino acid sequence comprising the $V_L$ of the antibody and an amino acid sequence comprising the $V_H$ of the antibody, or (2) a first vector comprising a nucleic acid that encodes an amino acid sequence comprising the $V_L$ of the antibody and a second vector comprising a nucleic acid that encodes an amino acid sequence comprising the $V_H$ of the antibody.

Also provided are methods of making the anti-ROR1 antibodies (including antigen-binding fragments). For recombinant production of the anti-ROR1 antibody, nucleic acid encoding an antibody, e.g., as described above, may be isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody). In some embodiments, a method of making the anti-ROR1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

In addition to prokaryotes, eukaryotic microbes such as filamentous fungi or yeast are suitable cloning or expression hosts for antibody-encoding vectors, including fungi and yeast strains whose glycosylation pathways have been modified to mimic or approximate those in human cells, resulting in the production of an antibody with a partially or fully human glycosylation pattern. See Gerngross, Nat. Biotech. 22:1409-1414 (2004), and Li et al., Nat. Biotech. 24:210-215 (2006).

Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells; and NSO cells. In some embodiments, the antibody heavy chains and/or light chains may be expressed in yeast. See, e.g., U.S. Publication No. US 2006/0270045 A1. In some embodiments, a particular eukaryotic host cell is selected based on its ability to make desired post-translational modifications to the heavy chains and/or light chains. For example, in some embodiments, CHO cells produce polypeptides that have a higher level of sialylation than the same polypeptide produced in 293 cells.

In some embodiments, the antibody is produced in a cell-free system. Exemplary cell-free systems are described, e.g., in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

The provided embodiments further include vectors and host cells and other expression systems for expressing and producing the antibodies and other binding proteins, including eukaryotic and prokaryotic host cells, including bacteria, filamentous fungi, and yeast, as well as mammalian cells such as human cells, as well as cell-free expression systems.

Exemplary Features

In some aspects, the provided antibodies have one or more specified functional features, such as binding properties, including binding to particular epitopes, such as epitopes that are similar to or overlap with those specifically bound by other antibodies such as reference antibodies, the ability to compete for binding with other antibodies such as reference antibodies, and/or particular binding affinities.

In some embodiments, the antibodies specifically bind to ROR1 protein. In some embodiments of any of the embodiments herein, ROR1 refers to human ROR1. The observation that an antibody or other binding molecule binds to ROR1 or specifically binds to ROR1 does not necessarily mean that it binds to ROR1 of every species. For example, in some embodiments, features of binding to ROR1, such as the ability to specifically bind thereto and/or to compete for binding thereto with a reference antibody, and/or to bind with a particular affinity or compete to a particular degree, in some embodiments, refers to the ability with respect to a human ROR1 protein and the antibody may not have this feature with respect to a ROR1 of another species such as mouse. In some embodiments, the antibody binds to human ROR1 and binds to ROR1 of another species, such as mouse.

In some embodiments, the antibodies specifically bind to human ROR1, such as to an epitope or region of human ROR1, such as the human ROR1 set forth in SEQ ID NO:103 (GenBank No. NP_005003.2, such as encoded by nucleotides set forth in GenBank No. NM_005012.3), or an allelic variant or splice variant thereof. In one embodiment, human ROR1 is a transcript variant or isoform that has the sequence of amino acids forth in SEQ ID NO:104 or SEQ ID NO:105.

In some embodiments, the antibody binds to non-human ROR1, such as monkey, rabbit, rat, mouse, or other species of ROR1. In some embodiments, the antibody binds to mouse ROR1, such as to an epitope or region of mouse ROR1, such as the mouse ROR1 set forth in SEQ ID NO: 106 (GenBank No. NP_038873, such as encoded by nucleotides set forth in GenBank No. NM_013845). In some embodiments, the antibody binds to human ROR1 and binds to mouse ROR1. In some embodiments, the extent of binding of an anti-ROR1 antibody to a non-human ROR1, such as mouse ROR1, is at least or about at least 75%, 80%, 90%, 95%, 100%, 110%, 120%, 130%, 140%, 150% or more of the binding of the antibody to ROR1.

In some embodiments, the antibodies do not bind to mouse ROR1, such as the mouse ROR1 set forth in SEQ ID NO:106 (GenBank No. NP_038873, such as encoded by nucleotides set forth in GenBank No. NM_013845).

In one embodiment, the extent of binding of an anti-ROR1 antibody to an unrelated, non-ROR1 protein or to anon-human ROR1 or other non-ROR1 protein, is less than at or about 10% of the binding of the antibody to human ROR1 as measured, e.g., by a radioimmunoassay (MA). In some embodiments, among provided antibodies are antibodies in which binding to mouse ROR1 is less than or at or about 10% of the binding of the antibody to human ROR1. In some embodiments, among provided antibodies are antibodies in which binding to a ROR2, such as a human ROR2, is less than or at or about 10% of the binding of the antibody to human ROR1.

In some embodiments, the provided antibodies are capable of binding ROR1, such as human ROR1 and/or mouse ROR1, with at least a certain affinity, as measured by any of a number of known methods. In some embodiments, the affinity is represented by a dissociation constant (Kd). In some embodiments, the affinity is represented by EC50.

In some embodiments, the binding affinity (EC50) and/or the dissociation constant of the antibody to ROR1, such as human ROR1 or mouse ROR1, is from or from about 0.1 nM to 500 nM, 0.1 nM to 100 nM, 0.1 nM to 50 nM, 0.1 nM to 10 nM, 0.1 nM to 1 nM, 1 nM to 500 nM, 1 nM to 100 nM, 1 nM to 50 nM, 1 nM to 10 nM, 10 nM to 500 nM, 10 nM to 100 nM, 10 nM to 50 nM, 50 nM to 500 nM, 50 nM to 100 nM or 100 nM to 500 nM. In certain embodiments, the binding affinity (EC50) and/or the dissociation constant of the antibody to ROR1, such as human ROR1 or mouse ROR1, is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM. In some embodiments, the antibodies bind to ROR1, such as human ROR1 or mouse ROR1, with a sub-nanomolar binding affinity, for example, with a binding affinity less than 1 nM, such as less than 0.9 nM, 0.8 nM, 0.7 nM, 0.6 nM, 0.5 nM, 0.4 nM, 0.3 nM, 0.2 nM or 0.1 nM.

In some embodiments, the antibodies, such as the human antibodies, specifically bind to a particular epitope or region of ROR1, such as generally an extracellular epitope or region. ROR1 is a type I membrane protein that contains an extracellular region containing an immunoglobulin (Ig) domain, a frizzled (Fz) domain and a kringle (Kr) domain followed by a transmembrane domain. With reference to human ROR1 set forth in SEQ ID NO:103, the extracellular region corresponds to amino acids 1-377, whereby amino acids 13-118 correspond to the Ig domain, amino acids 136-270 correspond to the Fz domain and amino acids 283-362 correspond to the Kr domain. In some embodiments, the antibodies, such as human antibodies, bind to an epitope comprising residues within the Ig domain, the Fz domain and/or the Kr domain. In some embodiments, the antibodies, such as human antibodies, bind to an epitope comprising residues with the Ig domain and/or Fz domain.

In some embodiments, the antibodies, such as human antibodies, bind to an epitope comprising residues within both the Ig and Fz domains.

In some embodiments, properties or features of the provided antibodies are described in relation to properties observed for another antibody, e.g., a reference antibody. In some embodiments, the reference antibody is a non-human anti-ROR1 antibody, such as a rabbit or chimeric or humanized anti-ROR1 antibody. In some aspects, the reference antibody is the chimeric rabbit/human IgG1 antibody designated R12 (see, e.g., Yang et al. (2011) *PloS ONE,* 6:e21018; U.S. Patent Application No. US 2013/0251642), and/or a fragment derived therefrom such as an scFv fragment thereof, and/or an antibody containing the $V_H$ and $V_L$ sequences of such an antibody and/or the heavy and light chain CDRs of such an antibody. A chimeric antigen receptor (CAR) containing an antigen-binding scFv fragment of R12 has been demonstrated to effectively promote antitumor reactivity in a CAR therapy (Hudecek et al. (2013) *Clin. Cancer Res.,* 19:3153; International published PCT Appl. No. WO2014031687).

For example, in some embodiments, the reference antibody has a $V_H$ region containing the sequence set forth in SEQ ID NO: 85, or comprises CDR1, CDR2, and/or CDR3 within such a sequence, and/or has a $V_L$ containing the sequence set forth in SEQ ID NO: 86, or comprises CDR1, CDR2, and/or CDR3 within such a sequence. For example, the reference antibody can be an antibody that contains a CDR-H1 sequence of AYYMS (SEQ ID NO:87), a CDR-H2 sequence of TIYPSSGKTYYATWVNG (set forth in SEQ ID NO:88), a CDR-H3 sequence of DSYADDGALFN (SEQ ID NO:72), a CDR-L1 sequence of TLSSAHKTDTID (SEQ ID NO:89), a CDR-L2 sequence of GSYTKRP (SEQ ID NO:90) and/or a CDR-L3 sequence of GADYIGGYV (SEQ ID NO:73). In some embodiments, the reference antibody is an scFv that comprises the sequence of amino acids set forth in SEQ ID NO:84.

In some embodiments, the reference antibody is the mouse anti-human ROR1 antibody designated 2A2, and/or a fragment derived therefrom such as an scFv fragment thereof, and/or an antibody containing the $V_H$ and $V_L$ sequences of such an antibody and/or the heavy and light chain CDRs of such an antibody (see, e.g., Baskar et al. (2012) I, 4:349-361; published U.S. Patent Appl. No. US2012/20058051).

For example, in some embodiments, the reference antibody has a $V_H$ region containing the sequence set forth in SEQ ID NO: 114, or comprises CDR1, CDR2, and/or CDR3 within such a sequence, and/or has a $V_L$ containing the sequence set forth in SEQ ID NO: 115, or comprises CDR1, CDR2, and/or CDR3 within such a sequence. For example, the reference antibody can be an antibody that contains a CDR-H1 sequence of DYEMH (SEQ ID NO:116), a CDR-H2 sequence of AIDPETGGTAYNQKFKG (set forth in SEQ ID NO:117), a CDR-H3 sequence of YYDYDSFTY (SEQ ID NO:118), a CDR-L1 sequence of KASQNVDAAVA (SEQ ID NO:119), a CDR-L2 sequence of SASNRYT (SEQ ID NO:120) and/or a CDR-L3 sequence of QQYDIYPYT (SEQ ID NO:121). In some embodiments, the reference antibody is an scFv form of antibody 2A2.

In some embodiments, the reference antibody is a human or humanized anti-ROR1 antibody. Exemplary humanized anti-ROR1 antibodies are described in International PCT Appl. No. WO2014/031174. In some embodiments, the reference antibody is a humanized variant of an antibody designated 99961. In some embodiments, the reference antibody has a $V_H$ region containing the sequence set forth in SEQ ID NO: 122, 123, 124 or 125, or comprises CDR1, CDR2, and/or CDR3 within such a sequence, and/or has a $V_L$ containing the sequence set forth in SEQ ID NO: 126, 127, 128 or 129, or comprises CDR1, CDR2, and/or CDR3 within such a sequence. In some embodiments, the reference antibody can be an antibody that contains a CDR-H1 sequence set forth in SEQ ID NO:130 or 133, a CDR-H2 sequence set forth in SEQ ID NO:131 or 134, a CDR-H3 sequence set forth in SEQ ID NO:132 or 135, a CDR-L1 sequence set forth in SEQ ID NO:136 or 139, a CDR-L2 sequence set forth in SEQ ID NO:137 or 140 and/or a CDR-L3 sequence set forth in SEQ ID NO:138 or 141.

In some embodiments, the provided antibody contains heavy and light chain CDRs that are distinct from the CDRs present in the reference antibody or antibodies. In some embodiments, the provided antibody contains heavy and light chain CDRs that are distinct from the CDRs present in the antibody designated R12, such as present in the $V_H$ region set forth in SEQ ID NO: 85 and/or the $V_L$ region set forth in SEQ ID NO: 86. In some embodiments, the provided antibody contains heavy and light chain CDRs that are distinct from the CDRs present in the antibody designated 2A2, such as present in the $V_H$ region set forth in SEQ ID NO: 104 and/or the $V_L$ region set forth in SEQ ID NO: 105. In some embodiments, the provided antibody contains heavy and light chain CDRs that are distinct from the CDRs present in a humanized variant of antibody designated 99961, such as present in the $V_H$ region set forth in SEQ ID NO: 122, 123, 124 or 125 and/or the $V_L$ region set forth in SEQ ID NO: 126, 127, 128 or 129.

Among the provided antibodies are those that compete for binding with and/or bind to the same or overlapping epitopes of ROR1 as those bound by a reference antibody or antibody, such as R12, but nonetheless contain distinct CDRs, e.g., distinct heavy and/or light chain CDR1, CDR2, and CDR3.

In some embodiments, the reference antibody has a sequence present in an antibody or portion thereof as described herein, such as any of the provided exemplary antibodies. For example, in some embodiments, the reference antibody contains a CDR-H1 comprising the amino acid sequence set forth in SEQ ID NO: 20, 27, or 33; a CDR-H2 comprising the amino acid sequence set forth in SEQ ID NO: 21, 26, 28, or 34; a CDR-H3 comprising the amino acid sequence set forth in SEQ ID NO: 22, 29, 35, 46, 50, 51, 52, 53, 54, 55, 56, 57, 58, 59, 60, 61, 62, 63, 64, 65, 66, 67, 68, 69, 70, 71 or 174; a CDR-L1 comprising the amino acid sequence set forth in SEQ ID NO: 23, 30, or 36; CDR-L2 comprising the amino acid sequence set forth in SEQ ID NO: 24, 31, or 37; and/or a CDR-L3 comprising the amino acid sequence set forth in SEQ ID NO: 25, 32, 38, 39, 40, 41, 42, 43, 44, 45, 47, 48, and 49. For example, in some embodiments, the reference antibody has a light chain variable ($V_L$) region amino acid sequence set forth in SEQ ID NO: 14, 16, or 18 and/or has a heavy chain variable ($V_H$) region set forth in SEQ ID NO: 8, 10, 13, 15, 17, or 19. In some such embodiments, the antibody has heavy and/or light chain CDRs 1, 2, and/or 3 as present in such an antibody.

In some embodiments, the antibody has an affinity, e.g., EC50 or Kd, about the same as or lower than that of the corresponding form of the reference antibody, e.g., no more than about 1.5-fold or no more than about 2-fold greater, no more than 3-fold greater, and/or no more than 10-fold greater, than the EC50 or Kd of the corresponding form of the reference antibody. In some embodiments, the antibody has an affinity, e.g., EC50 or Kd, that is greater than or greater than about 5-fold, 10-fold, 20-fold, 30-fold, 40-fold, 50-fold, 60-fold, 70-fold, 80-fold, 90-fold, 100-fold, 150-fold, 200-fold, 250-fold or greater than the EC50 or Kd of the corresponding form of the reference antibody.

In some embodiments, the antibodies display a binding preference for ROR1-expressing cells as compared to ROR1-negative cells, such as particular cells known and/or described herein to express ROR1 and known not to express ROR1. In some embodiments, the binding preference is observed where a significantly greater degree of binding is measured to the ROR1-expressing, as compared to the non-expressing, cells. In some embodiments, the fold change in degree of binding detected, for example, as measured by mean fluorescence intensity in a flow cytometry-based assay and/or dissociation constant or EC50, to the ROR1-expressing cells as compared to the non-ROR1-expressing cells, is at least at or about 1.5, 2, 3, 4, 5, 6, or more, and/or is about as great, about the same, at least as great or at least about as great, or greater, than the fold change observed for the corresponding form of the reference antibody. In some cases, the total degree of observed binding to ROR1 or to the ROR1-expressing cells is approximately the same, at least as great, or greater than that observed for the corresponding form of the reference antibody.

In some aspects, the affinity is at or about the same degree or substantially the same degree of affinity compared to the corresponding form of the reference antibody, such as rabbit ROR1 antibody. In some aspects, the affinity is at least 80, 85, 90, 95, or 99% the same as that of the corresponding form of the reference antibody.

In some embodiments, the antibody specifically binds to an epitope that overlaps with the epitope of ROR1 bound by a reference antibody. In some aspects, among such antibodies are antibodies that bind to the same or a similar epitope as the reference antibody. In some embodiments, two antibodies specifically bind to the same epitope and/or an overlapping epitope if all or essentially all amino acid mutations in the antigen that reduce or eliminate binding of one antibody reduce or eliminate binding of the other antibody.

In some embodiments, the antibodies bind to the same or a similar epitope or an epitope within the same region or containing residues within the same region of ROR1 as a reference antibody, such as anti-ROR1 antibody R12 or scFv fragment thereof (set forth in SEQ ID NO: 84; see e.g. Yang et al. (2011) *PloS ONE,* 6:e21018). In some such embodiments, the antibodies bind to an epitope that contains amino acids within the Ig domain and the Fz domain of a ROR1, such as a human ROR1, such as an epitope comprising residues from both such domains and/or at the conjunction of the Ig and Fz domains. In some embodiments, the antibodies bind to an epitope of the ROR1 that overlaps with the epitope specifically bound by R12 and/or an scFv fragment thereof and/or compete for binding with such an antibody.

In some embodiments, the antibody inhibits binding to and/or competes for binding to ROR1, such as human ROR1, with the reference antibody. In some embodiments, the antibody inhibits binding to and/or competes for binding to ROR1, such as human ROR1, with R12 or an IgG or antigen-binding fragment thereof.

An antibody "competes for binding" to ROR1 with a reference antibody if it competitively inhibits binding of the reference antibody to ROR1, and/or if the reference antibody competitively inhibits binding of the antibody to ROR1. An antibody competitively inhibits binding of a reference antibody to an antigen if the presence of the antibody in excess detectably inhibits (blocks) binding of the other antibody to its antigen. A particular degree of inhibition may be specified.

Competitive inhibition assays are known and include ELISA-based, flow cytometry-based assays, and RIA-based assays. In some aspects, competitive inhibition assays are carried out by incorporating an excess of an unlabeled form of one of the antibodies and assessing its ability to block binding of the other antibody, which is labeled with a detectable marker, such that degree of binding and reduction thereof can be assessed by detection of the label or marker.

In some embodiments, addition of the provided antibody in excess, e.g., 1-, 2-, 5-, 10-, 50- or 100-fold excess, as compared to the amount or concentration of the reference antibody, inhibits binding to the antigen by the reference antibody (or vice versa). In some embodiments, the inhibition of binding is by at least 50%, and in some embodiments by at least 75%, 90% or 99%. In some aspects, the competitive inhibition is as measured in a competitive binding assay (see, e.g., Junghans et al., Cancer Res. 1990:50:1495-1502).

In some embodiments, where the reference antibody is present at a concentration of or of about 2 nM, the provided antibody inhibits binding of the reference antibody with an IC50 of less than at or about 200 nM, 150 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, or 10 nM, or less than at or about 9 nM, 8 nM, 7 nM, 6 nM, or 5 nM. In some embodiments, where the provided antibody is present at a concentration of or about 2 nM, the reference antibody inhibits binding of the provided antibody with an IC50 of less than at or about 200 nM, 150 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, or 10 nM, or less than at or about 9 nM, 8 nM, 7 nM, 6 nM, or 5 nM.

In some embodiments, competitive inhibition of the reference antibody's binding by the provided antibody (or vice versa) is at or about or least at or about the same degree as the degree of competitive inhibition of the reference antibody's binding by the reference antibody itself, e.g., unlabeled reference antibody. In some embodiments, the provided antibody inhibits binding of the reference antibody, such as binding of R12 scFv, to human ROR1 by at least 70%, 75%, 80%, 85%, 90%, 91%, 92%, 93%, 94%, 95%, 96%, 97%, 98%, or 99%.

Anti-ROR1 antibodies provided herein may be identified, screened for, or characterized for their physical/chemical properties and/or biological activities by various known assays. In one aspect, the antibody is tested for its antigen binding activity, e.g., by known methods such as ELISA, Western blotting, and/or flow cytometric assays, including cell-based binding assays, for example, assessing binding of the antibody (e.g., conjugated to a fluorescent marker or tagged) to a cell expressing the target antigen, e.g., ROR1, in some cases compared to results using cells that do not express the target antigen, e.g., ROR1. Binding affinity may be measured as Kd or EC50.

Competition assays may be used to identify an antibody that competes with any of the antibodies described herein. Assays for mapping epitopes bound by the antibodies and reference antibodies also may be used and are known.

Immunoconjugates

In some embodiments, the antibody is or is part of an immunoconjugate, in which the antibody is conjugated to one or more heterologous molecule(s), such as, but not limited to, a cytotoxic or an imaging agent. Cytotoxic agents include, but are not limited to, radioactive isotopes (e.g., At211, I131, I125, Y90, Re186, Re188, Sm153, Bi212, P32, Pb212 and radioactive isotopes of Lu); chemotherapeutic agents (e.g., methotrexate, Adriamycin® (doxorubicin), vinca alkaloids (vincristine, vinblastine, etoposide), melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins. In some embodiments, the antibody is conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

Among the immunoconjugates are antibody-drug conjugates (ADCs), in which an antibody is conjugated to one or more drugs, including but not limited to a maytansinoid (see U.S. Pat. Nos. 5,208,020, 5,416,064 and European Patent EP 0 425 235 B1); an auristatin such as monomethyl auristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

Also among the immunoconjugates are those in which the antibody is conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

Also among the immunoconjugates are those in which the antibody is conjugated to a radioactive atom to form a radioconjugate. Exemplary radioactive isotopes include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu.

Conjugates of an antibody and cytotoxic agent may be made using any of a number of known protein coupling agents, e.g., linkers, (see Vitetta et al., *Science* 238:1098 (1987)), WO94/11026. The linker may be a "cleavable linker" facilitating release of a cytotoxic drug in the cell, such as acid-labile linkers, peptidase-sensitive linkers, photolabile linkers, dimethyl linkers, and disulfide-containing linkers (Chari et al., *Cancer Res.* 52:127-131 (1992); U.S. Pat. No. 5,208,020).

Multispecific Antibodies

In certain embodiments, the ROR1-binding molecules, e.g., antibodies or polypeptides such as chimeric receptors containing the same, are multispecific. Among the multispecific binding molecules are multispecific antibodies, including, e.g. bispecific. Multi specific binding partners, e.g., antibodies, have binding specificities for at least two different sites, which may be in the same or different antigens. In certain embodiments, one of the binding specificities is for ROR1 and the other is for another antigen. In certain embodiments, bispecific antibodies may bind to two different epitopes of ROR1. Bispecific antibodies may also be used to localize cytotoxic agents to cells which express ROR1. Bispecific antibodies can be prepared as full length antibodies or antibody fragments. Among the multispecific antibodies are multispecific single-chain antibodies, e.g., diabodies, triabodies, and tetrabodies, tandem di-scFvs, and tandem tri-scFvs. Also provided are multispecific chimeric receptors, such as multispecific CARs, containing the antibodies. Also provided are multispecific cells containing the antibodies or polypeptides including the same, such as cells containing a cell surface protein including the anti-ROR1 antibody and an additional cell surface protein, such as an additional chimeric receptor, which binds to a different antigen or a different epitope on ROR1.

Exemplary additional antigens include B cell specific antigens, other tumor-specific antigens, such as antigens expressed specifically on or associated with B cell leukemia, lymphoma, B cell chronic lymphocytic leukemia (CLL), AML, acute myeloid leukemia (AML), acute lymphocytic leukemia (ALL), Burkett's Lymphoma, mantle cell lymphoma (MCL), non-small cell lung cancer (NSCLC), neuroblastoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, uterine cancer, adrenal cancer and/or head and neck cancer, and antigens expressed on T cells. Exemplary antigens include CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC-1, Ia, HM1.24, HLA-DR, tenascin, an angiogenesis factor, VEGF, PIGF, ED-B fibronectin, an oncogene, an oncogene product, CD66a-d, necrosis antigens, Ii, IL-2, T101, TAC, IL-6, TRAIL-R1 (DR4) and TRAIL-R2 (DR5).

Variants

In certain embodiments, the antibodies include one or more amino acid variations, e.g., substitutions, deletions, insertions, and/or mutations, compared to the sequence of an antibody described herein. Exemplary variants include those designed to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, the antibodies include one or more amino acid substitutions, e.g., as compared to an antibody sequence described herein and/or compared to a sequence of a natural repertoire, e.g., human repertoire. Sites of interest for substitutional mutagenesis include the CDRs and FRs. Amino acid substitutions may be introduced into an antibody of interest and the products screened for a desired activity, e.g., retained/improved antigen binding, decreased immunogenicity, improved half-life, and/or improved effector function, such as the ability to promote antibody-dependent cellular cytotoxicity (ADCC) or complement-dependent cytotoxicity (CDC).

In some embodiments, one or more residues within a CDR of a parent antibody (e.g. a humanized or human antibody) is/are substituted. In some embodiments, the substitution is made to revert a sequence or position in the sequence to a germline sequence, such as an antibody sequence found in the germline (e.g., human germline), for example, to reduce the likelihood of immunogenicity, e.g., upon administration to a human subject.

In some embodiments, alterations are made in CDR "hotspots," residues encoded by codons that undergo mutation at high frequency during the somatic maturation process (see, e.g., Chowdhury, Methods Mol. Biol. 207:179-196 (2008)), and/or residues that contact antigen, with the resulting variant $V_H$ or $V_L$ being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may, for example, be outside of antigen contacting residues in the CDRs. In certain embodiments of the variant $V_H$ and $V_L$ sequences provided above, each CDR either is unaltered, or contains no more than one, two or three amino acid substitutions.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme or a polypeptide which increases the serum half-life of the antibody.

Modifications

In certain embodiments, the antibody is altered to increase or decrease the extent to which the antibody is glycosylated, for example, by removing or inserting one or more glycosylation sites by altering the amino acid sequence and/or by modifying the oligosaccharide(s) attached to the glycosylation sites, e.g., using certain cell lines.

In some embodiments, an N-linked glycosylation, which is a glycosylation site that occurs at asparagines in the consensus sequence -Asn-Xaa-Ser/Thr is removed or inserted. For example, an exemplary N-linked consensus sequence corresponds to residues N52/P52A/S53, by Kabat numbering, of the exemplary heavy chain set forth in SEQ ID NO: 17. In some embodiments, one or more residues corresponding to N52, P52A and/or S53 are replaced with another amino acid to remove the glycosylation site. Exemplary of a modification is S53N, such as is provided in the exemplary heavy chain set forth in SEQ ID NO: 19.

Exemplary modifications, variants, and cell lines are described, e.g., in Patent Publication Nos. US 2003/0157108, US 2004/0093621, US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Ripka et al. Arch. Biochem. Biophys. 249:533-545 (1986); US Pat Appl No US 2003/0157108 A1, Presta, L; and WO 2004/056312 A1, Yamane-Ohnuki et al. Biotech. Bioeng. 87: 614 (2004); Kanda, Y. et al., Biotechnol. Bioeng., 94(4):680-688 (2006); and WO2003/085107); WO 2003/011878 (Jean-Mairet et al.); U.S. Pat. No. 6,602,684 (Umana et al.); and US 2005/0123546 (Umana et al.); WO 1997/30087 (Patel et al.); WO 1998/58964 (Raju, S.); and WO 1999/22764 (Raju, S.).

Among the modified antibodies are those having one or more amino acid modifications in the Fc region, such as those having a human Fc region sequence or other portion of a constant region (e.g., a human IgG1, IgG2, IgG3 or IgG4 Fc region) comprising an amino acid modification (e.g. a substitution) at one or more amino acid positions.

Such modifications can be made, e.g., to improve half-life, alter binding to one or more types of Fc receptors, and/or alter effector functions.

Also among the variants are cysteine engineered antibodies such as "THIOMABS™" and other cysteine engineered variants, in which one or more residues of an antibody are substituted with cysteine residues, in order to generate reactive thiol groups at accessible sites, e.g., for use in conjugation of agents and linker-agents, to produce immunoconjugates. Cysteine engineered antibodies are described, e.g., in U.S. Pat. Nos. 7,855,275 and 7,521,541.

In some embodiments, the antibodies are modified to contain additional non proteinaceous moieties, including water soluble polymers. Exemplary polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyamino acids (either homopolymers or random copolymers), and dextran or poly(n-vinyl pyrrolidone) polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

B. Recombinant Receptors

Among the provided binding molecules, e.g., ROR1 binding molecules, are recombinant receptors, such as those that include one of the provided antibodies. The receptors include antigen receptors and other chimeric receptors that specifically bind to ROR1, such as receptors containing the provided anti-ROR1 antibodies, e.g., antibody fragments. Among the antigen receptors are functional non-TCR antigen receptors, such as chimeric antigen receptors (CARs). Also provided are cells expressing the recombinant receptors and uses thereof in adoptive cell therapy, such as treatment of diseases and disorders associated with ROR1 expression.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) *PLoS ONE* 8(4): e61338; Turtle et al., *Curr. Opin. Immunol.,* 2012 October; 24(5): 633-39; Wu et al., *Cancer,* 2012 Mar. 18(2): 160-75. In some aspects, the antigen receptors include a CAR as described in U.S. Pat. No. 7,446,190, and those described in International Patent Application Publication No.: WO/2014055668 A1. Exemplary of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, e.g., and in which the antigen-binding portion, e.g., scFv, is replaced by an antibody, e.g., as provided herein.

Among the chimeric receptors are chimeric antigen receptors (CARs). The chimeric receptors, such as CARs, generally include an extracellular antigen binding domain that includes, is, or is comprised within, one of the provided anti-ROR1 antibodies. Thus, the chimeric receptors, e.g., CARs, typically include in their extracellular portions one or more ROR1-binding molecules, such as one or more antigen-binding fragment, domain, or portion, or one or more antibody variable domains, and/or antibody molecules, such as those described herein. In some embodiments, the CAR includes a ROR1-binding portion or portions of the antibody molecule, such as a variable heavy ($V_H$) chain region and/or variable light ($V_L$) chain region of the antibody, e.g., an scFv antibody fragment.

ROR1-targeting CARs are described, for example, by Hudecek et al., *Clin Cancer Res,* 19(12), 3153-3164 (2013) and Baskar et al. *MAbs*. 4(3): 349-361 (2012). See also WO2014031687.

In some embodiments, the recombinant receptor such as the CAR, such as the antibody portion thereof, further includes a spacer, which may be or include at least a portion of an immunoglobulin constant region or variant or modified version thereof, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. (2013) *Clin. Cancer Res.,* 19:3153 or international patent application publication number WO2014031687. In some embodiments, the spacer has the sequence set forth in SEQ ID NO: 108, and is encoded by the sequence set forth in SEQ ID NO: 107. In some embodiments, the spacer has the sequence set forth in SEQ ID NO: 142. In some embodiments, the spacer has the sequence set forth in SEQ ID NO: 143.

In some embodiments, the constant region or portion is of IgD. In some embodiments, the spacer has the sequence set forth in SEQ ID NO:144. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 108, 142, 143 or 144.

The antigen recognition domain generally is linked to one or more intracellular signaling components, such as signaling components that mimic activation through an antigen receptor complex, such as a TCR complex, in the case of a CAR, and/or signal via another cell surface receptor. Thus, in some embodiments, the ROR1-specific binding component (e.g., antibody) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD5, CD9, CD 16, CD22, CD33, CD37, CD64, CD80, CD86, CD 134, CD137, CD 154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the ROR1-binding antibody is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR includes a chimeric molecule between CD3-zeta (CD3-ζ) or Fc receptor γ and CD8, CD4, CD25 or CD16.

In some embodiments, upon ligation of the CAR, the cytoplasmic domain or intracellular signaling domain of the CAR activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR or CD3 zeta, FcR gamma, FcR beta, CD3 gamma, CD3 delta, CD3 epsilon, CDS, CD22, CD79a, CD79b, and CD66d. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components.

In some embodiments, the activating domain is included within one CAR, whereas the costimulatory component is provided by another CAR recognizing another antigen. In some embodiments, the CARs include activating or stimulatory CARs, and costimulatory CARs, both expressed on the same cell (see WO2014/055668). In some aspects, the ROR1-targeting CAR is the stimulatory or activating CAR; in other aspects, it is the costimulatory CAR. In some embodiments, the cells further include inhibitory CARs (iCARs, see Fedorov et al., *Sci. Transl. Medicine,* 5(215) (December, 2013), such as a CAR recognizing an antigen other than ROR1, whereby an activating signal delivered through the ROR1-targeting CAR is diminished or inhibited by binding of the inhibitory CAR to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the CAR or other antigen receptor further includes a marker, such as a cell surface marker, which may be used to confirm transduction or engineering of the cell to express the receptor, such as a truncated version of a cell surface receptor, such as truncated EGFR (tEGFR). In some aspects, the marker includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. See WO2014031687. In some embodiments, introduction of a construct encoding the CAR and EGFRt separated by a T2A ribosome switch can express two proteins from the same construct, such that the EGFRt can be used as a marker to detect cells expressing such construct. In some embodiments, a marker, and optionally a linker sequence, can be any as disclosed in published patent application No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 154 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 154. An exemplary T2A linker sequence comprises the sequence of amino acids set forth in SEQ ID NO: 153 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 153.

In some embodiments, the marker is a molecule, e.g., cell surface protein, not naturally found on T cells or not naturally found on the surface of T cells, or a portion thereof.

In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR in some aspects is one that includes multiple costimulatory domains of different costimulatory receptors.

In some embodiments, the chimeric antigen receptor includes an extracellular portion containing the antibody or fragment described herein. In some aspects, the chimeric antigen receptor includes an extracellular portion containing the antibody or fragment described herein and an intracellular signaling domain. In some embodiments, the antibody or fragment includes an scFv or a single-domain $V_H$ antibody and the intracellular domain contains an ITAM. In some aspects, the intracellular signaling domain includes a signaling domain of a zeta chain of a CD3-zeta (CD3) chain. In some embodiments, the chimeric antigen receptor includes a transmembrane domain linking the extracellular domain and the intracellular signaling domain.

In some aspects, the transmembrane domain contains a transmembrane portion of CD28. The extracellular domain and transmembrane can be linked directly or indirectly. In some embodiments, the extracellular domain and transmembrane are linked by a spacer, such as any described herein. In some embodiments, the chimeric antigen receptor contains an intracellular domain of a T cell costimulatory molecule, such as between the transmembrane domain and intracellular signaling domain. In some aspects, the T cell costimulatory molecule is CD28 or 41BB.

In some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the receptor, e.g., the CAR is a transmembrane domain of human CD28 or variant thereof, e.g., a 27-amino acid transmembrane domain of a human CD28 (Accession No.: P10747.1), or is a transmembrane domain that comprises the sequence of amino acids set forth in SEQ ID NO: 145 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO:145; in some embodiments, the transmembrane-domain containing portion of the recombinant receptor comprises the sequence of amino acids set forth in SEQ ID NO: 146 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the chimeric antigen receptor contains an intracellular domain of a T cell costimulatory molecule. In some aspects, the T cell costimulatory molecule is CD28 or 41BB.

In some embodiments, the intracellular signaling domain comprises an intracellular costimulatory signaling domain of human CD28 or functional variant or portion thereof, such as a 41 amino acid domain thereof and/or such a domain with an LL to GG substitution at positions 186-187 of a native CD28 protein. In some embodiments, the intracellular signaling domain can comprise the sequence of amino acids set forth in SEQ ID NO: 147 or 148 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 147 or 148. In some embodiments, the intracellular domain comprises an intracellular costimulatory signaling domain of 41BB or functional variant or portion thereof, such as a 42-amino acid cytoplasmic domain of a human 4-1BB (Accession No. Q07011.1) or functional variant or portion thereof, such as the sequence of amino acids set forth in SEQ ID NO: 149 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 149.

In some embodiments, the intracellular signaling domain comprises a human CD3 zeta stimulatory signaling domain or functional variant thereof, such as an 112 AA cytoplasmic domain of isoform 3 of human CD3ζ (Accession No.: P20963.2) or a CD3 zeta signaling domain as described in U.S. Pat. No. 7,446,190 or 8,911,993. In some embodiments, the intracellular signaling domain comprises the sequence of amino acids set forth in SEQ ID NO: 150, 151 or 152 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 150, 151 or 152

In some aspects, the spacer contains only a hinge region of an IgG, such as only a hinge of IgG4 or IgG1, such as the hinge only spacer set forth in SEQ ID NO:108. In other embodiments, the spacer is an Ig hinge, e.g., and IgG4 hinge, linked to a CH2 and/or CH3 domains. In some embodiments, the spacer is an Ig hinge, e.g., an IgG4 hinge, linked to CH2 and CH3 domains, such as set forth in SEQ ID NO:143. In some embodiments, the spacer is an Ig hinge, e.g., an IgG4 hinge, linked to a CH3 domain only, such as set forth in SEQ ID NO:142. In some embodiments, the spacer is or comprises a glycine-serine rich sequence or other flexible linker such as known flexible linkers.

For example, in some embodiments, the CAR includes a ROR-1 antibody or fragment, such as any of the human ROR1 antibodies, including sdAbs (e.g. containing only the $V_H$ region) and scFvs, described herein, a spacer such as any of the Ig-hinge containing spacers, a CD28 transmembrane domain, a CD28 intracellular signaling domain, and a CD3 zeta signaling domain. In some embodiments, the CAR includes the ROR-1 antibody or fragment, such as any of the human ROR1 antibodies, including sdAbs and scFvs described herein, a spacer such as any of the Ig-hinge containing spacers, a CD28 transmembrane domain, a CD28 intracellular signaling domain, and a CD3 zeta signaling domain. In some embodiments, such CAR constructs further includes a T2A ribosomal skip element and/or a tEGFR sequence, e.g., downstream of the CAR.

C. Engineered Cells

Also provided are cells such as cells that contain an engineered antigen receptor, e.g., that contains an extracellular domain including the anti-ROR1 antibody or fragment, described herein. Also provided are populations of such cells, compositions containing such cells and/or enriched for such cells, such as in which cells expressing the ROR1 binding molecule make up at least 50, 60, 70, 80, 90, 91, 92, 93, 94, 95, 96, 97, 98, 99, or more percent of the total cells in the composition or cells of a certain type such as T cells or CD8+ or CD4+ cells. Among the compositions are pharmaceutical compositions and formulations for administration, such as for adoptive cell therapy. Also provided are therapeutic methods for administering the cells and compositions to subjects, e.g., patients.

Thus also provided are genetically engineered cells expressing the recombinant receptors containing the antibodies, e.g., cells containing the CARs. The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

Vectors and Methods for Genetic Engineering

Also provided are methods, nucleic acids, compositions, and kits, for expressing the binding molecules, including receptors comprising the antibodies, and for producing the genetically engineered cells expressing such binding molecules. The genetic engineering generally involves introduction of a nucleic acid encoding the recombinant or engineered component into the cell, such as by retroviral transduction, transfection, or transformation.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell II:223, 1977) which confers ganciclovir sensitivity; the cellular hypoxanthine phosphoribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some aspects, the cells further are engineered to promote expression of cytokines or other factors. Various methods for the introduction of genetically engineered components, e.g., antigen receptors, e.g., CARs, are well known and may be used with the provided methods and compositions. Exemplary methods include those for transfer of nucleic acids encoding the receptors, including via viral, e.g., retroviral or lentiviral, transduction, transposons, and electroporation.

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (VIPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) *J. Immunother.* 35(9): 689-701; Cooper et al. (2003) *Blood.* 101: 1637-1644; Verhoeyen et al. (2009) *Methods Mol Biol.* 506: 97-114; and Cavalieri et al. (2003) Blood. 102(2): 497-505.

In some embodiments, recombinant nucleic acids are transferred into T cells via electroporation (see, e.g., Chicaybam et al, (2013) *PLoS ONE* 8(3): e60298 and Van Tedeloo et al. (2000) *Gene Therapy* 7(16): 1431-1437). In some embodiments, recombinant nucleic acids are transferred into T cells via transposition (see, e.g., Manuri et al. (2010) Hum Gene Ther 21(4): 427-437; Sharma et al. (2013) *Molec Ther Nucl Acids* 2, e74; and Huang et al. (2009) *Methods Mol Biol* 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

Preparation of Cells for Engineering

In some embodiments, preparation of the engineered cells includes one or more culture and/or preparation steps. The cells for introduction of the ROR1-binding molecule, e.g., CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, or pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the COBE® 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a density gradient (Percoll® or Ficoll® gradient).

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using CD3/CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed ($marker^+$) at a relatively higher level ($marker^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) *J Immunother.* 35(9):689-701. In some embodiments, combining $T_{CM}$-enriched $CD8^+$ T cells and $CD4^+$ T cells further enhances efficacy.

In embodiments, memory T cells are present in both $CD62L^+$ and $CD62L^-$ subsets of $CD8^+$ peripheral blood lymphocytes. PBMC can be enriched for or depleted of $CD62L^-CD8^+$ and/or $CD62L^+CD8^+$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a $CD8^+$ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the $CD8^+$ cell population or subpopulation, also is used to generate the $CD4^+$ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of $CD4^+$ cells, where both the negative and positive fractions are retained. The negative fraction then is subjected to negative selection based on expression of CD14 and CD45RA or ROR1, and positive selection based on a marker characteristic of central memory T cells, such as CD62L or CCR7, where the positive and negative selections are carried out in either order.

$CD4^+$ T helper cells are sorted into naïve, central memory, and effector cells by identifying cell populations that have cell surface antigens. $CD4^+$ lymphocytes can be obtained by standard methods. In some embodiments, naive $CD4^+$ T lymphocytes are $CD45RO^-$, $CD45RA^+$, $CD62L^+$, $CD4^+$ T cells. In some embodiments, central memory $CD4^+$ cells are $CD62L^+$ and $CD45RO^+$. In some embodiments, effector $CD4^+$ cells are $CD62L^-$ and $CD45RO^-$.

In one example, to enrich for $CD4^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, N.J.).

In some aspects, the sample or composition of cells to be separated is incubated with small, magnetizable or magnetically responsive material, such as magnetically responsive particles or microparticles, such as paramagnetic beads (e.g., such as DYNABEADS® or MACS® beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS®) (Miltenyi Biotech, Auburn, Calif.). Magnetic Activated Cell Sorting (MACS®) systems are capable of high-purity selection of cells having magnetized particles attached thereto. In certain embodiments, MACS® operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS® system (Miltenyi Biotic), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS® system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy® system (Miltenyi Biotec). The CliniMACS Prodigy® system in some aspects is equipped with a cell processing unity that permits automated washing and fractionation of cells by centrifugation. The CliniMACS Prodigy® system can also include an onboard camera and image recognition software that determines the optimal cell fractionation endpoint by discerning the macroscopic layers of the source cell product. For example, peripheral blood may be automatically separated into erythrocytes, white blood cells and plasma layers. The CliniMACS Prodigy® system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood.1:72-82, and Wang et al. (2012) *J Immunother* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1° per minute and stored in the vapor phase of a liquid nitrogen storage tank.

In some embodiments, the provided methods include cultivation, incubation, culture, and/or genetic engineering steps. For example, in some embodiments, provided are methods for incubating and/or engineering the depleted cell populations and culture-initiating compositions.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood.1:72-82, and/or Wang et al. (2012) J Immunother. 35(9):689-701.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

II. COMPOSITIONS, METHODS AND USES

Also provided are compositions including the ROR1 binding molecules and engineered cells, including pharmaceutical compositions and formulations, and methods of using and uses of the molecules and compositions, such as in the treatment of diseases, conditions, and disorders in which ROR1 is expressed, and/or detection, diagnostic, and prognostic methods.

A. Pharmaceutical Compositions and Formulations

Provided are pharmaceutical formulations including the ROR1-binding molecule, e.g., antibody or chimeric receptor, and/or the engineered cells expressing the molecules. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell, binding molecule, and/or antibody, and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

Formulations of the antibodies can include lyophilized formulations and aqueous solutions.

The formulation or composition may also contain more than one active ingredient useful for the particular indication, disease, or condition being treated with the binding molecules or cells, preferably those with activities complementary to the binding molecule or cell, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the cells or antibodies are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

Active ingredients may be entrapped in microcapsules, in colloidal drug delivery systems (for example, liposomes, albumin microspheres, microemulsions, nano-particles and nanocapsules) or in macroemulsions. In certain embodiments, the pharmaceutical composition is formulated as an inclusion complex, such as cyclodextrin inclusion complex, or as a liposome. Liposomes can serve to target the host cells (e.g., T-cells or NK cells) to a particular tissue. Many methods are available for preparing liposomes, such as those described in, for example, Szoka et al., Ann. Rev. Biophys. Bioeng., 9: 467 (1980), and U.S. Pat. Nos. 4,235,871, 4,501,728, 4,837,028, and 5,019,369.

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known. Such systems can avoid repeated administrations of the composition, thereby increasing convenience to the subject and the physician.

The pharmaceutical composition in some embodiments contains the binding molecules and/or cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

In certain embodiments, in the context of genetically engineered cells containing the binding molecules, a subject is administered the range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges, and/or such a number of cells per kilogram of body weight of the subject.

The may be administered using standard administration techniques, formulations, and/or devices. Provided are formulations and devices, such as syringes and vials, for storage and administration of the compositions. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, intracranial, intrathoracic, and intraperitoneal administration. In some embodiments, the cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the binding molecule in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

B. Therapeutic and Prophylactic Methods and Uses

Also provided are methods of administering and uses, such as therapeutic and prophylactic uses, of the ROR1 binding molecules, including the anti-ROR1 antibodies, e.g., antibody fragments and proteins containing the same such as the chimeric receptors, and/or engineered cells expressing the recombinant receptors. Such methods and uses include therapeutic methods and uses, for example, involving administration of the molecules, cells, or compositions containing the same, to a subject having a disease, condition, or disorder expressing or associated with ROR1 expression, and/or in which cells or tissues express, e.g., specifically express, ROR1. In some embodiments, the molecule, cell, and/or composition is administered in an effective amount to effect treatment of the disease or disorder. Uses include uses of the binding molecules, CARs, antibodies, and cells in such methods and treatments, and in the preparation of a medicament in order to carry out such therapeutic methods. In some embodiments, the methods are carried out by administering the antibodies or cells, or compositions comprising the same, to the subject having, having hand, or suspected of having the disease or condition. In some embodiments, the methods thereby treat the disease or condition or disorder in the subject.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided molecules and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, an antibody or composition or cell which suppresses tumor growth reduces the rate of growth of the tumor compared to the rate of growth of the tumor in the absence of the antibody or composition or cell.

An "effective amount" of an agent, e.g., a pharmaceutical formulation, binding molecule, antibody, or cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation, antibody, or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the molecules, cells, and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

As used herein, a "subject" is a mammal, such as a human or other animal, and typically is human.

Among the diseases to be treated are any ROR1-associated disease or condition or disease or condition in which ROR1 is specifically expressed. In certain diseases and conditions, ROR1 is expressed on malignant cells and cancers. In some embodiments, the disease or condition is a ROR1-expressing cancer. Among the ROR1-associated diseases or conditions that can be treated include, but are not limited to, B cell leukemia, lymphoma, B cell chronic lymphocytic leukemia (CLL), AML, acute myeloid leukemia (AML), acute lymphocytic leukemia (ALL), Burkett's Lymphoma, mantle cell lymphoma (MCL), non-small cell lung cancer (NSCLC), neuroblastoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, uterine cancer, adrenal cancer and head and neck cancer.

In some embodiments, the methods may identify a subject who has, is suspected to have, or is at risk for developing a ROR1-associated disease or disorder. Hence, provided are methods for identifying subjects with diseases or disorders associated with elevated ROR1 expression and selecting them for treatment with a provided ROR1 binding molecule, including any of the anti-ROR1 antibodies, e.g., antibody fragments and proteins containing the same such as the chimeric receptors, and/or engineered cells expressing the recombinant receptors.

For example, a subject may be screened for the presence of a disease or disorder associated with elevated ROR1 expression, such as a ROR1-expressing cancer. In some embodiments, the methods include screening for or detecting the presence of a ROR1-associated disease, e.g. a tumor. Thus, in some aspects, a sample may be obtained from a patient suspected of having a disease or disorder associated with elevated ROR1 expression and assayed for the expression level of ROR1. In some aspects, a subject who tests positive for a ROR1-associated disease or disorder may be selected for treatment by the present methods, and may be administered a therapeutically effective amount of a ROR1 antibody, CAR expressing ROR1, cells containing a CAR or a pharmaceutical composition thereof as described herein. In some embodiments, the methods can be used to monitor the size or density of a ROR1-expressing tissue, e.g. tumor, over time, e.g., before, during, or after treatment by the methods.

In some embodiments, the subject has persistent or relapsed disease, e.g., following treatment with another ROR1-specific antibody and/or cells expressing a ROR1-targeting chimeric receptor and/or other therapy, including chemotherapy, radiation, and/or hematopoietic stem cell transplantation (HSCT), e.g., allogenic HSCT. In some embodiments, the administration effectively treats the subject despite the subject having become resistant to another ROR1-targeted therapy. In some embodiments, the subject has not relapsed but is determined to be at risk for relapse, such as at a high risk of relapse, and thus the compound or composition is administered prophylactically, e.g., to reduce the likelihood of or prevent relapse.

In some embodiments, the treatment does not induce an immune response by the subject to the therapy, and/or does not induce such a response to a degree that prevents effective treatment of the disease or condition. In some aspects, the degree of immunogenicity and/or graft versus host response is less than that observed with a different but comparable treatment. For example, in the case of adoptive cell therapy using cells expressing CARs including the provided anti-ROR1 antibodies, the degree of immunogenicity in some embodiments is reduced compared to CARs including a different antibody that binds to a similar, e.g., overlapping epitope and/or that competes for binding to ROR1 with the provided antibody, such as a mouse or rabbit or humanized antibody.

In some embodiments, the methods include adoptive cell therapy, whereby genetically engineered cells expressing the provided anti-ROR1-containing receptors (e.g., ROR1-targeted CARs) are administered to subjects. Such administration can promote activation of the cells (e.g., T cell activation) in a ROR1-targeted manner, such that the cells of the disease or disorder are targeted for destruction.

Thus, the provided methods and uses include methods and uses for adoptive cell therapy. In some embodiments, the methods include administration of the cells or a composition containing the cells to a subject, tissue, or cell, such as one having, at risk for, or suspected of having the disease, condition or disorder. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition. In some aspects, the methods thereby treat, e.g., ameliorate one or more symptom of the disease or condition, such as by lessening tumor burden in a ROR1-expressing cancer.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

In some embodiments, the cell therapy, e.g., adoptive cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject, to whom the cells, cell populations, or compositions are administered is a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent. In some examples, the patient or subject is a validated animal model for disease, adoptive cell therapy, and/or for assessing toxic outcomes such as cytokine release syndrome (CRS).

The ROR1-binding molecules, such as antibodies and chimeric receptors containing the antibodies and cells expressing the same, can be administered by any suitable means, for example, by injection, e.g., intravenous or subcutaneous injections, intraocular injection, periocular injection, subretinal injection, intravitreal injection, trans-septal injection, subscleral injection, intrachoroidal injection, intracameral injection, subconjunctival injection, subconjunctival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, intracranial, intrathoracic, or subcutaneous administration. Dosing and administration may depend in part on whether the administration is brief or chronic. Various dosing schedules include but are not limited to single or multiple administrations over various time-points, bolus administration, and pulse infusion.

For the prevention or treatment of disease, the appropriate dosage of the binding molecule or cell may depend on the type of disease to be treated, the type of binding molecule, the severity and course of the disease, whether the binding molecule is administered for preventive or therapeutic purposes, previous therapy, the patient's clinical history and response to the binding molecule, and the discretion of the attending physician. The compositions and molecules and cells are in some embodiments suitably administered to the patient at one time or over a series of treatments.

Depending on the type and severity of the disease, dosages of antibodies may include about 1 μg/kg to 15 mg/kg (e.g. 0.1 mg/kg-10 mg/kg), about 1 μg/kg to 100 mg/kg or more, about 0.05 mg/kg to about 10 mg/kg, 0.5 mg/kg, 2.0 mg/kg, 4.0 mg/kg or 10 mg/kg. Multiple doses may be administered intermittently, e.g. every week or every three weeks. An initial higher loading dose, followed by one or more lower doses may be administered.

In certain embodiments, in the context of genetically engineered cells containing the binding molecules, a subject is administered the range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Again, dosages may vary depending on attributes particular to the disease or disorder and/or patient and/or other treatments.

In some embodiments, the cells or antibodies are administered as part of a combination treatment, such as simultaneously with or sequentially with, in any order, another therapeutic intervention, such as another antibody or engineered cell or receptor or agent, such as a cytotoxic or therapeutic agent.

The cells or antibodies in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells or antibodies are administered prior to the one or more additional therapeutic agents. In some embodiments, the cells or antibodies are administered after to the one or more additional therapeutic agents.

Once the cells are administered to a mammal (e.g., a human), the biological activity of the engineered cell populations and/or antibodies in some aspects is measured by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285 (1): 25-40 (2004). In certain embodiments, the biological activity of the cells also can be measured by assaying expression and/or secretion of certain cytokines, such as CD 107a, IFNγ, IL-2, and TNF. In some aspects the biological activity is measured by assessing clinical outcome, such as reduction in tumor burden or load.

In certain embodiments, engineered cells are modified in any number of ways, such that their therapeutic or prophylactic efficacy is increased. For example, the engineered CAR or TCR expressed by the population in some embodiments are conjugated either directly or indirectly through a linker to a targeting moiety. The practice of conjugating compounds, e.g., the CAR or TCR, to targeting moieties is known in the art. See, for instance, Wadwa et al., J. Drug Targeting 3: 1 1 1 (1995), and U.S. Pat. No. 5,087,616.

C. Diagnostic and Detection Methods

Also provided are methods involving use of the provided binding molecules, e.g., antibodies, in detection of ROR1, for example, in diagnostic and/or prognostic methods in association with a ROR1-expressing disease or condition. The methods in some embodiments include incubating a biological sample with the antibody and/or administering the antibody to a subject. In certain embodiments, a biological sample includes a cell or tissue, such as tumor or cancer tissue. In certain embodiments, the contacting is under conditions permissive for binding of the anti-ROR1 antibody to ROR1, and detecting whether a complex is formed between the anti-ROR1 antibody and ROR1. Such a method may be an in vitro or in vivo method. In one embodiment, an anti-ROR1 antibody is used to select subjects eligible for therapy with an anti-ROR1 antibody or engineered antigen receptor, e.g. where ROR1 is a biomarker for selection of patients.

In some embodiments, a sample, such as a cell, tissue sample, lysate, composition, or other sample derived therefrom is contacted with the anti-ROR1 antibody and binding or formation of a complex between the antibody and the sample (e.g., ROR1 in the sample) is determined or detected. When binding in the test sample is demonstrated or detected as compared to a reference cell of the same tissue type, it may indicate the presence of an associated disease or condition. In some embodiments, the sample is from human tissues.

Various methods known in the art for detecting specific antibody-antigen binding can be used. Exemplary immunoassays include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (MA). An indicator moiety, or label group, can be attached to the subject antibodies and is selected so as to meet the needs of various uses of the method which are often dictated by the availability of assay equipment and compatible immunoassay procedures. Exemplary labels include radionuclides (e.g. $^{125}I$, $^{131}I$, $^{35}S$, $^{3}H$, or $^{32}P$), enzymes (e.g., alkaline phosphatase, horseradish peroxidase, luciferase, or β-galactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). General techniques to be used in performing the various immunoassays noted above are known to those of ordinary skill in the art.

For purposes of diagnosis, the antibodies can be labeled with a detectable moiety including but not limited to radioisotopes, fluorescent labels, and various enzyme-substrate labels know in the art. Methods of conjugating labels to an antibody are known in the art.

In some embodiments, antibodies need not be labeled, and the presence thereof can be detected using a labeled antibody which binds to the antibodies.

The provided antibodies in some embodiments can be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

The antibodies and polypeptides can also be used for in vivo diagnostic assays, such as in vivo imaging. Generally, the antibody is labeled with a radionuclide (such as $^{111}$In, $^{99}$Tc, $^{14}$C, $^{131}$I, $^{125}$I or $^{3}$H) so that the cells or tissue of interest can be localized in vivo following administration to a subject.

The antibody may also be used as staining reagent in pathology, e.g., using known techniques.

III. ARTICLES OF MANUFACTURE

Also provided are articles of manufacture containing the provided binding molecules, e.g., antibodies and CARs and/or genetically engineered cells, and/or compositions. The articles of manufacture may include a container and a label or package insert on or associated with the container. Suitable containers include, for example, bottles, vials, syringes, IV solution bags, etc. The containers may be formed from a variety of materials such as glass or plastic. The container in some embodiments holds a composition which is by itself or combined with another composition effective for treating, preventing and/or diagnosing the condition. In some embodiments, the container has a sterile access port. Exemplary containers include an intravenous solution bags, vials, including those with stoppers pierceable by a needle for injection. The label or package insert may indicate that the composition is used for treating the ROR1-expressing or -associated disease or condition. The article of manufacture may include (a) a first container with a composition contained therein, wherein the composition includes the antibody or engineered antigen receptor; and (b) a second container with a composition contained therein, wherein the composition includes a further agent, such as a cytotoxic or otherwise therapeutic agent. The article of manufacture may further include a package insert indicating that the compositions can be used to treat a particular condition. Alternatively, or additionally, the article of manufacture may further include another or the same container comprising a pharmaceutically-acceptable buffer. It may further include other materials such as other buffers, diluents, filters, needles, and/or syringes.

As used herein, reference to a "corresponding form" of an antibody means that when comparing a property or activity of two antibodies, the property is compared using the same form of the antibody. For example, if it is stated that an antibody has greater activity compared to the activity of the corresponding form of a first antibody, that means that a particular form, such as a scFv of that antibody, has greater activity compared to the scFv form of the first antibody.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

The terms "full length antibody," "intact antibody," and "whole antibody" are used herein interchangeably to refer to an antibody having a structure substantially similar to a native antibody structure or having heavy chains that contain an Fc region as defined herein.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-ROR1 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, "percent (%) amino acid sequence identity" and "percent identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR™) software. Those skilled in the art can determine appropriate parameters for aligning sequences, including any algorithms needed to achieve maximal alignment over the full length of the sequences being compared.

An amino acid substitution may include replacement of one amino acid in a polypeptide with another amino acid.

Exemplary substitutions are shown in Table 1. Amino acid substitutions may be introduced into a binding molecule, e.g., antibody, of interest and the products screened for a desired activity, e.g., retained/improved antigen binding, decreased immunogenicity, or improved ADCC or CDC.

Amino acids generally can be grouped according to the following common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative amino acid substitutions will involve exchanging a member of one of these classes for another class.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "package insert" is used to refer to instructions customarily included in commercial packages of therapeutic products, that contain information about the indications, usage, dosage, administration, combination therapy, contraindications and/or warnings concerning the use of such therapeutic products.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a composition refers to any mixture of two or more products, substances, or compounds, including cells. It may be a solution, a suspension, liquid, powder, a paste, aqueous, non-aqueous or any combination thereof.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

IV. EXEMPLARY EMBODIMENTS

Among the embodiments provided herein are:

1. An antibody or antigen-binding fragment thereof, said antibody or antigen-binding fragment comprising a heavy chain variable ($V_H$) region comprising:

a heavy chain complementarity determining region 3 (CDR-H3) comprising the amino acid sequence set forth in SEQ ID NO: 22, 29, 35, 45, 50, 51, 52, 53, 54, 55, 56, 57, 58, 59, 60, 61, 62, 63, 64, 65, 66, 67, 68, 69, 70, 71 or 174; or a CDR-H3 contained within the heavy chain variable ($V_H$) sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209.

2. An antibody or antigen-binding fragment thereof, said antibody or antigen-binding fragment comprising a heavy chain variable ($V_H$) region comprising at least 90% sequence identity to the $V_H$ region amino acid sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209.

3. The antibody or antigen-binding fragment thereof of embodiment 2, said antibody or antigen-binding fragment comprising a heavy chain variable ($V_H$) region comprising at least 90% sequence identity to the $V_H$ region amino acid sequence set forth in SEQ ID NO: 8, 10, 13, 15, 17, or 19.

4. The antibody or fragment of embodiment 2 or embodiment 3, wherein the $V_H$ region comprises a heavy chain complementarity determining region 3 (CDR-H3) comprising the amino acid sequence set forth in SEQ ID NO: 92, 93, 94, 109 or 110.

5. The antibody or fragment of any of embodiments 2-4, wherein the $V_H$ region comprises:

a heavy chain complementarity determining region 3 (CDR-H3) comprising the amino acid sequence set forth in SEQ ID NO: 22, 29, 35, 45, 50, 51, 52, 53, 54, 55, 56, 57, 58, 59, 60, 61, 62, 63, 64, 65, 66, 67, 68, 69, 70, 71 or 174; or a CDR-H3 contained within the $V_H$ sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209.

6. The antibody or fragment of any of embodiments 2-5, wherein the $V_H$ region comprises:

a heavy chain complementarity determining region 3 (CDR-H3) comprising the amino acid sequence set forth in SEQ ID NO: 22, 29, 35, 45, 50, 51, 52, 53, 54, 55, 56, 57, 58, 59, 60, 61, 62, 63, 64, 65, 66, 67, 68, 69, 70, 71 or 174; or a CDR-H3 contained within the $V_H$ sequence set forth in SEQ ID NO: 8, 10, 13, 15, 17, or 19.

7. The antibody or fragment of any of embodiments 2-6, wherein the $V_H$ region comprises:

a heavy chain complementarity determining region 3 (CDR-H3) comprising the amino acid sequence set forth in SEQ ID NO: 22, 29, 35 or 52; or a CDR-H3 contained within the $V_H$ sequence set forth in SEQ ID NO: 10, 13, 15 or 19.

8. The antibody or fragment of embodiment 2 or embodiment 3, wherein the $V_H$ region comprises a CDR-H3 comprising the amino acid sequence set forth in SEQ ID NO: 72 or a CDR-H3 contained within the $V_H$ sequence set forth in SEQ ID NO: 85.

9. The antibody or fragment of any of embodiments 1-8, wherein the $V_H$ region comprises:

a heavy chain complementarity determining region 1 (CDR-H1) comprising the amino acid sequence set forth in SEQ ID NO:95 or 97; and/or a heavy chain complementarity determining region 2 (CDR-H2) comprising the amino acid sequence set forth in SEQ ID NO: 96 or 98.

10. The antibody or fragment of any of embodiments 1-9, wherein the $V_H$ region comprises:

a heavy chain complementarity determining region 1 (CDR-H1) comprising the amino acid sequence set forth in SEQ ID NO: 20, 27, 33, 155, 156, 157, 158, 159, 160, 161, 162 or 163 and/or comprising the amino acid sequence set forth in SEQ ID NO: 269, 270, 271, 272, 273, 274, 275, 276, 278 or 279 and/or comprising the amino acid sequence set forth in SEQ ID NO: 75, 77, 79, 280, 281, 282, 283, 284, 285, 286, 287, 288 or 289 and/or a CDR-H1 contained within the $V_H$ sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209; and/or a heavy chain complementarity determining region 2 (CDR-H2) comprising the amino acid sequence set forth in SEQ ID NO: 21, 26, 28, 34, 164, 165, 166, 167, 168, 169, 170, 171, 172, 173, or 318 and/or comprising the amino acid sequence set forth in SEQ ID NO: 291, 292, 293, 294, 295, 296, 297, 298, 299, 300, 301, 302 or 303 and/or comprising the amino acid sequence set forth in SEQ ID NO: 304, 305, 306, 307, 308, 309, 310, 311, 312, 313, 314, 315, 316 or 317 and/or a CDR-H2 contained within the $V_H$ sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209.

11. The antibody or fragment of any of embodiments 1-10, wherein the $V_H$ region comprises:

a heavy chain complementarity determining region 1 (CDR-H1) comprising the amino acid sequence set forth in SEQ ID NO: 20, 27, or 33 and/or a CDR-H1 contained within the $V_H$ sequence set forth in SEQ ID NO: 8, 10, 13, 15, 17, or 19; and/or a heavy chain complementarity determining region 2 (CDR-H2) comprising the amino acid sequence set forth in SEQ ID NO: 21, 26, 28, or 34 and/or a CDR-H2 contained within the $V_H$ sequence set forth in SEQ ID NO: 8, 10, 13, 15, 17, or 19.

12. The antibody or fragment of any of embodiments 1-11, wherein the $V_H$ region comprises:

a heavy chain complementarity determining region 1 (CDR-H1) comprising the amino acid sequence set forth in SEQ ID NO: 20, 27, or 33 and/or a CDR-H1 contained within the $V_H$ sequence set forth in SEQ ID NO: 10, 13, 15 or 19; and/or a heavy chain complementarity determining region 2 (CDR-H2) comprising the amino acid sequence set forth in SEQ ID NO: 26, 28, or 34 and/or a CDR-H2 contained within the $V_H$ sequence set forth in SEQ ID NO: 10, 13, 15 or 19.

13. An antibody or antigen-binding fragment thereof, comprising a heavy chain variable ($V_H$) region comprising a heavy chain complementarity determining region 1 (CDR-H1), CDR-H2, and CDR-H3, wherein:

the CDR-H1 comprises the amino acid sequence set forth in SEQ ID NO: 20, 27, 33, 75, 77, 79, 155, 156, 157, 158, 159, 160, 161, 162, 163, 269, 270, 271, 272, 273, 274, 275, 276, 277, 278 or 279;

the CDR-H2 comprises the amino acid sequence set forth in SEQ ID NO: 21, 26. 28. 34, 80, 81, 82, 83, 164, 165, 166, 167, 168, 169, 170, 171, 172, 173, 291, 292, 293, 294, 295, 296, 297, 298, 299, 300, 301, 302, 303 or 318; and/or the CDR-H3 comprises the amino acid sequence set forth in SEQ ID NO: 22, 29, 35, 45, 50, 51, 52, 53, 54, 55, 56, 57, 58, 59, 60, 61, 62, 63, 64, 65, 66, 67, 68, 69, 70, 71 or 174.

14. The antibody or antigen-binding fragment of embodiment 11, wherein:

the CDR-H1 comprises the amino acid sequence set forth in SEQ ID NO: 20, 27, or 33;

the CDR-H2 comprises the amino acid sequence set forth in SEQ ID NO: 21, 26, 28, or 34; and/or the CDR-H3 comprises the amino acid sequence set forth in SEQ ID NO: 22, 29, 35, 45, 50, 51, 52, 53, 54, 55, 56, 57, 58, 59, 60, 61, 62, 63, 64, 65, 66, 67, 68, 69, 70 or 71.

15. The antibody or fragment of any of embodiments 1, 4-7 and 9-14, wherein the CDR-H3 comprises the amino acid sequence VSNYEYYFDY (SEQ ID NO: 29), DFGRWGYYFDY (SEQ ID NO: 52), DFGRWSYYFDY (SEQ ID NO:35) or DSSYDAFDI (SEQ ID NO:22).

16. The antibody or fragment of any of embodiments 1-7 and 9-15, comprising a heavy chain variable ($V_H$) region comprising a heavy chain complementarity determining region 1 (CDR-H1), CDR-H2, and CDR-H3, wherein:

the CDR-H1, CDR-H2, and CDR-H3 comprise the sequences of SEQ ID NOs: 20, 21, and 22, respectively;

the CDR-H1, CDR-H2, and CDR-H3 comprise the sequences of SEQ ID NOs: 20, 26, and 22, respectively;

the CDR-H1, CDR-H2, and CDR-H3 comprise the sequences of SEQ ID NOs: 27, 28, and 29, respectively;

the CDR-H1, CDR-H2, and CDR-H3 comprise the sequences of SEQ ID NOs: 33, 34, and 35, respectively; or the CDR-H1, CDR-H2, and CDR-H3 comprise the sequences of SEQ ID NOs: 33, 34, and 52, respectively;

the CDR-H1, CDR-H2, and CDR-H3 comprise the sequences of SEQ ID NOs: 27, 164 and 45, respectively;

the CDR-H1, CDR-H2, and CDR-H3 comprise the sequences of SEQ ID NOs: 27, 164 and 68, respectively;

the CDR-H1, CDR-H2, and CDR-H3 comprise the sequences of SEQ ID NOs: 27, 164 and 64, respectively;

the CDR-H1, CDR-H2, and CDR-H3 comprise the sequences of SEQ ID NOs: 27, 164 and 66, respectively;

the CDR-H1, CDR-H2, and CDR-H3 having the sequences of SEQ ID NOs: 33, 318, and 35, respectively;

the CDR-H1, CDR-H2, and CDR-H3 comprise the sequences of SEQ ID NOs: 33, 34 and 70, respectively;

the CDR-H1, CDR-H2, and CDR-H3 comprise the sequences of SEQ ID NOs: 33, 34 and 55, respectively;

the CDR-H1, CDR-H2, and CDR-H3 comprise the sequences of SEQ ID NOs: 33, 34 and 53, respectively;

the CDR-H1, CDR-H2, and CDR-H3 comprise the sequences of SEQ ID NOs: 33, 34 and 56, respectively;

the CDR-H1, CDR-H2, and CDR-H3 comprise the sequences of SEQ ID NOs: 33, 34 and 61, respectively;

the CDR-H1, CDR-H2, and CDR-H3 comprise the sequences of SEQ ID NOs: 33, 34 and 59, respectively;

the CDR-H1, CDR-H2, and CDR-H3 comprise the sequences of SEQ ID NOs: 33, 171 and 60, respectively;

the CDR-H1, CDR-H2, and CDR-H3 comprise the sequences of SEQ ID NOs: 155, 34 and 35, respectively;

the CDR-H1, CDR-H2, and CDR-H3 comprise the sequences of SEQ ID NOs: 156, 34 and 35, respectively;

the CDR-H1, CDR-H2, and CDR-H3 comprise the sequences of SEQ ID NOs: 162, 170 and 50, respectively;

the CDR-H1, CDR-H2, and CDR-H3 comprise the sequences of SEQ ID NOs: 162, 170 and 51, respectively;

the CDR-H1, CDR-H2, and CDR-H3 comprise the sequences of SEQ ID NOs: 161, 169 and 54, respectively;

the CDR-H1, CDR-H2, and CDR-H3 comprise the sequences of SEQ ID NOs:159, 167 and 57, respectively;

the CDR-H1, CDR-H2, and CDR-H3 comprise the sequences of SEQ ID NOs: 160, 168 and 58, respectively;

the CDR-H1, CDR-H2, and CDR-H3 comprise the sequences of SEQ ID NOs: 158, 166 and 62, respectively;

the CDR-H1, CDR-H2, and CDR-H3 comprise the sequences of SEQ ID NOs: 158, 166 and 63, respectively;

the CDR-H1, CDR-H2, and CDR-H3 comprise the sequences of SEQ ID NOs: 158, 166 and 65, respectively;

the CDR-H1, CDR-H2, and CDR-H3 comprise the sequences of SEQ ID NOs: 157, 165 and 67, respectively;

the CDR-H1, CDR-H2, and CDR-H3 comprise the sequences of SEQ ID NOs: 163, 173 and 69, respectively; or the CDR-H1, CDR-H2, and CDR-H3 comprise the sequences of SEQ ID NOs: 160, 172, 71, respectively; or the CDR-H1, CDR-H2, and CDR-H3 comprise the sequences of SEQ ID NOs: 160, 172, 174, respectively.

17. The antibody or fragment of any of embodiments 1-7 and 9-16, comprising a heavy chain variable ($V_H$) region comprising a heavy chain complementarity determining region 1 (CDR-H1), CDR-H2, and CDR-H3, wherein:

the CDR-H1, CDR-H2, and CDR-H3 comprise the sequences of SEQ ID NOs: 20, 21, and 22, respectively;

the CDR-H1, CDR-H2, and CDR-H3 comprise the sequences of SEQ ID NOs: 20, 26, and 22, respectively;

the CDR-H1, CDR-H2, and CDR-H3 comprise the sequences of SEQ ID NOs: 27, 28, and 29, respectively;

the CDR-H1, CDR-H2, and CDR-H3 comprise the sequences of SEQ ID NOs: 33, 34, and 35, respectively; or the CDR-H1, CDR-H2, and CDR-H3 comprise the sequences of SEQ ID NOs: 33, 34, and 52, respectively.

18. An antibody or antigen-binding fragment thereof, comprising a heavy chain variable ($V_H$) region comprising a heavy chain complementarity determining region 1 (CDR-H1), a CDR-H2, and a CDR-H3, respectively, comprising the amino acid sequences of a CDR-H1, a CDR-H2, and a CDR-H3 contained within the $V_H$ region amino acid sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209.

19. The antibody or antigen-binding fragment of embodiment 18, wherein the CDR-H1, CDR-H2, and CDR-H3, respectively, comprise the amino acid sequences of a CDR-H1, a CDR-H2, and a CDR-H3 contained within the $V_H$ region amino acid sequence set forth in SEQ ID NO: 8, 10, 13, 15, 17, or 19.

20. The antibody or fragment of any of embodiments 1-19, wherein the $V_H$ region comprises a framework region 1 (FR1), a FR2, a FR3, and/or a FR4 comprising at least 90% sequence identity, respectively, to a FR1, FR2, FR3, and/or FR4 of the amino acid sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209.

21. The antibody or fragment of any of embodiments 1-20, wherein the $V_H$ region comprises a framework region 1 (FR1), a FR2, a FR3, and/or a FR4 comprising at least 90% sequence identity, respectively, to a FR1, FR2, FR3, and/or FR4 of the amino acid sequence set forth in SEQ ID NO: 8, 10, 13, 15, 17 or 19.

22. The antibody or fragment of any of embodiments 1-7 and 9-21, wherein the $V_H$ region comprises the sequence of amino acids set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209.

23. The antibody or fragment of any of embodiments 1-7 and 9-22, wherein the $V_H$ region comprises the sequence of amino acids set forth in SEQ ID NO: 8, 10, 13, 15, 17, or 19.

24. The antibody or fragment of embodiment 23, wherein the $V_H$ region comprises the sequence of amino acids set forth in SEQ ID NO: 8 or 10.

25. The antibody or fragment of any of embodiments 1-7 and 9-24, wherein the $V_H$ region comprises the CDR-H1, CDR-H2, and CDR-H3 set forth in SEQ ID NOS: 20, 26, and 22, respectively, and/or the $V_H$ region comprises the sequence of amino acids set forth in SEQ ID NO: 19.

26. The antibody or fragment of any of embodiments 1-7 and 9-24, wherein the $V_H$ region comprises the CDR-H1, CDR-H2, and CDR-H3 set forth in SEQ ID NOS: 33, 34, and 52, respectively, and/or the $V_H$ region comprises the sequence of amino acids set forth in SEQ ID NO: 10.

27. The antibody or fragment of any of embodiments 1-7 and 9-24, wherein the $V_H$ region comprises the CDR-H1, CDR-H2, and CDR-H3 set forth in SEQ ID NOS: 33, 34, and 35, respectively, and/or the $V_H$ region comprises the sequence of amino acids set forth in SEQ ID NO: 13.

28. The antibody or fragment of any of embodiments 1-7 and 9-24, wherein the $V_H$ region comprises the CDR-H1, CDR-H2, and CDR-H3 set forth in SEQ ID NOS: 27, 28, and 29, respectively, and/or the $V_H$ region comprises the sequence of amino acids set forth in SEQ ID NO: 15.

29. The antibody or fragment of any of embodiments 1-28, wherein the antibody or fragment does not comprise a light chain variable (VL) region, does not comprise a CDR-L1, CDR-L2, and/or CDR-L3, and/or is a single-domain antibody (sdAb) comprising only the $V_H$ region.

30. The antibody or fragment of any of embodiments 1-29 that is a sdAb comprising only the $V_H$ region.

31. The antibody or fragment of any of embodiments 1-28, wherein the antibody or fragment further comprises a light chain variable (VL) region.

32. The antibody or fragment of embodiment 31, wherein the $V_L$ region comprises at least 90% sequence identity to the $V_L$ region amino acid sequence set forth in SEQ ID NO: 14, 16, 18, 234, 235, 236, 237, 238, 239, 240, 241, 242, 243, 244, 245, 246, 247 or 248.

33. The antibody or fragment of embodiment 31 or embodiment 32, wherein the $V_L$ region comprises at least 90% sequence identity to the $V_L$ region amino acid sequence set forth in SEQ ID NO: 14, 16, or 18.

34. The antibody of fragment of any of embodiments 31-33, wherein the $V_L$ region comprises a light chain complementarity determining region 3 (CDR-L3) comprising the amino acid sequence set forth in SEQ ID NO: 99 or 100.

35. The antibody or fragment of any of embodiments 31-34, wherein the $V_L$ region comprises a light chain complementarity determining region 3 (CDR-L3) comprising the amino acid sequence set forth in SEQ ID NO: 25, 32, 38, 39, 40, 41, 42, 43, 44, 46, 47, 48, 49, 232 or 233.

36. The antibody or fragment of any of embodiments 31-35, wherein the $V_L$ region comprises a light chain complementarity determining region 3 (CDR-L3) comprising the amino acid sequence set forth in SEQ ID NO: 25, 32, 38, 39, 40, 41, 42, 43, 44, 46, 47, 48 or 49.

37. The antibody or fragment of any of embodiments 31-36, wherein the $V_L$ region comprises a light chain complementarity determining region 1 (CDR-L1) comprising the amino acid sequence set forth in SEQ ID NO: 101 and/or a light chain complementarity determining region 2 (CDR-L2) comprising the amino acid sequence set forth in SEQ ID NO: 102.

38. The antibody or fragment of any of embodiments 31-38, wherein the $V_L$ region comprises:

a light chain complementarity determining region 1 (CDR-L1) comprising the amino acid sequence set forth in SEQ ID NO: 23, 30, 36, 210, 211, 212, 213, 214, 215, 217, 216, 218, 219 or 220 and/or a CDR-L1 contained within the $V_L$ sequence set forth in SEQ ID NO: 14, 16, 18, 234, 235, 236, 237, 238, 239, 240, 241, 242, 243, 244, 245, 246, 247 or 248; and/or a light chain complementarity determining region 2 (CDR-L2) comprising the amino acid sequence set forth in SEQ ID NO: 24, 31, 37, 221, 222, 223, 224, 225, 226, 227, 228, 229, 230 or 231 and/or a CDR-L2 contained within the $V_L$ sequence set forth in SEQ ID NO: 14, 16, 18, 234, 235, 236, 237, 238, 239, 240, 241, 242, 243, 244, 245, 246, 247 or 248.

39. The antibody or fragment of any of embodiments 31-38, wherein the $V_L$ region comprises:

a light chain complementarity determining region 1 (CDR-L1) comprising the amino acid sequence set forth in SEQ ID NO: 23, 30, or 36 and/or a CDR-L1 contained within the $V_L$ sequence set forth in SEQ ID NO: 14, 16, or 18; and/or a light chain complementarity determining region 2 (CDR-L2) comprising the amino acid sequence set forth in SEQ ID NO: 24, 31, or 37 and/or a CDR-L2 contained within the $V_L$ sequence set forth in SEQ ID NO: 14, 16, or 18.

40. The antibody or fragment of any of embodiments 31-39, wherein the $V_L$ region comprises:

a light chain complementarity determining region 1 (CDR-L1) comprising the amino acid sequence set forth in SEQ ID NO: 23, 30, 36, 210, 211, 212, 213, 214, 215, 217, 216, 218, 219 or 220;

a light chain complementarity determining region 2 (CDR-L2), comprising the amino acid sequence set forth in SEQ ID NO: 24, 31, 37, 221, 222, 223, 224, 225, 226, 227, 228, 229, 230 or 231; and a light chain complementarity determining region 3 (CDR-L3) comprising the amino acid sequence set forth in SEQ ID NO: 25, 32, 38, 39, 40, 41, 42, 43, 44, 46, 47, 48, 49, 232 or 233.

41. The antibody or fragment of any of embodiments 31-40, wherein the $V_L$ region comprises:

a light chain complementarity determining region 1 (CDR-L1) comprising the amino acid sequence set forth in SEQ ID NO: 23, 30, or 36;

a light chain complementarity determining region 2 (CDR-L2), comprising the amino acid sequence set forth in SEQ ID NO: 24, 31, or 37; and a light chain complementarity determining region 3 (CDR-L3) comprising the amino acid sequence set forth in SEQ ID NO: 25, 32, 38, 39, 40, 41, 42, 43, 44, 46, 47, 48, or 49.

42. The antibody or fragment of any of embodiments 36-41, wherein the CDR-L3 comprises the amino acid sequence set forth in SEQ ID NO: 25, 32 or 38.

43. The antibody or fragment of any of embodiments 31-42, wherein the $V_L$ region comprises a CDR-L1, CDR-L2, and CDR-L3 selected from:

the CDR-L1, CDR-L2, and CDR-L3 comprising the sequences of SEQ ID NOs: 23, 24, and 25, respectively;

the CDR-L1, CDR-L2, and CDR-L3 comprising the sequences of SEQ ID NOs: 30, 31, and 32, respectively;

the CDR-L1, CDR-L2, and CDR-L3 comprising the sequences of SEQ ID NOs: 36, 37, and 38, respectively;

the CDR-L1, CDR-L2 and CDR-L3 comprising the sequences of SEQ ID NOs: 216, 227, and 40, respectively;

the CDR-L1, CDR-L2 and CDR-L3 comprising the sequences of SEQ ID NOs: 218, 229, and 39, respectively;

the CDR-L1, CDR-L2 and CDR-L3 comprising the sequences of SEQ ID NOs: 219, 230, and 43, respectively;

the CDR-L1, CDR-L2 and CDR-L3 comprising the sequences of SEQ ID NOs: 220, 231, and 46, respectively;

the CDR-L1, CDR-L2 and CDR-L3 comprising the sequences of SEQ ID NOs: 210, 221, and 49, respectively;

the CDR-L1, CDR-L2 and CDR-L3 comprising the sequences of SEQ ID NOs: 210, 221, and 233, respectively;

the CDR-L1, CDR-L2 and CDR-L3 comprising the sequences of SEQ ID NOs: 211, 222, and 48, respectively;

the CDR-L1, CDR-L2 and CDR-L3 comprising the sequences of SEQ ID NOs: 212, 223, and 42, respectively;

the CDR-L1, CDR-L2 and CDR-L3 comprising the sequences of SEQ ID NOs: 214, 225, and 232, respectively;

the CDR-L1, CDR-L2 and CDR-L3 comprising the sequences of SEQ ID NOs: 215, 226, and 44, respectively;

the CDR-L1, CDR-L2 and CDR-L3 comprising the sequences of SEQ ID NOs: 217, 228, and 41, respectively; or the CDR-L1, CDR-L2 and CDR-L3 comprising the sequences of SEQ ID NOs: 213, 224, and 47, respectively.

44. The antibody or fragment of any of embodiments 31-43, wherein the $V_L$ region comprises a CDR-L1, CDR-L2, and CDR-L3 selected from:

the CDR-L1, CDR-L2, and CDR-L3 comprising the sequences of SEQ ID NOs: 23, 24, and 25, respectively;

the CDR-L1, CDR-L2, and CDR-L3 comprising the sequences of SEQ ID NOs: 30, 31, and 32, respectively; or the CDR-L1, CDR-L2, and CDR-L3 comprising the sequences of SEQ ID NOs: 36, 37, and 38, respectively.

45. The antibody or fragment of any of embodiments 31-44, wherein the $V_L$ region comprises light chain complementarity determining region 1 (CDR-L1), CDR-L2, and CDR-L3, respectively, contained within the $V_L$ region amino acid sequence set forth in SEQ ID NO: 14, 16, 18, 234, 235, 236, 237, 238, 239, 240, 241, 242, 243, 244, 245, 246, 247 or 248.

46. The antibody or fragment of any of embodiments 31-45, wherein the $V_L$ region comprises light chain complementarity determining region 1 (CDR-L1), CDR-L2, and CDR-L3, respectively, contained within the $V_L$ region amino acid sequence set forth in SEQ ID NO: 14, 16, or 18.

47. The antibody or fragment of any of embodiments 31-46, wherein the $V_L$ region comprises a framework region 1 (FR1), a FR2, a FR3, and/or a FR4 comprising at least 90% sequence identity, respectively, to the FR1, FR2, FR3, and/or FR4 of the amino acid sequence set forth in SEQ ID NO: 14, 16, or 18.

48. The antibody or fragment of any of embodiments 31-47, wherein the $V_L$ region comprises the amino acid sequence set forth in SEQ ID NO: 14, 16, 18, 234, 235, 236, 237, 238, 239, 240, 241, 242, 243, 244, 245, 246, 247 or 248.

49. The antibody or fragment of any of embodiments 31-48, wherein the $V_L$ region comprises the amino acid sequence set forth in SEQ ID NO: 14, 16, or 18.

50. An antibody or antigen-binding fragment thereof, comprising:

a heavy chain complementarity determining regions 1, 2, and 3 (CDR-H1, CDR-H2, and CDR-H3), respectively comprising the amino acid sequences of CDR-H1, CDR-H2, and CDR-H3 sequences contained within the $V_H$ region amino acid sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209; and/or a light chain complementarity determining regions 1, 2, and 3 (CDR-L1, CDR-L2, and CDR-L3), respectively comprising the amino acid sequences of CDR-L1, CDR-L2, and CDR-L3 sequences contained within the light chain variable (VL) region amino acid sequence set forth in SEQ ID NO: 14, 16, 18, 234, 235, 236, 237, 238, 239, 240, 241, 242, 243, 244, 245, 246, 247 or 248.

51. The antibody or antigen-binding fragment of embodiment 50, wherein:

the CDR-H1, CDR-H2, and CDR-H3, respectively, comprise the amino acid sequences of CDR-H1, CDR-H2, and CDR-H3 sequences contained within the $V_H$ region amino acid sequence set forth in SEQ ID NO: 8, 10, 13, 15, 17, or 19; and/or the CDR-L1, CDR-L2, and CDR-L3, respectively, comprise the amino acid sequences of CDR-L1, CDR-L2, and CDR-L3 sequences contained within the light chain variable (VL) region amino acid sequence set forth in SEQ ID NO: 14, 16, or 18.

52. An antibody or antigen-binding fragment thereof, comprising:

a $V_H$ and $V_L$ regions comprising amino acid sequences having at least 90% identity to SEQ ID NOs: 19 and 18, respectively;

a $V_H$ and $V_L$ regions comprising amino acid sequences having at least 90% identity to SEQ ID NOs: 17 and 18, respectively;

a $V_H$ and $V_L$ regions comprising amino acid sequences having at least 90% identity to SEQ ID NOs: 15 and 16, respectively; or a $V_H$ and $V_L$ regions comprising amino acid sequences having at least 90% identity to SEQ ID NOs: 13 and 14, respectively;

a $V_H$ and $V_L$ regions comprising amino acid sequences having at least 90% identity to SEQ ID NOs: 182 and 242 respectively;

a $V_H$ and $V_L$ regions comprising amino acid sequences having at least 90% identity to SEQ ID NOs: 182 and 246, respectively;

a $V_H$ and $V_L$ regions comprising amino acid sequences having at least 90% identity to SEQ ID NOs: 182 and 247, respectively;

a $V_H$ and $V_L$ regions comprising amino acid sequences having at least 90% identity to SEQ ID NOs: 185 and 248, respectively;

a $V_H$ and $V_L$ regions comprising amino acid sequences having at least 90% identity to SEQ ID NOs: 186 and 248, respectively;

a $V_H$ and $V_L$ regions comprising amino acid sequences having at least 90% identity to SEQ ID NOs: 175 and 234, respectively;

a $V_H$ and $V_L$ regions comprising amino acid sequences having at least 90% identity to SEQ ID NOs: 175 and 235, respectively;

a $V_H$ and $V_L$ regions comprising amino acid sequences having at least 90% identity to SEQ ID NOs: 176 and 236, respectively;

a $V_H$ and $V_L$ regions comprising amino acid sequences having at least 90% identity to SEQ ID NOs: 176 and 237, respectively;

a $V_H$ and $V_L$ regions comprising amino acid sequences having at least 90% identity to SEQ ID NOs: 177 and 238, respectively;

a $V_H$ and $V_L$ regions comprising amino acid sequences having at least 90% identity to SEQ ID NOs: 179 and 240 respectively;

a $V_H$ and $V_L$ regions comprising amino acid sequences having at least 90% identity to SEQ ID NOs: 180 and 241, respectively;

a $V_H$ and $V_L$ regions comprising amino acid sequences having at least 90% identity to SEQ ID NOs: 181 and 241, respectively;

a $V_H$ and $V_L$ regions comprising amino acid sequences having at least 90% identity to SEQ ID NOs: 183 and 243 respectively;

a $V_H$ and $V_L$ regions comprising amino acid sequences having at least 90% identity to SEQ ID NOs: 183 and 244 respectively;

a $V_H$ and $V_L$ regions comprising amino acid sequences having at least 90% identity to SEQ ID NOs: 184 and 243, respectively;

a $V_H$ and $V_L$ regions comprising amino acid sequences having at least 90% identity to SEQ ID NOs: 184 and 244 respectively;

a $V_H$ and $V_L$ regions comprising amino acid sequences having at least 90% identity to SEQ ID NOs: 183 and 245, respectively;

a $V_H$ and $V_L$ regions comprising amino acid sequences having at least 90% identity to SEQ ID NOs: 184 and 245, respectively; or a $V_H$ and $V_L$ regions comprising amino acid sequences having at least 90% identity to SEQ ID NOs: 178 and 239, respectively.

53. The antibody or antigen-binding fragment of embodiment 52, comprising:

a $V_H$ and $V_L$ regions comprising amino acid sequences having at least 90% identity to SEQ ID NOs: 19 and 18, respectively;

a $V_H$ and $V_L$ regions comprising amino acid sequences having at least 90% identity to SEQ ID NOs: 17 and 18, respectively;

a $V_H$ and $V_L$ regions comprising amino acid sequences having at least 90% identity to SEQ ID NOs: 15 and 16, respectively; or a $V_H$ and $V_L$ regions comprising amino acid sequences having at least 90% identity to SEQ ID NOs: 13 and 14, respectively.

54. The antibody or fragment of embodiment 52 or embodiment 53, wherein:

the $V_H$ and $V_L$ regions comprise the amino acid sequences of SEQ ID NOs: 19 and 18, respectively;

the $V_H$ and $V_L$ regions comprise the amino acid sequences of SEQ ID NOs: 17 and 18, respectively;

the $V_H$ and $V_L$ regions comprise the amino acid sequences of SEQ ID NOs: 15 and 16 respectively; or the $V_H$ and $V_L$ regions comprise the amino acid sequences of SEQ ID NOs: 13 and 14 respectively.

55. The antibody or fragment of any of embodiments 1-54, wherein said antibody or fragment specifically binds to a ROR1 protein.

56. The antibody or fragment of embodiment 55, wherein the ROR1 protein is a human ROR1 protein.

57. The antibody or fragment of embodiment 55, wherein the ROR1 protein is a mouse ROR1 protein.

58. The antibody or fragment of any of embodiments 1-57, wherein:

said antibody or fragment has a binding affinity for a ROR1 protein with an EC50 that is from or from about 0.1 nM to 100 nM, 0.5 nM to 50 nM or 1 nM to 10 nM; or said antibody or fragment has a binding affinity for a ROR1 protein with an EC50 that is less than or less than about 100 nM, less than or less than about 50 nM, less than or less than about 10 nM or less than or less than about 1 nM.

59. The antibody or fragment of any of embodiments 1-58, wherein said antibody or fragment has a binding affinity for a human ROR1 protein that is at least as high or substantially as high as the binding affinity for the ROR1 protein of the corresponding form of the anti-ROR1 antibody R12 or antigen-binding fragment thereof, which is optionally an scFv fragment of R12.
60. The antibody or fragment of any of embodiments 1-59, wherein said antibody or fragment specifically binds to the same or an overlapping epitope of a human ROR1 protein as the epitope specifically bound by the anti-ROR1 antibody R12 or an antigen-binding fragment thereof, which is optionally an scFv fragment of R12.
61. The antibody or fragment of any of embodiments 1-60, wherein said antibody or fragment competes for binding to a human ROR1 protein with anti-ROR1 antibody R12 or an antigen-binding fragment thereof, which is optionally an scFv fragment of R12.
62. The antibody or fragment of any of embodiments 1-61, wherein said antibody or fragment inhibits the binding of the anti-ROR1 antibody R12 or an antigen-binding fragment thereof, which is optionally an scFv fragment of R12, to a human ROR1 protein by greater than or greater than about 80% or greater than or greater than about 90%.
63. The antibody or fragment of any of embodiments 1-62, wherein the antibody or fragment binds to an overlapping epitope of a human ROR1 protein as the epitope specifically bound by the anti-ROR1 antibody R12 or an antigen-binding fragment thereof, which is optionally an scFv fragment of R12 and the antibody or fragment binds to mouse ROR1.
64. The antibody or antigen-binding fragment of any of embodiments 55, 56 and 58-63, wherein said human ROR1 protein comprises an amino acid sequence set forth in SEQ ID NO: 103.
65. The antibody or antigen-binding fragment of any of embodiments 55, 56 and 58-64, which binds an epitope within an extracellular portion of the ROR1 protein; and/or binds to an epitope of said ROR1 protein comprising residues within the fz domain or the Ig domain of the ROR1 protein.

66. The antibody or antigen-binding fragment of embodiment 65, wherein the epitope comprises a residue within the fz domain of the ROR1 protein and a residue within the Ig domain of the ROR1 protein.
67. The antibody or antigen-binding fragment thereof of embodiment 65 or embodiment 66, wherein said Ig domain comprises residues 13-118 of the amino acid sequence set forth in SEQ ID NO: 103; and/or said fz domain comprises residues 136-270 of the amino acid sequence set forth in SEQ ID NO:103.
68. The antibody or antigen binding fragment of embodiment 65, wherein the extracellular portion comprises amino acids 1-377 of SEQ ID NO:103.
69. The antibody or fragment thereof of any of embodiments 1-56, 58-62 and 64-68, wherein the antibody does not specifically bind to a mouse ROR1 protein or does not specifically bind to a protein having the amino acid sequence set forth in SEQ ID NO: 106.
70. The antibody or fragment of any of embodiments 1-7 and 9-69, which does not comprise the CDR-H1, CDR-H2, CDR-H3 and/or CDR-L1, CDR-L2, CDR-L3 sequences of the anti-ROR1 antibody, R12, and/or of the anti-ROR1 antibody 2A2.
71. The antibody or fragment of any of embodiments 1-7 and 9-70, which does not comprise CDR-H1, CDR-H2, CDR-H3 and/or CDR-L1, CDR-L2, CDR-L3 sequences having at least 90% identity to the CDR-H1, CDR-H2, CDR-H3 and/or CDR-L1, CDR-L2, CDR-L3 sequences of the anti-ROR1 antibody, R12, and/or of the anti-ROR1 antibody 2A2.
72. The antibody or fragment of any of embodiments 1-71, wherein the antibody or fragment is human.
73. A human antibody or antigen-binding fragment thereof that specifically binds to the same or an overlapping epitope of a ROR1 protein as the epitope specifically bound by a reference antibody, wherein the reference antibody is the antibody or fragment thereof of any of embodiments 1-72 or is the anti-ROR1 antibody, R12, or antigen binding fragment thereof, said human antibody or fragment comprising heavy and light chain CDRs that are distinct from the CDRs present in R12 and/or 2A2.
74. A human antibody or antigen-binding fragment thereof that specifically binds to ROR1 and competes for binding to ROR1 with a reference antibody, wherein the reference antibody is the antibody or fragment of any of embodiments 1-72 or is the anti-ROR1 antibody R12 or an antigen binding fragment thereof, said human antibody or fragment comprising heavy and light chain CDRs that are distinct from the CDRs present in R12 and/or 2A2.
75. The human antibody or fragment of any of embodiments 72-74, wherein:

the antibody comprises a heavy chain variable ($V_H$) region, said $V_H$ region comprises a portion having at least 95%, 96%, 97%, 98%, 99%, or 100% sequence identity to an amino acid sequence encoded by a germline nucleotide human heavy chain V segment, a portion with at least 95%, 96%, 97%, 98%, 99%, or 100% sequence identity to an amino acid sequence encoded by a germline nucleotide human heavy chain D segment, and/or a portion having at least 95%, 96%, 97%, 98%, 99%, or 100% sequence identity to an amino acid sequence encoded by a germline nucleotide human heavy chain J segment; and/or the antibody comprises a light chain variable ($V_L$) region, said $V_L$ region comprises a portion with at least 95%, 96%, 97%, 98%, 99%, or 100% sequence identity to an amino acid sequence encoded by a germline nucleotide human kappa or lambda chain V segment, and/or a portion with at least 95%, 96%, 97%, 98%, 99%, or 100% sequence identity to an amino acid sequence encoded by a germline nucleotide human kappa or lambda chain J segment.

76. The human antibody or fragment of any of embodiments 72-75, wherein:

the CDR-H1 and/or CDR-H2 comprises a sequence 100% identical or with no more than one amino acid difference as compared to an amino acid sequence of a CDR-H1 and/or CDR-H2, respectively, within a sequence encoded by a germline nucleotide human heavy chain V segment; and/or the CDR-L1 and/or CDR-L2 comprises a sequence 100% identical or with no more than one amino acid difference as compared to an amino acid sequence of a CDR-L1 and/or CDR-L2, respectively, within a sequence encoded by a germline nucleotide human kappa or lambda v segment.

77. The antibody or fragment of any of embodiments 1-76, wherein the antibody or fragment is recombinant.

78. The antibody or fragment of any of embodiments 1-77, which is monoclonal.
79. The antibody or fragment of any of embodiments 1-78 that is an antigen-binding fragment.
80. The antibody or fragment of any of any of embodiments 1-79, which is a single chain fragment.
81. The antibody or fragment of any of embodiments 31-80, which is a fragment comprising antibody $V_H$ and $V_L$ regions joined by a flexible linker.
82. The antibody or fragment of embodiment 80 or embodiment 81, wherein the fragment comprises an scFv.
83. The antibody or fragment of embodiment 82, wherein the scFv comprises a linker comprising the sequence set forth SEQ ID NO: 91.
84. The antibody or fragment of embodiment 82 or embodiment 83, wherein the scFv comprises the amino acid sequence set forth in SEQ ID NO: 2, 4, 6, 12, 249, 250, 251, 252, 253, 254, 255, 256, 257, 258, 259, 260, 261, 262, 263, 264, 265, 266, 267 or 268, or a sequence of amino acids that exhibits at least 90% sequence identity to the amino acid sequence set forth in SEQ ID NO: 2, 4, 6, 12, 249, 250, 251, 252, 253, 254, 255, 256, 257, 258, 259, 260, 261, 262, 263, 264, 265, 266, 267 or 268.
85. The antibody or fragment of any of embodiments 82-84, wherein the scFv comprises the amino acid sequence set forth in SEQ ID NO: 2, 4, 6, or 12, or a sequence of amino acids that exhibits at least 90% sequence identity to the amino acid sequence set forth in SEQ ID NO: 2, 4, 6, or 12.
86. The antibody or fragment of any of embodiments 82-85, wherein the scFv comprises the amino acid sequence set forth in SEQ ID NO: 2, 4, 6, or 12.
87. The antibody or fragment of any of embodiments 31-86, wherein the antibody or fragment comprises the $V_H$ region set forth in SEQ ID NO: 19 and the $V_L$ region set forth in SEQ ID NO: 18, and/or the antibody or fragment comprises the sequence of amino acids set forth in SEQ ID NO: 12.
88. The antibody or fragment of any of embodiments 31-86, wherein the antibody or fragment comprises the $V_H$ region set forth in SEQ ID NO: 13 and the $V_L$ region set forth in SEQ ID NO: 14, and/or the antibody or fragment comprises the sequence of amino acids set forth in SEQ ID NO: 6.
89. The antibody or fragment of any of embodiments 31-86, wherein the antibody or fragment comprises the $V_H$ region set forth in SEQ ID NO: 15 and the $V_L$ region set forth in SEQ ID NO: 16, and/or the antibody or fragment comprises the sequence of amino acids set forth in SEQ ID NO: 4.
90. The antibody or fragment of any of embodiments 31-86, wherein the antibody or fragment comprises the $V_H$ region set forth in SEQ ID NO: 17 and the $V_L$ region set forth in SEQ ID NO: 18, and/or the antibody or fragment comprises the sequence of amino acids set forth in SEQ ID NO: 2.
91. A single chain cell-surface protein, comprising the antibody or fragment of any of embodiments 1-90.
92. A single chain cell surface protein comprising the scFv sequence of SEQ ID NO: 2, 4, 6, 12, 249, 250, 251, 252, 253, 254, 255, 256, 257, 258, 259, 260, 261, 262, 263, 264, 265, 266, 267 or 268 or comprising the $V_H$ sequence set forth in SEQ ID NO: 8, 10, 13, 15, 17, 19, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 or 209.

93. The single chain cell surface protein of embodiment 92, comprising the scFv sequence of SEQ ID NO: 2, 4, 6 or 12 or comprising the $V_H$ sequence set forth in SEQ ID NO: 8, 10, 13, 15, 17, or 19.
94. The antibody or fragment of any of embodiments 1-90, which further comprises at least a portion of an immunoglobulin constant region.
95. The antibody or fragment of embodiment 94, further comprising a spacer set forth in SEQ ID NO:108.
96. The antibody or fragment of embodiment 94, wherein the at least a portion of an immunoglobulin constant region comprises an Fc region.
97. The antibody or fragment of embodiment 96, wherein the Fc region is an Fc region of a human IgG.
98. A conjugate, comprising the antibody or fragment of any of embodiments 1-97 and a heterologous molecule or moiety.
99. A chimeric antigen receptor (CAR) comprising an extracellular portion comprising the antibody or fragment of any of embodiments 1-97 and an intracellular signaling domain.
100. The chimeric antigen receptor of embodiment 99, wherein the antibody or fragment comprises a VH sdAb, an scFv and the intracellular signaling domain comprises an ITAM.
101. The chimeric antigen receptor of embodiment 99 or 100, wherein the intracellular signaling domain comprises a signaling domain of a zeta chain of a CD3-zeta (CD3) chain.
102. The chimeric antigen receptor of any of embodiments 99-101, further comprising a transmembrane domain linking the extracellular domain and the intracellular signaling domain.
103. The chimeric antigen receptor of embodiment 102, wherein the transmembrane domain comprises a transmembrane portion of CD28.
104. The chimeric antigen receptor of any of embodiments 99-103, further comprising an intracellular signaling domain of a T cell costimulatory molecule.
105. The chimeric antigen receptor of embodiment 104, wherein the T cell costimulatory molecule is selected from the group consisting of CD28 and 41BB.
106. A nucleic acid encoding the antibody or fragment thereof of any of embodiments 1-97, conjugate of embodiment 98 or the chimeric antigen receptor of any of embodiments 99-105.
107. An engineered cell expressing a receptor comprising the antibody or fragment of any of embodiments 1-97, conjugate of embodiment 98 or the chimeric antigen receptor of any of embodiments 99-105.
108. The engineered cell of embodiment 107, which is a T cell. 109. A composition comprising the antibody or fragment thereof of any of embodiments 1-97, conjugate of embodiment 98, the CAR of any of embodiments 99-105, or the cell of embodiment 107 or 108.
110. The composition of embodiment 109, further comprising a pharmaceutically acceptable excipient.
111. A method of treatment, comprising administering the composition of embodiment 109 or embodiment 110 to a subject having a disease or disorder associated with ROR1.
112. A method of treatment, comprising administering an antibody or fragment of any of embodiments 1-97, conjugate of embodiment 98, a CAR of any of embodiments 99-103 or the cell of embodiment 107 or 108 to a subject having a disease or disorder associated with ROR1.

113. A method of treatment, comprising administering the cell of embodiment 107 or embodiment 108 to a subject having a disease or disorder associated with ROR1.

114. The method of any of embodiments 112-113, wherein the disease or disorder is a ROR1-expressing cancer.

115. The method of embodiment any of embodiments 112-114, wherein the ROR1-expressing cancer is selected from the group consisting of B cell leukemia, lymphoma, B cell chronic lymphocytic leukemia (CLL), AML, acute myeloid leukemia (AML), acute lymphocytic leukemia (ALL), Burkett's Lymphoma, mantle cell lymphoma (MCL), non-small cell lung cancer (NSCLC), neuroblastoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, uterine cancer, adrenal cancer and head and neck cancer.

116. A composition of embodiment 109 or embodiment 110 for use in treating a disease or disorder associated with ROR1.

117. Use of a composition of embodiment 109 or embodiment 110 for the manufacture of a medicament for treating a disease or disorder associated with ROR1.

118. The composition for use of embodiment 116 or the use of embodiment 117, wherein the disease or disorder is a ROR1-expressing cancer.

119. The composition for use or use of embodiment 118, wherein the ROR1-expressing cancer is selected from the group consisting of B cell leukemia, lymphoma, B cell chronic lymphocytic leukemia (CLL), AML, acute myeloid leukemia (AML), acute lymphocytic leukemia (ALL), Burkett's Lymphoma, mantle cell lymphoma (MCL), non-small cell lung cancer (NSCLC), neuroblastoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, uterine cancer, adrenal cancer and head and neck cancer.

V. EXAMPLES

The following examples are included for illustrative purposes only and are not intended to limit the scope of the invention.

Example 1: Generation and Assessment of Anti-ROR1 Antibodies (VHs)

Exemplary anti-ROR1 antibodies, variable heavy (VH) chains that specifically bound to ROR1, even in the absence of a variable light ($V_L$) chain, were generated and assessed. The anti-ROR1 antibodies (VHs) resulted from selections based on ability to specifically bind to ROR1-expressing cells, and/or to compete for binding with a rabbit-derived anti-ROR1 reference antibody.

1A. Library Selection, Antibody Generation

Exemplary anti-ROR1 antibodies (VHs) were generated through a series of selection steps carried out on dsDNA-encoded human naïve antibody $V_H$ libraries displayed in a cell-free system. Members of a $V_H$ library were selected for binding to live cells through five successive rounds, enriching for members that bound specifically to stably-transfected ROR1-expressing CHOK1, K562, and/or HEK293 cells, but not parental K562 and/or CHOK1 cells that did not express ROR1. To recover $V_H$ binders, a further selection was performed. In branch (a), surface stripping was applied to all 5 rounds of selection to recover ROR1 $V_H$ binders that cover broad epitopes and affinity ranges. In another branch (b), after two rounds of surface stripping, competitive elution was applied using a rabbit anti-ROR1 antibody, R12 scFv (having the sequence set forth in SEQ ID NO: 84, including the $V_H$ and $V_L$ sequences from the rabbit-human antibody designated R12), to enrich for binders that competed with R12 scFv for binding to ROR1, such as to the R12 scFv epitope.

Certain resulting clones were sequenced using forward and reverse primers to determine amino acid sequences. Table 2A lists sequence identifiers of the $V_H$ sequence of exemplary clones and the corresponding exemplary CDR-H1, CDR-H2 and CDR-H3 therein. Table 2B lists sequence identifiers corresponding to exemplary CDR-H3 (Kabat) amino acid sequences for exemplary clones. A $V_H$ sequence for clone V70 is set forth in SEQ ID NO: 8, which had CDR-H1 and CDR-H2 (Kabat) sequences as set forth in SEQ ID NOs: 27 and 28, respectively. A $V_H$ sequence for clone V353 is set forth in SEQ ID NO: 10, which had CDR-H1 and CDR-H2 (Kabat) sequences set forth in SEQ ID NOs: 33 and 34, respectively. Table 2B also lists a CDR-H3 (Kabat) sequence of a rabbit-derived reference antibody R12 (which has a $V_H$ sequence set forth in SEQ ID NO: 85), an scFv fragment of which was used as a control in this study. Clone V355 had a heavy chain framework with a sequence derived from a $V_H1$ sequence; clones V331 and V345 had heavy chain frameworks with sequences derived from human $V_H4$ sequences. All other clones (aside from R12) listed in Table 2A and 2B contained frameworks with sequences derived from human $V_H3$ sequences.

TABLE 2A

Sequences for Exemplary Clones (SEQ ID NO.)

| Clone # | Heavy Chain Variable ($V_H$) Region (Amino Acid) | Heavy Chain Variable ($V_H$) Region (nucleotide) | CDR-H (1, 2, 3) (Kabat) (Amino Acid) | Heavy Chain Framework Derived From |
|---|---|---|---|---|
| V70 | 8 | 7 | 27, 28, 29 | $V_H3$ |
| V420 | 206 | | 162, 170, 50 | $V_H3$ |
| V282 | 203 | | 162, 170, 51 | $V_H3$ |
| V353 | 10 | 9 | 33, 34, 52 | $V_H3$ |
| V163 | 193 | | 33, 34, 53 | $V_H3$ |
| V355 | 201 | | 161, 169, 54 | $V_H1$ |
| V18 | 179 | | 33, 34, 35 | $V_H3$ |
| V224 | 192 | | 33, 34, 55 | $V_H3$ |
| V95 | 194 | | 33, 34, 56 | $V_H3$ |
| V316 | 198 | | 159, 167, 57 | $V_H3$ |
| V331 | 199 | | 160, 168, 58 | $V_H4$ |
| V357 | 202 | | 33, 34, 59 | $V_H3$ |
| V397 | 205 | | 33, 171, 60 | $V_H3$ |
| V312 | 197 | | 33, 34, 61 | $V_H3$ |
| V278 | 200 | | 158, 166, 62 | $V_H3$ |
| V86 | 191 | | 158, 166, 63 | $V_H3$ |
| V102 | 195 | | 27, 164, 64 | $V_H3$ |
| V365 | 204 | | 158, 166, 65 | $V_H3$ |
| V181 | 196 | | 27, 164, 66 | $V_H3$ |
| V128 | 188 | | 156, 34, 35 | $V_H3$ |
| V71 | 190 | | 157, 165, 67 | $V_H3$ |
| V68 | 189 | | 27, 164, 68 | $V_H3$ |

TABLE 2A-continued

| Sequences for Exemplary Clones (SEQ ID NO.) | | | | |
|---|---|---|---|---|
| | Heavy Chain Variable ($V_H$) Region | | CDR-H (1, 2, 3) (Kabat) | Heavy Chain Framework Derived |
| Clone # | (Amino Acid) | (nucleotide) | (Amino Acid) | From |
| V336 | 208/209 | | 163, 173, 69/174 | $V_H3$ |
| V9 | 187 | | 33, 34, 70 | $V_H3$ |
| V345 | 207 | | 160, 172, 71 | $V_H4$ |

TABLE 2B

| Clone# | CDR-H3 Sequence (Kabat) | SEQ ID NO: |
|---|---|---|
| V70 | VSNYEYYFDY | 29 |
| V420 | VNGGEYYFDY | 50 |
| V282 | VRGSEYYFDY | 51 |
| V353 | DFGRWGYYFDY | 52 |
| V163 | QGDSSSWYVEVYYFDY | 53 |
| V355 | ITPPDAFDI | 54 |
| V18 | DFGRWSYYFDY | 35 |
| V224 | TYSSSWYESLLFDY | 55 |
| V95 | GSGELRFLESYYFDY | 56 |
| V316 | VDSERFLEWYYFDY | 57 |
| V331 | GQIAAHVWGWFDP | 58 |
| V357 | DMVGAWLVLSYFDY | 59 |
| V397 | AKGLWFGESYYFDY | 60 |
| V312 | TSRGRFLEWLLFDY | 61 |
| V278 | ERSRWGDNWFDP | 62 |
| V86 | VIFGVVNIPDY | 63 |
| V102 | VGPSWDYYFDY | 64 |
| V365 | GIGYSSSWYEIWTFDY | 65 |
| V181 | DFEVREAHLSYFDY | 66 |
| V128 | DFGRWSYYFDY | 35 |
| V71 | VLRSGFLEWNLFDY | 67 |

TABLE 2B-continued

| Clone# | CDR-H3 Sequence (Kabat) | SEQ ID NO: |
|---|---|---|
| V68 | DFEVRGAHLSYFDY | 68 |
| V336 | VYGYDYRDFGWFDP | 69 |
| V9 | GSNERFLEWLNFDY | 70 |
| V345 | GPLRPQKVLPFQI | 71 |
| R12 scFv reference antibody | DSYADDGALFNI | 72 |

1B. Binding Affinities, Competition with Reference Antibody

Exemplary ROR1 binding $V_H$ clones, generated in the selection process described in Example 1A, were further assessed. Clones were purified and titrated, and their binding affinities ($EC_{50}$) to ROR1-expressing K562 and CHOK1 cells assessed by flow cytometry, with $EC_{50}$ of the reference antibody (R12 scFv) serving as a positive control.

Assays also were performed to assess competition of the clones with the reference antibody (R12 scFv), for binding to ROR1-expressing cells. $V_H$ clones were titrated against 2 nM Myc-R12 on ROR1/K562 cells and competition assessed with an anti-Myc-Alexa Fluor™ 647 secondary antibody, and the half maximal inhibitory concentration ($IC_{50}$) determined for respective clones.

Additionally, percent (%) maximum (max) binding to ROR1-expressing cells and % max competition with the reference antibody (R12 scFv) were calculated. Percent max binding and competition values were calculated based on predicted plateaus (measured by GraphPad Prism® using four parameter non-linear regression), relative to values for R12 scFv binding and inhibition, respectively, assigned as 100% in each study.

Results are presented in Table 2C, listing mean $EC_{50}$ (binding affinity), $IC_{50}$ (competition), % max binding, and % max competition values, based on the indicated number of experiments for various clones. As expected, the reference antibody (R12 scFv) was confirmed in this study to specifically bind to ROR1 and compete with itself. The results demonstrated ROR1-specific binding and competition with the R12 scFv reference antibody, to varying degrees for various clones. Among the clones generated were those exhibiting similar affinity ($EC_{50}$) for ROR1 and similar levels of competition for binding to ROR1 with the reference antibody.

Two preps of clone V9 were tested in a single R12 scFv competition assay and found not to have any detectable competitive binding activity.

TABLE 2C

| Results from Various Binding and Competition Assays | | | | |
|---|---|---|---|---|
| | Binding affinity to ROR1-Expressing Cells | | Competition for binding with R12 scFv | |
| Clone # | $EC_{50}$ (nM) | % Max Binding | $IC_{50}$ (nM) | % Max Competition |
| V70 | 3.1 ± 0.3 (n = 7) | 92 ± 6 | 38.2 ± 4.8 (n = 8) | 92 ± 12 |
| V420 | 8.0 (n = 1) | 74 | 71.5 (n = 1) | 58 |
| V282 | 13.1 (n = 1) | 64 | 94.3 (n = 1) | 48 |
| V353 | 0.7 (n = 2) | 35 ± 5 | .4 (n = 2) | 62 |

TABLE 2C-continued

Results from Various Binding and Competition Assays

| | Binding affinity to ROR1-Expressing Cells | | Competition for binding with R12 scFv | |
|---|---|---|---|---|
| Clone # | $EC_{50}$ (nM) | % Max Binding | $IC_{50}$ (nM) | % Max Competition |
| V163 | 92.9 (n = 1) | 122 | 154.2 (n = 1) | 58 |
| V355 | 0.9 (n = 1) | 54 | 1.9 ± 0.4 (n = 2) | 53 ± 8 |
| V18 | 0.2 ± 0.1 (n = 2) | 37 ± 12 | 3.4 ± 0.8 (n = 3) | 54 ± 6 |
| V224 | 46.2 (n = 1) | 74 | 94.6 ± 56.7 | 32 ± 17 |
| V95 | 35.5 ± 2.1 (n = 2) | 61 ± 14 | 19.0 ± 2.1 (n = 2) | 36 ± 7 |
| V316 | 28.7 (n = 1) | 78 | 28.8 ± 4.9 (n = 2) | 37 ± 14 |
| V331 | 18.8 (n = 1) | 70 | 32.4 (n = 1) | 31 |
| V357 | 46.0 (n = 1) | 22 | 74.0 (n = 1) | 44 |
| V397 | 49.7 (n = 1) | 18 | 25.2 (n = 1) | 18 |
| V312 | 23.7 (n = 1) | 29 | 5.6 (n = 1) | 19 |
| V278 | 31.5 (n = 1) | 22 | ND (n = 2) | |
| V86 | 97.7 ± 62.1 (n = 2) | | ND (n = 2) | |
| V102 | 128.9 ± 46.0 (n = 2) | | ND (n = 1) | |
| V365 | >200 (n = 1) | 8 | ND (n = 1) | |
| V181 | >200 (n = 1) | | >200 (n = 1) | 76 |
| V128 | >200 (n = 1) | | >200 (n = 1) | |
| V71 | >200 (n = 2) | | ND (n = 2) | |
| V68 | >200 (n = 2) | | ND (n = 2) | |
| V336 | >200 (n = 1) | 72 | ND (n = 1) | |
| V345 | ND (n = 1) | | ND (n = 1) | |
| R12 scFv reference antibody | 0.8 ± 0.1 (n = 20) | 100 | 3.3 ± 0.2 (n = 17) | 100 |

ND = not detected

Example 2: Generation and Assessment of Anti-ROR1 Antibodies (scFvs)

Exemplary anti-ROR1 antibodies (scFvs) that specifically bound to ROR1 were generated and assessed, including those that competed for binding with the R12 scFv reference antibody.

2A. Library Selection, Antibody Generation

Exemplary anti-ROR1 scFv antibodies were generated through various selection approaches, carried out on dsDNA-encoded human naïve antibody libraries displayed in a cell-free system. In some approaches, $V_L$ library members were paired with ROR1-specific $V_H$-only antibodies generated in the study described in Example 1.

In one approach, a $V_H$ library was enriched through three successive rounds for members that bound specifically to stably-transfected ROR1-expressing CHOK1, K562, and/or HEK293 cells, but not parental ROR1-negative cells. The resulting enriched $V_H$ libraries were converted to scFv libraries by shuffling with a naïve human $V_L$ library, in $V_H$-$(G4S)_3$-$V_L$ format. The shuffled scFv libraries then were enriched in a fourth and fifth round of selection for specific binding to ROR1-expressing (but not parental) CHOK1 cells, with elution by surface stripping. In a sixth round, negative selection enriched for members that did not bind parental cells (K562, CHOK1), followed by positive selection for binding to ROR1-expressing K562 and/or CHOK1 cells. Elution pools were generated by either (a) surface stripping, or (b) R12 competitive elution.

In another approach, de novo selection was carried out by enriching a naïve human scFv library for ROR1-specific binding with ROR1-HEK293, ROR1-CHO, and ROR1-K562 cells and not HEK293, CHO-K1, and K562 parental cells over multiple rounds by alternating cell lines each round, followed by a combination of surface stripping (R1), competitive elution with R12 scFv (R2-4) and immunoprecipitation (R5) to recover scFv binders.

In another approach, ROR1-specific $V_H$-only antibodies generated in the study described in Example 1B were non-covalently paired with members of a human naïve $V_L$ library (constructed from the same set of donors as naïve $V_H$ library) by dsDNA display, followed by selection for ROR1 binding for 3 successive rounds with ROR1-HEK293 and ROR1-CHO cells. Sequences of selected $V_L$s were used to generate scFv clones.

For scFv clones selected in these various approaches, specific binding to ROR1-expressing K562 cells, as compared to control cells not expressing ROR1, was assessed by flow cytometry either with in vitro translated crude cell lysate or with bacterially-produced supernatant. Certain clones displaying binding preference for ROR1 were further analyzed.

Clones were sequenced using forward and reverse primers. Exemplary CDR-H3 (Kabat) amino acid sequences for exemplary clones and respective sequence identifiers are listed Table 3A. Clone "83B," a de-glycosylation variant of clone 83, was generated by a introducing a serine (S) to asparagine (N) substitution at $V_H$ position 53 (Kabat) to remove the N-glycosylation motif of clone 83. Table 3B lists sequence identifiers for $V_H$ and $V_L$ sequences and exemplary CDR-H 1, 2, and 3 (Kabat) and CDR-L sequences of exemplary clones. Table 3A also lists the respective light chain human v-segment from which framework sequences of individual antibodies were derived. Each antibody in this table included a heavy chain framework sequence derived from a human VH3 sequence.

TABLE 3A

| Clone/ Antibody | CDR-H3 | SEQ ID NO. | CDR-L3 | SEQ ID NO: | Light Chain Framework Derived From |
|---|---|---|---|---|---|
| Exemplary Clones | | | | | |
| 83B | DSSYDAFDI | 22 | QQYESLPYT | 25 | Vk1 |
| 83 | DSSYDAFDI | 22 | QQYESLPYT | 25 | Vk1 |
| 305 | VSNYEYYFDY | 29 | QVWDNDSDHRV | 40 | Vλ3 |
| 298 | VSNYEYYFDY | 29 | QVWDDTGDHPV | 32 | Vλ3 |
| 350 | VSNYEYYFDY | 29 | QSYDSSNHV | 41 | Vλ6 |
| 20 | DFGRWSYYFDY | 35 | QQLKSRPLS | 42 | Vk1 |
| 16 | DFGRWSYYFDY | 35 | QQLNSYPLT | 43 | Vk1 |
| 48 | DFGRWSYYFDY | 35 | AAWDDSLSGVV | 39 | Vλ3 |
| 43 | DFGRWSYYFDY | 35 | AAWDDSLSGVV | 39 | Vλ1 |
| 366 | VSNYEYYFDY | 29 | AAWDDSLNGYV | 44 | Vλ1 |
| 40 | DFGRWSYYFDY | 35 | QSYDGRNLM | 45 | Vλ6 |
| 461 | DFEVREAHLSYFDY | 46 | QVWDSSSDHRV | 47 | Vλ3 |
| 65 | DFGRWSYYFDY | 35 | KSWDSSGSLYV | 48 | Vλ3 |
| 81 | DFGRWSYYFDY | 35 | QVWDSSSDHYV | 49 | Vλ3 |
| 7 | DFGRWSYYFDY | 35 | QAWDSSTVV | 50 | Vλ3 |
| R12 scFv reference antibody | DSYADDGALFN | 73 | GADYIGGYV | 74 | Rb |

TABLE 3B

| Clone # | Heavy Chain Variable (VH) Region (Amino Acid) | Light Chain Variable (VL) Region (Amino Acid) | ScFv Sequence Amino Acid (Nucleotide) | CDR-H (1, 2, 3) (Kabat) (Amino Acid) | CDR-L (1, 2, 3) (Kabat) (Amino Acid) | Heavy Chain Framework Derived From | Light Chain Framework Derived From |
|---|---|---|---|---|---|---|---|
| Sequences for Exemplary Clones and Reference Antibody (SEQ ID NO:) | | | | | | | |
| 83 | 17 | 18 | 2 (1) | 20, 21, 22 | 23, 24, 25 | $V_H3$ | Vk1 |
| 83B | 19 | 18 | 12 (11) | 20, 26, 22 | 23, 24, 25 | $V_H3$ | Vk1 |
| 305 | 182 | 246 | 265 | 27, 28, 29 | 218, 229, 39 | $V_H3$ | Vλ3 |
| 298 | 15 | 16 | 4 (3) | 27, 28, 29 | 30, 31, 32 | $V_H3$ | Vλ3 |
| 350 | 182 | 242 | 258 | 27, 28, 29 | 216, 227, 40 | $V_H3$ | Vλ6 |
| 20 | 183/184 | 243/244 | 259/260/261/262 | 33, 34, 35 | 217, 228, 41 | $V_H3$ | Vk1 |
| 16 | 177 | 238 | 253 | 33, 34, 35 | 212, 223, 42 | $V_H3$ | Vk1 |
| 48 | 13 | 14 | 6 (5) | 33, 34, 35 | 36, 37, 38 | $V_H3$ | Vλ3 |
| 43 | 183/184 | 245 | 263/264 | 33, 34, 35 | 36, 37, 38 | $V_H3$ | Vλ1 |
| 366 | 182 | 247 | 266 | 27, 28, 29 | 219, 230, 43 | $V_H3$ | Vλ1 |
| 40 | 180/181 | 241 | 256/257 | 33, 34, 35 | 215, 226, 44 | $V_H3$ | Vλ6 |
| 461 | 185/186 | 248 | 267/268 | 27, 164, 45 | 220, 231, 46 | $V_H3$ | Vλ3 |
| 65 | 178 | 239 | 254 | 155, 34, 35 | 213, 224, 47 | $V_H3$ | Vλ3 |
| 81 | 176 | 236/237 | 251/252 | 33, 34, 35 | 211, 222, 48 | $V_H3$ | Vλ3 |
| 7 | 175 | 234/235 | 249/250 | 33, 318, 35 | 210, 221, 49/233 | $V_H3$ | Vλ3 |
| R12 scFv reference antibody | 85 | 86 | 84 | 87, 88, 72 | 89, 90, 73 | Rb | Rb |

2B. Binding Affinities, Competition with Reference Antibody

Clones were purified and titrated, and their binding affinities ($EC_{50}$) to ROR1-expressing K562 and CHOK1 cells assessed by flow cytometry. $EC_{50}$ for the R12 scFv reference antibody in this study served as a positive control.

Assays also were performed to assess competition (measured as half maximal inhibitory concentration ($IC_{50}$)) of the clones with the R12 scFv reference antibody for binding to ROR1-expressing cells, as described in Example 1. Percent (%) max ROR1 and % max competition, as compared to the R12 scFv reference antibody, were determined as described in Example 1.

Results are presented in Table 3C, listing mean $EC_{50}$ (binding affinity), $IC_{50}$ (competition), % max binding, and % max competition values for various clones, as determined over a plurality of experiments. As expected, the reference antibody was confirmed to exhibited ROR1-specific binding and competition with itself in this study. The results demonstrated varying degrees of ROR1-specific binding affinities and competition with the R12 scFv reference antibody among the various clones. Among the assayed clones were those with similar ROR1 binding affinity as compared to the reference antibody and those that competed for binding with the reference antibodies to similar degrees as compared to the reference antibody itself.

TABLE 3C

Results from Various Binding and Competition Assays

| | Binding affinity to ROR1-Expressing Cells | | Competition for binding with R12 scFv | |
|---|---|---|---|---|
| Clone# | $EC_{50}$ (nM) | % Max | $IC_{50}$ (nM) | % Max |
| 83B | 6.4 (n = 1) | 140 | 15.0 (n = 1) | 103 |
| 83 | 2.5 ± 0.3 (n = 2) | 70 ± 7 | 11.1 ± 3.4 (n = 3) | 103 ± 3 |
| 305 | 5.1 (n = 1) | 86 | 62.5 (n = 1) | 97 |
| 298 | 5.9 (n = 1) | 96 | 41.3 (n = 1) | 88 |
| 350 | 22.9 (n = 1) | 137 | 49.1 (n = 1) | 80 |
| 20 | 2.6 ± 1.1 (n = 9) | 97 ± 18 | 4.7 ± 2.2 (n = 5) | 77 ± 7 |
| 16 | 3.7 ± 1.3 (n = 6) | 91 ± 23 | 4.2 ± 1.8 (n = 4) | 71 ± 8 |
| 48 | 9.2 ± 1.9 (n = 4) | 69 ± 24 | 53.7 ± 18.7 (n = 3) | 55 ± 11 |
| 43 | 10.6 ± 3.4 (n = 4) | 66 ± 14 | 56.1 ± 28.4 | 56 ± 17 |
| 366 | 10.0 (n = 1) | 104 | 53.9 (n = 1) | 71 |
| 40 | 3.2 ± 0.8 (n = 4) | 81 ± 20 | 22.8 ± 11.2 (n = 4) | 70 ± 11 |
| 461 | 22.8 (n = 1) | 63 | 99.8 (n = 1) | 48 |
| 65 | 18.4 ± 11.6 (n = 2) | | ND (n = 3) | |
| 81 | >200 (n = 2) | | not assayed | |
| R12 scFv reference antibody | 0.8 ± 0.1 (n = 20) | 100 | 3.3 ± 0.2 (n = 17) | 100 |

ND = none detected

Example 3: Generation of Chimeric Antigen Receptors (CARs) Against ROR1, Engineering of Cells Expressing Such CARs, and Assessment of Effector Functions of Such CAR-Expressing Cells Various exemplary chimeric antigen receptors (CARs) were generated, with antigen-binding regions containing human anti-ROR1 antigen-binding domains as described in Example 1. Specifically, nucleic acid molecules were generated that encoded CARs containing either an scFv antigen-binding domains in the VH-VL format (Clone 83B, Clone 298 or Clone 48) or a VH only antigen-binding domain (Clone V70 and Clone V353). For exemplary scFv antigen-binding domains, constructs encoding a CAR having the same VH and VL sequences, but present in the reverse orientation (VL-VH), also were generated. A CAR containing a rabbit anti-ROR1 scFv (R12) (in the VH-VL orientation) was used as a control. Each CAR further contained an Ig-derived hinge only spacer, a human CD28-derived transmembrane domain, a human 4-1BB-derived intracellular signaling domain, a human CD3 zeta-derived signaling domain, and a truncated EGFR (tEGFR) sequence for use as a transduction marker, separated from the CAR sequence by a self-cleaving T2A sequence.

Primary human T cell populations expressing the various CARs were generated. Nucleic acid molecules encoding each CAR were individually cloned into a lentiviral vector, which was used to transduce CD8+ T cells in populations isolated from human PBMC samples obtained from healthy donors (essentially as described by Yam et al. (2002) Mol. Ther. 5:479; WO2015/095895). As a control, a lentiviral vector containing nucleic acid encoding only the tEGFR sequence was used to generate control cells expressing the tEGFR only. The genetically engineered human CD8+ T cells expressing various CARs containing human anti-ROR1 antigen-binding domains, produced as described above, were assessed for various responses following co-culture with ROR1-expressing cells.

A. Cytolytic Activity

ROR1-expressing target cells were incubated with CD8+ T cells expressing the various CARs or tEGFR alone (negative control). Following incubation, lysis of target cells was monitored. Specifically, lysis of ROR1-transduced K562 cells (K562/ROR1), JeKo-1 (mantle cell lymphoma line) cells, and non-transduced K562 control cells (negative control) (FIG. 1A) were tested.

The target cells (K562/ROR1, JeKo-1, or non-transduced K562 control cells) were labeled overnight with $^{51}Cr$. Labeled cells were washed and incubated with effector T cells (CAR-expressing and negative control CD8+ cells) at a single effector to target (E:T) ratio. To measure spontaneous lysis, target cells were incubated with an equal volume of media but without effector cells and maximum lysis was determined following incubation of target cells with detergent to completely lyse the target cells. Supernatants were harvested for γ-counting after a 4 hour incubation. The percent specific lysis for the experimental conditions was calculated as:

$$[(\text{Experimental Release}-\text{Spontaneous Release})/(\text{Maximum Release}-\text{Spontaneous Release})]\times 100.$$

The results are set forth in FIG. 1A. As shown in FIG. 1A, engineered CD8+ T cells expressing various human anti-ROR1 antigen-binding domain-containing CARs exhibited antigen-specific cytolytic activity against K562/ROR1 cells, as did cells expressing the CAR containing the rabbit anti-ROR1 (R12) scFv. This cytotoxic activity was generally not observed against control K562 cells not expressing ROR1. The results showed that cells engineered with a CAR containing the exemplary V353 clone containing only the VH domain exhibited comparable cytolytic activity to CARs containing an antigen-binding domain in the scFv format. The degree of cytolytic activity observed for cells expressing a CAR with a given human scFv in the VH-VL orientation was generally greater than that observed for cells expressing a CAR with the corresponding scFv in the reverse VL-VH orientation (LH).

B. Cytokine Release

Cytokine release was assessed following incubation of the CAR-expressing cells with antigen-expressing and control target cells. Transduced CD8+ T cells were co-cultured with target cells (K562, K562/ROR1, JeKo-1) at a single effector to target (E:T) ratio. The co-cultured cells were incubated for about 24 hours, and then supernatants were collected for measurement of IFN-γ using a cytokine immunoassay.

Figure 1B:
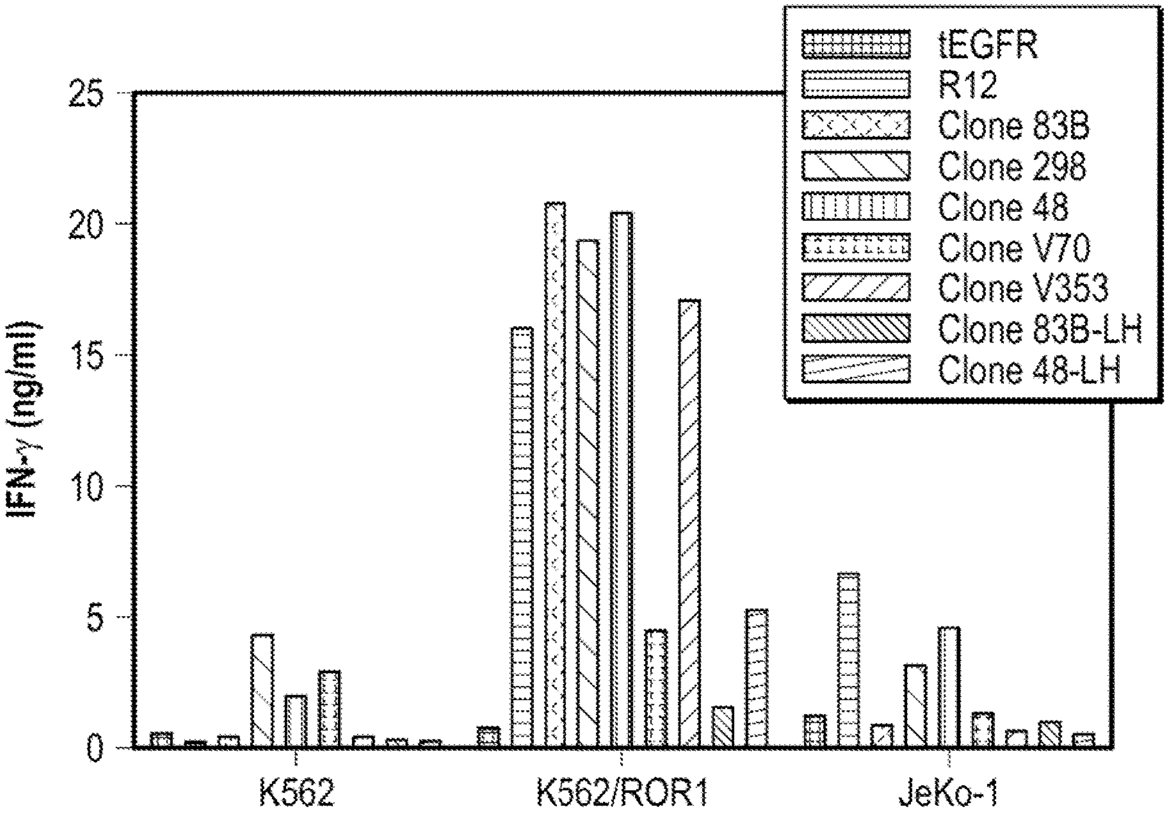
FIG. 1B shows cytokine secretion of primary human CD8+ T cells expressing various anti-ROR1 specific CARs after co-culture with ROR1-expressing cells. tEGFR alone is a negative control; R12 is R12 scFv CAR.

The results are set forth in FIG. 1B. Engineered CD8+ T cells expressing various human anti-ROR1 antigen-binding domain-containing CARs were observed to secrete IFN-γ in an antigen-specific manner following incubation with K562/ROR1 cells, as did cells expressing the CAR containing the rabbit anti-ROR1 (R12) scFv. The cytokine secretion was generally not observed following incubation with control K562 cells not expressing ROR1. The results showed that cells engineered with a CAR containing the exemplary V353 clone containing only the VH domain exhibited comparable levels of IFN-γ secretion to CARs containing an antigen-binding domain in the scFv format. The degree of IFNγ secretion observed for cells expressing a CAR with a given human scFv in the VH-VL orientation was generally greater that observed for cells expressing a CAR with the corresponding scFv in the reverse (VL-VH) orientation.

Example 4: Assessment of Effector Functions of CAR-Expressing Cells Against Cells Expressing Human or Mouse ROR1

Various exemplary chimeric antigen receptors (CARs) were generated and used to generate CAR-expressing CD8+ T cells as described in Example 3.

Cytokine release was assessed following incubation of the CAR-expressing cells with either K562/human ROR1 (hROR1) or K562/mouse ROR1 (mROR1) antigen-expressing cells. Transduced CD8+ T cells were co-cultured with antigen-expressing cells at a single effector to target (E:T). The co-cultured cells were incubated for about 24 hours, and then supernatants were collected for measurement of IFN-γ using a cytokine immunoassay.

Figure 2:
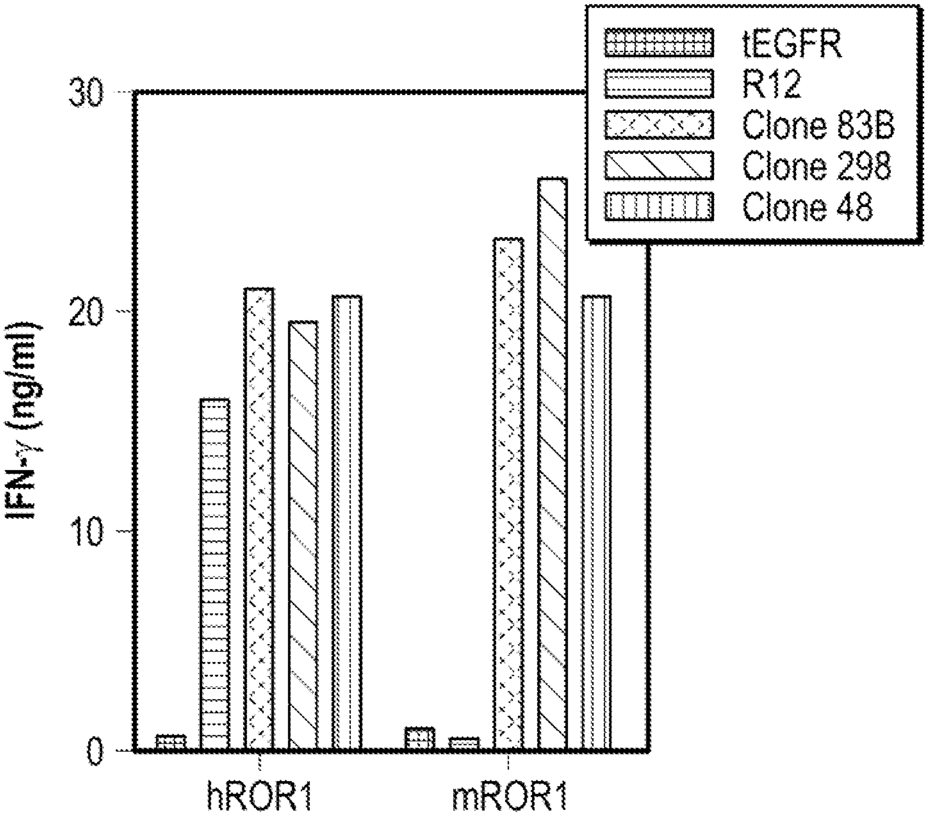
FIG. 2 shows cytokine secretion of primary human CD8+ T cells expressing various anti-ROR1 specific CARs after co-culture with human ROR1-expressing cells (hROR1) or mouse ROR1-expressing cells (mROR1). tEGFR alone is a negative control; R12 is R12 scFv CAR.

The results are set forth in FIG. 2. Engineered CD8+ T cells expressing the various human anti-ROR1 antigen-binding domain-containing CARs were observed to secrete IFN-γ at comparable levels following incubation with either hROR1-expressing cells or mROR1-expressing cells. In contrast, cells engineered with the rabbit anti-ROR1 (R12) scFv were observed to secrete IFN-γ only following incubation with hROR-1-expressing cells and not following incubation with mROR-1-expressing cells. This result is consistent with the reported specificity of R12 for human and not mouse ROR1 (Yang et al. (2011) PLoS ONE, 6:e21018). Thus, together with the results in Example 2, the results showed that the tested human anti-ROR1 antigen-binding binding domains of the CARs bind to an epitope in human ROR1 that may overlap with R12, but also bind to an epitope in mouse ROR1 that is not recognized by R12.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| SEQ ID NO: | Sequence | Description |
|---|---|---|
| 1 | CAGGTCCAGCTTGTGCAGTCTGGGGCTGAGGTGAAGAAGCCTGGGGCCT<br>CAGTGAAGGTTTCCTGCAAGGCATCTGGATACACCTTCACCAGCTACTA<br>TATGCACTGGGTGCGACAGGCCCCTGGACAAGGGCTTGAGTGGATGGG<br>AATAATCAACCCTAGTGGTGGTAGCACAAGCTACGCACAGAAGTTCCAG<br>GGCAGAGTCACCATGACCAGGGACACGTCCACGAGCACAGTCTACATG<br>GAGCTGAGCAGCCTGAGATCTGAGGACACGGCCGTGTATTACTGTGCGA<br>GAGATAGCAGCTATGATGCTTTTGATATCTGGGGCCAAGGGACAATGGT<br>CACCGTCTCCTCAGGTGGAGGCGGTTCAGGCGGAGGTGGCTCTGGCGGT<br>GGCGGATCGGCCATCCAGTTGACCCAATCTCCTTCCACCCTGTCTGCATC<br>TGTAGGAGACAGAGTCACCATCACTTGCCAGGCGAGTCAGGACATCAGC<br>AATTATTTAAATTGGTATCAGCAGAAACCAGGGAAAGCCCCTAAACTCC<br>TGATCAACGATGCATCCTATTTGGAGACAGGGGTCCCATCAAGGTTCAG<br>TGGAAGTGGATCTGGGACAGATTTTACTTTAACCATCAGCAGCCTGCAG<br>CCTGAAGATATTGCAACATATTACTGTCAACAGTATGAAAGTCTCCCGT<br>ACACTTTTGGCCAGGGGACCAAGCTGGAGATCAAA | Clone 83 scFv |
| 2 | QVQLVQSGAEVKKPGASVKVSCKASGYTFTSYYMHWVRQAPGQGLEWM<br>GIINPSGGSTSYAQKFQGRVTMTRDTSTSTVYMELSSLRSEDTAVYYCARDS<br>SYDAFDIWGQGTMVTVSSGGGGSGGGGSGGGGSAIQLTQSPSTLSASVGDR<br>VTITCQASQDISNYLNWYQQKPGKAPKLLINDASYLETGVPSRFSGSGSGTD<br>FTLTISSLQPEDIATYYCQQYESLPYTFGQGTKLEIK | Clone 83 scFv |
| 3 | GAGGTGCAGCTGGTGGAGTCTGGGGGAGGCTTGGTACAGCCAGGGCGG<br>TCCCTGAGACTCTCCTGTACAGCTTCTGGATTCACCTTTGGTGATTATGC<br>GATGAGCTGGGTCCGCCAGGCTCCAGGGAAGGGGCTGGAGTGGGTCTC<br>AAGTATTAGTGGTAGTGGTCGTAGCACAGACCACGCAGACTACGTGAAG | Clone 298 scFv |

-continued

SEQUENCES

| SEQ ID NO: | Sequence | Description |
|---|---|---|
| | GGCCGGTTCACCATCTCCAGAGACAATTCCAAGAACACGGTATATCTGC<br>AAATGAACAGGCTGAGAGCCGAGGACACGGCCGTGTATTACTGTGCAA<br>AAGTCAGTAACTACGAGTATTACTTTGACTACTGGGCCCAGGGAACCCT<br>GGTCACCGTCTCCTCAGGTGGAGGCGGTTCAGGCGGAGGTGGCTCTGGC<br>GGTGGCGGATCGGAAATTGTGCTGACTCAGTCTCCCTCGGTGTCAGTGG<br>CCCCAGGACAGACGGCCAGAATTACCTGTGGGGGAAGCAACATTGGAT<br>CTGAGAGTGTCAACTGGTACCAGTGGAAGTCGGGCCAGGTTCCTGTCTT<br>GGTCGTCTCTGACACTACCGACCGACCCTCAGGGATCCCTGGGCGATTC<br>ACTGGCACCCGGTCTGGGACCACGGCCACCTTGACCATCAGTGGGGTCG<br>AAGCCGGGGATGAGGCCGACTATCACTGTCAGGTGTGGGATGACACTG<br>GTGATCATCCTGTCTTCGGCGGAGGGACCAAGCTGACCGTCCTA | |
| 4 | EVQLVESGGGLVQPGRSLRLSCTASGFTFGDYAMSWVRQAPGKGLEWVSS<br>ISGSGRSTDHADYVKGRFTISRDNSKNTVYLQMNRLRAEDTAVYYCAKVS<br>NYEYYFDYWAQGTLVTVSSGGGGSGGGGSGGGGSEIVLTQSPSVSVAPGQ<br>TARITCGGSNIGSESVNWYQWKSGQVPVLVVSDTTDRPSGIPGRFTGTRSGT<br>TATLTISGVEAGDEADYHCQVWDDTGDHPVFGGGTKLTVL | Clone 298<br>scFv |
| 5 | CAGGTCACCTTGAAGGAGTCTGGGGGAGGCTTGGTAAAGCCTGGGGGG<br>TCCCTTAGACTCTCCTGTGCAGCCTCTGGATTCACTTTCAGTAACGCCTG<br>GATGAGCTGGGTCCGCCAGGCTCCAGGGAAGGGGCTGGAGTGGGTTGG<br>CCGTATTAAAAGCAAAACTGATGGTGGGACAACAGACTACGCTGCACCC<br>GTGAAAGGCAGATTCACCATCTCAAGAGATGATTCAAAAAACACGCTGT<br>ATCTGCAAATGAACAGCCTGAAAACCGAGGACACAGCCGTGTATTACTG<br>TGCGAGAGATTTCGGACGATGGAGCTACTACTTTGACTACTGGAGCCAG<br>GGAACCCTGGTCACCGTCTCCTCAGGTGGAGGCGGTTCAGGCGGAGGTG<br>GCTCTGGCGGTGGCGGATCGCAGTCTGTGCTGACTCAGCCATCCTCAGT<br>GTCTGGGACCCCCGGGCAGAGGGTCACCATCTCTTGTTCTGGAAGCAGC<br>TCCAACATCGGAAGTAATTATGTATACTGGTACCAGCAGCTCCCAGGAA<br>CGGCCCCCAAACTCCTCATCTATAGGAATAATCAGCGGCCCTCAGGGGT<br>CCCTGACCGATTCTCTGGCTCCAAGTCTGGCACCTCAGCCTCCCTGGCCA<br>TCAGTGGGCTCCGGTCCGAGGATGAGGCTGATTATTACTGTGCAGCATG<br>GGATGACAGCCTGAGTGGTGTGGTATTCGGCGGAGGGACCAAGCTCACC<br>GTCCTA | Clone 48 scFv |
| 6 | QVTLKESGGGLVKPGGSLRLSCAASGFTFSNAWMSWVRQAPGKGLEWVG<br>RIKSKTDGGTTDYAAPVKGRFTISRDDSKNTLYLQMNSLKTEDTAVYYCAR<br>DFGRWSYYFDYWSQGTLVTVSSGGGGSGGGGSGGGGSQSVLTQPSSVSGT<br>PGQRVTISCSGSSSNIGSNYVYWYQQLPGTAPKLLIYRNNQRPSGVPDRFSG<br>SKSGTSASLAISGLRSEDEADYYCAAWDDSLSGVVFGGGTKLTVL | Clone 48 scFv<br>(aa) |
| 7 | CAGGTGCAGCTGTTGGAGTCTGGGGGAGGCTTGGTACAGCCAGGGCGGT<br>CCCTGAGACTCTCCTGTACAGCTTCTGGATTCACCTTTGGTGATTATGCG<br>ATGAGCTGGGTCCGCCAGGCTCCAGGGAAGGGGCTGGAGTGGGTCTCA<br>AGTATTAGTGGTAGTGGTCGTAGCACAGACCACGCAGACTACGTGAAGG<br>GCCGGTTCACCATCTCCAGAGACAATTCCAAGAACACGGTATATCTGCA<br>AATGAACAGGCTGAGAGCCGAGGACACGGCCGTGTATTACTGTGCAAA<br>AGTCAGTAACTACGAGTATTACTTTGACTACTGGGCCCAGGGAACCCTG<br>GTCACCGTCTCCTCA | Clone V70 $V_H$ |
| 8 | QVQLLESGGGLVQPGRSLRLSCTASGFTFGDYAMSWVRQAPGKGLEWVSS<br>ISGSGRSTDHADYVKGRFTISRDNSKNTVYLQMNRLRAEDTAVYYCAKVS<br>NYEYYFDYWAQGTLVTVSS | Clone V70 $V_H$ |
| 9 | CAGGTCACCTTGAAGGAGTCTGGGGGAGGCTTGGTAAAGCCTGGGGGG<br>TCCCTTAGACTCTCCTGTGCAGCCTCTGGATTCACTTTCAGTAACGCCTG<br>GATGAGCTGGGTCCGCCAGGCTCCAGGGAAGGGGCTGGAGTGGGTTGG<br>CCGTATTAAAAGCAAAACTGATGGTGGGACAACAGACTACGCTGCACCC<br>GTGAAAGGCAGATTCACCATCTCAAGAGATGATTCAAAAAACACGCTGT<br>ATCTGCAAATGAACAGCCTGAAAACCGAGGACACAGCCGTGTATTACTG<br>TGCGAGAGATTTCGGACGATGGGGCTACTACTTTGACTACTGGAGCCAG<br>GGAACCCTGGTCACCGTCTCCTCA | Clone V353<br>$V_H$ |
| 10 | QVTLKESGGGLVKPGGSLRLSCAASGFTFSNAWMSWVRQAPGKGLEWVG<br>RIKSKTDGGTTDYAAPVKGRFTISRDDSKNTLYLQMNSLKTEDTAVYYCAR<br>DFGRWGYYFDYWSQGTLVTVSS | Clone V353<br>$V_H$ |
| 11 | CAGGTCCAGCTTGTGCAGTCTGGGGCTGAGGTGAAGAAGCCTGGGGCCT<br>CAGTGAAGGTTTCCTGCAAGGCATCTGGATACACCTTCACCAGCTACTA<br>TATGCACTGGGTGCGACAGGCCCCTGGACAAGGGCTTGAGTGGATGGG<br>AATAATCAACCCTAATGGTGGTAGCACAAGCTACGCACAGAAGTTCCAG<br>GGCAGAGTCACCATGACCAGGGACACGTCCACGAGCACAGTCTACATG<br>GAGCTGAGCAGCCTGAGATCTGAGGACACGGCCGTGTATTACTGTGCGA | Clone 83B<br>scFv |

-continued

| SEQ ID NO: | Sequence | Description |
|---|---|---|
| | GAGATAGCAGCTATGATGCTTTTGATATCTGGGGCCAAGGGACAATGGT<br>CACCGTCTCCTCAGGTGGAGGCGGTTCAGGCGGAGGTGGCTCTGGCGGT<br>GGCGGATCGGCCATCCAGTTGACCCAATCTCCTTCCACCCTGTCTGCATC<br>TGTAGGAGACAGAGTCACCATCACTTGCCAGGCGAGTCAGGACATCAGC<br>AATTATTTAAATTGGTATCAGCAGAAACCAGGGAAAGCCCCTAAACTCC<br>TGATCAACGATGCATCCTATTTGGAGACAGGGGTCCCATCAAGGTTCAG<br>TGGAAGTGGATCTGGGACAGATTTTACTTTAACCATCAGCAGCCTGCAG<br>CCTGAAGATATTGCAACATATTACTGTCAACAGTATGAAAGTCTCCCGT<br>ACACTTTTGGCCAGGGGACCAAGCTGGAGATCAAA | |
| 12 | QVQLVQSGAEVKKPGASVKVSCKASGYTFTSYYMHWVRQAPGQGLEWM<br>GIINPNGGSTSYAQKFQGRVTMTRDTSTSTVYMELSSLRSEDTAVYYCARD<br>SSYDAFDIWGQGTMVTVSSGGGGSGGGGSGGGGSAIQLTQSPSTLSASVGD<br>RVTITCQASQDISNYLNWYQQKPGKAPKLLINDASYLETGVPSRFSGSGSGT<br>DFTLTISSLQPEDIATYYCQQYESLPYTFGQGTKLEIK | Clone 83B scFv |
| 13 | QVTLKESGGGLVKPGGSLRLSCAASGFTFSNAWMSWVRQAPGKGLEWVG<br>RIKSKTDGGTTDYAAPVKGRFTISRDDSKNTLYLQMNSLKTEDTAVYYCAR<br>DFGRWSYYFDYWSQGTLVTVSS | Clone 48 $V_H$ |
| 14 | QSVLTQPSSVSGTPGQRVTISCSGSSSNIGSNYVYWYQQLPGTAPKLLIYRN<br>NQRPSGVPDRFSGSKSGTSASLAISGLRSEDEADYYCAAWDDSLSGVVFGG<br>GTKLTVL | Clone 48 $V_L$ |
| 15 | EVQLVESGGGLVQPGRSLRLSCTASGFTFGDYAMSWVRQAPGKGLEWVSS<br>ISGSGRSTDHADYVKGRFTISRDNSKNTVYLQMNRLRAEDTAVYYCAKVS<br>NYEYYFDYWAQGTLVTVSS | Clone 298 $V_H$ |
| 16 | EIVLTQSPSVSVAPGQTARITCGGSNIGSESVNWYQWKSGQVPVLVVSDTT<br>DRPSGIPGRFTGTRSGTTATLTISGVEAGDEADYHCQVWDDTGDHPVFGGG<br>TKLTVL | Clone 298 $V_L$ |
| 17 | QVQLVQSGAEVKKPGASVKVSCKASGYTFTSYYMHWVRQAPGQGLEWM<br>GIINPSGGSTSYAQKFQGRVTMTRDTSTSTVYMELSSLRSEDTAVYYCARDS<br>SYDAFDIWGQGTMVTVSS | Clone 83 $V_H$ |
| 18 | AIQLTQSPSTLSASVGDRVTITCQASQDISNYLNWYQQKPGKAPKLLINDAS<br>YLETGVPSRFSGSGSGTDFTLTISSLQPEDIATYYCQQYESLPYTFGQGTKLEI<br>K | Clone 83, 83B $V_L$ |
| 19 | QVQLVQSGAEVKKPGASVKVSCKASGYTFTSYYMHWVRQAPGQGLEWM<br>GIINPNGGSTSYAQKFQGRVTMTRDTSTSTVYMELSSLRSEDTAVYYCARD<br>SSYDAFDIWGQGTMVTVSS | Clone 83B $V_H$ |
| 20 | SYYMH | Clone 83, 83B CDR-H1 |
| 21 | IINPSGGSTSYAQKFQG | Clone 83 CDR-H2 |
| 22 | DSSYDAFDI | Clone 83, 83B CDR-H3 |
| 23 | QASQDISNYLN | Clone 83, 83B CDR-L1 |
| 24 | DASYLET | Clone 83, 83B CDR-L2 |
| 25 | QQYESLPYT | Clone 83, 83B CDR-L3 |
| 26 | IINPNGGSTSYAQKFQG | Clone 83B CDR-H2 |
| 27 | DYAMS | Clone 298, V70, 350, 305, 366, 461, V68, V102, V181 CDR-H1 |

-continued

SEQUENCES

| SEQ ID NO: | Sequence | Description |
|---|---|---|
| 28 | SISGSGRSTDHADYVKG | Clone 298, V70, 350, 305, 366 CDR-H2 |
| 29 | VSNYEYYFDY | Clone 298, 305, 350, 366, V70 CDR-H3 |
| 30 | GGSNIGSESVN | Clone 298 CDR-L1 |
| 31 | DTTDRPS | Clone 298 CDR-L2 |
| 32 | QVWDDTGDHPV | Clone 298 CDR-L3 |
| 33 | NAWMS | Clone 48, V353, 7, 81, 16, V18, 40, 20, 43, V9, V224, V163, V95, V312, V357, V397 CDR-H1 |
| 34 | RIKSKTDGGTTDYAAPVKG | Clone 48, V353, 81, 16, 65, V18, 40, 20, 43, V9, V128, V224, V163, V95, V312, V357 CDR-H2 |
| 35 | DFGRWSYYFDY | Clones 16, 20, 43, 48, 40, 65, 81, 7, V128, V18 CDR-H3 |
| 36 | SGSSSNIGSNYVY | Clone 48, 43 CDR-L1 |
| 37 | RNNQRPS | Clone 48, 43 CDR-L2 |
| 38 | AAWDDSLSGVV | Clones 43, 48 CDR-L3 |
| 39 | QVWDNDSDHRV | Clone 305 CDR-L3 |
| 40 | QSYDSSNHV | Clone 350 CDR-L3 |
| 41 | QQLKSRPLS | Clone 20 CDR-L3 |
| 42 | QQLNSYPLT | Clone 16 CDR-L3 |
| 43 | AAWDDSLNGYV | Clone 366 CDR-L3 |
| 44 | QSYDGRNLM | Clone 40 CDR-L3 |
| 45 | DFEVREAHLSYFDY | Clone 461 CDR-H3 |
| 46 | QVWDSSSDHRV | Clone 461 CDR-L3 |

-continued

| SEQUENCES | | |
|---|---|---|
| SEQ ID NO: | Sequence | Description |
| 47 | KSWDSSGSLYV | Clone 65 CDR-L3 |
| 48 | QVWDSSSDHYV | Clone 81 CDR-L3 |
| 49 | QAWDSSTVV | Clone 7 CDR-L3 |
| 50 | VNGGEYYFDY | Clone V420 CDR-H3 |
| 51 | VRGSEYYFDY | Clone V282 CDR-H3 |
| 52 | DFGRWGYYFDY | Clone V353 CDR-H3 |
| 53 | QGDSSSWYVEVYYFDY | Clone V163 CDR-H3 |
| 54 | ITPPDAFDI | Clone V355 CDR-H3 |
| 55 | TYSSSWYESLLFDY | Clone V224 CDR-H3 |
| 56 | GSGELRFLESYYFDY | Clone V95 CDR-H3 |
| 57 | VDSERFLEWYYFDY | Clone V316 CDR-H3 |
| 58 | GQIAAHVWGWFDP | Clone V331 CDR-H3 |
| 59 | DMVGAWLVLSYFDY | Clone V357 CDR-H3 |
| 60 | AKGLWFGESYYFDY | Clone V397 CDR-H3 |
| 61 | TSRGRFLEWLLFDY | Clone V312 CDR-H3 |
| 62 | ERSRWGDNWFDP | Clone V278 CDR-H3 |
| 63 | VIFGVVNIPDY | Clone V86 CDR-H3 |
| 64 | VGPSWDYYFDY | Clone V102 CDR-H3 |
| 65 | GIGYSSSWYEIWTFDY | Clone V365 CDR-H3 |
| 66 | DFEVREAHLSYFDY | Clone V181 CDR-H3 |
| 67 | VLRSGFLEWNLFDY | Clone V71 CDR-H3 |
| 68 | DFEVRGAHLSYFDY | Clone V68 CDR-H3 |
| 69 | VYGYDYRDFGWFDP | Clone V336 CDR-H3 |
| 70 | GSNERFLEWLNFDY | Clone V9 CDR-H3 |

-continued

SEQUENCES

| SEQ ID NO: | Sequence | Description |
|---|---|---|
| 71 | GPLRPQKVLPFQI | Clone V345 CDR-H3 |
| 72 | DSYADDGALFNI | R12 CDR-H3 |
| 73 | GADYIGGYV | R12 CDR-L3 |
| 74 | GYTFTS | Clone 83, 83B CDR-H1 |
| 75 | GYTFTSYYMH | Clone 83, 83B CDR-H1 |
| 76 | GFTFGD | Clone 298, V70, 350, 305, 366, 461, V68, V102, V181 CDR-H1 |
| 77 | GFTFGDYAMS | Clone 298, V70, 350, 305, 366, 461, V68, V102, V181 CDR-H1 |
| 78 | GFTFSN | Clone 48, V353, 7, 81, 16, V18, 40, 20, 43, V9, V163, V95, V312, V357, V397 CDR-H1 |
| 79 | GFTFSNAWMS | Clone 48, V353, 7, 81, 16, V18, 40, 20, 43, V9, V163, V95, V312, V357, V397 CDR-H1 |
| 80 | IINPSGGS | Clone 83 CDR-H2 |
| 81 | SISGSGRS | Clone 298, V70 CDR-H2 |
| 82 | RIKSKTDGGT | Clone 48, V353 CDR - H2 |
| 83 | IINPNGGS | Clone 83B CDR-H2 |
| 84 | QEQLVESGGRLVTPGGSLTLSCKASGFDFSAYYMSWVRQAPGKGLEWIATI YPSSGKTYYATWVNGRFTISSDNAQNTVDLQMNSLTAADRATYFCARDSY ADDGALFNIWGPGTLVTISSGGGGSGGGGSGGGGSELVLTQSPSVSAALGS PAKITCTLSSAHKTDTIDWYQQLQGEAPRYLMQVQSDGSYTKRPGVPDRFS GSSSGADRYLIIPSVQADDEADYYCGADYIGGYVFGGGTQLTVTG | R12 scFv |
| 85 | QEQLVESGGRLVTPGGSLTLSCKASGFDFSAYYMSWVRQAPGKGLEWIATI YPSSGKTYYATWVNGRFTISSDNAQNTVDLQMNSLTAADRATYFCARDSY ADDGALFNIWGPGTLVTISS | R12 $V_H$ |
| 86 | ELVLTQSPSVSAALGSPAKITCTLSSAHKTDTIDWYQQLQGEAPRYLMQVQ SDGSYTKRPGVPDRFSGSSSGADRYLIIPSVQADDEADYYCGADYIGGYVF GGGTQLTVTG | R12 $V_L$ |
| 87 | AYYMS | R12 CDR-H1 |
| 88 | TIYPSSGKTYYATWVNG | R12 CDR-H2 |

-continued

SEQUENCES

| SEQ ID NO: | Sequence | Description |
|---|---|---|
| 89 | TLSSAHKTDTID | R12 CDR-L1 |
| 90 | GSYTKRP | R12 CDR-L2 |
| 91 | GGGGSGGGGSGGGGS | Linker |
| 92 | $X_1X_2X_3X_4X_5X_6X_7X_8X_9X_{10}X_{11}X_{12}X_{13}X_{14}$ $X_{15}$ $X_{16}$<br>$X_1$ = D, V, Q, I, T, G, A, or E;<br>$X_2$ = S, F, N, R, G, T, Y, D, Q, M, K, I, L, or P;<br>$X_3$ = S, N, G, E, D, P, I, V, R, F, N, or L;<br>$X_4$ = Y, R, V, G, S, P, E, A, or L;<br>$X_5$ = D, E, W, R, S, L, A, V, G, or P;<br>$X_6$ = A, W, S, E, G, Y, R, F, H, V, D, S, or Q;<br>$X_7$ = F, Y, A, W, L, G, D, V, N, S, K, or R;<br>$X_8$ = F, Y, H, E, L, W, V, N, I, D, or null;<br>$X_9$ = F, L, V, S, E, W, G, P, Y, or null;<br>$X_{10}$ = S, E, L, Y, W, F, N, G, P, or null;<br>$X_{11}$ = Y, V, L, F, I, W, N, or null;<br>$X_{12}$ = F, Y, W, or null;<br>$X_{13}$ = Y, F, T, or null;<br>$X_{14}$ = F or null;<br>$X_{15}$ = D or Q;<br>$X_{16}$ = I, Y, or P | Consensus CDR-H3 |
| 93 | $X_1X_2X_3X_4X_5X_6X_7X_8X_9X_{10}X_{11}X_{12}DX_{14}$<br>$X_1$ = D or V;<br>$X_2$ = S or F;<br>$X_3$ = S, N, G, or E;<br>$X_4$ = Y, R, or V;<br>$X_5$ = D, E, W, or R;<br>$X_6$ = A, Y, S, or E;<br>$X_7$ = F, Y, or A;<br>$X_8$ = F, Y, H, or null;<br>$X_9$ = F, L, or null;<br>$X_{10}$ = S or null;<br>$X_{11}$ = Y or null;<br>$X_{12}$ = F or null;<br>$X_{14}$ = I or Y | Consensus CDR-H3 |
| 94 | $X_1X_2X_3X_4X_5X_6YX_8X_9DY$<br>$X_1$ = V or D;<br>$X_2$ = S or F;<br>$X_3$ = N or G;<br>$X_4$ = Y or R;<br>$X_5$ = E or W;<br>$X_6$ = Y or G;<br>$X_8$ = F or Y;<br>$X_9$ = F or null | Consensus CDR-H3 |
| 95 | $X_1X_2X_3MX_5$<br>$X_1$ = S, D, or N;<br>$X_2$ = Y or A;<br>$X_3$ = Y, A, or W;<br>$X_5$ = H or S | Consensus CDR-H1 |
| 96 | $X_1IX_3X_4X_5X_6X_7GX_9X_{10}TX_{12}X_{13}AX_{15}X_{16}X_{17}X_{18}G$<br>$X_1$ = I, S, or R;<br>$X_3$ = N, S, or K;<br>$X_4$ = P, G, or S;<br>$X_5$ = K or null;<br>$X_6$ = T or null;<br>$X_7$ = S, D, or N;<br>$X_9$ = G or R;<br>$X_{10}$ = S or T;<br>$X_{12}$ = S or D;<br>$X_{13}$ = Y or H;<br>$X_{15}$ = Q, D, or A;<br>$X_{16}$ = K, Y, or P;<br>$X_{17}$ = F or V;<br>$X_{18}$ = Q or K | Consensus CDR-H2 |

-continued

SEQUENCES

| SEQ ID NO: | Sequence | Description |
| --- | --- | --- |
| 97 | $X_1X_2X_3MS$<br>$X_1$ = D or N;<br>$X_2$ = Y or A;<br>$X_3$ = A or W | Consensus CDR-H1 |
| 98 | $X_1IX_3X_4X_5X_6X_7GX_9X_{10}TX_{12}X_{13}AX_{15}X_{16}X_{17}X_{18}G$<br>$X_1$ = I, S, or R;<br>$X_3$ = N, S, or K;<br>$X_4$ = P, G, or S;<br>$X_5$ = K or null;<br>$X_6$ = T or null;<br>$X_7$ = S, D, or N;<br>$X_9$ = G or R;<br>$X_{10}$ = S or T;<br>$X_{12}$ = S or D;<br>$X_{13}$ = Y or H;<br>$X_{15}$ = Q, D, or A;<br>$X_{16}$ = K, Y, or P;<br>$X_{17}$ = F or V;<br>$X_{18}$ = Q or K | Consensus CDR-H2 |
| 99 | $X_1X_2X_3X_4X_5X_6X_7X_8X_9X_{10}X_{11}X_{12}X_{13}X_{14}$<br>$X_1$ = Q, A, or K;<br>$X_2$ = Q, V, A, or S;<br>$X_3$ = Y, W, or L;<br>$X_4$ = E, D, K, or N;<br>$X_5$ = S, D, N, or G;<br>$X_6$ = L, T, S, D, R, or Y;<br>$X_7$ = P, G, L, S, N, or T;<br>$X_8$ = D, S, N, or null;<br>$X_9$ = H, G, L, or null;<br>$X_{10}$ = Y, P, V, R, H, or L;<br>$X_{11}$ = T, V, S, or M | Consensus CDR-L3 |
| 100 | $X_1X_2X_3X_4X_5X_6X_7X_8X_9X_{10}X_{11}X_{12}X_{13}X_{14}$<br>$X_1$ = Q or A;<br>$X_2$ = Q, V, or A;<br>$X_3$ = Y or W;<br>$X_4$ = E or D;<br>$X_5$ = S or D;<br>$X_6$ = L, T, or S;<br>$X_7$ = P, G, or L;<br>$X_8$ = D, S, or null;<br>$X_9$ = H, G, or null;<br>$X_{10}$ = Y, P, or V;<br>$X_{11}$ = T or V | Consensus CDR-L3 |
| 101 | $X_1X_2SX_4X_5X_6X_7X_8SX_{10}X_{11}X_{12}X_{13}$<br>$X_1$ = Q, G, or S;<br>$X_2$ = A or G;<br>$X_4$ = Q, N, or S;<br>$X_5$ = S or null;<br>$X_6$ = N or null;<br>$X_7$ = D or I;<br>$X_8$ = I or G;<br>$X_{10}$ = N or E;<br>$X_{11}$ = Y or S;<br>$X_{12}$ = L or V;<br>$X_{13}$ = N or Y | Consensus CDR-L1 |
| 102 | $X_1X_2X_3X_4X_5X_6X_7$<br>$X_1$ = D or R;<br>$X_2$ = A, T, or N;<br>$X_3$ = S, T, or N;<br>$X_4$ = Y, D, or Q;<br>$X_5$ = L or R;<br>$X_6$ = E or P;<br>$X_7$ = T or S | Consensus CDR-L2 |

-continued

SEQUENCES

| SEQ ID NO: | Sequence | Description |
|---|---|---|
| 103 | QETELSVSAELVPTSSWNISSELNKDSYLTLDEPMNNITTSLGQTAELHCKV SGNPPPTIRWFKNDAPVVQEPRRLSFRSTIYGSRLRIRNLDTTDTGYFQCVAT NGKEVVSSTGVLFVKFGPPPTASPGYSDEYEEDGFCQPYRGIACARFIGNRT VYMESLHMQGEIENQITAAFTMIGTSSHLSDKCSQFAIPSLCHYAFPYCDET SSVPKPRDLCRDECEILENVLCQTEYIFARSNPMILMRLKLPNCEDLPQPESP EAANCIRIGIPMADPINKNHKCYNSTGVDYRGTVSVTKSGRQCQPWNSQYP HTHTFTALRFPELNGGHSYCRNPGNQKEAPWCFTLDENFKSDLCDIPACDS KDSKEKNKMEILYILVPSVAIPLAIALLFFFICVCRNNQKSSSAPVQRQPKHV RGQNVEMSMLNAYKPKSKAKELPLSAVRFMEELGECAFGKIYKGHLYLPG MDHAQLVAIKTLKDYNNPQQWTEFQQEASLMAELHHPNIVCLLGAVTQEQ PVCMLFEYINQGDLHEFLIMRSPHSDVGCSSDEDGTVKSSLDHGDFLHIAIQI AAGMEYLSSHFFVHKDLAARNILIGEQLHVKISDLGLSREIYSADYYRVQSK SLLPIRWMPPEAIMYGKFSSDSDIWSFGVVLWEIFSFGLQPYYGFSNQEVIE MVRKRQLLPCSEDCPPRMYSLMTECWNEIPSRRPRFKDIHVRLRSWEGLSS HTSSTTPSGGNATTQTTSLSASPVSNLSNPRYPNYMFPSQGITPQGQIAGFIG PPIPQNQRFIPINGYPIPPGYAAFPAAHYQPTGPPRVIQHCPPPKSRSPSSASGS TSTGHVTSLPSSGSNQEANIPLLPHMSIPNHPGGMGIT VFGNKSQKPYKIDSKQASLLGDANIHGHTESMISAEL | Human ROR1; GenBank No. NP_005003.2 |
| 104 | QETELSVSAELVPTSSWNISSELNKDSYLTLDEPMNNITTSLGQTAELHCKV SGNPPPTIRWFKNDAPVVQEPRRLSFRSTIYGSRLRIRNLDTTDTGYFQCVAT NGKEVVSSTGVLFVKFGPPPTASPGYSDEYEEDGFCQPYRGIACARFIGNRT VYMESLHMQGEIENQITAAFTMIGTSSHLSDKCSQFAIPSLCHYAFPYCDET SSVPKPRDLCRDECEILENVLCQTEYIFARSNPMILMRLKLPNCEDLPQPESP EAANCIRIGIPMADPINKNHKCYNSTGVDYRGTVSVTKSGRQCQPWNSQYP HTHTFTALRFPELNGGHSYCRNPGNQKEAPWCFTLDENFKSDLCDIPACDS KDSKEKNKMEILYILVPSVAIPLAIALLFFFICVCRNNQKSSSAPVQRQPKHV RGQNVEMSMLNAYKPKSKAKELPLSAVRFMEELGECAFGKIYKGHLYLPG MDHAQLVAIKTLKDYNNPQQWTEFQQEASLMAELHHPNIVCLLGAVTQEQ PVC | ROR1 Isoform short |
| 105 | QETELSVSAELVPTSSWNISSELNKDSYLTLDEPMNNITTSLGQTAELHCKV SGNPPPTIRWFKNDAPVVQEPRRLSFRSTIYGSRLRIRNLDTTDTGYFQCVAT NGKEVVSSTGVLFVKFGPPPTASPGYSDEYEEDGFCQPYRGIACARFIGNRT VYMESLHMQGEIENQITAAFTMIGTSSHLSDKCSQFAIPSLCHYAFPYCDET SSVPKPRDLCRDECEILENVLCQTEYIFARSNPMILMRLKLPNCEDLPQPESP EAANCIRIGIPMADPINKNHKCYNSTGVDYRGTVSVTKSGRQCQPWNSQYP HTHTFTALRFPELNGGHSYCRNPGNQKEAPWCFTLDENFKSDLCDIPACGK | ROR1 isoform 3 |
| 106 | QETELSVSAELVPTSSWNTSSEIDKGSYLTLDEPMNNITTSLGQTAELHCKV SGNPPPSIRWFKNDAPVVQEPRRISFRATNYGSRLRIRNLDTTDTGYFQCVA TNGKKVVSTTGVLFVKFGPPPTASPGSSDEYEEDGFCQPYRGIACARFIGNR TVYMESLHMQGEIENQITAAFTMIGTSSHLSDKCSQFAIPSLCHYAFPYCDE TSSVPKPRDLCRDECEVLENVLCQTEYIFARSNPMILMRLKLPNCEDLPQPE SPEAANCIRIGIPMADPINKNHKCYNSTGVDYRGTVSVTKSGRQCQPWNSQ YPHTHSFTALRFPELNGGHSYCRNPGNQKEAPWCFTLDENFKSDLCDIPAC DSKDSKEKNKMEILYILVPSVAIPLAIAFLFFFICVCRNNQKSSSPPVQRQPKP VRGQNVEMSMLNAYKPKSKAKELPLSAVRFMEELGECTFGKIYKGHLYLP GMDHAQLVAIKTLKDYNNPQQWTEFQQEASLMAELHHPNIVCLLGAVTQE QPVCMLFEYMNQGDLHEFLIMRSPHSDVGCSSDEDGTVKSSLDHGDFLHIA IQIAAGMEYLSSHFFVHKDLAARNILIGEQLHVKISDLGLSREIYSADYYRVQ SKSSLPIRWMPPEAIMYGKFSSDSDIWSFGVVLWEIFSFGLQPYYGFSNQEVI EMVRKRQLLPCSEDCPPRMYSLMTECWNEIPSRRPRFKDIHVRLRSWEGLS SHTSSTTPSGGNATTQTTSLSASPVSNLSNPRFPNYMFPSQGITPQGQIAGFIG PAIPQNQRFIPINGYPIPPGYAAFPAAHYQPAGPPRVIQHCPPPKSRSPSSASG STSTGHVASLPSSGSNQEANVPLLPHMSIPNHPGGMGITVFGNKSQKPYKID SKQSSLLGDSHIHGHTESMISAEV | Mouse ROR1; GenBank No. NP_038873 |
| 107 | GAATCTAAGTACGGACCGCCCTGCCCCCCTTGCCCT | spacer (IgG4hinge) |
| 108 | ESKYGPPCPPCP | spacer (IgG4hinge) |
| 109 | $X_1SX_3YX_5X_6X_7X_8DX_{10}$<br>$X_1$ = V or D;<br>$X_3$ = S or N;<br>$X_5$ = D or E;<br>$X_6$ = Y or A;<br>$X_7$ = F or Y;<br>$X_8$ = F or null;<br>$X_{10}$ = I or Y; | Consensus CDR-H3 |

-continued

SEQUENCES

| SEQ ID NO: | Sequence | Description |
|---|---|---|
| 110 | $VX_2X_3X_4EYYFDY$<br>$X_2$ = S, N, or R;<br>$X_3$ = N or G;<br>$X_4$ = Y, G, or S; | Consensus CDR-H3 |
| 111 | GGGGS | 4GS linker |
| 112 | GGGS | 3GS linker |
| 113 | GSTSGSGKPGSGEGSTKG | Linker |
| 114 | QVQLQQSGAELVRPGASVTLSCKASGYTFSDYEMHWVIQTPVHGLEWIGAI<br>DPETGGTAYNQKFKGKAILTADKSSSTAYMELRSLTSEDSAVYYCTGYYD<br>YDSFTYWGQGTLVTVSA | 2A2 $V_H$ |
| 115 | DIVMTQSQKIMSTTVGDRVSITCKASQNVDAAVAWYQQKPGQSPKLLIYSA<br>SNRYTGVPDRFTGSGSGTDFTLTISNMQSEDLADYFCQQYDIYPYTFGGGT<br>KLEIK | 2A2 $V_L$ |
| 116 | DYEMH | 2A2 CDR-H1 |
| 117 | AIDPETGGTAYNQKFKG | 2A2 CDR-H2 |
| 118 | YYDYDSFTY | 2A2 CDR-H3 |
| 119 | KASQNVDAAVA | 2A2 CDR-LI |
| 120 | SASNRYT | 2A2 CDR-L2 |
| 121 | QQYDIYPYT | 2A2 CDR-L3 |
| 122 | QVQLQESGPGLVKPSQTLSLTCTVSGYAFTAYNIHWVRQAPGQGLEWMGS<br>FDPYDGGSSY<br>NQKFKDRLTISKDTSKNQVVLTMTNMDPVDTATYYCARGWYYFDYWGH<br>GTLVTVSS | 99961 humanized $V_H$ |
| 123 | QVQLQESGPGLVKPSQTLSLTCTVSGYAFTAYNIHWVRQAPGQGLEWMGS<br>FDPYDGGSSY<br>NQKFKDRLTISKDTSKNQVVLTMTNMDPVDTATYYCARGWYYFDYWGH<br>GTLVTVSS | 99961 humanized $V_H$ |
| 124 | QVQLQESGPGLVKPSQTLSLTCTVSGYAFTAYNIHWIRQPPGKGLEWIGSFD<br>PYDGGSSY<br>NQKFKDRLTISKDTSKNQVVLTMTNMDPVDTATYYCARGWYYFDYWGH<br>GTLVTVSS | 99961 humanized $V_H$ |
| 125 | QVQLQESGPGLVKPSQTLSLTCTVSGYAFTAYNIHWIRQPPGKGLEWIGSFD<br>PYDGGSSY<br>NQKFKDRLTISKDTSKNQVVLTMTNMDPVDTATYYCARGWYYFDYWGH<br>GTLVTVSS | 99961 humanized $V_H$ |
| 126 | DIVMTQTPLSLPVTPGEPASISCRASKSISKYLAWYQQKPGQAPRLLIYSGST<br>LQSGIPP<br>RFSGSGYGTDFTLTINNIESEDAAYYFCQQHDESPYTFGEGTKVEIK | 99961 humanized $V_L$ |
| 127 | DVVMTQSPLSLPVTLGQPASISCRASKSISKYLAWYQQKPGKAPKLLIYSGS<br>TLQSGIPP<br>RFSGSGYGTDFTLTINNIESEDAAYYFCQQHDESPYTFGEGTKVEIK | 99961 humanized $V_L$ |
| 128 | DIVMTQTPLSLPVTPGEPASISCRASKSISKYLAWYQQKPGQAPRLLIYSGST<br>LQSGIPP<br>RFSGSGYGTDFTLTINNIESEDAAYYFCQQHDESPYTFGEGTKVEIK | 99961 humanized $V_L$ |
| 129 | DVVMTQSPLSLPVTLGQPASISCRASKSISKYLAWYQQKPGKAPKLLIYSGS<br>TLQSGIPP<br>RFSGSGYGTDFTLTINNIESEDAAYYFCQQHDESPYTFGEGTKVEIK | 99961 humanized $V_L$ |
| 130 | SGYAFTAYNIHWVRQ | 99961 humanized CDR-H1 |

-continued

| SEQUENCES | | |
|---|---|---|
| SEQ ID NO: | Sequence | Description |
| 131 | GSFDPYDGGSSYNQKFKD | 99961 humanized CDR-H2 |
| 132 | YYCARGWYYFDYWGHGTLVTVSS | 99961 humanized CDR-H3 |
| 133 | GYAFTAYN | 99961 humanized CDR-H1 |
| 134 | FDPYDGGS | 99961 humanized CDR-H2 |
| 135 | GWYYFDY | 99961 humanized CDR-H3 |
| 136 | CRASKSISKYLAWY | 99961 humanized CDR-L1 |
| 137 | LLIYSGSTLQSG | 99961 humanized CDR-L2 |
| 138 | CQQHDESPYTFGEGTK | 99961 humanized CDR-L3 |
| 139 | KSISKY | 99961 humanized CDR-L1 |
| 140 | SGS | 99961 humanized CDR-L2 |
| 141 | QQHDESPY | 99961 humanized CDR-L3 |
| 142 | ESKYGPPCPPCPGQPREPQVYTLPPSQEEMTKNQVSLTCLVKGFYPSDIAVE WESNGQPENNYKTTPPVLDSDGSFFLYSRLTVDKSRWQEGNVFSCSVMHE ALHNHYTQKSLSLSLGK | Hinge-CH3 spacer |
| 143 | ESKYGPPCPPCPAPEFLGGPSVFLFPPKPKDTLMISRTPEVTCVVVDVSQEDP EVQFNWYVDGVEVHNAKTKPREEQFNSTYRVVSVLTVLHQDWLNGKEYK CKVSNKGLPSSIEKTISKAKGQPREPQVYTLPPSQEEMTKNQVSLTCLVKGF YPSDIAVEWESNGQPENNYKTTPPVLDSDGSFFLYSRLTVDKSRWQEGNVF SCSVMHEALHNHYTQKSLSLSLGK | Hinge-CH2-CH3 spacer |
| 144 | RWPESPKAQASSVPTAQPQAEGSLAKATTAPATTRNTGRGGEEKKKEKEK EEQEERETKTPECPSHTQPLGVYLLTPAVQDLWLRDKATFTCFVVGSDLKD AHLTWEVAGKVPTGGVEEGLLERHSNGSQSQHSRLTLPRSLWNAGTSVTC TLNHPSLPPQRLMALREPAAQAPVKLSLNLLASSDPPEAASWLLCEVSGFSP PNILLMWLEDQREVNTSGFAPARPPPQPGSTTFWAWSVLRVPAPPSPQPAT YTCVVSHEDSRTLLNASRSLEVSYVTDH | IgD-hinge-Fc |
| 145 | FWVLVVVGGVLACYSLLVTVAFIIFWV | CD28 (amino acids 153-179 of Accession No. P10747) |
| 146 | IEVMYPPPYLDNEKSNGTIIHVKGKHLCPSPLFPGPSKP FWVLVVVGGVLACYSLLVTVAFIIFWV | CD28 (amino acids 114-179 of Accession No. P10747) |

-continued

| SEQUENCES | | |
|---|---|---|
| SEQ ID NO: | Sequence | Description |
| 147 | RSKRSRLLHSDYMNMTPRRPGPTRKHYQPYAPPRDFAAYRS | CD28 (amino acids 180-220 of P10747) |
| 148 | RSKRSRGGHSDYMNMTPRRPGPTRKHYQPYAPPRDFAAYRS | CD28 (LL to GG) |
| 149 | KRGRKKLLYIFKQPFMRPVQTTQEEDGCSCRFPEEEEGGCEL | 4-1BB (amino acids 214-255 of Q07011.1) |
| 150 | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | CD3 zeta |
| 151 | RVKFSRSAEPPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | CD3 zeta |
| 152 | RVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | CD3 zeta |
| 153 | LEGGGEGRGSLLTCGDVEENPGPR | T2A |
| 154 | MLLLVTSLLLCELPHPAFLLIPRKVCNGIGIGEFKDSLSINATNIKHFKNCTSISGDLHILPVAFRGDSFTHTPPLDPQELDILKTVKEITGFLLIQAWPENRTDLHAFENLEIIRGRTKQHGQFSLAVVSLNITSLGLRSLKEISDGDVIISGNKNLCYANTINWKKLFGTSGQKTKIISNRGENSCKATGQVCHALCSPEGCWGPEPRDCVSCRNVSRGRECVDKCNLLEGEPREFVENSECIQCHPECLPQAMNITCTGRGPDNCIQCAHYIDGPHCVKTCPAGVMGENNTLVWKYADAGHVCHLCHPNCTYGCTGPGLEGCPTNGPKIPSIATGMVGALLLLLVVALGIGLFM | tEGFR |
| 155 | XaaRLDE | Clone 65 CDR-H1 |
| 156 | TFWMS | Clone V128 CDR-H1 |
| 157 | TSAMS | Clone V71 CDR-H1 |
| 158 | SYAMS | Clone V86, V278, V365 CDR-H1 |
| 159 | RTWMS | Clone V316 CDR-H1 |
| 160 | GYYWS | Clone V331, V345 CDR-H1 |
| 161 | SYAIS | Clone V355 CDR-H1 |
| 162 | SYWMS | Clone V420, V282 CDR-H1 |
| 163 | SYAMH | Clone V336 CDR-H1 |
| 164 | FIRSKAYGGTTEYAASVKG | Clone 461, V68, V102, V181 CDR-H2 |
| 165 | TISTDGATTWYADSVRG | Clone V71 CDR-H2 |
| 166 | AISGSGGSTYYADSVKG | Clone V86, V278, V365 CDR-H2 |

-continued

SEQUENCES

| SEQ ID NO: | Sequence | Description |
|---|---|---|
| 167 | SINDDGSEKYYVDSVKG | Clone V316 CDR-H2 |
| 168 | KINHSGSTNYNPSLKS | Clone V331 CDR-H2 |
| 169 | GIIPIFGTANYAQKFQG | Clone V355 CDR-H2 |
| 170 | NIKQDGSEKYYVDSVKG | Clone V282, V420 CDR-H2 |
| 171 | RIKSKTDGGTTDYAAPLKG | Clone V397 CDR-H2 |
| 172 | EINHSGSTNYNPSLKS | Clone V345 CDR-H2 |
| 173 | VISYDGSTNYNPSLX$_{aa}$S | Clone V336 CDR-H2 |
| 174 | VYGYDYX$_{aa}$DFGWFDP | Clone V336 CDR-H3 |
| 175 | QITLKESGGGLVKPGGSLRLSCAASGFTFSNAWMSWVRQAPGKGLEWVGR IRSKTDGGTTDYAALVKGRFTISRDDSENTLYLQMNSLKTEDTAVYYCARD FGRWSYYFDYWSQGTLVTVSS | Clone 7 VH |
| 176 | QITLKESGGGLVKPGGSLRLSCAASGFTFSNAWMSWVRQAPGKGLEWVGR IKSKTDGGTTDYAAPVKGRFTISRDDSKNTLYLQMNSLKTEDTAVYYCARD FGRWSYYFDYWSQGTLVTVSS | Clone 81 VH |
| 177 | RSPX$_{aa}$RSLGEAX$_{aa}$VKPGGSLRLSCAASGFTFSNAWMSGSAQAPGKGLEWV GRIKSKTDGGTTDYAAPVKGRFTISRDDSKNTLYLQMNSLKTEDTAVYYCA RDFGRWSYYFDYWSQGTLVTVSS | Clone 16 VH |
| 178 | QVTLKESGGGLVKPGGSLRLSCAASGFTFQX$_{aa}$RLDEWVRQAPGKGLEWVG RIKSKTDGGTTDYAAPVKGRFTISRDDSKNTLYLQMNSLKTEDTAVYYCAR DFGRWSYYFDYWSQGTLVTVSS | Clone 65 VH |
| 179 | QVQLVESGGGLVKPGGSLRLSCAASGFTFSNAWMSWVRQAPGKGLEWVG RIKSKTDGGTTDYAAPVKGRFTISRDDSKNSLYLQMNSLKTEDTAVYYCAR DFGRWSYYFDYWGQGTLVTVSS | Clone V18 VH |
| 180 | QVTLKESGGGLVKPGGSLRLSCAASGFTFSNAWMSWVRQAPGKGLEWVG RIKSKTDGGTTDYAAPVKGRFTISRDDSKNTLYLQMNSLRTEDTAVYYCAR DFGRWSYYFDYWSQGTLVTVSS | Clone 40 VH |
| 181 | EVQLVESGGGLVKPGGSLRLSCAASGFTFSNAWMSWVRQAPGKGLEWVG RIKSKTDGGTTDYAAPVKGRFTISRDDSKNTLYLQMNSLRTEDTAVYYCAR DFGRWSYYFDYWSQGTLVTVSS | Clone 40 VH |
| 182 | EVQLVESGGGLVQPGRSLRLSCTASGFTFGDYAMSWVRQAPGKGLEWVSS ISGSGRSTDHADYVKGRFTISRDNSKNTVYLQMNRLRAEDTAVYYCAKVS NYEYYFDYWAQGTLVTVSS | Clone 350, 305, 366 VH |
| 183 | QVTLKESGGGLVKPGGSLRLSCAASGFTFSNAWMSWVRQAPGKGLEWVG RIKSKTDGGTTDYAAPVKGRFTISRDDSKNTLYLQMNSLKTEDTAVYYCAR DFGRWSYYFDYWSQGTLVTVSS | Clone 20, 43 VH |
| 184 | EVQLVESGGGLVKPGGSLRLSCAASGFTFSNAWMSWVRQAPGKGLEWVG RIKSKTDGGTTDYAAPVKGRFTISRDDSKNTLYLQMNSLKTEDTAVYYCAR DFGRWSYYFDYWSQGTLVTVSS | Clone 20, 43 VH |
| 185 | QVQLVESGGGLVKPGRSLRLSCTASGFTFGDYAMSWFRQAPGKGLEWVGF IRSKAYGGTTEYAASVKGRFTISRDDSKSIAYLQMNSLKTEDTAVYYCAKD FEVREAHLSYFDYWGQGTLVTVSS | Clone 461 VH |
| 186 | EVQLVESGGGLVKPGRSLRLSCTASGFTFGDYAMSWFRQAPGKGLEWVGF IRSKAYGGTTEYAASVKGRFTISRDDSKSIAYLQMNSLKTEDTAVYYCAKD FEVREAHLSYFDYWGQGTLVTVSS | Clone 461 VH |

-continued

| SEQUENCES | | |
|---|---|---|
| SEQ ID NO: | Sequence | Description |
| 187 | QVTLKESGGGLVKPGGSLRLSCAASGFTFSNAWMSWVRQAPGKELEWVG RIKSKTDGGTTDYAAPVKGRFTISRDDSKKTLYLQMNSLKTEDTAVYYCAR GSNERFLEWLNFDYWGQGTLVTVSS | Clone V9 VH |
| 188 | EVQLLESGGGVVQPGGSLRLSCAASGFTFDTFWMSWVRQAPGKGLEWVG RIKSKTDGGTTDYAAPVKGRFTISRDDSKNTLYLQMNSLKTEDTAVYYCAR DFGRWSYYFDYWSQGTLVTVSS | Clone V128 VH |
| 189 | QITLKESGGGLVKPGRSLRLSCTASGFTFGDYAMSWFRQAPGKGLEWVGFI RSKAYGGTTEYAASVKGRFTISRDDSKSIAYLQMNSLKTEDTAVYYCAKDF EVRGAHLSYFDYWGQGTLVTVSS | Clone V68 VH |
| 190 | QVQLVESGGGLVQPGGSLRLSCAASGFTFSTSAMSWVRQAPGKGLEWVSTI STDGATTWYADSVRGRFSVSRDNSKNTLYLQMTGLRAEDTAVYYCARVL RSGFLEWNLFDYWGQGTLVTVSS | Clone V71 VH |
| 191 | QVQLLESGGGLVQPGGSLRLSCAASGFTFSSYAMSWVRQAPGKGLEWVSA ISGSGGSTYYADSVKGRFTISRDNSKNTLYLQMNSLRAEDTAVYYCARVIF GVVNIPDYWGQGTLVTVSS | Clone V86 VH |
| 192 | QVQLVESGGGLVKPGGSLRLSCAASGFTFINAWMSWVRQAPGKGLEWVG RIKSKTDGGTTDYAAPVKGRFTISRDDSKNTLYLQMNSLKTEDTAVYYCAR TYSSSWYESLLFDYWGQGTLVTVSS | Clone V224 VH |
| 193 | QVQLVESGGGLVKPGGSLRLSCAASGFTFSNAWMSWVRQAPGKGLEWVG RIKSKTDGGTTDYAAPVKGRFTISRDDSKNTLYLQMNSLKTEDTAVYYCAR QGDSSSWYVEVYYFDYWGQGTLVTVSS | Clone V163 VH |
| 194 | QVQLVESGGGLVKPGGSLRLSCAASGFTFSNAWMSWVRQAPGKGLEWVG RIKSKTDGGTTDYAAPVKGRFTISRDDSKKTLYLQMNSLKTEDTAVYYCAR GSGELRFLESYYFDYWGQGTLVTVSS | Clone V95 VH |
| 195 | QVQLVESGGGLVQPGRSLRLSCTASGFTFGDYAMSWVRQAPGKGLEWVG FIRSKAYGGTTEYAASVKGRFTISRDDSQSIAYLQMDSLKTEDTAVYYCAK VGPSWDYYFDYWGQGTLVTVSS | Clone V102 VH |
| 196 | QITLKESGGGLVKPGRSLRLSCTASGFTFGDYAMSWFRQAPGKGLEWVGFI RSKAYGGTTEYAASVKGRFTISRDDSKSIAYLQMNSLKTEDTAVYYCAKDF EVREAHLSYFDYWGQGTLVTVSS | Clone V181 VH |
| 197 | EVQLVESGGGLVKPRGSLRLSCAASGFTFSNAWMSWVRQAPGKGLEWVG RIKSKTDGGTTDYAAPVKGRFTISRDDSKNTLYLQMNSLKTEDTAVYYCAR TSRGRFLEWLLFDYWGQGTLVTVSS | Clone V312 VH |
| 198 | EVQLVESGGGLVRPGGSLRLSCAASGLTFSRTWMSWVRQAPGKGLEWVAS INDDGSEKYYVDSVKGRFTISRDNARNSLYLQMNRLRAEDTAVYYCARVD SERFLEWYYFDYWGQGTLVTVSS | Clone V316 VH |
| 199 | QVQLQQWGAGLLKPSETLSLTCAVYGGSFSGYYWSWIRQPPGKGLEWIGK INHSGSTNYNPSLKSRVTISVDTSKNQFSLKLSSVTAADTAVYYCARGQIAA HVWGWFDPWGQGTLVTVSS | Clone V331 VH |
| 200 | QITLKESGGGLVQPGGSLRLSCAASGFTFSSYAMSWVRQAPGKGLEWVSAI SGSGGSTYYADSVKGRFTISRDNSKNTLYLQMNSLRAEDTAVYYCAKERSR WGDNWFDPWGQGTLVTVSS | Clone V278 VH |
| 201 | EVQLVESGAEVKKPGSSVKVSCKASGGTFSSYAISWVRQAPGQGLEWMGG IIPIFGTANYAQKFQGRVTITADESTSTAYMELSSLRSEDTAVYYCARIYPPD AFDIWGQGTMVTVSS | Clone V355 VH |
| 202 | EVQLVESGGGLVKPGGSLRLSCAASGFTFSNAWMSWVRQAPGKGLEWVG RIKSKTDGGTTDYAAPVKGRFTISRDDSKNTLYLQMNSLKTEDTAVYYCAR DMVGAWLVLSYFDYWGQGTLVTVSS | Clone V357 VH |
| 203 | EVQLVESGGGLVQPGGSLRLSCAASGFTFSSYWMSWVRQAPGKGLEWVA NIKQDGSEKYYVDSVKGRFTISRDNAKNSLYLQMNSLRAEDTAVYYCARV RGSEYYFDYWGQGTLVTVSS | Clone V282 VH |
| 204 | QVQLVESGGGLVQPGGSLRLSCAASGFTFSSYAMSWVRQAPGKGLEWVSA ISGSGGSTYYADSVKGRFTISRDNSKNTLYLQMNSLRAEDTAVYYCAKGIG YSSSWYEIWTFDYWGQGTLVTVSS | Clone V365 VH |

-continued

| SEQUENCES | | |
|---|---|---|
| SEQ ID NO: | Sequence | Description |
| 205 | QITLKESGGGLVQPGGSLRLSCAASGFTFSNAWMSWVRQAPGKGLEWVGR IKSKTDGGTTDYAAPLKGRFTISRDDSKNTLYLQMNSLKTEDTAVYYCARA KGLWFGESYYFDYWGQGTLVTVSS | Clone V397 VH |
| 206 | QVQLVESGGGLVQPGGSLRLSCAASGFTFSSYWMSWVRQAPGKGLEWVA NIKQDGSEKYYVDSVKGRFTISRDNAKNSLYLQMNSLRAEDTAVYYCARV NGGEYYFDYWGQGTLVTVSS | Clone V420 VH |
| 207 | QVQLQQWGAGLLKPSETLSLTCAVYGGSFSGYYWSWIRQPPGKGLEWIGEI NHSGSTNYNPSLKSRVTISVDTSKNQFSLKLSSVTAEDTAVYYCARGPLRPQ KVLPFQIGAQGTLVTVSS | Clone V345 VH |
| 208 | QVQLVESGGGVVQPGRSLRLSCAASGFTFSSYAMHWVRQAPGKGLEWVA VISYDGSTNYNPSLX$_{aa}$SRVTISVDTSKNQFSLKLSSVTAADTAVYYCARVYG YDYRDFGWFDPWGQGTLVTVSS | Clone V336 VH |
| 209 | QVQLVESGGGVVQPGRSLRLSCAASGFTFSSYAMHWVRQAPGKGLEWVA VISYDGSTNYNPSLX$_{aa}$SRVTISVDTSKNQFSLKLSSVTAADTAVYYCARVYG YDYX$_{aa}$DFGWFDPWGQGTLVTVSS | Clone V336 VH |
| 210 | SGDKLGDKYAC | Clone 7 CDR-L1 |
| 211 | GGNNIGTKSVH | Clone 81 CDR-L1 |
| 212 | RASQGISSYLA | Clone 16 CDR-L1 |
| 213 | PRRQPQKTIMQ | Clone 65 CDR-L1 |
| 214 | GGNNLGSKNVH | Clone V18 CDR-L1 |
| 215 | TRSSGNIASNFVQ | Clone 40 CDR-L1 |
| 216 | TRSSGSIASNYVQ | Clone 350 CDR-L1 |
| 217 | RASQSINKWLA | Clone 20 CDR-L1 |
| 218 | GGNNIGSTSVH | Clone 305 CDR-L1 |
| 219 | SGSRFNIGSNTVN | Clone 366 CDR-L1 |
| 220 | GGNRIGTKAVH | Clone 461 CDR-L1 |
| 221 | QDSKRPS | Clone 7 CDR-L2 |
| 222 | DESDRPS | Clone 81 CDR-L2 |
| 223 | AASTLQS | Clone 16 CDR-L2 |
| 224 | GKNDRPS | Clone 65 CDR-L2 |
| 225 | DDDNRPS | Clone V18 CDR-L2 |
| 226 | EDTQRPS | Clone 40 CDR-L2 |
| 227 | EDNQRPS | Clone 350 CDR-L2 |

-continued

SEQUENCES

| SEQ ID NO: | Sequence | Description |
|---|---|---|
| 228 | DASTLES | Clone 20 CDR-L2 |
| 229 | DDSDRPS | Clone 305 CDR-L2 |
| 230 | SNNQRPS | Clone 366 CDR-L2 |
| 231 | DDTDRPS | Clone 461 CDR-L2 |
| 232 | QVWDSSSRHVV | Clone V18 CDR-L3 |
| 233 | $X_{aa}$AWDSSTVV | Clone 7 CDR-L3 |
| 234 | SYELTQPPSVSVSPGQTASITCSGDKLGDKYACWYQQKPGQSPVLVIYQDS KRPSGIPERFSGSNSGNTATLTISGTQAMDEADYXaaXaaXaaAWDSSTVVFG GGTKLTVL | Clone 7 VL |
| 235 | SYELTQPPSVSVSPGQTASITCSGDKLGDKYACWYQQKPGQSPVLVIYQDS KRPSGIPERFSGSNSGNTATLTISGTQAMDEADYXaaXaaQAWDSSTVVFGG GTKLTVL | Clone 7 VL |
| 236 | QSVLTQPPSVSVAPGQTARITCGGNNIGTKSVHWYQQKPGQAPVLVLYDES DRPSGIPERFSGS$X_{aa}$SGNTATLTISRVEAGDEAD$X_{aa}$LLSGVG$X_{aa}$$X_{aa}$$X_{aa}$$X_{aa}$SLC FGSGTKLTVL | Clone 81 VL |
| 237 | QSVLTQPPSVSVAPGQTARITCGGNNIGTKSVHWYQQKPGQAPVLVLYDES DRPSGIPERFSGS$X_{aa}$SGNTATLTISRVEAGDEAD$X_{aa}$LLQVWDSSSDHYVFGS GTKLTVL | Clone 81 VL |
| 238 | EIVMTQSPSFLSASVGDRVTITCRASQGISSYLAWYQQKPGKAPKLLIYAAS TLQSGSHQGFSGSGSGTEFTLTISSLQPEDFATYYC | Clone 16 VL |
| 239 | QSALTQDPAVSVALGTDSQDHMPRRQPQKTIMQWYQQKPGQAPALVIYGK NDRPSGIPDRFSGSTSGNTASLTITGAQAEDEADYY$X_{aa}$ | Clone 65 VL |
| 240 | VLTQPPSVSVAPGKTARITCGGNNLGSKNVHWYQQKPGQAPVLVIYDDDN RPSGIPERFSGSNSGNTATLTISRVEAGDEADYYCQVWDSSSRHVVFGGGT KLTVL | Clone V18 VL |
| 241 | QPVLTQPHSVSESPGKTVTISCTRSSGNIASNFVQWYQRRPDGATTNVIYED TQRPSGVSGRFSGSIDRSSNSASLTISGLRAEDEADYYCQSYDGRNLMFGGG TKVTVL | Clone 40 VL |
| 242 | QPVLTQPHSVSESPGKTVTISCTRSSGSIASNYVQWYQQRPGSAPTTVIYED NQRPSGVPDRFSGSIDSSSNSASLTISGLKTEDEADYYCQSYDSSNHVFGTGT KLTVL | Clone 350 VL |
| 243 | NIQMTQSPSSLSASVGDRVTITCRASQSINKWLAWYQQKPGKAPKLLIHDA STLESGVPSRFSGSGSGTEFTLTISSLHPDDSATYYCQQLKSPPAQFGEGTKL EIK | Clone 20 VL |
| 244 | NIQMTQSPSSLSASVGDRVTITCRASQSINKWLAWYQQKPGKAPKLLIHDA STLESGVPSRFSGSGSGTEFTLTISSLHPDDSATYYCQQLKSRPLSFGEGTKL EIK | Clone 20 VL |
| 245 | QSVLTQPSSVSGTPGQRVTISCSGSSSNIGSNYVYWYQQLPGTAPKLLIYRN NQRPSGVPDRFSGSKSGTSASLGHQWAPGPRMRLIITAAWDDSLSGVVFGG GTKLTVL | Clone 43 VL |
| 246 | QSVLTQPPSVSVAPGQTARITCGGNNIGSTSVHWFQQKPGQAPVLVVYDDS DRPSGIPERFSGSNSGNTATLTISRVEAGDEADYYCQVWDNDSDHRVFGGG TKLTVL | Clone 305 VL |
| 247 | QSVLTQPPSVPGTPGQRVTITCSGSRFNIGSNTVNWYQQLPGTAPKLLIYSN NQRPSGVPDRFSGSKSGTSASLAISGLQSEDEADYYCAAWDDSLNGYVFGT GTKLTVL | Clone 366 VL |

-continued

| SEQUENCES | | |
|---|---|---|
| SEQ ID NO: | Sequence | Description |
| 248 | QSVLTQPPSVSVAPGQTARITCGGNRIGTKAVHWYQQKSGQAPVLVVRDD<br>TDRPSGSLRDSLAPTLGT$X_{aa}$ATLTISGVEAGDEADYYQVWDSSSDHRVFGG<br>GTKLTVL | Clone 461 VL |
| 249 | QITLKESGGGLVKPGGSLRLSCAASGFTFSNAWMSWVRQAPGKGLEWVGR<br>IRSKTDGGTTDYAALVKGRFTISRDDSENTLYLQMNSLKTEDTAVYYCARD<br>FGRWSYYFDYWSQGTLVTVSSSYELTQPPSVSVSPGQTASITCSGDKLGDK<br>YACWYQQKPGQSPVLVIYQDSKRPSGIPERFSGSNSGNTATLTISGTQAMDE<br>ADYXaaXaaXaaAWDSSTVVFGGGTKLTVL | Clone 7 scFv |
| 250 | QITLKESGGGLVKPGGSLRLSCAASGFTFSNAWMSWVRQAPGKGLEWVGR<br>IRSKTDGGTTDYAALVKGRFTISRDDSENTLYLQMNSLKTEDTAVYYCARD<br>FGRWSYYFDYWSQGTLVTVSSSYELTQPPSVSVSPGQTASITCSGDKLGDK<br>YACWYQQKPGQSPVLVIYQDSKRPSGIPERFSGSNSGNTATLTISGTQAMDE<br>ADYXaaXaaQAWDSSTVVFGGGTKLTVL | Clone 7 scFv |
| 251 | QITLKESGGGLVKPGGSLRLSCAASGFTFSNAWMSWVRQAPGKGLEWVGR<br>IKSKTDGGTTDYAAPVKGRFTISRDDSKNTLYLQMNSLKTEDTAVYYCARD<br>FGRWSYYFDYWSQGTLVTVSSQSVLTQPPSVSVAPGQTARITCGGNNIGTK<br>SVHWYQQKPGQAPVLVLYDESDRPSGIPERFSGS$X_{aa}$SGNTATLTISRVEAGD<br>EAD$X_{aa}$LLSGVG$X_{aa}X_{aa}X_{aa}X_{aa}$SLCFGSGTKLTVL | Clone 81 scFv |
| 252 | QITLKESGGGLVKPGGSLRLSCAASGFTFSNAWMSWVRQAPGKGLEWVGR<br>IKSKTDGGTTDYAAPVKGRFTISRDDSKNTLYLQMNSLKTEDTAVYYCARD<br>FGRWSYYFDYWSQGTLVTVSSQSVLTQPPSVSVAPGQTARITCGGNNIGTK<br>SVHWYQQKPGQAPVLVLYDESDRPSGIPERFSGS$X_{aa}$SGNTATLTISRVEAGD<br>EAD$X_{aa}$LLQVWDSSSDHYVFGSGTKLTVL | Clone 81 scFv |
| 253 | RSP$X_{aa}$RSLGEA$X_{aa}$VKPGGSLRLSCAASGFTFSNAWMSGSAQAPGKGLEWV<br>GRIKSKTDGGTTDYAAPVKGRFTISRDDSKNTLYLQMNSLKTEDTAVYYCA<br>RDFGRWSYYFDYWSQGTLVTVSSEIVMTQSPSFLSASVGDRVTITCRASQGI<br>SSYLAWYQQKPGKAPKLLIYAASTLQSGSHQGFSGSGSGTEFTLTISSLQPE<br>DFATYYC | Clone 16 scFv |
| 254 | QVTLKESGGGLVKPGGSLRLSCAASGFTFQ*RLDEWVRQAPGKGLEWVGR<br>IKSKTDGGTTDYAAPVKGRFTISRDDSKNTLYLQMNSLKTEDTAVYYCARD<br>FGRWSYYFDYWSQGTLVTVSSQSALTQDPAVSVALGTDSQDHMPRRQPQK<br>TIMQWYQQKPGQAPALVIYGKNDRPSGIPDRFSGSTSGNTASLTITGAQAED<br>EADYY$X_{aa}$ | Clone 65 scFv |
| 255 | QVQLVESGGGLVKPGGSLRLSCAASGFTFSNAWMSWVRQAPGKGLEWVG<br>RIKSKTDGGTTDYAAPVKGRFTISRDDSKNSLYLQMNSLKTEDTAVYYCAR<br>DFGRWSYYFDYWGQGTLVTVSSVLTQPPSVSVAPGKTARITCGGNNLGSK<br>NVHWYQQKPGQAPVLVIYDDDNRPSGIPERFSGSNSGNTATLTISRVEAGD<br>EADYYCQVWDSSSRHVVFGGGTKLTVL | Clone V18<br>scFv |
| 256 | QVTLKESGGGLVKPGGSLRLSCAASGFTFSNAWMSWVRQAPGKGLEWVG<br>RIKSKTDGGTTDYAAPVKGRFTISRDDSKNTLYLQMNSLRTEDTAVYYCAR<br>DFGRWSYYFDYWSQGTLVTVSSQPVLTQPHSVSESPGKTVTISCTRSSGNIA<br>SNFVQWYQRRPDGATTNVIYEDTQRPSGVSGRFSGSIDRSSNSASLTISGLR<br>AEDEADYYCQSYDGRNLMFGGGTKVTVL | Clone 40 scFv |
| 257 | EVQLVESGGGLVKPGGSLRLSCAASGFTFSNAWMSWVRQAPGKGLEWVG<br>RIKSKTDGGTTDYAAPVKGRFTISRDDSKNTLYLQMNSLRTEDTAVYYCAR<br>DFGRWSYYFDYWSQGTLVTVSSQPVLTQPHSVSESPGKTVTISCTRSSGNIA<br>SNFVQWYQRRPDGATTNVIYEDTQRPSGVSGRFSGSIDRSSNSASLTISGLR<br>AEDEADYYCQSYDGRNLMFGGGTKVTVL | Clone 40 scFv |
| 258 | EVQLVESGGGLVQPGRSLRLSCTASGFTFGDYAMSWVRQAPGKGLEWVSS<br>ISGSGRSTDHADYVKGRFTISRDNSKNTVYLQMNRLRAEDTAVYYCAKVS<br>NYEYYFDYWAQGTLVTVSSQPVLTQPHSVSESPGKTVTISCTRSSGSIASNY<br>VQWYQQRPGSAPTTVIYEDNQRPSGVPDRFSGSIDSSSNSASLTISGLKTEDE<br>ADYYCQSYDSSNHVFGTGTKLTVL | Clone 350<br>scFv |
| 259 | QVTLKESGGGLVKPGGSLRLSCAASGFTFSNAWMSWVRQAPGKGLEWVG<br>RIKSKTDGGTTDYAAPVKGRFTISRDDSKNTLYLQMNSLKTEDTAVYYCAR<br>DFGRWSYYFDYWSQGTLVTVSSNIQMTQSPSSLSASVGDRVTITCRASQSIN<br>KWLAWYQQKPGKAPKLLIHDASTLESGVPSRFSGSGSGTEFTLTISSLHPDD<br>SATYYCQQLKSPPAQFGEGTKLEIK | Clone 20 scFv |

-continued

SEQUENCES

| SEQ ID NO: | Sequence | Description |
|---|---|---|
| 260 | QVTLKESGGGLVKPGGSLRLSCAASGFTFSNAWMSWVRQAPGKGLEWVG RIKSKTDGGTTDYAAPVKGRFTISRDDSKNTLYLQMNSLKTEDTAVYYCAR DFGRWSYYFDYWSQGTLVTVSSNIQMTQSPSSLSASVGDRVTITCRASQSIN KWLAWYQQKPGKAPKLLIHDASTLESGVPSRFSGSGSGTEFTLTISSLHPDD SATYYCQQLKSRPLSFGEGTKLEIK | Clone 20 scFv |
| 261 | EVQLVESGGGLVKPGGSLRLSCAASGFTFSNAWMSWVRQAPGKGLEWVG RIKSKTDGGTTDYAAPVKGRFTISRDDSKNTLYLQMNSLKTEDTAVYYCAR DFGRWSYYFDYWSQGTLVTVSSNIQMTQSPSSLSASVGDRVTITCRASQSIN KWLAWYQQKPGKAPKLLIHDASTLESGVPSRFSGSGSGTEFTLTISSLHPDD SATYYCQQLKSPPAQFGEGTKLEIK | Clone 20 scFv |
| 262 | EVQLVESGGGLVKPGGSLRLSCAASGFTFSNAWMSWVRQAPGKGLEWVG RIKSKTDGGTTDYAAPVKGRFTISRDDSKNTLYLQMNSLKTEDTAVYYCAR DFGRWSYYFDYWSQGTLVTVSSNIQMTQSPSSLSASVGDRVTITCRASQSIN KWLAWYQQKPGKAPKLLIHDASTLESGVPSRFSGSGSGTEFTLTISSLHPDD SATYYCQQLKSRPLSFGEGTKLEIK | Clone 20 scFv |
| 263 | QVTLKESGGGLVKPGGSLRLSCAASGFTFSNAWMSWVRQAPGKGLEWVG RIKSKTDGGTTDYAAPVKGRFTISRDDSKNTLYLQMNSLKTEDTAVYYCAR DFGRWSYYFDYWSQGTLVTVSSQSVLTQPSSVSGTPGQRVTISCSGSSSNIG SNYVYWYQQLPGTAPKLLIYRNNQRPSGVPDRFSGSKSGTSASLGHQWAP GPRMRLIITAAWDDSLSGVVFGGGTKLTVL | Clone 43 scFv |
| 264 | EVQLVESGGGLVKPGGSLRLSCAASGFTFSNAWMSWVRQAPGKGLEWVG RIKSKTDGGTTDYAAPVKGRFTISRDDSKNTLYLQMNSLKTEDTAVYYCAR DFGRWSYYFDYWSQGTLVTVSSQSVLTQPSSVSGTPGQRVTISCSGSSSNIG SNYVYWYQQLPGTAPKLLIYRNNQRPSGVPDRFSGSKSGTSASLGHQWAP GPRMRLIITAAWDDSLSGVVFGGGTKLTVL | Clone 43 scFv |
| 265 | EVQLVESGGGLVQPGRSLRLSCTASGFTFGDYAMSWVRQAPGKGLEWVSS ISGSGRSTDHADYVKGRFTISRDNSKNTVYLQMNRLRAEDTAVYYCAKVS NYEYYFDYWAQGTLVTVSSQSVLTQPPSVSVAPGQTARITCGGNNIGSTSV HWFQQKPGQAPVLVVYDDSDRPSGIPERFSGSNSGNTATLTISRVEAGDEA DYYCQVWDNDSDHRVFGGGTKLTVL | Clone 305 scFv |
| 266 | EVQLVESGGGLVQPGRSLRLSCTASGFTFGDYAMSWVRQAPGKGLEWVSS ISGSGRSTDHADYVKGRFTISRDNSKNTVYLQMNRLRAEDTAVYYCAKVS NYEYYFDYWAQGTLVTVSSQSVLTQPPSVPGTPGQRVTITCSGSRFNIGSNT VNWYQQLPGTAPKLLIYSNNQRPSGVPDRFSGSKSGTSASLAISGLQSEDEA DYYCAAWDDSLNGYVFGTGTKLTVL | Clone 366 scFv |
| 267 | QVQLVESGGGLVKPGRSLRLSCTASGFTFGDYAMSWFRQAPGKGLEWVGF IRSKAYGGTTEYAASVKGRFTISRDDSKSIAYLQMNSLKTEDTAVYYCAKD FEVREAHLSYFDYWGQGTLVTVSSQSVLTQPPSVSVAPGQTARITCGGNRI GTKAVHWYQQKSGQAPVLVVRDDTDRPSGSLRDSLAPTLGT$X_{aa}$ATLTISGV EAGDEADYYQVWDSSSDHRVFGGGTKLTVL | Clone 461 scFv |
| 268 | EVQLVESGGGLVKPGRSLRLSCTASGFTFGDYAMSWFRQAPGKGLEWVGF IRSKAYGGTTEYAASVKGRFTISRDDSKSIAYLQMNSLKTEDTAVYYCAKD FEVREAHLSYFDYWGQGTLVTVSSQSVLTQPPSVSVAPGQTARITCGGNRI GTKAVHWYQQKSGQAPVLVVRDDTDRPSGSLRDSLAPTLGT$X_{aa}$ATLTISGV EAGDEADYYQVWDSSSDHRVFGGGTKLTVL | Clone 461 scFv |
| 269 | GYTFTSY | Clone 83, 83B CDR-H1 |
| 270 | GFTFGDY | Clone 298, V70, 350, 305, 366, 461, V68, V102, V181 CDR-H1 |
| 271 | GFTFSNA | Clone 48, V353, 7, 81, 16, V18, 40, 20, 43, V9, V163, V95, V312, V357, V397 CDR-H1 |

-continued

| SEQUENCES | | |
|---|---|---|
| SEQ ID NO: | Sequence | Description |
| 272 | GFTFSTS | Clone V71 CDR-H1 |
| 273 | GFTFSSY | Clone V86, V278, V282, V365, V420, V336 CDR-H1 |
| 274 | GFTFQXaaR | Clone 65 CDR-H1 |
| 275 | GFTFDTF | Clone V128 CDR-H1 |
| 276 | GFTFINA | Clone V224 CDR-H1 |
| 277 | GLTFSRT | Clone V316 CDR-H1 |
| 278 | GGSFSGY | Clone V331, V345 CDR-H1 |
| 279 | GGTFSSY | Clone V355 CDR-H1 |
| 280 | GFTFQXaaRLDE | Clone 65 CDR-H1 |
| 281 | GFTFSTSAMS | Clone V71 CDR-H1 |
| 282 | GFTFSSYAMS | Clone 86, V278, V365 CDR-H1 |
| 283 | GFTFDTFWMS | Clone V128 CDR-H1 |
| 284 | GFTFINAWMS | Clone V224 CDR-H1 |
| 285 | GLTFSRTWMS | Clone V316 CDR-H1 |
| 286 | GGSFSGYYWS | Clone V331 CDR-H1 |
| 287 | GGTFSSYAIS | Clone V355 CDR-H1 |
| 288 | GFTFSSYWMS | Clone V282, V420 CDR-H1 |
| 289 | GGSFSGYYWS | Clone V345 CDR-H1 |
| 290 | GFTFSSYAMH | Clone V336 CDR-H1 |
| 291 | KSKTDGGT | Clone V353, V48, V81, V16, V65, V18, V40, V20, V43, 9, 128, V224, V163, V95, V312, V357, V397 CDR-H2 |

-continued

SEQUENCES

| SEQ ID NO: | Sequence | Description |
|---|---|---|
| 292 | SGSGRS | Clone V298, V70, V350, V305, V366 CDR-H2 |
| 293 | NPSGGS | Clone V83 CDR-H2 |
| 294 | NPNGGS | Clone V83B CDR-H2 |
| 295 | RSKTDGGT | Clone 7 CDR-H2 |
| 296 | RSKAYGGT | Clone V68, V102, 461, 181 CDR-H2 |
| 297 | STDGAT | Clone V71 CDR-H2 |
| 298 | SGSGGS | Clone V86, V278, V365 CDR-H2 |
| 299 | NDDGSE | Clone V316 CDR-H2 |
| 300 | NHSGS | Clone V331, V345 CDR-H2 |
| 301 | IPIFGT | Clone V355 CDR-H2 |
| 302 | KQDGSE | Clone V282, V420 CDR-H2 |
| 303 | SYDGS | Clone V336 CDR-H2 |
| 304 | RIKSKTDGGTTD | Clone V353, V48, V81, V16, V65, V18, V40, V20, V43, 9, 128, V224, V163, V95, V312, V357, V397 CDR-H2 |
| 305 | SISGSGRSTD | Clone 298, V70, V350, V305, V366 CDR-H2 |
| 306 | IINPSGGSTS | Clone V83 CDR-H2 |
| 307 | IINPNGGSTS | Clone V83B CDR-H2 |
| 308 | RIRSKTDGGTTD | Clone 7 CDR-H2 |
| 309 | FIRSKAYGGTTE | Clone V68, V102, V181, 461 CDR-H2 |
| 310 | TISTDGATTW | Clone V71 CDR-H2 |

-continued

SEQUENCES

| SEQ ID NO: | Sequence | Description |
|---|---|---|
| 311 | AISGSGGSTY | Clone V86, V278, V365 CDR-H2 |
| 312 | SINDDGSEKY | Clone V316 CDR-H2 |
| 313 | KINHSGSTN | Clone V331 CDR-H2 |
| 314 | GIIPIFGTAN | Clone V355 CDR-H2 |
| 315 | NIKQDGSEKY | Clone V282, V420 CDR-H2 |
| 316 | EINHSGSTN | Clone V345 CDR-H2 |
| 317 | VISYDGSTN | Clone V336 CDR-H2 |
| 318 | RIRSKTDGGTTDYAALVKG | Clone 7 CDR-H2 |

The invention claimed is:

1. A chimeric antigen receptor (CAR) comprising an extracellular portion comprising an anti-human receptor tyrosine kinase-like orphan receptor 1 (ROR1) antibody or an antigen-binding fragment thereof, an intracellular signaling domain, and a transmembrane domain linking the extracellular portion and the intracellular signaling domain, wherein the anti-ROR1 antibody or antigen-binding fragment thereof comprises:

- a heavy chain variable ($V_H$) region comprising a CDR-H1, a CDR-H2, and a CDR-H3 comprising the amino acid sequences set forth in SEQ ID NOs: 20, 21, and 22, respectively, and a light chain variable ($V_L$) region comprising a CDR-L1, a CDR-L2, and a CDR-L3 comprising the amino acid sequences set forth in SEQ ID NOs: 23, 24, and 25 respectively;
- a heavy chain variable ($V_H$) region comprising a CDR-H1, a CDR-H2, and a CDR-H3 comprising the amino acid sequences set forth in SEQ ID NOs: 20, 26, and 22, respectively, and a light chain variable ($V_L$) region comprising a CDR-L1, a CDR-L2, and a CDR-L3 comprising the amino acid sequences set forth in SEQ ID NOs: 23, 24, and 25, respectively;
- a heavy chain variable ($V_H$) region comprising a CDR-H1, a CDR-H2, and a CDR-H3 comprising the amino acid sequences set forth in SEQ ID NOs: 27, 28, and 29, respectively, and a light chain variable ($V_L$) region comprising a CDR-L1, a CDR-L2, and a CDR-L3 comprising the amino acid sequences set forth in SEQ ID NOs: 218, 229, and 39, respectively;
- a heavy chain variable ($V_H$) region comprising a CDR-H1, a CDR-H2, and a CDR-H3 comprising the amino acid sequences set forth in SEQ ID NOs: 27, 28, and 29, respectively, and a light chain variable ($V_L$) region comprising a CDR-L1, a CDR-L2, and a CDR-L3 comprising the amino acid sequences set forth in SEQ ID NOs: 30, 31, and 32, respectively;

a heavy chain variable ($V_H$) region comprising a CDR-H1, a CDR-H2, and a CDR-H3 comprising the amino acid sequences set forth in SEQ ID NOs: 27, 28, and 29, respectively, and a light chain variable ($V_L$) region comprising a CDR-L1, a CDR-L2, and a CDR-L3 comprising the amino acid sequences set forth in SEQ ID NOs: 216, 227, and 40, respectively;

a heavy chain variable ($V_H$) region comprising a CDR-H1, a CDR-H2, and a CDR-H3 comprising the amino acid sequences set forth in SEQ ID NOs: 27, 28, and 29, respectively, and a light chain variable ($V_L$) region comprising a CDR-L1, a CDR-L2, and a CDR-L3 comprising the amino acid sequences set forth in SEQ ID NOs: 219, 230, and 43, respectively;

a heavy chain variable ($V_H$) region comprising a CDR-H1, a CDR-H2, and a CDR-H3 comprising the amino acid sequences set forth in SEQ ID NOs: 33, 34, and 35, respectively, and a light chain variable ($V_L$) region comprising a CDR-L1, a CDR-L2, and a CDR-L3 comprising the amino acid sequences set forth in SEQ ID NOs: 217, 228, and 41, respectively;

a heavy chain variable ($V_H$) region comprising a CDR-H1, a CDR-H2, and a CDR-H3 comprising the amino acid sequences set forth in SEQ ID NOs: 33, 34, and 35, respectively, and a light chain variable ($V_L$) region comprising a CDR-L1, a CDR-L2, and a CDR-L3 comprising the amino acid sequences set forth in SEQ ID NOs: 212, 223, and 42, respectively;

a heavy chain variable ($V_H$) region comprising a CDR-H1, a CDR-H2, and a CDR-H3 comprising the amino acid sequences set forth in SEQ ID NOs: 33, 34, and 35, respectively, and a light chain variable ($V_L$) region comprising a CDR-L1, a CDR-L2, and a CDR-L3 comprising the amino acid sequences set forth in SEQ ID NOs: 36, 37, and 38, respectively;

a heavy chain variable ($V_H$) region comprising a CDR-H1, a CDR-H2, and a CDR-H3 comprising the amino acid sequences set forth in SEQ ID NOs: 33, 34, and 35, respectively, and a light chain variable ($V_L$) region comprising a CDR-L1, a CDR-L2, and a CDR-L3 comprising the amino acid sequences set forth in SEQ ID NOs: 215, 226, and 44, respectively;

a heavy chain variable ($V_H$) region comprising a CDR-H1, a CDR-H2, and a CDR-H3 comprising the amino acid sequences set forth in SEQ ID NOs: 33, 34, and 35, respectively, and a light chain variable ($V_L$) region comprising a CDR-L1, a CDR-L2, and a CDR-L3 comprising the amino acid sequences set forth in SEQ ID NOs: 211, 222, and 48, respectively;

a heavy chain variable ($V_H$) region comprising a CDR-H1, a CDR-H2, and a CDR-H3 comprising the amino acid sequences set forth in SEQ ID NOs: 27, 164, and 45, respectively, and a light chain variable ($V_L$) region comprising a CDR-L1, a CDR-L2, and a CDR-L3 comprising the amino acid sequences set forth in SEQ ID NOs: 220, 231, and 46, respectively;

a heavy chain variable ($V_H$) region comprising a CDR-H1, a CDR-H2, and a CDR-H3 comprising the amino acid sequences set forth in SEQ ID NOs: 33, 318, and 35, respectively, and a light chain variable ($V_L$) region comprising a CDR-L1, a CDR-L2, and a CDR-L3 comprising the amino acid sequences set forth in SEQ ID NOs: 210, 221, and 49, respectively;

a heavy chain variable ($V_H$) region comprising a CDR-H1, a CDR-H2, and a CDR-H3 comprising the amino acid sequences set forth in SEQ ID NOs: 33, 318, and 35, respectively, and a light chain variable ($V_L$) region comprising a CDR-L1, a CDR-L2, and a CDR-L3 comprising the amino acid sequences set forth in SEQ ID NOs: 210, 221, and 233, respectively; or a heavy chain variable ($V_H$) region comprising a CDR-H1, a CDR-H2, and a CDR-H3 comprising the amino acid sequences set forth in SEQ ID NOs: 155, 34 and 35, respectively, and a light chain variable ($V_L$) region comprising a CDR-L1, a CDR-L2, and a CDR-L3 comprising the amino acid sequences set forth in SEQ ID NOs: 213, 224, and 47, respectively.

2. The CAR of claim 1, wherein:

the $V_H$ and $V_L$ regions comprise amino acid sequences having at least 90% identity to SEQ ID NOs: 19 and 18, respectively;

the $V_H$ and $V_L$ regions comprise amino acid sequences having at least 90% identity to SEQ ID NOs: 17 and 18, respectively;

the $V_H$ and $V_L$ regions comprise amino acid sequences having at least 90% identity to SEQ ID NOs: 15 and 16, respectively;

the $V_H$ and $V_L$ regions comprise amino acid sequences having at least 90% identity to SEQ ID NOs: 13 and 14, respectively;

the $V_H$ and $V_L$ regions comprise amino acid sequences having at least 90% identity to SEQ ID NOs: 182 and 242 respectively;

the $V_H$ and $V_L$ regions comprise amino acid sequences having at least 90% identity to SEQ ID NOs: 182 and 246, respectively;

the $V_H$ and $V_L$ regions comprise amino acid sequences having at least 90% identity to SEQ ID NOs: 182 and 247, respectively;

the $V_H$ and $V_L$ regions comprise amino acid sequences having at least 90% identity to SEQ ID NOs: 185 and 248, respectively;

the $V_H$ and $V_L$ regions comprise amino acid sequences having at least 90% identity to SEQ ID NOs: 186 and 248, respectively;

the $V_H$ and $V_L$ regions comprise amino acid sequences having at least 90% identity to SEQ ID NOs: 175 and 234, respectively;

the $V_H$ and $V_L$ regions comprise amino acid sequences having at least 90% identity to SEQ ID NOs: 175 and 235, respectively;

the $V_H$ and $V_L$ regions comprise amino acid sequences having at least 90% identity to SEQ ID NOs: 176 and 236, respectively;

the $V_H$ and $V_L$ regions comprise amino acid sequences having at least 90% identity to SEQ ID NOs: 176 and 237, respectively;

the $V_H$ and $V_L$ regions comprise amino acid sequences having at least 90% identity to SEQ ID NOs: 177 and 238, respectively;

the $V_H$ and $V_L$ regions comprise amino acid sequences having at least 90% identity to SEQ ID NOs: 179 and 240 respectively;

the $V_H$ and $V_L$ regions comprise amino acid sequences having at least 90% identity to SEQ ID NOs: 180 and 241, respectively;

the $V_H$ and $V_L$ regions comprise amino acid sequences having at least 90% identity to SEQ ID NOs: 181 and 241, respectively;

the $V_H$ and $V_L$ regions comprise amino acid sequences having at least 90% identity to SEQ ID NOs: 183 and 243 respectively;

the $V_H$ and $V_L$ regions comprise amino acid sequences having at least 90% identity to SEQ ID NOs: 183 and 244 respectively;

the $V_H$ and $V_L$ regions comprise amino acid sequences having at least 90% identity to SEQ ID NOs: 184 and 243, respectively;

the $V_H$ and $V_L$ regions comprise amino acid sequences having at least 90% identity to SEQ ID NOs: 184 and 244 respectively;

the $V_H$ and $V_L$ regions comprise amino acid sequences having at least 90% identity to SEQ ID NOs: 183 and 245, respectively;

the $V_H$ and $V_L$ regions comprise amino acid sequences having at least 90% identity to SEQ ID NOs: 184 and 245, respectively; or the $V_H$ and $V_L$ regions comprise amino acid sequences having at least 90% identity to SEQ ID NOs: 178 and 239, respectively.

3. The CAR of claim 1, wherein:

the $V_H$ and $V_L$ regions comprise the amino acid sequences set forth in SEQ ID NOs: 19 and 18, respectively;

the $V_H$ and $V_L$ regions comprise the amino acid sequences set forth in SEQ ID NOs: 17 and 18, respectively;

the $V_H$ and $V_L$ regions comprise the amino acid sequences set forth in SEQ ID NOs: 15 and 16, respectively;

the $V_H$ and $V_L$ regions comprise the amino acid sequences set forth in SEQ ID NOs: 13 and 14, respectively;

the $V_H$ and $V_L$ regions comprise the amino acid sequences set forth in SEQ ID NOs: 182 and 242 respectively;

the $V_H$ and $V_L$ regions comprise the amino acid sequences set forth in SEQ ID NOs: 182 and 246, respectively;

the $V_H$ and $V_L$ regions comprise the amino acid sequences set forth in SEQ ID NOs: 182 and 247, respectively;

the $V_H$ and $V_L$ regions comprise the amino acid sequences set forth in SEQ ID NOs: 185 and 248, respectively;

the $V_H$ and $V_L$ regions comprise the amino acid sequences set forth in SEQ ID NOs: 186 and 248, respectively;

the $V_H$ and $V_L$ regions comprise the amino acid sequences set forth in SEQ ID NOs: 175 and 234, respectively;

the $V_H$ and $V_L$ regions comprise the amino acid sequences set forth in SEQ ID NOs: 175 and 235, respectively;

the $V_H$ and $V_L$ regions comprise the amino acid sequences set forth in SEQ ID NOs: 176 and 236, respectively;

the $V_H$ and $V_L$ regions comprise the amino acid sequences set forth in SEQ ID NOs: 176 and 237, respectively;

the $V_H$ and $V_L$ regions comprise the amino acid sequences set forth in SEQ ID NOs: 177 and 238, respectively;

the $V_H$ and $V_L$ regions comprise the amino acid sequences set forth in SEQ ID NOs: 179 and 240 respectively;

the $V_H$ and $V_L$ regions comprise the amino acid sequences set forth in SEQ ID NOs: 180 and 241, respectively;

the $V_H$ and $V_L$ regions comprise the amino acid sequences set forth in SEQ ID NOs: 181 and 241, respectively;

the $V_H$ and $V_L$ regions comprise the amino acid sequences set forth in SEQ ID NOs: 183 and 243 respectively;

the $V_H$ and $V_L$ regions comprise the amino acid sequences set forth in SEQ ID NOs: 183 and 244 respectively;

the $V_H$ and $V_L$ regions comprise the amino acid sequences set forth in SEQ ID NOs: 184 and 243, respectively;

the $V_H$ and $V_L$ regions comprise the amino acid sequences set forth in SEQ ID NOs: 184 and 244 respectively;

the $V_H$ and $V_L$ regions comprise the amino acid sequences set forth in SEQ ID NOs: 183 and 245, respectively;

the $V_H$ and $V_L$ regions comprise the amino acid sequences set forth in SEQ ID NOs: 184 and 245, respectively; or the $V_H$ and $V_L$ regions comprise the amino acid sequences set forth in SEQ ID NOs: 178 and 239, respectively.

4. The CAR of claim 1, wherein the anti-ROR1 antibody or antigen-binding fragment thereof is human.

5. The CAR of claim 1, wherein the anti-ROR1 antibody or antigen-binding fragment thereof is a single chain fragment.

6. The CAR of claim 5, wherein the single chain fragment is a single chain variable fragment (scFv).

7. The CAR of claim 6, wherein the scFv comprises the amino acid sequence set forth in SEQ ID NO: 2, 4, 6, 12, 249, 250, 251, 252, 253, 254, 255, 256, 257, 258, 259, 260, 261, 262, 263, 264, 265, 266, 267, or 268, or a sequence of amino acids that has at least 90% sequence identity to the amino acid sequence set forth in SEQ ID NO: 2, 4, 6, 12, 249, 250, 251, 252, 253, 254, 255, 256, 257, 258, 259, 260, 261, 262, 263, 264, 265, 266, 267, or 268.

8. The CAR of claim 1, wherein:

(a) the anti-ROR1 antibody or antigen-binding fragment thereof has a binding affinity for a human ROR1 protein that is equal to or higher than the binding affinity for the ROR1 protein of the corresponding form of the anti-ROR1 antibody R12 or antigen-binding fragment thereof; and/or (b) the anti-ROR1 antibody or antigen-binding fragment thereof specifically binds to the same or an overlapping epitope of a human ROR1 protein as the epitope specifically bound by the anti-ROR1 antibody R12 or an antigen-binding fragment thereof;

wherein the anti-ROR1 antibody R12 or antigen-binding fragment thereof comprises a VH region comprising the amino acid sequence set forth in SEQ ID NO: 85 and a VL region comprising the amino acid sequence set forth in SEQ ID NO: 86.

9. The CAR of claim 1, wherein the anti-ROR1 antibody or antigen binding fragment thereof binds an epitope within an extracellular portion of the ROR1 protein, wherein the epitope comprises a residue within the fz domain of the ROR1 protein and a residue within the Ig domain of the ROR1 protein.

10. The CAR of claim 1, wherein the intracellular signaling domain comprises a signaling domain of a zeta chain of a CD3-zeta (CD3ζ) chain.

11. The chimeric antigen receptor of claim 10, further comprising an intracellular signaling domain of a T cell costimulatory molecule.

12. The chimeric antigen receptor of claim 11, wherein the T cell costimulatory molecule is selected from the group consisting of CD28 and 4-1BB.

13. A nucleic acid molecule(s) encoding the CAR of claim 1.

14. An engineered cell expressing the CAR of claim 1.

15. The engineered cell of claim 14, wherein the cell is a T cell.

16. A composition comprising the engineered cell of claim 14.

17. A method of treatment, comprising administering a composition comprising the engineered cell of claim 14 to a subject having a disease or disorder associated with ROR1.

18. The method of claim 17, wherein the disease or disorder is a ROR1-expressing cancer.

19. The method of claim 18, wherein the ROR1-expressing cancer is selected from the group consisting of B cell leukemia, lymphoma, B cell chronic lymphocytic leukemia (CLL), acute myeloid leukemia (AML), acute lymphocytic leukemia (ALL), Burkitt Lymphoma, mantle cell lymphoma (MCL), non-small cell lung cancer (NSCLC), neuroblastoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, uterine cancer, adrenal cancer, and head and neck cancer.

20. A method of treatment, comprising administering a composition comprising an anti-human receptor tyrosine kinase-like orphan receptor 1 (ROR1) antibody or an antigen-binding fragment thereof to a subject having a disease or disorder associated with ROR1, wherein the anti-ROR1 antibody or antigen-binding fragment comprises:

a heavy chain variable ($V_H$) region comprising a CDR-H1, a CDR-H2, and a CDR-H3 comprising the amino acid sequences set forth in SEQ ID NOs: 20, 21, and 22, respectively, and a light chain variable ($V_L$) region comprising a CDR-L1, a CDR-L2, and a CDR-L3 comprising the amino acid sequences set forth in SEQ ID NOs: 23, 24, and 25 respectively;

a heavy chain variable ($V_H$) region comprising a CDR-H1, a CDR-H2, and a CDR-H3 comprising the amino acid sequences set forth in SEQ ID NOs: 20, 26, and 22, respectively, and a light chain variable ($V_L$) region comprising a CDR-L1, a CDR-L2, and a CDR-L3 comprising the amino acid sequences set forth in SEQ ID NOs: 23, 24, and 25, respectively;

a heavy chain variable ($V_H$) region comprising a CDR-H1, a CDR-H2, and a CDR-H3 comprising the amino acid sequences set forth in SEQ ID NOs: 27, 28, and 29, respectively, and a light chain variable ($V_L$) region comprising a CDR-L1, a CDR-L2, and a CDR-L3 comprising the amino acid sequences set forth in SEQ ID NOs: 218, 229, and 39, respectively;

a heavy chain variable ($V_H$) region comprising a CDR-H1, a CDR-H2, and a CDR-H3 comprising the amino acid sequences set forth in SEQ ID NOs: 27, 28, and 29, respectively, and a light chain variable ($V_L$) region comprising a CDR-L1, a CDR-L2, and a CDR-L3 comprising the amino acid sequences set forth in SEQ ID NOs: 30, 31, and 32, respectively;

a heavy chain variable ($V_H$) region comprising a CDR-H1, a CDR-H2, and a CDR-H3 comprising the amino acid sequences set forth in SEQ ID NOs: 27, 28, and 29, respectively, and a light chain variable ($V_L$) region comprising a CDR-L1, a CDR-L2, and a CDR-L3 comprising the amino acid sequences set forth in SEQ ID NOs: 216, 227, and 40, respectively;

a heavy chain variable ($V_H$) region comprising a CDR-H1, a CDR-H2, and a CDR-H3 comprising the amino acid sequences set forth in SEQ ID NOs: 27, 28, and 29, respectively, and a light chain variable ($V_L$) region comprising a CDR-L1, a CDR-L2, and a CDR-L3 comprising the amino acid sequences set forth in SEQ ID NOs: 219, 230, and 43, respectively;

a heavy chain variable ($V_H$) region comprising a CDR-H1, a CDR-H2, and a CDR-H3 comprising the amino acid sequences set forth in SEQ ID NOs: 33, 34, and 35, respectively, and a light chain variable ($V_L$) region comprising a CDR-L1, a CDR-L2, and a CDR-L3 comprising the amino acid sequences set forth in SEQ ID NOs: 217, 228, and 41, respectively;

a heavy chain variable ($V_H$) region comprising a CDR-H1, a CDR-H2, and a CDR-H3 comprising the amino acid sequences set forth in SEQ ID NOs: 33, 34, and 35, respectively, and a light chain variable ($V_L$) region comprising a CDR-L1, a CDR-L2, and a CDR-L3 comprising the amino acid sequences set forth in SEQ ID NOs: 212, 223, and 42, respectively;

a heavy chain variable ($V_H$) region comprising a CDR-H1, a CDR-H2, and a CDR-H3 comprising the amino acid sequences set forth in SEQ ID NOs: 33, 34, and 35, respectively, and a light chain variable ($V_L$) region comprising a CDR-L1, a CDR-L2, and a CDR-L3 comprising the amino acid sequences set forth in SEQ ID NOs: 36, 37, and 38, respectively;

a heavy chain variable ($V_H$) region comprising a CDR-H1, a CDR-H2, and a CDR-H3 comprising the amino acid sequences set forth in SEQ ID NOs: 33, 34, and 35, respectively, and a light chain variable ($V_L$) region comprising a CDR-L1, a CDR-L2, and a CDR-L3 comprising the amino acid sequences set forth in SEQ ID NOs: 215, 226, and 44, respectively;

a heavy chain variable ($V_H$) region comprising a CDR-H1, a CDR-H2, and a CDR-H3 comprising the amino acid sequences set forth in SEQ ID NOs: 33, 34, and 35, respectively, and a light chain variable ($V_L$) region comprising a CDR-L1, a CDR-L2, and a CDR-L3 comprising the amino acid sequences set forth in SEQ ID NOs: 211, 222, and 48, respectively;

a heavy chain variable ($V_H$) region comprising a CDR-H1, a CDR-H2, and a CDR-H3 comprising the amino acid sequences set forth in SEQ ID NOs: 27, 164, and 45, respectively, and a light chain variable ($V_L$) region comprising a CDR-L1, a CDR-L2, and a CDR-L3 comprising the amino acid sequences set forth in SEQ ID NOs: 220, 231, and 46, respectively;

a heavy chain variable ($V_H$) region comprising a CDR-H1, a CDR-H2, and a CDR-H3 comprising the amino acid sequences set forth in SEQ ID NOs: 33, 318, and 35, respectively, and a light chain variable ($V_L$) region comprising a CDR-L1, a CDR-L2, and a CDR-L3 comprising the amino acid sequences set forth in SEQ ID NOs: 210, 221, and 49, respectively;

a heavy chain variable ($V_H$) region comprising a CDR-H1, a CDR-H2, and a CDR-H3 comprising the amino acid sequences set forth in SEQ ID NOs: 33, 318, and 35, respectively, and a light chain variable ($V_L$) region comprising a CDR-L1, a CDR-L2, and a CDR-L3 comprising the amino acid sequences set forth in SEQ ID NOs: 210, 221, and 233, respectively; or a heavy chain variable ($V_H$) region comprising a CDR-H1, a CDR-H2, and a CDR-H3 comprising the amino acid sequences set forth in SEQ ID NOs: 155, 34 and 35, respectively, and a light chain variable ($V_L$) region comprising a CDR-L1, a CDR-L2, and a CDR-L3 comprising the amino acid sequences set forth in SEQ ID NOs: 213, 224, and 47, respectively.

21. The method of claim 20, wherein the disease or disorder is a ROR1-expressing cancer.

22. The method of claim 21, wherein the ROR1-expressing cancer is selected from the group consisting of B cell leukemia, lymphoma, B cell chronic lymphocytic leukemia (CLL), acute myeloid leukemia (AML), acute lymphocytic leukemia (ALL), Burkitt Lymphoma, mantle cell lymphoma (MCL), non-small cell lung cancer (NSCLC), neuroblastoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, uterine cancer, adrenal cancer and head and neck cancer.

23. An anti-human receptor tyrosine kinase-like orphan receptor 1 (ROR1) antibody or an antigen-binding fragment thereof, wherein the anti-ROR1 antibody or antigen-binding fragment thereof comprises a heavy chain variable ($V_H$) region comprising a heavy chain complementarity determining region 1 (CDR-H1), CDR-H2, and CDR-H3, wherein:
- the CDR-H1, CDR-H2, and CDR-H3 comprise the amino acid sequences set forth in SEQ ID NOs: 27, 28, and 29, respectively;
- the CDR-H1, CDR-H2, and CDR-H3 comprise the amino acid sequences set forth in SEQ ID NOs: 27, 164, and 64, respectively;
- the CDR-H1, CDR-H2, and CDR-H3 comprise the amino acid sequences set forth in SEQ ID NOs: 27, 164, and 66, respectively;
- the CDR-H1, CDR-H2, and CDR-H3 comprise the amino acid sequences set forth in SEQ ID NOs: 27, 164, and 68, respectively;
- the CDR-H1, CDR-H2, and CDR-H3 comprise the amino acid sequences set forth in SEQ ID NOs: 33, 34, and 35, respectively;
- the CDR-H1, CDR-H2, and CDR-H3 comprise the amino acid sequences set forth in SEQ ID NOs: 33, 34, and 52, respectively;
- the CDR-H1, CDR-H2, and CDR-H3 comprise the amino acid sequences set forth in SEQ ID NOs: 33, 34 and 55, respectively;
- the CDR-H1, CDR-H2, and CDR-H3 comprise the amino acid sequences set forth in SEQ ID NOs: 33, 34 and 53, respectively;
- the CDR-H1, CDR-H2, and CDR-H3 comprise the amino acid sequences set forth in SEQ ID NOs: 33, 34 and 56, respectively;
- the CDR-H1, CDR-H2, and CDR-H3 comprise the amino acid sequences set forth in SEQ ID NOs: 33, 34 and 61, respectively;
- the CDR-H1, CDR-H2, and CDR-H3 comprise the amino acid sequences set forth in SEQ ID NOs: 33, 34 and 59, respectively;
- the CDR-H1, CDR-H2, and CDR-H3 comprise the amino acid sequences set forth in SEQ ID NOs: 33, 171 and 60, respectively;
- the CDR-H1, CDR-H2, and CDR-H3 comprise the amino acid sequences set forth in SEQ ID NOs: 156, 34, and 35, respectively;
- the CDR-H1, CDR-H2, and CDR-H3 comprise the amino acid sequences set forth in SEQ ID NOs: 157, 165, and 67, respectively;
- the CDR-H1, CDR-H2, and CDR-H3 comprise the amino acid sequences set forth in SEQ ID NOs: 158, 166 and 62, respectively;
- the CDR-H1, CDR-H2, and CDR-H3 comprise the amino acid sequences set forth in SEQ ID NOs: 158, 166, and 63, respectively;
- the CDR-H1, CDR-H2, and CDR-H3 comprise the amino acid sequences set forth in SEQ ID NOs: 158, 166, and 65, respectively;
- the CDR-H1, CDR-H2, and CDR-H3 comprise the amino acid sequences set forth in SEQ ID NOs: 159, 167 and 57, respectively;
- the CDR-H1, CDR-H2, and CDR-H3 comprise the amino acid sequences set forth in SEQ ID NOs: 160, 168 and 58, respectively;
- the CDR-H1, CDR-H2, and CDR-H3 comprise the amino acid sequences set forth in SEQ ID NOs: 161, 169 and 54, respectively;
- the CDR-H1, CDR-H2, and CDR-H3 comprise the amino acid sequences set forth in SEQ ID NOs: 162, 170 and 50, respectively;
- the CDR-H1, CDR-H2, and CDR-H3 comprise the amino acid sequences set forth in SEQ ID NOs: 162, 170 and 51, respectively;
- the CDR-H1, CDR-H2, and CDR-H3 comprise the amino acid sequences set forth in SEQ ID NOs: 163, 173, and 69, respectively; or
- the CDR-H1, CDR-H2, and CDR-H3 comprise the amino acid sequences set forth in SEQ ID NOs: 163, 173, and 174, respectively.

24. The anti-ROR1 antibody or antigen-binding fragment thereof of claim 23, wherein the $V_H$ region comprises a sequence of amino acids that exhibits at least 90% sequence identity to the amino acid sequence set forth in SEQ ID NO: 8, 10, 179, 188, 189, 190, 191, 192, 193, 194, 195, 196, 197, 198, 199, 200, 201, 202, 203, 204, 205, 206, 208 or 209.

25. The anti-ROR1 antibody or antigen-binding fragment thereof of claim 23, wherein the $V_H$ region comprises the amino acid sequence set forth in SEQ ID NO: 8, 10, 179, 188, 189, 190, 191, 192, 193, 194, 195, 196, 197, 198, 199, 200, 201, 202, 203, 204, 205, 206, 208 or 209.

26. The anti-ROR1 antibody or antigen-binding fragment thereof of claim 23, wherein the anti-ROR1 antibody or antigen-binding fragment thereof does not comprise a light chain variable ($V_L$) region, does not comprise a CDR-L1, CDR-L2, and/or CDR-L3, and/or is a single-domain antibody (sdAb) comprising only the $V_H$ region.

27. The anti-ROR1 antibody or antigen-binding fragment thereof of claim 23 that is a sdAb comprising only a $V_H$ region.

28. The anti-ROR1 antibody or antigen-binding fragment thereof of claim 23, wherein the anti-ROR1 antibody or antigen-binding fragment thereof specifically binds to a human ROR1 protein.

29. The anti-ROR1 antibody or antigen-binding fragment thereof of claim 23, wherein:
- (a) the anti-ROR1 antibody or antigen-binding fragment thereof has a binding affinity for a human ROR1 protein that is equal to or higher than the binding affinity for the ROR1 protein of the corresponding form of the anti-ROR1 antibody R12 or antigen-binding fragment thereof;
- (b) the anti-ROR1 antibody or antigen-binding fragment thereof specifically binds to the same or an overlapping epitope of a human ROR1 protein as the epitope specifically bound by the anti-ROR1 antibody R12 or an antigen-binding fragment thereof;
- wherein the anti-ROR1 antibody R12 or antigen-binding fragment thereof comprises a VH region comprising the amino acid sequence set forth in SEQ ID NO: 85 and a VL region comprising the amino acid sequence set forth in SEQ ID NO: 86.

30. A conjugate, comprising the anti-ROR1 antibody or antigen-binding fragment thereof of claim 23 and a heterologous molecule or moiety.

31. A chimeric antigen receptor (CAR) comprising an extracellular portion comprising the anti-ROR1 antibody or antigen-binding fragment thereof of claim 23, an intracellular signaling domain, and a transmembrane domain linking the extracellular portion and the intracellular signaling domain.

32. A nucleic acid molecule(s) encoding the anti-ROR1 antibody or antigen-binding fragment thereof of claim 23.

33. A nucleic acid molecule(s) encoding the CAR of claim 31.

34. An engineered cell expressing the CAR of claim 31.

35. A composition comprising the anti-ROR1 antibody or antigen-binding fragment thereof of claim 23.

36. A composition comprising the engineered cell of claim 34.

37. A method of treatment, comprising administering a composition comprising the anti-ROR1 antibody or antigen-binding fragment thereof of claim 23 to a subject having a disease or disorder associated with ROR1.

38. A method of treatment, comprising administering a composition comprising the engineered cell of claim 34 to a subject having a disease or disorder associated with ROR1.

39. A nucleic acid molecule(s) encoding an anti-human receptor tyrosine kinase-like orphan receptor 1 (ROR1) antibody or an antigen-binding fragment thereof, wherein the anti-ROR1 antibody or antigen binding fragment thereof comprises:

a heavy chain variable ($V_H$) region comprising a CDR-H1, a CDR-H2, and a CDR-H3 comprising the amino acid sequences set forth in SEQ ID NOs: 20, 21, and 22, respectively, and a light chain variable ($V_L$) region comprising a CDR-L1, a CDR-L2, and a CDR-L3 comprising the amino acid sequences set forth in SEQ ID NOs: 23, 24, and 25 respectively;

a heavy chain variable ($V_H$) region comprising a CDR-H1, a CDR-H2, and a CDR-H3 comprising the amino acid sequences set forth in SEQ ID NOs: 20, 26, and 22, respectively, and a light chain variable ($V_L$) region comprising a CDR-L1, a CDR-L2, and a CDR-L3 comprising the amino acid sequences set forth in SEQ ID NOs: 23, 24, and 25, respectively;

a heavy chain variable ($V_H$) region comprising a CDR-H1, a CDR-H2, and a CDR-H3 comprising the amino acid sequences set forth in SEQ ID NOs: 27, 28, and 29, respectively, and a light chain variable ($V_L$) region comprising a CDR-L1, a CDR-L2, and a CDR-L3 comprising the amino acid sequences set forth in SEQ ID NOs: 218, 229, and 39, respectively;

a heavy chain variable ($V_H$) region comprising a CDR-H1, a CDR-H2, and a CDR-H3 comprising the amino acid sequences set forth in SEQ ID NOs: 27, 28, and 29, respectively, and a light chain variable ($V_L$) region comprising a CDR-L1, a CDR-L2, and a CDR-L3 comprising the amino acid sequences set forth in SEQ ID NOs: 30, 31, and 32, respectively;

a heavy chain variable ($V_H$) region comprising a CDR-H1, a CDR-H2, and a CDR-H3 comprising the amino acid sequences set forth in SEQ ID NOs: 27, 28, and 29, respectively, and a light chain variable ($V_L$) region comprising a CDR-L1, a CDR-L2, and a CDR-L3 comprising the amino acid sequences set forth in SEQ ID NOs: 216, 227, and 40, respectively;

a heavy chain variable ($V_H$) region comprising a CDR-H1, a CDR-H2, and a CDR-H3 comprising the amino acid sequences set forth in SEQ ID NOs: 27, 28, and 29, respectively, and a light chain variable ($V_L$) region comprising a CDR-L1, a CDR-L2, and a CDR-L3 comprising the amino acid sequences set forth in SEQ ID NOs: 219, 230, and 43, respectively;

a heavy chain variable ($V_H$) region comprising a CDR-H1, a CDR-H2, and a CDR-H3 comprising the amino acid sequences set forth in SEQ ID NOs: 33, 34, and 35, respectively, and a light chain variable ($V_L$) region comprising a CDR-L1, a CDR-L2, and a CDR-L3 comprising the amino acid sequences set forth in SEQ ID NOs: 217, 228, and 41, respectively;

a heavy chain variable ($V_H$) region comprising a CDR-H1, a CDR-H2, and a CDR-H3 comprising the amino acid sequences set forth in SEQ ID NOs: 33, 34, and 35, respectively, and a light chain variable ($V_L$) region comprising a CDR-L1, a CDR-L2, and a CDR-L3 comprising the amino acid sequences set forth in SEQ ID NOs: 212, 223, and 42, respectively;

a heavy chain variable ($V_H$) region comprising a CDR-H1, a CDR-H2, and a CDR-H3 comprising the amino acid sequences set forth in SEQ ID NOs: 33, 34, and 35, respectively, and a light chain variable ($V_L$) region comprising a CDR-L1, a CDR-L2, and a CDR-L3 comprising the amino acid sequences set forth in SEQ ID NOs: 36, 37, and 38, respectively;

a heavy chain variable ($V_H$) region comprising a CDR-H1, a CDR-H2, and a CDR-H3 comprising the amino acid sequences set forth in SEQ ID NOs: 33, 34, and 35, respectively, and a light chain variable ($V_L$) region comprising a CDR-L1, a CDR-L2, and a CDR-L3 comprising the amino acid sequences set forth in SEQ ID NOs: 215, 226, and 44, respectively;

a heavy chain variable ($V_H$) region comprising a CDR-H1, a CDR-H2, and a CDR-H3 comprising the amino acid sequences set forth in SEQ ID NOs: 33, 34, and 35, respectively, and a light chain variable ($V_L$) region comprising a CDR-L1, a CDR-L2, and a CDR-L3 comprising the amino acid sequences set forth in SEQ ID NOs: 211, 222, and 48, respectively;

a heavy chain variable ($V_H$) region comprising a CDR-H1, a CDR-H2, and a CDR-H3 comprising the amino acid sequences set forth in SEQ ID NOs: 27, 164, and 45, respectively, and a light chain variable ($V_L$) region comprising a CDR-L1, a CDR-L2, and a CDR-L3 comprising the amino acid sequences set forth in SEQ ID NOs: 220, 231, and 46, respectively;

a heavy chain variable ($V_H$) region comprising a CDR-H1, a CDR-H2, and a CDR-H3 comprising the amino acid sequences set forth in SEQ ID NOs: 33, 318, and 35, respectively, and a light chain variable ($V_L$) region comprising a CDR-L1, a CDR-L2, and a CDR-L3 comprising the amino acid sequences set forth in SEQ ID NOs: 210, 221, and 49, respectively;

a heavy chain variable ($V_H$) region comprising a CDR-H1, a CDR-H2, and a CDR-H3 comprising the amino acid sequences set forth in SEQ ID NOs: 33, 318, and 35, respectively, and a light chain variable ($V_L$) region comprising a CDR-L1, a CDR-L2, and a CDR-L3 comprising the amino acid sequences set forth in SEQ ID NOs: 210, 221, and 233, respectively; or a heavy chain variable ($V_H$) region comprising a CDR-H1, a CDR-H2, and a CDR-H3 comprising the amino acid sequences set forth in SEQ ID NOs: 155, 34 and 35, respectively, and a light chain variable ($V_L$) region comprising a CDR-L1, a CDR-L2, and a CDR-L3 comprising the amino acid sequences set forth in SEQ ID NOs: 213, 224, and 47, respectively.

40. A single chain cell-surface protein, comprising an anti-human receptor tyrosine kinase-like orphan receptor 1 (ROR1) antibody or an antigen-binding fragment thereof, wherein the anti-ROR1 antibody or antigen-binding fragment thereof comprises:

a heavy chain variable ($V_H$) region comprising a CDR-H1, a CDR-H2, and a CDR-H3 comprising the amino acid sequences set forth in SEQ ID NOs: 20, 21, and 22, respectively, and a light chain variable ($V_L$) region comprising a CDR-L1, a CDR-L2, and a CDR-L3 comprising the amino acid sequences set forth in SEQ ID NOs: 23, 24, and 25 respectively;

a heavy chain variable ($V_H$) region comprising a CDR-H1, a CDR-H2, and a CDR-H3 comprising the amino acid sequences set forth in SEQ ID NOs: 20, 26, and 22, respectively, and a light chain variable ($V_L$) region comprising a CDR-L1, a CDR-L2, and a CDR-L3 comprising the amino acid sequences set forth in SEQ ID NOs: 23, 24, and 25, respectively;

a heavy chain variable ($V_H$) region comprising a CDR-H1, a CDR-H2, and a CDR-H3 comprising the amino acid sequences set forth in SEQ ID NOs: 27, 28, and 29, respectively, and a light chain variable ($V_L$) region comprising a CDR-L1, a CDR-L2, and a CDR-L3 comprising the amino acid sequences set forth in SEQ ID NOs: 218, 229, and 39, respectively;

a heavy chain variable ($V_H$) region comprising a CDR-H1, a CDR-H2, and a CDR-H3 comprising the amino acid sequences set forth in SEQ ID NOs: 27, 28, and 29, respectively, and a light chain variable ($V_L$) region comprising a CDR-L1, a CDR-L2, and a CDR-L3 comprising the amino acid sequences set forth in SEQ ID NOs: 30, 31, and 32, respectively;

a heavy chain variable ($V_H$) region comprising a CDR-H1, a CDR-H2, and a CDR-H3 comprising the amino acid sequences set forth in SEQ ID NOs: 27, 28, and 29, respectively, and a light chain variable ($V_L$) region comprising a CDR-L1, a CDR-L2, and a CDR-L3 comprising the amino acid sequences set forth in SEQ ID NOs: 216, 227, and 40, respectively;

a heavy chain variable ($V_H$) region comprising a CDR-H1, a CDR-H2, and a CDR-H3 comprising the amino acid sequences set forth in SEQ ID NOs: 27, 28, and 29, respectively, and a light chain variable ($V_L$) region comprising a CDR-L1, a CDR-L2, and a CDR-L3 comprising the amino acid sequences set forth in SEQ ID NOs: 219, 230, and 43, respectively;

a heavy chain variable ($V_H$) region comprising a CDR-H1, a CDR-H2, and a CDR-H3 comprising the amino acid sequences set forth in SEQ ID NOs: 33, 34, and 35, respectively, and a light chain variable ($V_L$) region comprising a CDR-L1, a CDR-L2, and a CDR-L3 comprising the amino acid sequences set forth in SEQ ID NOs: 217, 228, and 41, respectively;

a heavy chain variable ($V_H$) region comprising a CDR-H1, a CDR-H2, and a CDR-H3 comprising the amino acid sequences set forth in SEQ ID NOs: 33, 34, and 35, respectively, and a light chain variable ($V_L$) region comprising a CDR-L1, a CDR-L2, and a CDR-L3 comprising the amino acid sequences set forth in SEQ ID NOs: 212, 223, and 42, respectively;

a heavy chain variable ($V_H$) region comprising a CDR-H1, a CDR-H2, and a CDR-H3 comprising the amino acid sequences set forth in SEQ ID NOs: 33, 34, and 35, respectively, and a light chain variable ($V_L$) region comprising a CDR-L1, a CDR-L2, and a CDR-L3 comprising the amino acid sequences set forth in SEQ ID NOs: 36, 37, and 38, respectively;

a heavy chain variable ($V_H$) region comprising a CDR-H1, a CDR-H2, and a CDR-H3 comprising the amino acid sequences set forth in SEQ ID NOs: 33, 34, and 35, respectively, and a light chain variable ($V_L$) region comprising a CDR-L1, a CDR-L2, and a CDR-L3 comprising the amino acid sequences set forth in SEQ ID NOs: 215, 226, and 44, respectively;

a heavy chain variable ($V_H$) region comprising a CDR-H1, a CDR-H2, and a CDR-H3 comprising the amino acid sequences set forth in SEQ ID NOs: 33, 34, and 35, respectively, and a light chain variable ($V_L$) region comprising a CDR-L1, a CDR-L2, and a CDR-L3 comprising the amino acid sequences set forth in SEQ ID NOs: 211, 222, and 48, respectively;

a heavy chain variable ($V_H$) region comprising a CDR-H1, a CDR-H2, and a CDR-H3 comprising the amino acid sequences set forth in SEQ ID NOs: 27, 164, and 45, respectively, and a light chain variable ($V_L$) region comprising a CDR-L1, a CDR-L2, and a CDR-L3 comprising the amino acid sequences set forth in SEQ ID NOs: 220, 231, and 46, respectively;

a heavy chain variable ($V_H$) region comprising a CDR-H1, a CDR-H2, and a CDR-H3 comprising the amino acid sequences set forth in SEQ ID NOs: 33, 318, and 35, respectively, and a light chain variable ($V_L$) region comprising a CDR-L1, a CDR-L2, and a CDR-L3 comprising the amino acid sequences set forth in SEQ ID NOs: 210, 221, and 49, respectively;

a heavy chain variable ($V_H$) region comprising a CDR-H1, a CDR-H2, and a CDR-H3 comprising the amino acid sequences set forth in SEQ ID NOs: 33, 318, and 35, respectively, and a light chain variable ($V_L$) region comprising a CDR-L1, a CDR-L2, and a CDR-L3 comprising the amino acid sequences set forth in SEQ ID NOs: 210, 221, and 233, respectively; or a heavy chain variable ($V_H$) region comprising a CDR-H1, a CDR-H2, and a CDR-H3 comprising the amino acid sequences set forth in SEQ ID NOs: 155, 34 and 35, respectively, and a light chain variable ($V_L$) region comprising a CDR-L1, a CDR-L2, and a CDR-L3 comprising the amino acid sequences set forth in SEQ ID NOs: 213, 224, and 47, respectively.

* * * * *